US006683165B1

(12) United States Patent
Keith et al.

(10) Patent No.: US 6,683,165 B1
(45) Date of Patent: Jan. 27, 2004

(54) HUMAN GENE RELATING TO RESPIRATORY DISEASES AND OBESITY

(75) Inventors: Tim Keith, Bedford, MA (US); Randall Little, Newtonville, MA (US); Paul Van Eerdewegh, Weston, MA (US); Josée Dupuis, Newton, MA (US); Richard Del Mastro, Norfolk, MA (US); Jason Simon, Westfield, NJ (US); Kristina Allen, Hopkinton, MA (US); Sunil Pandit, Gaithersburg, MD (US)

(73) Assignee: Genome Therapeutics Corporation, Waltham, MA (US)

( * ) Notice: Subject to any disclaimer, the term of this patent is extended or adjusted under 35 U.S.C. 154(b) by 0 days.

(21) Appl. No.: 09/548,797

(22) Filed: Apr. 13, 2000

(Under 37 CFR 1.47)

Related U.S. Application Data

(60) Provisional application No. 60/129,391, filed on Apr. 13, 1999.

(51) Int. Cl.[7] .................. C07H 19/00; C07H 21/00; C07H 21/02; C12Q 1/68
(52) U.S. Cl. .............. 536/22.1; 536/23.1; 536/24.3; 536/24.33; 435/6
(58) Field of Search ............... 435/6; 536/22.1, 536/23.1, 24.3, 24.33

(56) References Cited

U.S. PATENT DOCUMENTS

| 5,552,526 A | 9/1996 | Nakamura et al. .......... 530/350 |
| 6,420,154 B1 | 7/2002 | Sheppard et al. ........... 435/212 |

FOREIGN PATENT DOCUMENTS

| WO | WO 97/09420 | 3/1997 | ............ C12N/9/00 |
| WO | WO 97/31109 | 8/1997 | ............ C12N/15/12 |
| WO | WO 99/03878 | 1/1999 | ............ C07K/5/00 |
| WO | WO 01/09293 | 2/2001 | ............ C12N/9/00 |
| WO | WO 01/83782 | 11/2001 | ............ C12N/15/57 |
| WO | WO 02/38744 | 5/2002 | ............ C12N/9/00 |

OTHER PUBLICATIONS

GenBank Accession No. AA44255, Jun. 4, 1997, Hiller et al.
GenBank Accession No. AL117415, Sep. 15, 1999, Blum et al.
GenBank Accession No. AC017113, Dec. 14, 1999, Waterston.
GenBank Accession No. AC055771, Apr. 20, 2000, Birren et al.
Eerdewegh et al., 2002, Nature, 418:426–430.
Alfandari et al., 1997, Devel. Biol., 182:314–330.
Collins et al., 2000, Genetics and Mol. Biol., 23:1–10.
D. R. Dunbar et al., 1997, "In situ hybridization mapping of genomic clones for five human respiratory chain complex 1 genes" *Cytogenet. Cell Genet.* 78:21–24.
A.V. Lembertas et al., 1997, "Identification of an obesity quantitative trail locus on mouse chromosome 2 and evidence of linkage to body fat and insulin on the human homologous region 20q" *J. Clin. Invest.* 100:1240–1247.

*Primary Examiner*—Jezia Riley
(74) *Attorney, Agent, or Firm*—Morgan & Finnegan, L.L.P.

(57) ABSTRACT

This invention relates to isolated nucleic acids comprising genes of human chromosome 20p13-p12 and the proteins encoded by these genes. Expression vectors and host cells containing such genes or fragments thereof, as well as antibodies to the proteins encoded by these nucleic acids are also included herein.

17 Claims, 59 Drawing Sheets

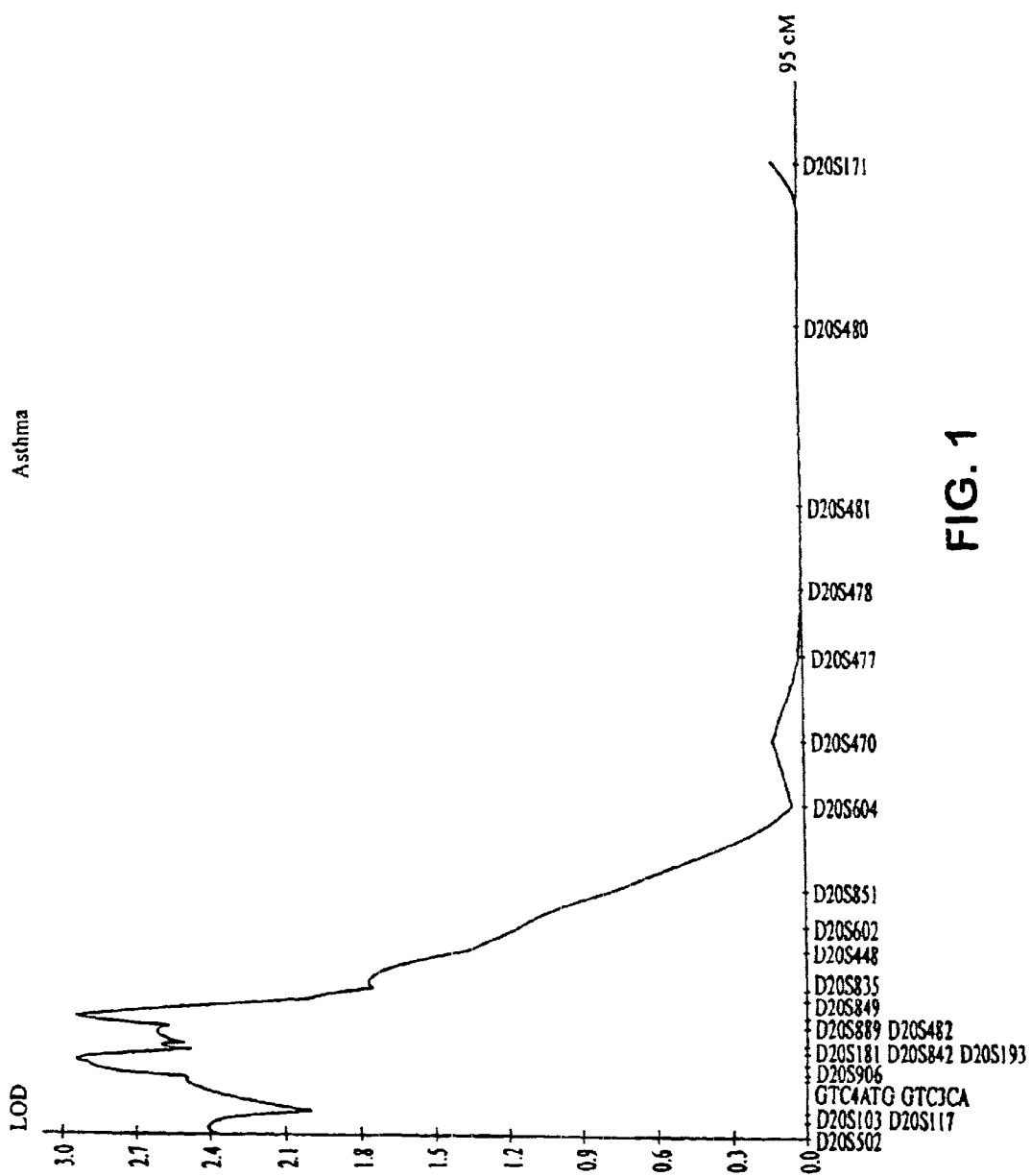

- B0586O20AX
- STSG4244
- SHGC11829
- WI13669
- AFM240ZF4 (D20S181)
- STSF16794
- B688D18AL
- STSG34957
- IB607
- STSG9697
- CDY1EG05
- WI18442
- STSG25155
- WI8344
- AFM308WE1
- B0599O09AX
- B688D18AR
- ATRNMOST5
- B849D17AR
- CHLCATA21E04
- PRG5599PRG5600
- PRG5527PRG5528
- STSG24277
- STSG408
- A005O05
- B849D17AL — 216
- SN2
- AFMB026XH5
- SN1
- STSH22126
- WI4876
- STSG30448
- WI18677
- BDYC4E10
- SGC30160
- B721H02AL
- B0950I22AX
- WI17681
- B0614A04AY
- B1097D08AY
- A009O14
- STSG20327
- AFM248TD1
- STSG30106
- STSG2202
- SHGC2666
- WI17847
- AFM234TF10
- SGC32955
- STSG25313
- STSG8000
- B721H02AR
- B1097D08AX
- B1082K09AR
- B0950I22AY
- B0800D14A3Y

- B0624E22A2X
- B0870L06A2Y
- WI3772
- B768F06AL
- WI2640
- STSG25189
- RM8ARM8B
- AFM036YA3
- UT235
- STSG25337
- UT1704
- CHLCGATA149E11
- CHLCGATA51D03 (D20S482)
- B819A20AL
- B583H11AR
- B715K24AR
- B0934N19A2X
- B1122K02A2Y
- B736H10AR
- STSG20232
- STSG20381
- WI8738
- PDG3PDG6
- EST498946
- WI7784
- WI3651
- SGC34960
- B727P10AR
- B583H11AL
- B819A20AR
- B715K24AL
- B772K01AR
- B1122K02A2X
- B780N09AL
- B736H10AL
- B602E18AL
- B1033I16AY
- STSR73406
- B0686P06AY
- B732A06AR
- SHGC16916
- R79078
- SGC35090
- WI11626
- STSG8643
- STSG5017
- AFMB352XD9 D20S895)
- STSG42745
- STSG10203
- B602E18AR

```
         10                   30                    50
          .                    .                     .
ATGGGCTGGAGGCCCCGGAGAGCTCGGGGGACCCCGTTGCTGCTGCTGCTACTACTGCTG
MetGlyTrpArgProArgArgAlaArgGlyThrProLeuLeuLeuLeuLeuLeuLeuLeu 70                   90                   110
          .                    .                     .
CTGCTCTGGCCAGTGCCAGGCGCCGGGGTGCTTCAAGGACATATCCCTGGGCAGCCAGTC
LeuLeuTrpProValProGlyAlaGlyValLeuGlnGlyHisIleProGlyGlnProVal 130                  150                  170
          .                    .                     .
ACCCCGCACTGGGTCCTGGATGGACAACCCTGGCGCACCGTCAGCCTGGAGGAGCCGGTC
ThrProHisTrpValLeuAspGlyGlnProTrpArgThrValSerLeuGluGluProVal 190                  210                  230
          .                    .                     .
TCGAAGCCAGACATGGGGCTGGTGGCCCTGGAGGCTGAAGGCCAGGAGCTCCTGCTTGAG
SerLysProAspMetGlyLeuValAlaLeuGluAlaGluGlyGlnGluLeuLeuLeuGlu 250                  270                  290
          .                    .                     .
CTGGAGAAGAACCACAGGCTGCTGGCCCCAGGATACATAGAAACCCACTACGGCCCAGAT
LeuGluLysAsnHisArgLeuLeuAlaProGlyTyrIleGluThrHisTyrGlyProAsp 310                  330                  350
          .                    .                     .
GGGCAGCCAGTGGTGCTGGCCCCCAACCACACGGATCATTGCCACTACCAAGGGCGAGTA
GlyGlnProValValLeuAlaProAsnHisThrAspHisCysHisTyrGlnGlyArgVal 370                  390                  410
          .                    .                     .
AGGGGCTTCCCCGACTCCTGGGTAGTCCTCTGCACCTGCTCTGGGATGAGTGGCCTGATC
ArgGlyPheProAspSerTrpValValLeuCysThrCysSerGlyMetSerGlyLeuIle 430                  450                  470
          .                    .                     .
ACCCTCAGCAGGAATGCCAGCTATTATCTGCGTCCCTGGCCACCCCGGGGCTCCAAGGAC
ThrLeuSerArgAsnAlaSerTyrTyrLeuArgProTrpProProArgGlySerLysAsp 490                  510                  530
          .                    .                     .
TTCTCAACCCACGAGATCTTTCGGATGGAGCAGCTGCTCACCTGGAAAGGAACCTGTGGC
PheSerThrHisGluIlePheArgMetGluGlnLeuLeuThrTrpLysGlyThrCysGly 550                  570                  590
```

FIG. 3A

```
CACAGGGATCCTGGGAACAAAGCGGGCATGACCAGCCTTCCTGGTGGTCCCCAGAGCAGG
HisArgAspProGlyAsnLysAlaGlyMetThrSerLeuProGlyGlyProGlnSerArg 610                   630                   650
          .                     .                     .
GGCAGGCGAGAAGCGCGCAGGACCCGGAAGTACCTGGAACTGTACATTGTGGCAGACCAC
GlyArgArgGluAlaArgArgThrArgLysTyrLeuGluLeuTyrIleValAlaAspHis 670                   690                   710
          .                     .                     .
ACCCTGTTCTTGACTCGGCACCGAAACTTGAACCACACCAAACAGCGTCTCCTGGAAGTC
ThrLeuPheLeuThrArgHisArgAsnLeuAsnHisThrLysGlnArgLeuLeuGluVal 730                   750                   770
          .                     .                     .
GCCAACTACGTGGACCAGCTTCTCAGGACTCTGGACATTCAGGTGGCGCTGACCGGCCTG
AlaAsnTyrValAspGlnLeuLeuArgThrLeuAspIleGlnValAlaLeuThrGlyLeu 790                   810                   830
          .                     .                     .
GAGGTGTGGACCGAGCGGGACCGCAGCCGCGTCACGCAGGACGCCAACGCCACGCTCTGG
GluValTrpThrGluArgAspArgSerArgValThrGlnAspAlaAsnAlaThrLeuTrp 850                   870                   890
          .                     .                     .
GCCTTCCTGCAGTGGCGCCGGGGGCTGTGGGCGCAGCGGCCCCACGACTCCGCGCAGCTG
AlaPheLeuGlnTrpArgArgGlyLeuTrpAlaGlnArgProHisAspSerAlaGlnLeu 910                   930                   950
          .                     .                     .
CTCACGGGCCGCGCCTTCCAGGGCGCCACAGTGGGCCTGGCGCCCGTCGAGGGCATGTGC
LeuThrGlyArgAlaPheGlnGlyAlaThrValGlyLeuAlaProValGluGlyMetCys 970                   990                   1010
          .                     .                     .
CGCGCCGAGAGCTCGGGAGGCGTGAGCACGGACCACTCGGAGCTCCCCATCGGCGCCGCA
ArgAlaGluSerSerGlyGlyValSerThrAspHisSerGluLeuProIleGlyAlaAla 1030                  1050                  1070
          .                     .                     .
GCCACCATGGCCCATGAGATCGGCCACAGCCTCGGCCTCAGCCACGACCCCGACGGCTGC
AlaThrMetAlaHisGluIleGlyHisSerLeuGlyLeuSerHisAspProAspGlyCys 1090                  1110                  1130
          .                     .                     .
TGCGTGGAGGCTGCGGCCGAGTCCGGAGGCTGCGTCATGGCTGCGGCCACCGGGCACCCG
CysValGluAlaAlaAlaGluSerGlyGlyCysValMetAlaAlaAlaThrGlyHisPro
```

FIG. 3B

```
              1150                1170                1190
                .                  .                    .
TTTCCGCGCGTGTTCAGCGCCTGCAGCCGCCGCCAGCTGCGCGCCTTCTTCCGCAAGGGG
PheProArgValPheSerAlaCysSerArgArgGlnLeuArgAlaPhePheArgLysGly 1210                1230                1250
                .                  .                    .
GGCGGCGCTTGCCTCTCCAATGCCCCGGACCCCGGACTCCCGGTGCCGCCGGCGCTCTGC
GlyGlyAlaCysLeuSerAsnAlaProAspProGlyLeuProValProProAlaLeuCys 1270                1290                1310
                .                  .                    .
GGGAACGGCTTCGTGGAAGCGGGCGAGGAGTGTGACTGCGGCCCTGGCCAGGAGTGCCGC
GlyAsnGlyPheValGluAlaGlyGluGluCysAspCysGlyProGlyGlnGluCysArg 1330                1350                1370
                .                  .                    .
GACCTCTGCTGCTTTGCTCACAACTGCTCGCTGCGCCCGGGGGCCCAGTGCGCCCACGGG
AspLeuCysCysPheAlaHisAsnCysSerLeuArgProGlyAlaGlnCysAlaHisGly 1390                1410                1430
                .                  .                    .
GACTGCTGCGTGCGCTGCCTGCTGAAGCCGGCTGGAGCGCTGTGCCGCCAGGCCATGGGT
AspCysCysValArgCysLeuLeuLysProAlaGlyAlaLeuCysArgGlnAlaMetGly 1450                1470                1490
                .                  .                    .
GACTGTGACCTCCCTGAGTTTTGCACGGGCACCTCCTCCCACTGTCCCCCAGACGTTTAC
AspCysAspLeuProGluPheCysThrGlyThrSerSerHisCysProProAspValTyr 1510                1530                1550
                .                  .                    .
CTACTGGACGGCTCACCCTGTGCCAGGGGCAGTGGCTACTGCTGGGATGGCGCATGTCCC
LeuLeuAspGlySerProCysAlaArgGlySerGlyTyrCysTrpAspGlyAlaCysPro 1570                1590                1610
                .                  .                    .
ACGCTGGAGCAGCAGTGCCAGCAGCTCTGGGGGCCTGATGGCCAGGAAGTGACTTGTCGG
ThrLeuGluGlnGlnCysGlnGlnLeuTrpGlyProAspGlyGlnGluValThrCysArg 1630                1650                1670
                .                  .                    .
GGAGCCTTGGCACTCCCCAGTGCCCAGCTGGACCTGCTTGGCCTGGGCCTGGTAGAGCCA
GlyAlaLeuAlaLeuProSerAlaGlnLeuAspLeuLeuGlyLeuGlyLeuValGluPro 1690                1710                1730
```

FIG. 3C

```
GGCACCCAGTGTGGACCTAGAATGGTGTGCCAGAGCAGGCGCTGCAGGAAGAATGCCTTC
GlyThrGlnCysGlyProArgMetValCysGlnSerArgArgCysArgLysAsnAlaPhe 1750              1770              1790

CAGGAGCTTCAGCGCTGCCTGACTGCCTGCCACAGCCACGGGGTTTGCAATAGCAACCAT
GlnGluLeuGlnArgCysLeuThrAlaCysHisSerHisGlyValCysAsnSerAsnHis 1810              1830              1850

AACTGCCACTGTGCTCCAGGCTGGGCTCCACCCTTCTGTGACAAGCCAGGCTTTGGTGGC
AsnCysHisCysAlaProGlyTrpAlaProProPheCysAspLysProGlyPheGlyGly 1870              1890              1910

AGCATGGACAGTGGCCCTGTGCAGGCTGAAAACCATGACACCTTCCTGCTGGCCATGCTC
SerMetAspSerGlyProValGlnAlaGluAsnHisAspThrPheLeuLeuAlaMetLeu 1930              1950              1970

CTCAGCGTCCTGCTGCCTCTGCTCCCAGGGGCCGGCCTGGCCTGGTGTTGCTACCGACTC
LeuSerThrLeuLeuProLeuLeuProGlyAlaGlyLeuAlaTrpCysCysTyrArgLeu 1990              2010              2030

CCAGGAGCCCATCTGCAGCGATGCAGCTGGGGCTGCAGAAGGGACCCTGCGTGCAGTGGC
ProGlyAlaHisLeuGlnArgCysSerTrpGlyCysArgArgAspProAlaCysSerGly 2050              2070              2090

CCCAAAGATGGCCCACACAGGGACCACCCCCTGGGCGGCGTTCACCCCATGGAGTTGGGC
ProLysAspGlyProHisArgAspHisProLeuGlyGlyValHisProMetGluLeuGly 2110              2130              2150

CCCACAGCCACTGGACAGCCCTGGCCCCTGGACCCTGAGAACTCTCATGAGCCCAGCAGC
ProThrAlaThrGlyGlnProTrpProLeuAspProGluAsnSerHisGluProSerSer 2170              2190              2210

CACCCTGAGAAGCCTCTGCCAGCAGTCTCGCCTGACCCCCAAGCAGATCAAGTCCAGATG
HisProGluLysProLeuProAlaValSerProAspProGlnAlaAspGlnValGlnMet 2230              2250              2270

CCAAGATCCTGCCTCTGGTGAGAGGTAGCTCCTAAAATGAACAGATTTAAAGACAGGTGG
ProArgSerCysLeuTrpEnd
```

FIG. 3D

```
                2290                    2310                    2330
                  .                       .                       .
CCACTGACAGCCACTCCAGGAACTTGAACTGCAGGGGCAGAGCCAGTGAATCACCGGACC 2350                    2370                    2390
                  .                       .                       .
TCCAGCACCTGCAGGCAGCTTGGAAGTTTCTTCCCCGAGTGGAGCTTCGACCCACCCACT 2410                    2430                    2450
                  .                       .                       .
CCAGGAACCCAGAGCCACATTAGAAGTTCCTGAGGGCTGCAGAACACTGCTGGGCACACT 2470                    2490                    2510
                  .                       .                       .
CTCCAGCTCAATAAACCATCAGTCCCAGAAGCAAAGGTCACACAGCCCCTGACCTCCCTC 2530                    2550                    2570
                  .                       .                       .
ACCAGTGGAGGCTGGGTAGTGCTGGCCATCCCAAAAGGGCTCTGTCCTGGGAGTCTGGTG 2590                    2610                    2630
                  .                       .                       .
TGTCTCCTACATGCAATTTCCACGGACCCAGCTCTGTGGAGGGCATGACTGCTGGCCAGA 2650                    2670                    2690
                  .                       .                       .
AGCTAGTGGTCCTGGGGCCCTATGGTTCGACTGAGTCCACACTCCCCTGCAGCCTGGCTG 2710                    2730                    2750
                  .                       .                       .
GCCTCTGCAAACAAACATAATTTTGGGGACCTTCCTTCCTGTTTCTTCCCACCCTGTCTT 2770                    2790                    2810
                  .                       .                       .
CTCCCCTAGGTGGTTCCTGAGCCCCCACCCCCAATCCCAGTGCTACACCTGAGGTTCTGG 2830                    2850                    2870
                  .                       .                       .
AGCTCAGAATCTGACAGCCTCTCCCCCATTCTGTGTGTGTCGGGGGACAGAGGGAACCA 2890                    2910                    2930
                  .                       .                       .
TTTAAGAAAAGATACCAAAGTAGAAGTCAAAAGAAAGACATGTTGGCTATAGGCGTGGTG
```

FIG. 3E

```
         2950                  2970                  2990
          .                     .                     .
GCTCATGCCTATAATCCCAGCACTTTGGGAAGCCGGGGTAGGAGGATCACCAGAGGCCAG 3010                  3030                  3050
          .                     .                     .
GAGGTCCACACCAGCCTGGGCAACACAGCAAGACACCGCATCTACAGAAAAATTTTAAAA 3070                  3090                  3110
          .                     .                     .
TTAGCTGGGCGTGGTGGTGTGTACCTGTAGGCCTAGCTGCTCAGGAGGCTGAAGCAGGAG 3130                  3150                  3170
          .                     .                     .
GATCACTTGAGCCTGAGTTCAACACTGCAGTGAGCTATGGTGGCACCACTGCACTCCAGC 3190                  3210                  3230
          .                     .                     .
CTGGGTGACAGAGCAAGACCCTGTCTCTAAAATAAATTTTAAAAAGACATATTAAAAAAA 3250                  3270
          .                     .
AAAAAAAAAAAAAAAAAAAAAAAAAAAAAA
```

FIG. 3F

```
         10                  30                  50
          .                   .                   .
ATGGGCTGGAGGCCCCGGAGAGCTCGGGGGACCCCGTTGCTGCTGCTGCTACTACTGCTG
MetGlyTrpArgProArgArgAlaArgGlyThrProLeuLeuLeuLeuLeuLeuLeuLeu 70                  90                 110
          .                   .                   .
CTGCTCTGGCCAGTGCCAGGCGCCGGGGTGCTTCAAGGACATATCCCTGGGCAGCCAGTC
LeuLeuTrpProValProGlyAlaGlyValLeuGlnGlyHisIleProGlyGlnProVal 130                 150                 170
          .                   .                   .
ACCCCGCACTGGGTCCTGGATGGACAACCCTGGCGCACCGTCAGCCTGGAGGAGCCGGTC
ThrProHisTrpValLeuAspGlyGlnProTrpArgThrValSerLeuGluGluProVal 190                 210                 230
          .                   .                   .
TCGAAGCCAGACATGGGGCTGGTGGCCCTGGAGGCTGAAGGCCAGGAGCTCCTGCTTGAG
SerLysProAspMetGlyLeuValAlaLeuGluAlaGluGlyGlnGluLeuLeuLeuGlu 250                 270                 290
          .                   .                   .
CTGGAGAAGAACCACAGGCTGCTGGCCCCAGGATACATAGAAACCCACTACGGCCCAGAT
LeuGluLysAsnHisArgLeuLeuAlaProGlyTyrIleGluThrHisTyrGlyProAsp 310                 330                 350
          .                   .                   .
GGGCAGCCAGTGGTGCTGGCCCCCAACCACACGGATCATTGCCACTACCAAGGGCGAGTA
GlyGlnProValValLeuAlaProAsnHisThrAspHisCysHisTyrGlnGlyArgVal 370                 390                 410
          .                   .                   .
AGGGGCTTCCCCGACTCCTGGGTAGTCCTCTGCACCTGCTCTGGGATGAGTGGCCTGATC
ArgGlyPheProAspSerTrpValValLeuCysThrCysSerGlyMetSerGlyLeuIle 430                 450                 470
          .                   .                   .
ACCCTCAGCAGGAATGCCAGCTATTATCTGCGTCCCTGGCCACCCCGGGGCTCCAAGGAC
ThrLeuSerArgAsnAlaSerTyrTyrLeuArgProTrpProProArgGlySerLysAsp 490                 510                 530
          .                   .                   .
TTCTCAACCCACGAGATCTTTCGGATGGAGCAGCTGCTCACCTGGAAAGGAACCTGTGGC
PheSerThrHisGluIlePheArgMetGluGlnLeuLeuThrTrpLysGlyThrCysGly 550                 570                 590
```

FIG. 4A

```
CACAGGGATCCTGGGAACAAAGCGGGCATGACCAGCCTTCCTGGTGGTCCCCAGAGCAGG
HisArgAspProGlyAsnLysAlaGlyMetThrSerLeuProGlyGlyProGlnSerArg 610               630               650
GGCAGGCGAGAAGCGCGCAGGACCCGGAAGTACCTGGAACTGTACATTGTGGCAGACCAC
GlyArgArgGluAlaArgArgThrArgLysTyrLeuGluLeuTyrIleValAlaAspHis 670               690               710
ACCCTGTTCTTGACTCGGCACCGAAACTTGAACCACACCAAACAGCGTCTCCTGGAAGTC
ThrLeuPheLeuThrArgHisArgAsnLeuAsnHisThrLysGlnArgLeuLeuGluVal 730               750               770
GCCAACTACGTGGACCAGCTTCTCAGGACTCTGGACATTCAGGTGGCGCTGACCGGCCTG
AlaAsnTyrValAspGlnLeuLeuArgThrLeuAspIleGlnValAlaLeuThrGlyLeu 790               810               830
GAGGTGTGGACCGAGCGGGACCGCAGCCGCGTCACGCAGGACGCCAACGCCACGCTCTGG
GluValTrpThrGluArgAspArgSerArgValThrGlnAspAlaAsnAlaThrLeuTrp 850               870               890
GCCTTCCTGCAGTGGCGCCGGGGGCTGTGGGCGCAGCGGCCCCACGACTCCGCGCAGCTG
AlaPheLeuGlnTrpArgArgGlyLeuTrpAlaGlnArgProHisAspSerAlaGlnLeu 910               930               950
CTCACGGGCCGCGCCTTCCAGGGCGCCACAGTGGGCCTGGCGCCCGTCGAGGGCATGTGC
LeuThrGlyArgAlaPheGlnGlyAlaThrValGlyLeuAlaProValGluGlyMetCys 970               990              1010
CGCGCCGAGAGCTCGGGAGGCGTGAGCACGGACCACTCGGAGCTCCCCATCGGCGCCGCA
ArgAlaGluSerSerGlyGlyValSerThrAspHisSerGluLeuProIleGlyAlaAla 1030              1050              1070
GCCACCATGGCCCATGAGATCGGCCACAGCCTCGGCCTCAGCCACGACCCCGACGGCTGC
AlaThrMetAlaHisGluIleGlyHisSerLeuGlyLeuSerHisAspProAspGlyCys 1090              1110              1130
TGCGTGGAGGCTGCGGCCGAGTCCGGAGGCTGCGTCATGGCTGCGGCCACCGGGCACCCG
CysValGluAlaAlaAlaGluSerGlyGlyCysValMetAlaAlaAlaThrGlyHisPro
```

FIG. 4B

```
       1150                1170                1190
         .                   .                   .
TTTCCGCGCGTGTTCAGCGCCTGCAGCCGCCGCCAGCTGCGCGCCTTCTTCCGCAAGGGG
PheProArgValPheSerAlaCysSerArgArgGlnLeuArgAlaPhePheArgLysGly 1210                1230                1250
         .                   .                   .
GGCGGCGCTTGCCTCTCCAATGCCCCGGACCCCGGACTCCCGGTGCCGCCGGCGCTCTGC
GlyGlyAlaCysLeuSerAsnAlaProAspProGlyLeuProValProProAlaLeuCys 1270                1290                1310
         .                   .                   .
GGGAACGGCTTCGTGGAAGCGGGCGAGGAGTGTGACTGCGGCCCTGGCCAGGAGTGCCGC
GlyAsnGlyPheValGluAlaGlyGluGluCysAspCysGlyProGlyGlnGluCysArg 1330                1350                1370
         .                   .                   .
GACCTCTGCTGCTTTGCTCACAACTGCTCGCTGCGCCCGGGGGCCCAGTGCGCCCACGGG
AspLeuCysCysPheAlaHisAsnCysSerLeuArgProGlyAlaGlnCysAlaHisGly 1390                1410                1430
         .                   .                   .
GACTGCTGCGTGCGCTGCCTGCTGAAGCCGGCTGGAGCGCTGTGCCGCCAGGCCATGGGT
AspCysCysValArgCysLeuLeuLysProAlaGlyAlaLeuCysArgGlnAlaMetGly 1450                1470                1490
         .                   .                   .
GACTGTGACCTCCCTGAGTTTTGCACGGGCACCTCCTCCCACTGTCCCCCAGACGTTTAC
AspCysAspLeuProGluPheCysThrGlyThrSerSerHisCysProProAspValTyr 1510                1530                1550
         .                   .                   .
CTACTGGACGGCTCACCCTGTGCCAGGGGCAGTGGCTACTGCTGGGATGGCGCATGTCCC
LeuLeuAspGlySerProCysAlaArgGlySerGlyTyrCysTrpAspGlyAlaCysPro 1570                1590                1610
         .                   .                   .
ACGCTGGAGCAGCAGTGCCAGCAGCTCTGGGGGCCTGGCTCCCACCCAGCTCCCGAGGCC
ThrLeuGluGlnGlnCysGlnGlnLeuTrpGlyProGlySerHisProAlaProGluAla 1630                1650                1670
         .                   .                   .
TGTTTCCAGGTGGTGAACTCTGCGGGAGATGCTCATGGAAACTGCGGCCAGGACAGCGAG
CysPheGlnValValAsnSerAlaGlyAspAlaHisGlyAsnCysGlyGlnAspSerGlu 1690                1710                1730
```

FIG. 4C

```
GGCCACTTCCTGCCCTGTGCAGGGAGGGATGCCCTGTGTGGGAAGCTGCAGTGCCAGGGT
GlyHisPheLeuProCysAlaGlyArgAspAlaLeuCysGlyLysLeuGlnCysGlnGly 1750                1770                1790
GGAAAGCCCAGCCTGCTCGCACCGCACATGGTGCCAGTGGACTCTACCGTTCACCTAGAT
GlyLysProSerLeuLeuAlaProHisMetValProValAspSerThrValHisLeuAsp 1810                1830                1850
GGCCAGGAAGTGACTTGTCGGGGAGCCTTGGCACTCCCCAGTGCCCAGCTGGACCTGCTT
GlyGlnGluValThrCysArgGlyAlaLeuAlaLeuProSerAlaGlnLeuAspLeuLeu 1870                1890                1910
GGCCTGGGCCTGGTAGAGCCAGGCACCCAGTGTGGACCTAGAATGGTTTGCAATAGCAAC
GlyLeuGlyLeuValGluProGlyThrGlnCysGlyProArgMetValCysAsnSerAsn 1930                1950                1970
CATAACTGCCACTGTGCTCCAGGCTGGGCTCCACCCTTCTGTGACAAGCCAGGCTTTGGT
HisAsnCysHisCysAlaProGlyTrpAlaProProPheCysAspLysProGlyPheGly 1990                2010                2030
GGCAGCATGGACAGTGGCCCTGTGCAGGCTGAAAACCATGACACCTTCCTGCTGGCCATG
GlySerMetAspSerGlyProValGlnAlaGluAsnHisAspThrPheLeuLeuAlaMet 2050                2070                2090
CTCCTCAGCGTCCTGCTGCCTCTGCTCCCAGGGGCCGGCCTGGCCTGGTGTTGCTACCGA
LeuLeuSerValLeuLeuProLeuLeuProGlyAlaGlyLeuAlaTrpCysCysTyrArg 2110                2130                2150
CTCCCAGGAGCCCATCTGCAGCGATGCAGCTGGGGCTGCAGAAGGGACCCTGCGTGCAGT
LeuProGlyAlaHisLeuGlnArgCysSerTrpGlyCysArgArgAspProAlaCysSer 2170                2190                2210
GGCCCCAAAGATGGCCCACACAGGGACCACCCCTGGGCGGCGTTCACCCCATGGAGTTG
GlyProLysAspGlyProHisArgAspHisProLeuGlyGlyValHisProMetGluLeu 2230                2250                2270
GGCCCCACAGCCACTGGACAGCCCTGGCCCCTGGACCCTGAGAACTCTCATGAGCCCAGC
GlyProThrAlaThrGlyGlnProTrpProLeuAspProGluAsnSerHisGluProSer
```

FIG. 4D

```
              2290                    2310                   2330
               .                       .                      .
AGCCACCCTGAGAAGCCTCTGCCAGCAGTCTCGCCTGACCCCCAAGCAGATCAAGTCCAG
SerHisProGluLysProLeuProAlaValSerProAspProGlnAlaAspGlnValGln 2350                    2370                   2390
               .                       .                      .
ATGCCAAGATCCTGCCTCTGGTGAGAGGTAGCTCCTAAAATGAACAGATTTAAAGACAGG
MetProArgSerCysLeuTrpEnd 2410                    2430                   2450
               .                       .                      .
TGGCCACTGACAGCCACTCCAGGAACTTGAACTGCAGGGGCAGAGCCAGTGAATCACCGG 2470                    2490                   2510
               .                       .                      .
ACCTCCAGCACCTGCAGGCAGCTTGGAAGTTTCTTCCCCGAGTGGAGCTTCGACCCACCC 2530                    2550                   2570
               .                       .                      .
ACTCCAGGAACCCAGAGCCACATTAGAAGTTCCTGAGGGCTGGAGAACACTGCTGGGCAC 2590                    2610                   2630
               .                       .                      .
ACTCTCCAGCTCAATAAACCATCAGTCCCAGAAGCAAAGGTCACACAGCCCCTGACCTCC 2650                    2670                   2690
               .                       .                      .
CTCACCAGTGGAGGCTGGGTAGTGCTGGCCATCCCAAAAGGGCTCTGTCCTGGGAGTCTG 2710                    2730                   2750
               .                       .                      .
GTGTGTCTCCTACATGCAATTTCCACGGACCCAGCTCTGTGGAGGGCATGACTGCTGGCC 2770                    2790                   2810
               .                       .                      .
AGAAGCTAGTGGTCCTGGGGCCCTATGGTTCGACTGAGTCCACACTCCCCTGCAGCCTGG 2830                    2850                   2870
               .                       .                      .
CTGGCCTCTGCAAACAAACATAATTTTGGGGACCTTCCTTCCTGTTTCTTCCCACCCTGT 2890                    2910                   2930
               .                       .                      .
CTTCTCCCCTAGGTGGTTCCTGAGCCCCCACCCCCAATCCCAGTGCTACACCTGAGGTTC
```

FIG. 4E

```
         2950                2970                  2990
          .                   .                     .
TGGAGCTCAGAATCTGACAGCCTCTCCCCATTCTGTGTGTGTCGGGGGGACAGAGGGAA 3010                3030                  3050
          .                   .                     .
CCATTTAAGAAAAGATACCAAAGTAGAAGTCAAAAGAAAGACATGTTGGCTATAGGCGTG 3070                3090                  3110
          .                   .                     .
GTGGCTCATGCCTATAATCCCAGCACTTTGGGAAGCCGGGGTAGGAGGATCACCAGAGGC 3130                3150                  3170
          .                   .                     .
CAGGAGGTCCACACCAGCCTGGGCAACACAGCAAGACACCGCATCTACAGAAAAATTTTA 3190                3210                  3230
          .                   .                     .
AAATTAGCTGGGCGTGGTGGTGTGTACCTGTAGGCCTAGCTGCTCAGGAGGCTGAAGCAG 3250                3270                  3290
          .                   .                     .
GAGGATCACTTGAGCCTGAGTTCAACACTGCAGTGAGCTATGGTGGCACCACTGCACTCC 3310                3330                  3350
          .                   .                     .
AGCCTGGGTGACAGAGCAAGACCCTGTCTCTAAAATAAATTTTAAAAAGACATATTAAAA 3370                3390
          .                   .
AAAAAAAAAAAAAAAAAAAAAAAAAAAAAA
```

FIG. 4F

```
         10                   30                    50
          .                    .                     .
ATGGGCTGGAGGCCCCGGAGAGCTCGGGGGACCCCGTTGCTGCTGCTGCTACTACTGCTG
MetGlyTrpArgProArgArgAlaArgGlyThrProLeuLeuLeuLeuLeuLeuLeuLeu 70                   90                   110
          .                    .                     .
CTGCTCTGGCCAGTGCCAGGCGCCGGGGTGCTTCAAGGTGAGGACGCGGGCGGGGTCCCC
LeuLeuTrpProValProGlyAlaGlyValLeuGlnGlyGluAspAlaGlyGlyValPro 130                  150                   170
          .                    .                     .
CTCACCCTGTGCTCTGTCTTTACTCCAGGACATATCCCTGGGCAGCCAGTCACCCCGCAC
LeuThrLeuCysSerValPheThrProGlyHisIleProGlyGlnProValThrProHis 190                  210                   230
          .                    .                     .
TGGGTCCTGGATGGACAACCCTGGCGCACCGTCAGCCTGGAGGAGCCGGTCTCGAAGCCA
TrpValLeuAspGlyGlnProTrpArgThrValSerLeuGluGluProValSerLysPro 250                  270                   290
          .                    .                     .
GACATGGGGCTGGTGGCCCTGGAGGCTGAAGGCCAGGAGCTCCTGCTTGAGCTGGAGAAG
AspMetGlyLeuValAlaLeuGluAlaGluGlyGlnGluLeuLeuLeuGluLeuGluLys 310                  330                   350
          .                    .                     .
AACCACAGGCTGCTGGCCCCAGGATACATAGAAACCCACTACGGCCCAGATGGGCAGCCA
AsnHisArgLeuLeuAlaProGlyTyrIleGluThrHis<u>Tyr</u>GlyProAspGlyGlnPro 370                  390                   410
          .                    .                     .
GTGGTGCTGGCCCCCAACCACACGGATCATTGCCACTACCAAGGGCGAGTAAGGGGCTTC
ValValLeuAlaProAsnHisThrAspHisCysHisTyrGlnGlyArgValArgGlyPhe 430                  450                   470
          .                    .                     .
CCCGACTCCTGGGTAGTCCTCTGCACCTGCTCTGGGATGAGTGGCCTGATCACCCTCAGC
ProAspSerTrpValValLeuCysThrCysSerGlyMetSerGlyLeuIleThrLeuSer 490                  510                   530
          .                    .                     .
AGGAATGCCAGCTATTATCTGCGTCCCTGGCCACCCCGGGGCTCCAAGGACTTCTCAACC
ArgAsnAlaSerTyrTyrLeuArgProTrpProProArgGlySerLysAspPheSerThr 550                  570                   590
```

FIG. 5A

CACGAGATCTTTCGGATGGAGCAGCTGCTCACCTGGAAAGGAACCTGTGGCCACAGGGAT
HisGluIlePheArgMetGluGlnLeuLeuThrTrpLysGlyThrCysGlyHisArgAsp 610                 630                 650
CCTGGGAACAAAGCGGGCATGACCAGCCTTCCTGGTGGTCCCCAGAGCAGGGGCAGGCGA
ProGlyAsnLysAlaGlyMetThrSerLeuProGlyGlyProGlnSerArgGlyArgArg 670                 690                 710
GAAGCGCGCAGGACCCGGAAGTACCTGGAACTGTACATTGTGGCAGACCACACCCTGTTC
GluAlaArgArgThrArgLysTyrLeuGluLeuTyrIleValAlaAspHisThrLeuPhe 730                 750                 770
TTGACTCGGCACCGAAACTTGAACCACACCAAACAGCGTCTCCTGGAAGTCGCCAACTAC
LeuThrArgHisArgAsnLeuAsnHisThrLysGlnArgLeuLeuGluValAlaAsnTyr 790                 810                 830
GTGGACCAGCTTCTCAGGACTCTGGACATTCAGGTGGCGCTGACCGGCCTGGAGGTGTGG
ValAspGlnLeuLeuArgThrLeuAspIleGlnValAlaLeuThrGlyLeuGluValTrp 850                 870                 890
ACCGAGCGGGACCGCAGCCGCGTCACGCAGGACGCCAACGCCACGCTCTGGGCCTTCCTG
ThrGluArgAspArgSerArgValThrGlnAspAlaAsnAlaThrLeuTrpAlaPheLeu 910                 930                 950
CAGTGGCGCCGGGGGCTGTGGGCGCAGCGGCCCCACGACTCCGCGCAGCTGCTCACGGGC
GlnTrpArgArgGlyLeuTrpAlaGlnArgProHisAspSerAlaGlnLeuLeuThrGly 970                 990                 1010
CGCGCCTTCCAGGGCGCCACAGTGGGCCTGGCGCCCGTCGAGGGCATGTGCCGCGCCGAG
ArgAlaPheGlnGlyAlaThrValGlyLeuAlaProValGluGlyMetCysArgAlaGlu 1030                1050                1070
AGCTCGGGAGGCGTGAGCACGGACCACTCGGAGCTCCCCATCGGCGCCGCAGCCACCATG
SerSerGlyGlyValSerThrAspHisSerGluLeuProIleGlyAlaAlaAlaThrMet 1090                1110                1130
GCCCATGAGATCGGCCACAGCCTCGGCCTCAGCCACGACCCCGACGGCTGCTGCGTGGAG
AlaHisGluIleGlyHisSerLeuGlyLeuSerHisAspProAspGlyCysCysValGlu

FIG. 5B

```
              1150                1170                1190
GCTGCGGCCGAGTCCGGAGGCTGCGTCATGGCTGCGGCCACCGGGCACCCGTTTCCGCGC
AlaAlaAlaGluSerGlyGlyCysValMetAlaAlaAlaThrGlyHisProPheProArg 1210                1230                1250
GTGTTCAGCGCCTGCAGCCGCCGCCAGCTGCGCGCCTTCTTCCGCAAGGGGGGCGGCGCT
ValPheSerAlaCysSerArgArgGlnLeuArgAlaPhePheArgLysGlyGlyGlyAla 1270                1290                1310
TGCCTCTCCAATGCCCCGGACCCCGGACTCCCGGTGCCGCCGGCGCTCTGCGGGAACGGC
CysLeuSerAsnAlaProAspProGlyLeuProValProProAlaLeuCysGlyAsnGly 1330                1350                1370
TTCGTGGAAGCGGGCGAGGAGTGTGACTGCGGCCCTGGCCAGGAGTGCCGCGACCTCTGC
PheValGluAlaGlyGluGluCysAspCysGlyProGlyGlnGluCysArgAspLeuCys 1390                1410                1430
TGCTTTGCTCACAACTGCTCGCTGCGCCCGGGGGCCCAGTGCGCCCACGGGGACTGCTGC
CysPheAlaHisAsnCysSerLeuArgProGlyAlaGlnCysAlaHisGlyAspCysCys 1450                1470                1490
GTGCGCTGCCTGCTGAAGCCGGCTGGAGCGCTGTGCCGCCAGGCCATGGGTGACTGTGAC
ValArgCysLeuLeuLysProAlaGlyAlaLeuCysArgGlnAlaMetGlyAspCysAsp 1510                1530                1550
CTCCCTGAGTTTTGCACGGGCACCTCCTCCCACTGTCCCCCAGACGTTTACCTACTGGAC
LeuProGluPheCysThrGlyThrSerSerHisCysProProAspValTyrLeuLeuAsp 1570                1590                1610
GGCTCACCCTGTGCCAGGGGCAGTGGCTACTGCTGGGATGGCGCATGTCCCACGCTGGAG
GlySerProCysAlaArgGlySerGlyTyrCysTrpAspGlyAlaCysProThrLeuGlu 1630                1650                1670
CAGCAGTGCCAGCAGCTCTGGGGGCCTGGCTCCCACCCAGCTCCCGAGGCCTGTTTCCAG
GlnGlnCysGlnGlnLeuTrpGlyProGlySerHisProAlaProGluAlaCysPheGln 1690                1710                1730
```

FIG. 5C

```
GTGGTGAACTCTGCGGGAGATGCTCATGGAAACTGCGGCCAGGACAGCGAGGGCCACTTC
ValValAsnSerAlaGlyAspAlaHisGlyAsnCysGlyGlnAspSerGluGlyHisPhe 1750                1770                1790
           .                   .                   .
CTGCCCTGTGCAGGGAGGGATGCCCTGTGTGGGAAGCTGCAGTGCCAGGGTGGAAAGCCC
LeuProCysAlaGlyArgAspAlaLeuCysGlyLysLeuGlnCysGlnGlyGlyLysPro 1810                1830                1850
           .                   .                   .
AGCCTGCTCGCACCGCACATGGTGCCAGTGGACTCTACCGTTCACCTAGATGGCCAGGAA
SerLeuLeuAlaProHisMetValProValAspSerThrValHisLeuAspGlyGlnGlu 1870                1890                1910
           .                   .                   .
GTGACTTGTCGGGGAGCCTTGGCACTCCCCAGTGCCCAGCTGGACCTGCTTGGCCTGGGC
ValThrCysArgGlyAlaLeuAlaLeuProSerAlaGlnLeuAspLeuLeuGlyLeuGly 1930                1950                1970
           .                   .                   .
CTGGTAGAGCCAGGCACCCAGTGTGGACCTAGAATGGTGTGCCAGAGCAGGCGCTGCAGG
LeuValGluProGlyThrGlnCysGlyProArgMetValCysGlnSerArgArgCysArg 1990                2010                2030
           .                   .                   .
A;GAATGCCTTCCAGGAGCTTCAGCGCTGCCTGACTGCCTGCCACAGCCACGGGGTTTGC
LysAsnAlaPheGlnGluLeuGlnArgCysLeuThrAlaCysHisSerHisGlyValCys 2050                2070                2090
           .                   .                   .
AATAGCAACCATAACTGCCACTGTGCTCCAGGCTGGGCTCCACCCTTCTGTGACAAGCCA
AsnSerAsnHisAsnCysHisCysAlaProGlyTrpAlaProProPheCysAspLysPro 2110                2130                2150
           .                   .                   .
GGCTTTGGTGGCAGCATGGACAGTGGCCCTGTGCAGGCTGAAAACCATGACACCTTCCTG
GlyPheGlyGlySerMetAspSerGlyProValGlnAlaGluAsnHisAspThrPheLeu 2170                2190                2210
           .                   .                   .
CTGGCCATGCTCCTCAGCGTCCTGCTGCCTCTGCTCCCAGGGGCCGGCCTGGCCTGGTGT
LeuAlaMetLeuLeuSerValLeuLeuProLeuLeuProGlyAlaGlyLeuAlaTrpCys 2230                2250                2270
           .                   .                   .
TGCTACCGACTCCCAGGAGCCCATCTGCAGCGATGCAGCTGGGGCTGCAGAAGGGACCCT
CysTyrArgLeuProGlyAlaHisLeuGlnArgCysSerTrpGlyCysArgArgAspPro
```

FIG. 5D

```
              2290                   2310                   2330
               .                      .                      .
GCGTGCAGTGGCCCCAAAGATGGCCCACACAGGGACCACCCCTGGGCGGCGTTCACCCC
AlaCysSerGlyProLysAspGlyProHisArgAspHisProLeuGlyGlyValHisPro 2350                   2370                   2390
               .                      .                      .
ATGGAGTTGGGCCCCACAGCCACTGGACAGCCCTGGCCCCTGGCCCCAGGGTCTCCTGCT
MetGluLeuGlyProThrAlaThrGlyGlnProTrpProLeuAlaProGlySerProAla 2410                   2430                   2450
               .                      .                      .
GACCATATTCACAACATTTACCCTCCACCATTTCTCCCAGACCCTGAGAACTCTCATGAG
AspHisIleHisAsnIleTyrProProProPheLeuProAspProGluAsnSerHisGlu 2470                   2490                   2510
               .                      .                      .
CCCAGCAGCCACCCTGAGAAGCCTCTGCCAGCAGTCTCGCCTGACCCCCAAGCAGATCAA
ProSerSerHisProGluLysProLeuProAlaValSerProAspProGlnAlaAspGln 2530                   2550                   2570
               .                      .                      .
GTCCAGATGCCAAGATCCTGCCTCTGGTGAGAGGTAGCTCCTAAAATGAACAGATTTAAA
ValGlnMetProArgSerCysLeuTrpEnd 2590                   2610                   2630
               .                      .                      .
GACAGGTGGCCACTGACAGCCACTCCAGGAACTTGAACTGCAGGGGCAGAGCCAGTGAAT 2650                   2670                   2690
               .                      .                      .
CACCGGACCTCCAGCACCTGCAGGCAGCTTGGAAGTTTCTTCCCCGAGTGGAGCTTCGAC 2710                   2730                   2750
               .                      .                      .
CCACCCACTCCAGGAACCCAGAGCCACACTAGAAGTTCCTGAGGGCTGGAGAACACTGCT 2770                   2790                   2810
               .                      .                      .
GGGCACACTCTCCAGCTCAATAAACCATCAGTCCCAGAAGCAAAGGTCACACAGCCCCTG 2830                   2850                   2870
               .                      .                      .
ACCTCCCTCACCAGTGGAGGCTGGGTAGTGCTGGCCATCCCAAAAGGGCTCTGTCCTGGG
```

FIG. 5E

```
           2890                2910                2930
AGTCTGGTGTGTCTCCTACATGCAATTTCCACGGACCCAGCTCTGTGGAGGGCATGACTG 2950                2970                2990
CTGGCCAGAAGCTAGTGGTCCTGGGGCCCTATGGTTCGACTGAGTCCACACTCCCCTGSA 3010                3030                3050
GCCTGGCTGGCCTCTGCAAACAAACATAATTTTGGGGACCTTCCTTCCTGTTTCTTCCCA 3070                3090                3110
CCCTGTCTTCTCCCCTAGGTGGTTCCTGAGCCCCCACCCCCAATCCCAGTGCTACACCTG 3130                3150                3170
AGGTTCTGGAGCTCAGAATCTGACAGCCTCTCCCCCATTCTGTGTGTGTCGGGGGGACAG 3190                3210                3230
AGGGAACCATTTAAGAAAAGATACCAAAGTAGAAGTCAAAAGAAAGACATGTTGGCTATA 3250                3270                3290
GGCGTGGTGGCTCATGCCTATAATCCCAGCACTTTGGGAAGCYGGGGTAGGAGGATCACC 3310                3330                3350
AGAGGCCAGSAGGTCCACACCAGCCTGGGCAACACAGCAAGACACCGCATCTACARAAAA 3370                3390                3410
ATTTTAAAATTAGCTGGGCGTGGTGGTGTGTACCTGTAGGCCTAGCTGCTCAGGAGGCTG 3430                3450                3470
AAGCAGGAGGATCACTTGAGCCTGAGTTCAACACTGCAGTGAGCTATGGTGGCACCACTG 3490                3510                3530
CACTCCAGCCTGGGTGACAGAGCAAGACCCTGTCTCTAAAATAAATTTTAAAAAGACATA 3550                3570
```

FIG. 5F

TTAAAAAAAAAAAAAAAAAAAAAAAAAAAAAAAAAAAAAAAAA

FIG. 5G

>Gene216_A
ATGGGCTGGAGGCCCCGGAGAGCTCGGGGGACCCCGTTGCTGCTGCTGCTACTACTGCTGCTGCTCTGGCCAGTGCCAGG
CGCCGGGGTGCTTCAAG >Gene216_B
GACATATCCCTGGGCAGCCAGTCACCCCGCACTGGGTCCTGGATGGACAACCCTGGCGCACCGTCAGCCTGGAGGAGCCG >Gene216_C
GTCTCGAAGCCAGACATGGGGCTGGTGGCCCTGGAGGCTGAAGGCCAGGAGCTCCTGCTTGAGCTGGAGAAGAACCA >Gene216_D
CAGGCTGCTGGCCCCAGGATACATAGAAACCCACTACGGCCCAGATGGGCAGCCAGTGGTGCTGGCCCCAACCACACG >Gene216_E
GATCATTGCCACTACCAAGGGCGAGTAAGGGGCTTCCCCGACTCCTGGGTAGTCCTCTGCACCTGCTCTGGGATGAG >Gene216_F
TGGCCTGATCACCCTCAGCAGGAATGCCAGCTATTATCTGCGTCCCTGGCCACCCCGGGGCTCCAAGGACTTCTCAACCC
ACGAGATCTTTCGGATGGAGCAGCTGCTCACCTGGAAAGGAACCTGTGGCCACAGGGATCCTGGGAACAAAGCGGGCATG
ACCAGCCTTCCTGGTGGTCCCCAGAGCAGG >Gene216_G
GGCAGGCGAGAAGCGCGCAGGACCCGGAAGTACCTGGAACTGTACATTGTGGCAGACCACACCCTG >Gene216_H
TTCTTGACTCGGCACCGAAACTTGAACCACACCAAACAGCGTCTCCTGGAAGTCGCCAACTACGTGGACCAG >Gene216_I
CTTCTCAGGACTCTGGACATTCAGGTGGCGCTGACCGGCCTGGAGGTGTGGACCGAGCGGGACCGCAGCCGCGTCACGCA
GGACGCCAACGCCACGCTCTGGGCCTTCCTGCAGTGGCGCCGGGGGCTGTGGGCGCAGCGGCCCCACGACTCCGCGCAGC
TGCTCAC >Gene216_J
GGGCCGCGCCTTCCAGGGCGCCACAGTGGGCCTGGCGCCCGTCGAGGGCATGTGCCGCGCCGAGAGCTCGGGAGGCGTGA
GCACG >Gene216_K
GACCACTCGGAGCTCCCCATCGGCGCCGCAGCCACCATGGCCCATGAGATCGGCCACAGCCTCGGCCTCAGCCACGACCC
CGACGGCTGCTGCGTGGAGGCTGCGGCCGAGTCCGGAGGCTGCGTCATGGCTGCGGCCACCGG >Gene216_L1
GCACCCGTTTCCGCGCGTGTTCAGCGCCTGCAGCCGCCGCCAGCTGCGCGCCTTCTTCCGCAAGGGGGGCGGCGCTTGCC
TCTCCAATGCCCCGGACCCCGGACTCCCGGTGCCGCCGGCGCTCTGCGGGAACGGCTTCGTGGAAGCGGGCGAGGAGTGT
GACTGCGGCCCTGGCCAG >Gene216_L2
GAGTGCCGCGACCTCTGCTGCTTTGCTCACAACTGCTCGCTGCGCCCGGGGGCCCAGTGCGCCCACGGGGACTGCTGCGT
GCGCTGCCTG >Gene216_M
CTGAAGCCGGCTGGAGCGCTGTGCCGCCAGGCCATGGGTGACTGTGACCTCCCTGAGTTTTG:ACGGGCACCTCCTCCCA
CTGTCCCCCAGACGTTTACCTACTGGACGGCTCACCCTGTGCCAGGGGCAGTGGCTACTGCTGGGATGGCGCATGTCCCA
CGCTGGAGCAGCAGTGCCAGCAGCTCTGGGGGCCTG >Gene216_O

```
ATGGCCAGGAAGTGACTTGTCGGGGAGCCTTGGCACTCCCCAGTGCCCAGCTGGACCTGCTTGGCCTGGGCCTGGTAGAG
CCAGGCACCCAGTGTGGACCTAGAATG

>Gene216_U_Alt
GTGTGCCAGAGCAGGCGCTGCAGGAAGAATGCCTTCCAGGAGCTTCAGCGCTGCCTGACTGCCTGCCACAGCCACGGG >Gene216_P
GTTTGCAATAGCAACCATAACTGCCACTGTGCTCCAGGCTGGGCTCCACCCTTCTGTGACAAGCCAGGCTTTGGTGGCAG
CATGGACAGTGGCCCTGTGCAGGCTGAAA >Gene216_Q
ACCATGACACCTTCCTGCTGGCCATGCTCCTCAGCGTCCTGCTGCCTCTGCTCCCAGGGGCCGGCCTGGCCTGGTGTTGC
TACCGACTCCCAGGAGCCCATCTGCAGCGATGCAGCTGGGGCTGCAGAAGGGACCCTGCGTGCAGTGG >Gene216_R
CCCCAAAGATGGCCCACACAGGGACCACCCCTGGGCGGCGTTCACCCCATGGAGTTGGGCCCCACAGCCACTGGACAGC
CCTGGCCCCTGG >Gene216_S
ACCCTGAGAACTCTCATGAGCCCAGCAGCCACCCTGAGAAGCCTCTGCCAGCAGTCTCGCCTGACCCCCAAG >Gene216_T
CAGATCAAGTCCAGATGCCAAGATCCTGCCTCTGGTGAGAGGTAGCTCCTAAAATGAACAGATTTAAAGACAGGTGGCCA
CTGACAGCCACTCCAGGAACTTGAACTGCAGGGGCAGAGCCAGTGAATCACCGGACCTCCAGCACCTGCAGGCAGCTTGG
AAGTTTCTTCCCCGAGTGGAGCTTCGACCCACCCACTCCAGGAACCCAGAGCCACACTAGAAGTTCCTGAGGGCTGGAGA
ACACTGCTGGGCACACTCTCCAGCTCAATAAACCATCAGTCCCAGAAGCAAAGGTCACACAGCCCTGACCTCCCTCACC
AGTGGAGGCTGGGTAGTGCTGGCCATCCCAAAAGGGCTCTGTCCTGGGAGTCTGGTGTGTCTCCTACATGCAATTTCCAC
GGACCCAGCTCTGTGGAGGGCATGACTGCTGGCCAGAAGCTAGTGGTCCTGGGGCCCTATGGTTCGACTGAGTCCACACT
CCCCTGGAGCCTGGCTGGCCTCTGCAAACAAACATAATTTTGGGGACCTTCCTTCCTGTTTCTTCCCACCCTGTCTTCTC
CCCTAGGTGGTTCCTGAGCCCCCACCCCCAATCCCAGTGCTACACCTGAGGTTCTGGAGCTCAGAATCTGACAGCCTCTC
CCCCATTCTGTGTGTGTCGGGGGGACAGAGGGAACCATTTAAGAAAAGATACCAAAGTAGAAGTCAAAAGAAAGACATGT
TGGCTATAGGCGTGGTGGCTCATGCCTATAATCCCAGCACTTTGGGAAGCTGGGGTAGGAGGATCACCAGAGGCCAGGAG
GTCCACACCAGCCTGGGCAACACAGCAAGACACCGCATCTACAGAAAAATTTTAAAATTAGCTGGGCGTGGTGGTGTGTA
CCTGTAGGCCTAGCTGCTCAGGAGGCTGAAGCAGGAGGATCACTTGAGCCTGAGTTCAACACTGCAGTGAGCTATGGTGG
CACCACTGCACTCCAGCCTGGGTGACAGAGCAAGACCCTGTCTCTAAAATAAATTTTAAAAAGACATATTA
```

FIG. 7B

>Gene216_A
ATGGGCTGGAGGCCCCGGAGAGCTCGGGGGACCCCGTTGCTGCTGCTGCTACTACTGCTGCTGCTCTGGCCAGTGCCAGG
CGCCGGGGTGCTTCAAG >Gene216_B
GACATATCCCTGGGCAGCCAGTCACCCCGCACTGGGTCCTGGATGGACAACCCTGGCGCACCGTCAGCCTGGAGGAGCCG >Gene216_C
GTCTCGAAGCCAGACATGGGGCTGGTGGCCCTGGAGGCTGAAGGCCAGGAGCTCCTGCTTGAGCTGGAGAAGAACCA >Gene216_D
CAGGCTGCTGGCCCCAGGATACATAGAAACCCACTACGGCCCAGATGGGCAGCCAGTGGTGCTGGCCCCCAACCACACG >Gene216_E
GATCATTGCCACTACCAAGGGCGAGTAAGGGGCTTCCCCGACTCCTGGGTAGTCCTCTGCACCTGCTCTGGGATGAG >Gene216_F
TGGCCTGATCACCCTCAGCAGGAATGCCAGCTATTATCTGCGTCCCTGGCCACCCCGGGGCTCCAAGGACTTCTCAACCC
ACGAGATCTTTCGGATGGAGCAGCTGCTCACCTGGAAAGGAACCTGTGGCCACAGGGATCCTGGGAACAAAGCGGGCATG
ACCAGCCTTCCTGGTGGTCCCCAGAGCAGG >Gene216_G
GGCAGGCGAGAAGCGCGCAGGACCCGGAAGTACCTGGAACTGTACATTGTGGCAGACCACACCCTG >Gene216_H
TTCTTGACTCGGCACCGAAACTTGAACCACACCAAACAGCGTCTCCTGGAAGTCGCCAACTACGTGGACCAG >Gene216_I
CTTCTCAGGACTCTGCACATTCAGGTGGCGCTGACCGGCCTGGAGGTGTGGACCGAGCGGGACCGCAGCCGCGTCACGCA
GGACGCCAACGCCACGCTCTGGGCCTTCCTGCAGTGGCGCCGGGGGCTGTGGGCGCAGCGGCCCCACGACTCCGCGCAGC
TGCTCAC >Gene216_J
GGGCCGCGCCTTCCAGGGCGCCACAGTGGGCCTGGCGCCCGTCGAGGGCATGTGCCGCGCCGAGAGCTCGGGAGGCGTGA
GCACG >Gene216_K
GACCACTCGGAGCTCCCCATCGGCGCCGCAGCCACCATGGCCCATGAGATCGGCCACAGCCTCGGCCTCAGCCACGACCC
CGACGGCTGCTGCGTGGAGGCTGCGGCCGAGTCCGGAGGCTGCGTCATGGCTGCGGCCACCGG >Gene216_L1
GCACCCGTTTCCGCGCGTGTTCAGCGCCTGCAGCCGCCGCCAGCTGCGCGCCTTCTTCCGCAAGGGGGGCGGCGCTTGCC
TCTCCAATGCCCCGGACCCCGGACTCCCGGTGCCGCCGGCGCTCTGCGGGAACGGCTTCGTGGAAGCGGGCGAGGAGTGT
GACTGCGGCCCTGGCCAG >Gene216_L2
GAGTGCCGCGACCTCTGCTGCTTTGCTCACAACTGCTCGCTGCGCCCGGGGGCCCAGTGCGCCCACGGGGACTGCTGCGT
GCGCTGCCTG >Gene216_M
CTGAAGCCGGCTGGAGCGCTGTGCCGCCAGGCCATGGGTGACTGTGACCTCCCTGAGTTTTGCACGGGCACCTCCTCCCA
CTGTCCCCCAGACGTTTACCTACTGGACGGCTCACCCTGTGCCAGGGGCAGTGGCTACTGCTGGGATGGCGCATGTCCCA
CGCTGGAGCAGCAGTGCCAGCAGCTCTGGGGGCCTG

FIG. 8A

>Gene216_N_Alt
GCTCCCACCCAGCTCCCGAGGCCTGTTTCCAGGTGGTGAACTCTGCGGGAGATGCTCATGGAAACTGCGGCCAGGACAGC
GAGGGCCACTTCCTGCCCTGTGCAGGGAG >Gene216_O_Alt
GGATGCCCTGTGTGGGAAGCTGCAGTGCCAGGGTGGAAAGCCCAGCCTGCTCGCACCGCACATGGTGCCAGTGGACTCTA
CCGTTCACCTAGATGGCCAGGAAGTGACTTGTCGGGGAGCCTTGGCACTCCCCAGTGCCCAGCTGGACCTGCTTGGCCTG
GGCCTGGTAGAGCCAGGCACCCAGTGTGGACCTAGAATG >Gene216_P
GTTTGCAATAGCAACCATAACTGCCACTGTGCTCCAGGCTGGGCTCCACCCTTCTGTGACAAGCCAGGCTTTGGTGGCAG
CATGGACAGTGGCCCTGTGCAGGCTGAAA >Gene216_Q
ACCATGACACCTTCCTGCTGGCCATGCTCCTCAGCGTCCTGCTGCCTCTGCTCCCAGGGGCCGGCCTGGCCTGGTGTTGC
TACCGACTCCCAGGAGCCCATCTGCAGCGATGCAGCTGGGGCTGCAGAAGGGACCCTGCGTGCAGTGG >Gene216_R
CCCCAAAGATGGCCCACACAGGGACCACCCCCTGGGCGGCGTTCACCCCATGGAGTTGGGCCCCACAGCCACTGGACAGC
CCTGGCCCCTGG >Gene216_S
ACCCTGAGAACTCTCATGAGCCCAGCAGCCACCCTGAGAAGCCTCTGCCAGCAGTCTCGCCTGACCCCCAAG >Gene216_T
CAGATCAAGTCCAGATGCCAAGATCCTGCCTCTGGTGAGAGGTAGCTCCTAAAATGAACAGATTTAAAGACAGGTGGCCA
CTGACAGCCACTCCAGGAACTTGAACTGCAGGGGCAGAGCCAGTGAATCACCGGACCTCCAGCACCTGCAGGCAGCTTGG
AAGTTTCTTCCCCGAGTGGAGCTTCGACCCACCCACTCCAGGAACCCAGAGCCACACTAGAAGTTCCTGAGGGCTGGAGA
ACACTGCTGGGCACACTCTCCAGCTCAATAAACCATCAGTCCCAGAAGCAAAGGTCACACAGCCCCTGACCTCCCTCACC
AGTGGAGGCTGGGTAGTGCTGGCCATCCCAAAAGGGCTCTGTCCTGGGAGTCTGGTGTGTCTCCTACATGCAATTTCCAC
GGACCCAGCTCTGTGGAGGGCATGACTGCTGGCCAGAAGCTAGTGGTCCTGGGGCCCTATGGTTCGACTGAGTCCACACT
CCCCTGGAGCCTGGCTGGCCTCTGCAAACAAACATAATTTTGGGGACCTTCCTTCCTGTTTCTTCCCACCCTGTCTTCTC
CCCTAGGTGGTTCCTGAGCCCCCACCCCCAATCCCAGTGCTACACCTGAGGTTCTGGAGCTCAGAATCTGACAGCCTCTC
CCCCATTCTGTGTGTGTCGGGGGACAGAGGGAACCATTTAAGAAAAGATACCAAAGTAGAAGTCAAAAGAAAGACATGT
TGGCTATAGGCGTGGTGGCTCATGCCTATAATCCCAGCACTTTGGGAAGCTGGGGTAGGAGGATCACCAGAGGCCAGGAG
GTCCACACCAGCCTGGGCAACACAGCAAGACACCGCATCTACAGAAAAATTTTAAAATTAGCTGGGCGTGGTGGTGTGTA
CCTGTAGGCCTAGCTGCTCAGGAGGCTGAAGCAGGAGGATCACTTGAGCCTGAGTTCAACACTGCAGTGAGCTATGGTGG
CACCACTGCACTCCAGCCTGGGTGACAGAGCAAGACCCTGTCTCTAAAATAAATTTTAAAAAGACATATTA

FIG. 8B

>Gene216_A_Alt
ATGGGCTGGAGGCCCCGGAGAGCTCGGGGGACCCCGTTGCTGCTGCTGCTACTACTGCTGCTGCTCTGGCCAGTGCCAGG
CGCCGGGGTGCTTCAAGGTGAGGACGCGGGCGGG >Gene216_B_Alt
GTCCCCCTCACCCTGTGCTCTGTCTTTACTCCAGGACATATCCCTGGGCAGCCAGTCACCCCGCACTGGGTCCTGGATGG
ACAACCCTGGCGCACCGTCAGCCTGGAGGAGCCG >Gene216_C
GTCTCGAAGCCAGACATGGGGCTGGTGGCCCTGGAGGCTGAAGGCCAGGAGCTCCTGCTTGAGCTGGAGAAGAACCA >Gene216_D
CAGGCTGCTGGCCCCAGGATACATAGAAACCCACTACGGCCCAGATGGGCAGCCAGTGGTGCTGGCCCCCAACCACACG >Gene216_E
GATCATTGCCACTACCAAGGGCGAGTAAGGGGCTTCCCCGACTCCTGGGTAGTCCTCTGCACCTGCTCTGGGATGAG >Gene216_F
TGGCCTGATCACCCTCAGCAGGAATGCCAGCTATTATCTGCGTCCCTGGCCACCCCGGGGCTCCAAGGACTTCTCAACCC
ACGAGATCTTTCGGATGGAGCAGCTGCTCACCTGGAAAGGAACCTGTGGCCACAGGGATCCTGGGAACAAAGCGGGCATG
ACCAGCCTTCCTGGTGGTCCCCAGAGCAGG >Gene216_G
GGCAGGCGAGAAGCGCGCAGGACCCGGAAGTACCTGGAACTGTACATTGTGGCAGACCACACCCTG >Gene216_H
TTCTTGACTCGGCACCGAAACTTGAACCACACCAAACAGCGTCTCCTGGAAGTCGCCAACTACGTGGACCAG >Gene216_I
CTTCTCAGGACTCTGGACATTCAGGTGGCGCTGACCGGCCTGGAGGTGTGGACCGAGCGGGACCGCAGCCGCGTCACGCA
GGACGCCAACGCCACGCTCTGGGCCTTCCTGCAGTGGCGCCGGGGGCTGTGGGCGCAGCGGCCCCACGACTCCGCGCAGC
TGCTCAC >Gene216_J
GGGCCGCGCCTTCCAGGGCGCCACAGTGGGCCTGGCGCCCGTCGAGGGCATGTGCCGCGCCGAGAGCTCGGGAGGCGTGA
GCACG >Gene216_K
GACCACTCGGAGCTCCCCATCGGCGCCGCAGCCACCATGGCCCATGAGATCGGCCACAGCCTCGGCCTCAGCCACGACCC
CGACGGCTGCTGCGTGGAGGCTGCGGCCGAGTCCGGAGGCTGCGTCATGGCTGCGGCCACCGG >Gene216_L1
GCACCCGTTTCCGCGCGTGTTCAGCGCCTGCAGCCGCCGCCAGCTGCGCGCCTTCTTCCGCAAGGGGGGCGGCGCTTGCC
TCTCCAATGCCCCGGACCCCGGACTCCCGGTGCCGCCGGCGCTCTGCGGGAACGGCTTCGTGGAAGCGGGCGAGGAGTGT
GACTGCGGCCCTGGCCAG >Gene216_L2
GAGTGCCGCGACCTCTGCTGCTTTGCTCACAACTGCTCGCTGCGCCCGGGGGCCCAGTGCGCCCACGGGGACTGCTGCGT
GCGCTGCCTG >Gene216_M
CTGAAGCCGGCTGGAGCGCTGTGCCGCCAGGCCATGGGTGACTGTGACCTCCCTGAGTTTTG:ACGGGCACCTCCTCCCA
CTGTCCCCCAGACGTTTACCTACTGGACGGCTCACCCTGTGCCAGGGGCAGTGGCTACTGCTGGGATGGCGCATGTCCCA
CGCTGGAGCAGCAGTGCCAGCAGCTCTGGGGGCCTG

FIG. 9A

>Gene216_N_Alt
GCTCCCACCCAGCTCCCGAGGCCTGTTTCCAGGTGGTGAACTCTGCGGGAGATGCTCATGGAAACTGCGGCCAGGACAGC
GAGGGCCACTTCCTGCCCTGTGCAGGGAG >Gene216_O_Alt
GGATGCCCTGTGTGGGAAGCTGCAGTGCCAGGGTGGAAAGCCCAGCCTGCTCGCACCGCACATGGTGCCAGTGGACTCTA
CCGTTCACCTAGATGGCCAGGAAGTGACTTGTCGGGGAGCCTTGGCACTCCCCAGTGCCCAGCTGGACCTGCTTGGCCTG
GGCCTGGTAGAGCCAGGCACCCAGTGTGGACCTAGAATG >Gene216_U_Alt
GTGTGCCAGAGCAGGCGCTGCAGGAAGAATGCCTTCCAGGAGCTTCAGCGCTGCCTGACTGCCTGCCACAGCCACGGG >Gene216_P
GTTTGCAATAGCAACCATAACTGCCACTGTGCTCCAGGCTGGGCTCCACCCTTCTGTGACAAGCCAGGCTTTGGTGGCAG
CATGGACAGTGGCCCTGTGCAGGCTGAAA >Gene216_Q
ACCATGACACCTTCCTGCTGGCCATGCTCCTCAGCGTCCTGCTGCCTCTGCTCCCAGGGGCCGGCCTGGCCTGGTGTTGC
TACCGACTCCCAGGAGCCCATCTGCAGCGATGCAGCTGGGGCTGCAGAAGGGACCCTGCGTGCAGTGG >Gene216_R
CCCCAAAGATGGCCCACACAGGGACCACCCCCTGGGCGGCGTTCACCCCATGGAGTTGGGCCCCACAGCCACTGGACAGC
CCTGGCCCCTGG >Gene216_S_Alt
CCCCAGGGTCTCCTGCTGACCATATTCACAACATTTACCCTCCACCATTTCTCCCAGACCCTGAGAACTCTCATGAGCCC
AGCAGCCACCCTGAGAAGCCTCTGCCAGCAGTCTCGCCTGACCCCCAAG >Gene216_T
CAGATCAAGTCCAGATGCCAAGATCCTGCCTCTGGTGAGAGGTAGCTCCTAAAATGAACAGATTTAAAGACAGGTGGCCA
CTGACAGCCACTCCAGGAACTTGAACTGCAGGGGCAGAGCCAGTGAATCACCGGACCTCCAGCACCTGCAGGCAGCTTGG
AAGTTTCTTCCCCGAGTGGAGCTTCGACCCACCCACTCCAGGAACCCAGAGCCACACTAGAAGTTCCTGAGGGCTGGAGA
ACACTGCTGGGCACACTCTCCAGCTCAATAAACCATCAGTCCCAGAAGCAAAGGTCACACAGCCCCTGACCTCCCTCACC
AGTGGAGGCTGGGTAGTGCTGGCCATCCCAAAAGGGCTCTGTCCTGGGAGTCTGGTGTGTCTCCTACATGCAATTTCCAC
GGACCCAGCTCTGTGGAGGGCATGACTGCTGGCCAGAAGCTAGTGGTCCTGGGGCCCTATGGTTCGACTGAGTCCACACT
CCCCTGGAGCCTGGCTGGCCTCTGCAAACAAACATAATTTTGGGGACCTTCCTTCCTGTTTCTTCCCACCCTGTCTTCTC
CCCTAGGTGGTTCCTGAGCCCCCACCCCCAATCCCAGTGCTACACCTGAGGTTCTGGAGCTCAGAATCTGACAGCCTCTC
CCCCATTCTGTGTGTGTCGGGGGACAGAGGGAACCATTTAAGAAAAGATACCAAAGTAGAAGTCAAAAGAAAGACATGT
TGGCTATAGGCGTGGTGGCTCATGCCTATAATCCCAGCACTTTGGGAAGCTGGGGTAGGAGGATCACCAGAGGCCAGGAG
GTCCACACCAGCCTGGGCAACACAGCAAGACACCGCATCTACAGAAAAATTTTAAAATTAGCTGGGCGTGGTGGTGTGTA
CCTGTAGGCCTAGCTGCTCAGGAGGCTGAAGCAGGAGGATCACTTGAGCCTGAGTTCAACACTGCAGTGAGCTATGGTGG
CACCACTGCACTCCAGCCTGGGTGACAGAGCAAGACCCTGTCTCTAAAATAAATTTTAAAAAGACATATTA

FIG. 9B

Signal sequence ⟶

```
             1                                                          50
adam28    M----------  ----------  ------LQG  LLPVSLLLSV  AVSAIKELPG
adam7     ----------  ----------  ----------  ----------  ----------
gene216b  MGWRPRRARG  TPLLLLLLLL  LLWPVPGAGV  LQ........  .........G
gene216c  MGWRPRRARG  TPLLLLLLLL  LLWPVPGAGV  LQGEDAGGVP  LTLCSVFTPG
gene216a  MGWRPRRARG  TPLLLLLLLL  LLWPVPGAGV  LQ........  .........G
adam12    M---------  -----AARP   LPVSPARALL  LALAGALLAP  CEARGVSLWN
adam19    ----------  ----------  ----------  ----------  ----------
adam15    M---------  ---RLALLW   ALGLLGAGSP  LPSWPLPNIG  GTEEQQAESE
adam8     M---------  ----------  -----RGLG   LWLLGAMMLP  AIAPSRPWAL
```

Pro-domain ⟶

```
             51                                                         100
adam28    VKKYEVVYPI  RLHPLHKREA  KEPEQQEQFE  TELKYKMTIN  GKIAVLYLKK
adam7     ----------  ----------  ----------  ----------  ----------
gene216b  HIPGQPVTPH  WVLDGQPWRT  VSLEEPVSKP  DMGLVALEAE  GQELLLELEK
gene216c  HIPGQPVTPH  WVLDGQPWRT  VSLEEPVSKP  DMGLVALEAE  GQELLLELEK
gene216a  HIPGQPVTPH  WVLDGQPWRT  VSLEEPVSKP  DMGLVALEAE  GQELLLELEK
adam12    EGRADEVVSA  SVRSGDLWIP  VKSFDSKNHP  EVLNIRLQRE  SKELIINLER
adam19    ----------  ----------  ----------  ----------  ----------
adam15    KAPREPLEPQ  VLQDDLP.IS  LKKVLQTSLP  EPLRIKLELD  GDSHILELLQ
adam8     MEQYEVVLPR  RLPGPRVRRA  LPSHLGL.HP  ERVSYVLGAT  GHNFTLHLRK
```

```
             101                                                        150
adam28    NKNLLAPGYT  ETYYNSTGKE  ITTSP...QI  MDDCYYQGHI  LNEKVSDASI
adam7     ----------  ----------  ----------  ----------  ----------
gene216b  NHRLLAPGYI  ETHYGPDGQP  VVLAPNHT..  .DHCHYQGRV  RGFPDSWVVL
gene216c  NHRLLAPGYI  ETHYGPDGQP  VVLAPNHT..  .DHCHYQGRV  RGFPDSWVVL
gene216a  NHRLLAPGYI  ETHYGPDGQP  VVLAPNHT..  .DHCHYQGRV  RGFPDSWVVL
adam12    NEGLIASSFT  ETHYLQDGTD  VSLARNYTVI  LGHCYYHGHV  RGYSDSAVSL
adam19    ----------  --------S   GNPQTTTRKL  EDHCFYHGTV  RETELSSVTL
adam15    NRELVPGRPT  LVWYQPDGTR  VV...SEGHT  LENCCYQGRV  RGYAGSWVSI
adam8     NRDLLGSGYT  ETYTAANGSE  VTEQP...RG  QDHCLYQGHV  EGYPDSAASL
```

Cysteine switch

```
                                                                        200
adam28    STCRGLRGYF  SQG.DQRYFI  EPLSPIHRDG  QEHALFKYNP  DEKNYDSTCG
adam7     --C-------  ----------  ----------  ----------  ----------
gene216b  CTCSGMSGLI  TLSRNASYYL  RPWPPRGSKD  FSTHEIFRME  QLLTWKGTCG
gene216c  CTCSGMSGLI  TLSRNASYYL  RPWPPRGSKD  FSTHEIFRME  QLLTWKGTCG
gene216a  CTCSGMSGLI  TLSRNASYYL  RPWPPRGSKD  FSTHEIFRME  QLLTWKGTCG
adam12    STCSGLRGLI  .VFENESYVL  EPMKSATNR.  ...YKLFPAK  KLKSVRGSCG
adam19    STCRGIRGLI  TVSSNLSYVI  EPLPDSKGQ.  ...HLIYRSE  HLKPPPGNCG
adam15    CTCSGLRGLV  VLTPERSYTL  EQGP...GDL  QGPPIISRIQ  DLHLPGHTCA
adam8     STCAGLRGFF  QVGSDL.HLI  EPLDEGG..E  GGRHAVYQAE  HLLQTAGTCG
```

Catalytic domain

```
             201
adam28    MDGVLWAHDL  QQNIALPATK  LV.KLKDRKV  QEHEKYIEYY  LVLDNGEFKR
adam7     -NYSCTELNF  TRKTVPGDNE  SE.EDSKIKG  IHDEKYVELF  IVADDTVYRR
gene216b  ..HRDPGNKA  GMTSLPGGPQ  SRGRREARRT  ...RKYLELY  IVADHTLFLT
gene216c  ..HRDPGNKA  GMTSLPGGPQ  SRGRREARRT  ...RKYLELY  IVADHTLFLT
gene216a  ..HRDPGNKA  GMTSLPGGPQ  SRGRREARRT  ...RKYLELY  IVADHTLFLT
adam12    SHHNTPNLAA  KNV.FPPPSQ  TWARRHKRET  LKATKYVELV  IVADNREFQR
adam19    FEHSKPTTRD  WALQFTQQTK  KRPRRMKRED  LNSMKYVELY  LVADYLEFQK
adam15    LSWRESVHTQ  TPPEHPLGQR  HIRRR..RDV  VTETKTVELV  IVADHSE.AQ
adam8     VSDDSLGSLL  GPRT...AAV  FRPRPGDSLP  SRETRYVELY  VVVDNAEFQM
```

FIG. 11A

```
            251                                                      300
adam28      YNENQDEIRK  RVFEMANYVN  MLYKKLNTHV  ALVGMEIWTD  KDKIKITPNA
adam7       NGHPHNKLRN  RIWGMVNFVN  MIYKTLNIHV  TLVGIEIWTH  EDKIELYSNI
gene216b    RHRNLNHTKQ  RLLEVANYVD  QLLRTLDIQV  ALTGLEVWTE  RDRSRVTQDA
gene216c    RHRNLNHTKQ  RLLEVANYVD  QLLRTLDIQV  ALTGLEVWTE  RDRSRVTQDA
gene216a    RHRNLNHTKQ  RLLEVANYVD  QLLRTLDIQV  ALTGLEVWTE  RDRSRVTQDA
adam12      QGKDLEKVKQ  RLIEIANHVD  KFYRPLNIRI  VLVGVEVWND  MDKCSVSQDP
adam19      NRRDQDATKH  KLIEIANYVD  KFYRSLNIRI  ALVGLEVWTH  GNMCEVSENP
adam15      KYRDFQHLLN  RTLEVALLLD  TFFRPLNVRV  ALVGLEAWTQ  RDLVEISPNP
adam8       LGSEA.AVRH  RVLEVVNHVD  KLYQKLNFRV  VLVGLEIWNS  QDRFHVSPDP 301                                                      350
adam28      SFTLENFSKW  RGSVLSRRKR  HDIAQLITAT  ELAGTTVGLA  FMSTMCSP.Y
adam7       ETTLLRFSFW  QEKILKTRKD  FDHVVLLSGK  WLYSHVQGIS  YPGGMCLPYY
gene216b    NATLWAFLQW  RRG.LWAQRP  HDSAQLLTGR  AFQGATVGLA  PVEGMCRAES
gene216c    NATLWAFLQW  RRG.LWAQRP  HDSAQLLTGR  AFQGATVGLA  PVEGMCRAES
gene216a    NATLWAFLQW  RRG.LWAQRP  HDSAQLLTGR  AFQGATVGLA  PVEGMCRAES
adam12      FTSLHEFLDW  RKMKLLPRKS  HDNAQLVSGV  YFQGTTIGMA  PIMSMCTADQ
adam19      YSTLWSFLSW  RR.KLLAQKY  HDNAQLITGM  SFHGTTIGLA  PLMAMCSVYQ
adam15      AVTLENFLHW  RRAHLLPRLP  HDSAQLVTGT  SFSGPTVGMA  IQNSICSPDF
adam8       SVTLENLLTW  QARQRTRRHL  HDNVQLITGV  DFTGTTVGFA  RVSAMCS.HS 351              Metalloprotease domain                  400
adam28      SVGVVQDHSD  NLLRVAGTMA  HEMGHNFGMF  HDDYSCKC..  ....PSTICV
adam7       STSIIKDLLP  DTNIIANRMA  HQLGHNLGMQ  HDEFPCTC..  ....PSGKCV
gene216b    SGGVSTDHSE  LPIGAAATMA  HEIGHSLGLS  HD..PDGCCV  EAAAESGGCV
gene216c    SGGVSTDHSE  LPIGAAATMA  HEIGHSLGLS  HD..PDGCCV  EAAAESGGCV
gene216a    SGGVSTDHSE  LPIGAAATMA  HEIGHSLGLS  HD..PDGCCV  EAAAESGGCV
adam12      SGGIVMDHSD  NPLGAAVTLA  HELGHNFGMN  HDTLDRGCSC  QMAVEKGGCI
adam19      SGGVNMDHSE  NAIGVAATMA  HEMGHNFGMT  HDSAD...CC  SASAADGGCI
adam15      SGGVNMDHST  SILGVASSIA  HELGHSLGLD  HDLPGNSCPC  PGPAPAKTCI
adam8       SGAVNQDHSK  NPVGVACTMA  HEMGHNLGMD  HDENVQGCRC  QERFEAGRCI "Met-turn"                                               450
adam28      MDKALSFYIP  TDFSSCSRLS  YDKFFEDKLS  NCLFNAPLPT  DIISTPICGN
adam7       MDSDGSI.PA  LDLSKCRQNQ  YHQYLKDYKP  TCMLNIPFPY  NFHDFQFCGN
gene216b    MAAATGHPFP  RVFSACSRRQ  LRAFFRKGGG  ACLSNAPDPG  LPVPPALCGN
gene216c    MAAATGHPFP  RVFSACSRRQ  LRAFFRKGGG  ACLSNAPDPG  LPVPPALCGN
gene216a    MAAATGHPFP  RVFSACSRRQ  LRAFFRKGGG  ACLSNAPDPG  LPVPPALCGN
adam12      MNASTGYPFP  MVFSSCSRKD  LETSLEKGMG  VCLFNLPEVR  ESFGGQKCGN
adam19      MAAATGHPFP  KVFNGCNRRE  LDRYLQSGGG  MCLSNMPDTR  MLYGGRRCGN
adam15      MEASTDFLPG  LNFSNCSRRA  LEKALLDGMG  SCLFERL.PS  LPPMAAFCGN
adam8       MAGSIGSSFP  RMFSDCSQAY  LESFLERPQS  VCLANAPDLS  HLVGGPVCGN 451                               Disintegrin domain ─→ 500
adam28      QLVEMGEDCD  CGTSEECTNI  CCDAKTCKIK  ATFQCAL.GE  CCEKCQFKKA
adam7       KKLDEGEECD  CGPAQECTNP  CCDAHTCVLK  PGFTCAE.GE  CCESCQIKKA
gene216b    GFVEAGEECD  CGPGQECRDL  CCFAHNCSLR  PGAQCA.HGD  CCVRCLLKPA
gene216c    GFVEAGEECD  CGPGQECRDL  CCFAHNCSLR  PGAQCA.HGD  CCVRCLLKPA
gene216a    GFVEAGEECD  CGPGQECRDL  CCFAHNCSLR  PGAQCA.HGD  CCVRCLLKPA
adam12      RFVEEGEECD  CGEPEECMNR  CCNATTCTLK  PDAVCA.HGL  CCEDCQLKPA
adam19      GYLEDGEECD  CGEEEECNNP  CCNASNCTLR  PGAECA.HGS  CCHQCKLLAP
adam15      MFVEPGEQCD  CGFLDDCVDP  CCDSLTCQLR  PGAQCASDGP  CCQNCQLRPS
adam8       LFVERGEQCD  CGPPEDCRNR  CCNSTTCQLA  EGAQCA.HGT  CCQECKVKPA
```

FIG. 11B

```
              501                                                    550
    adam28    GMVCRPAKDE  CDLPEMCNGK  SGNCPDDRFQ  VNGFPCHHGK  GHCLMGTCPT
     adam7    GSICRPAKDE  CDFPEMCTGH  SPACPKDQFR  VNGFPCKNSE  GYCFMGKCPT
  gene216b    GALCRQAMGD  CDLPEFCTGT  SSHCPPDVYL  LDGSPCARGS  GYCWDGACPT
  gene216c    GALCRQAMGD  CDLPEFCTGT  SSHCPPDVYL  LDGSPCARGS  GYCWDGACPT
  gene216a    GALCRQAMGD  CDLPEFCTGT  SSHCPPDVYL  LDGSPCARGS  GYCWDGACPT
    adam12    GTACRDSSNS  CDLPEFCTGA  SPHCPANVYL  HDGHSCQDVD  GYCYNGICQT
    adam19    GTLCREQARQ  CDLPEFCTGK  SPHCPTNFYQ  MDGTPCEGGQ  AYCYNGMCLT
    adam15    GWQCRPTRGD  CDLPEFCPGD  SSQCPPDVSL  GDGEPCAGGQ  AVCMHGRCAS
     adam8    GELCRPKKDM  CDLEEFCDGR  HPECPEDAFQ  ENGTPCSGG.  .YCYNGACPT
```

Cysteine rich domain

```
                                                                     600
    adam28    LQEQCTELWG  PGTEVADKSC  YNR.NEGGSK  YGYC.RRVDD  TLIPCKANDT
     adam7    REDQCSELFD  DEAIESHDIC  YKM.NTKGNK  FGYC.KNKEN  RFLPCEEKDV
  gene216b    LEQQCQQLWG  PGSHPAPEAC  FQVVNSAGDA  HGNCGQDSEG  HFLPCAGRDA
  gene216c    LEQQCQQLWG  PGSHPAPEAC  FQVVNSAGDA  HGNCGQDSEG  HFLPCAGRDA
  gene216a    LEQQCQQLWG  P.........  ..........  ..........  ..........
    adam12    HEQQCVTLWG  PGAKPAPGIC  FERVNSAGDP  YGNCGKVSKS  SFAKCEMRDA
    adam19    YQEQCQQLWG  PGARPAPDLC  FEKVNVAGDT  FGNCGKVMNG  EHRKCNMRDA
    adam15    YAQQCQSLWG  PGAQPAAPLC  LQTANTRGNA  FGSCGRNPSG  SYVSCTPRDA
     adam8    LAQQCQAFWG  PGGQAAEESC  FSYDILPG..  ..........  .CKASRYRAD 601                                                    650
    adam28    MCGKLFCQGG  S.DNLPWKGR  ..IV......  ..TFLTCKTF  ......DPED
     adam7    RCGKIYCTGG  ELSSLLGEDK  ..TYHLKDPQ  KNATVKCKTI  ......FLYH
  gene216b    LCGKLQCQGG  KP.SLLAPHM  VPVDSTVHL.  DGQEVTCRGA  LAL..PSAQL
  gene216c    LCGKLQCQGG  KP.SLLAPHM  VPVDSTVHL.  DGQEVTCRGA  LAL..PSAQL
  gene216a    ..........  ..........  ..........  DGQEVTCRGA  LAL..PSAQL
    adam12    KCGKIQCQGG  ASRPVIGTNA  VSIETNIPLQ  QGGRILCRGT  HVYLG....D
    adam19    KCGKIQCQSS  EARP.LESNA  VPIDTTI.IM  NGRQIQCRGT  HVYRGPEEEG
    adam15    ICGQLQCQTG  RTQPLLGSIR  DLLWETIDV.  NGTELNCSWV  HLDLGS....
     adam8    MCGVLQCKGG  QQPLGRAICI  VDVCHALTTE  DGTAYE....  ..........
```

EGF-like domain

```
                                                                     700
    adam28    TSQEIGMVAN  GTKCGDNKVC  INAECVDIEK  AYKSTNCSSK  CKGHAVCDHE
     adam7    DSTDIGLVAS  GTKCGEGMVC  NNGECLNMEK  VYISTNCPSQ  CNENPVDGHG
  gene216b    DLLGLGLVEP  GTQCGPRM..  ..........  ..........  .....VCNSN
  gene216c    DLLGLGLVEP  GTQCGPRMVC  QSRRCRKNA.  FQELQRCLTA  CHSHGVCNSN
  gene216a    DLLGLGLVEP  GTQCGPRMVC  QSRRCRKNA.  FQELQRCLTA  CHSHGVCNSN
    adam12    DMPDPGLVLA  GTKCADGKIC  LNRQCQNIS.  VFGVHECAMQ  CHGRGVCNNR
    adam19    DMLNPGLVMT  GTKCGYNHIC  FEGQCRNTS.  FFETEGCGKK  CNGHGVCNNN
    adam15    DVAQPLLTLP  GTACGPGLVC  IDHRCQRVD.  LLGAQECRSK  CHGHGVCDSN
     adam8    ......PVPE  GTRCGPEKVC  WKGRCQDLH.  VYRSSNCSAQ  CHNHGVCNHK
```

Transmembrane

```
              701
    adam28    LQCQCEEGWI  PPDCDDSSVV  FHFSIVVGVL  FPMAVIFVVV  AMVIRHQSSR
     adam7    LQCHCEEGQA  PVACEETLHV  TNITILVVVL  VLVIVGIGVL  ILLVRYRKCI
  gene216b    HNCHCAPGWA  PPFCDKPGFG  GSMD.SGPVQ  AENHDTFLLA  MLLSVLLPLL
  gene216c    HNCHCAPGWA  PPFCDKPGFG  GSMD.SGPVQ  AENHDTFLLA  MLLSVLLPLL
  gene216a    HNCHCAPGWA  PPFCDKPGFG  GSMD.SGPVQ  AENHDTFLLA  MLLSVLLPLL
    adam12    KNCHCEAHWA  PPFCDKFGFG  GSTD.SGPIR  QAEARQEAAE  SNRERGQGQE
    adam19    QNCHCLPGWA  PPFCNTPGHG  GSID.SGPM.  PPESVGPVVA  GVLVAILVLA
    adam15    RHCYCEEGWA  PPDCTTQLKA  TSSL.TTGLL  L.SLLVLLVL  VMLGAGYWYR
     adam8    QECHCAGWA   PPHCAKLLTE  VHAA.SGSLP  VLVVVVLVLL  AVVLVTLAGI
```

FIG. 11C

```
                  Domain →        Cytoplasmic domain →
                                                      800
   adam28   EKQKKDQRPL STTGTRPHKQ KRKPQMVKAV QPQEMSQMKP HVYDLPVEGN
    adam7   KLKQVQSPPT ETLGVENKGY FGDEQQIRTE PILPEIHFLN KPASKDSRGI
 gene216b   PGAGLAWCCY RLPGAHLQRC SWGCRRDPAC SGPKDGPHRD HPLGGVHPME
 gene216c   PGAGLAWCCY RLPGAHLQRC SWGCRRDPAC SGPKDGPHRD HPLGGVHPME
 gene216a   PGAGLAWCCY RLPGAHLQRC SWGCRRDPAC SGPKDGPHRD HPLGGVHPME
   adam12   PVGSQEHAST ASLTLI---- ---------- ---------- ----------
   adam19   VLMLMYYCCR QNNKLGQLKP SALPSKLRQQ FSCPFRVSQN SGTGHANPTF
   adam15   ARLHQRLCQL KGPTCQYRAA QSGPSERPGP PQRALLARGT KSQGPAKPPP
    adam8   IVYRKARSRI LSRNVAPKTT MGRSNPLFHQ AASRVPAKGG APAPSRGPQE 801                                        Putative SH₃
   adam28   EPPASFHKDT NALPPTVFKD NPMSTPKDSN PKA------- ----------
    adam7   ADPNQSAK-- ---------- ---------- ---------- ----------
 gene216b   LGPTATGQPW PL........ .......... .DPENSHEPS SHPEKPLPAV
 gene216c   LGPTATGQPW PLAPGSPADH IHNIYPPPFL PDPENSHEPS SHPEKPLPAV
 gene216a   LGPTATGQPW PL........ .......... .DPENSHEPS SHPEKPLPAV
   adam12   ---------- ---------- ---------- ---------- ----------
   adam19   KLQTPQGKRK VINTPEILRK PSQPPPRPPP DYLRGGSPPA PLPAHLSRAA
   adam15   PRKPLPADPQ GRCPSGDLPG PGAGIPPLVV PSRPAPPPPT VSSLYL----
    adam8   LVPTTHPGQP ARHPASSVAL KRPPPAPPVT VSSPPFPVPV YTRQAPKQVI 851                                                900
           binding domain
   adam28   ---------- ---------- ---------- ---------- ----------
    adam7   ---------- ---------- ---------- ---------- ----------
 gene216b   SPDPQADQVQ MPRSCLW--- ---------- ---------- ----------
 gene216c   SPDPQADQVQ MPRSCLW--- ---------- ---------- ----------
 gene216a   SPDPQADQVQ MPRSCLW--- ---------- ---------- ----------
   adam12   ---------- ---------- ---------- ---------- ----------
   adam19   RNSPGPGSQI ERTESSRRPP PSRPIPPAPN CIVSQDFSRP RPPQKALPAN
   adam15   ---------- ---------- ---------- ---------- ----------
    adam8   KPTFAPPVPP VKPGAGAANP GPAEGAVGPK VALKPPIQRK QGAGAPTAP- 901                                                950
   adam28   ---------- ---------- ---------- ---------- ----------
    adam7   ---------- ---------- ---------- ---------- ----------
 gene216b   ---------- ---------- ---------- ---------- ----------
 gene216c   ---------- ---------- ---------- ---------- ----------
 gene216a   ---------- ---------- ---------- ---------- ----------
   adam12   ---------- ---------- ---------- ---------- ----------
   adam19   PVPGRRSLPR PGGASPLRPP GAGPQQSRPL AALAPKVSPR EALKVKAGTR
   adam15   ---------- ---------- ---------- ---------- ----------
    adam8   ---------- ---------- ---------- ---------- ----------

951                                       990
   adam28   ---------- ---------- ---------- ----------
    adam7   ---------- ---------- ---------- ----------
 gene216b   ---------- ---------- ---------- ----------
 gene216c   ---------- ---------- ---------- ----------
 gene216a   ---------- ---------- ---------- ----------
   adam12   ---------- ---------- ---------- ----------
   adam19   GLQGGRCRVE KTKQFMLLVV WTELPEQKPR AKHSCFLVPA
   adam15   ---------- ---------- ---------- ----------
    adam8   ---------- ---------- ---------- ----------
```

FIG. 11D

```
mGene216    M--L.------ SPVLLLLLPLL LPSCPLRSAR MFPASIPKPH LHIPTCTWLT    50
Gene 216c   MGWR------ ---------- ---P-RRAR- ----GTP--- ----------    12
Gene 216b   MGWR------ ---------- ---P-RRAR- ----GTP--- ----------    12
Gene 216a   MGWR------ ---------- ---P-RRAR- ----GTP--- ----------    12 mGene216    NYEAHVTLRT RFLELLLFQI LKMYMSVLPA HASVYRGGNA HG--------    92
Gene 216c   ---------- --L-LLLLLL LLLW--PVPG -AGVLQ-GED AGGVPLTLCS    45
Gene 216b   ---------- --L-LLLLLL LLLW--PVPG -AGVLQ-GHI PG--------    37
Gene 216a   ---------- --L-LLLLLL LLLW--PVPG -AGVLQ-GHI PG--------    37 mGene216    --------E- LVTPHWILEG RLWLKVTLEE PILKPDSVLV ALEAEGQDLL   133
Gene 216c   VFTPGHIPGQ PVTPHWVLDG QPWRTVSLEE PVSKPDMGLV ALEAEGQELL    95
Gene 216b   --------Q- PVTPHWVLDG QPWRTVSLEE PVSKPDMGLV ALEAEGQELL    78
Gene 216a   --------Q- PVTPHWVLDG QPWRTVSLEE PVSKPDMGLV ALEAEGQELL    78 mGene216    LELEKKHKLL APGYIETHYR PDGHPVVLSP NHTDHCQYHG RVRGFRESWV   183
Gene 216c   LELEKNHRLL APGYIETHYG PDGQPVVLAP NHTDHCHYQG RVRGFPDSWV   145
Gene 216b   LELEKNHRLL APGYIETHYG PDGQPVVLAP NHTDHCHYQG RVRGFPDSWV   128
Gene 216a   LELEKNHRLL APGYIETHYG PDGQPVVLAP NHTDHCHYQG RVRGFPDSWV   128 mGene216    VLSTCSGMSG LIVLSSKVSY YLQPRTPGDT KDFPTHEIFR MEQLFTWRGV   233
Gene 216c   VLQTCSGMSG LITLSRNASY YLRPWPPRGS KDFSTHEIFR MEQLLTWKGT   195
Gene 216b   VLQTCSGMSG LITLSRNASY YLRPWPPRGS KDFSTHEIFR MEQLLTWKGT   178
Gene 216a   VLQTCSGMSG LITLSRNASY YLRPWPPRGS KDFSTHEIFR MEQLLTWKGT   178 mGene216    QRDKNSQYKA GMASLPHVPQ SRVRREARRS PRYLELYIVA DHTLV-----   278
Gene 216c   CGHRDPGNKA GMTSLPGGPQ SRGRREARRT RKYLELYIVA DHTLFLTRHR   245
Gene 216b   CGHRDPGNKA GMTSLPGGPQ SRGRREARRT RKYLELYIVA DHTLFLTRHR   228
Gene 216a   CGHRDPGNKA GMTSLPGGPQ SRGRREARRT RKYLELYIVA DHTLFLTRHR   228 mGene216    SPSDSQD--- --SGY----- -TVGVDRA-G SVD-RAGSQS HHSGRKRNA-   314
Gene 216c   NLNHTKQRLL EVANYVDQLL RTLDIQMALT GLEVWIERDR SRVTQDANAT   295
Gene 216b   NLNHTKQRLL EVANYVDQLL RTLDIQMALT GLEVWIERDR SRVTQDANAT   278
Gene 216a   NLNHTKQRLL EVANYVDQLL RTLDIQMALT GLEVWIERDR SRVTQDANAT   278 mGene216    L-GF------ ----PT---- -VAPR--G-- -VG----QE  TIRLHTT--   335
Gene 216c   LWAFLQWRRG LWAQRPHDSA QILTGRAFCG ATVGLAPVEG MCRAESSGGV   345
Gene 216b   LWAFLQWRRG LWAQRPHDSA QILTGRAFCG ATVGLAPVEG MCRAESSGGV   328
Gene 216a   LWAFLQWRRG LWAQRPHDSA QILTGRAFCG ATVGLAPVEG MCRAESSGGV   328 mGene216    AHDHSELPIG TAATMAHEIG HSLGLHHDPE GCCVQADAEQ GGCVMEAATG   385
Gene 216c   STDHSELPIG AAATMAHEIG HSLGLSHDPD GCCVEAAAES GGCVMAAATG   395
Gene 216b   STDHSELPIG AAATMAHEIG HSLGLSHDPD GCCVEAAAES GGCVMAAATG   378
Gene 216a   STDHSELPIG AAATMAHEIG HSLGLSHDPD GCCVEAAAES GGCVMAAATG   378 mGene216    HPFPRVFSAC SRRQLRTFFR KGGGPCLSNT SAPGLLMLPS RCGNGFLEAG   435
Gene 216c   HPFPRVFSAC SRRQLRAFFR KGGGACLSNA PDPGLPVPPA LCGNGFVEAG   445
Gene 216b   HPFPRVFSAC SRRQLRAFFR KGGGACLSNA PDPGLPVPPA LCGNGFVEAG   428
Gene 216a   HPFPRVFSAC SRRQLRAFFR KGGGACLSNA PDPGLPVPPA LCGNGFVEAG   428 mGene216    EECDCGSGQ- ---------- ---------- -------L-  KSAGTPCRPA   455
Gene 216c   EECDCGPGQE CRDLCCFAHN CSLRPGAQCA HGDCCVRCLL KPAGALCRQA   495
Gene 216b   EECDCGPGQE CRDLCCFAHN CSLRPGAQCA HGDCCVRCLL KPAGALCRQA   478
Gene 216a   EECDCGPGQE CRDLCCFAHN CSLRPGAQCA HGDCCVRCLL KPAGALCRQA   478
```

FIG. 12A

```
mGene216   ATDCDLPEFC TGTSPYCPAD VYLLDGSPCA HRGYCLDCW  CPTLEQQCQQ   505
Gene 216c  MGDCDLPEFC TGTSSHCPPD VYLLDGSPCA RSGYCWDGA  CPTLEQQCQQ   545
Gene 216b  MGDCDLPEFC TGTSSHCPPD VYLLDGSPCA RSGYCWDGA  CPTLEQQCQQ   528
Gene 216a  MGDCDLPEFC TGTSSHCPPD VYLLDGSPCA RSGYCWDGA  CPTLEQQCQQ   528 mGene216   LWGPGSKPAP EPCFQQMNSM GNSQGNCGQD HKGSFLPCAQ RDALCGKLLC   555
Gene 216c  LWGPGSHPAP EACFQVVNSA GDAHGNCGQD SEGHFLPCAG RDALCGKLQC   595
Gene 216b  LWGPGSHPAP EACFQVVNSA GDAHGNCGQD SEGHFLPCAG RDALCGKLQC   578
Gene 216a  LWGPDGQ--- ---------- ---------- ---------- ----------   535 mGene216   QGGEPNPLVP HIVTMDSTIL LEGREVVCRG AFVLPDSHLD QLLGLVEPG    605
Gene 216c  QGGKPSLLAP HMVPVDSTVH LDGQEVICRG ALALPSAQLD LLLGLVEPG    645
Gene 216b  QGGKPSLLAP HMVPVDSTVH LDGQEVICRG ALALPSAQLD LLLGLVEPG    628
Gene 216a  ---------- ---------- ---EVICRG ALALPSAQLD LLLGLVEPG     561 mGene216   TCGPRM---- ---------- ---------- ---------- --------P     613
Gene 216c  TQCGPRMVCQ SRRCRKNAFQ ELQRCLTACH SHGVCNSNHN CHCAPGWAFP    695
Gene 216b  TQCGPRMVCN SNHNCHCA-- ---------- ---------- ----PGWAFP    652
Gene 216a  TQCGPRMVCQ SRRCRKNAFQ ELQRCLTACH SHGVCNSNHN CHCAPGWAFP    611 mGene216   --HGP-LANS VRTLHLLTCS QT--LRTLSL PCNYPL---- -------KQP    647
Gene 216c  FCDKPGFGGS MDSGPVQAEN HDTFLLAMLL SVLIPL---- --------LP    733
Gene 216b  FCDKPGFGGS MDSGPVQAEN HDTFLLAMLL SVLIPLLPGA GLAWCCYRLP    702
Gene 216a  FCDKPGFGGS MDSGPVQAEN HDTFLLAMLL SVLIPLLPGA GLAWCCYRLP    661 mGene216   GLQIEF---- ---------- ------QTC- -PI--PMRED K-CAIL-PCDL  671
Gene 216c  GAGLAWCCYR LPGAHLQRCS WGCRRDPACS GPKDGHHRDH PLGGVHPMEL    783
Gene 216b  GAHLQRC--- ---------S WGCRRDPACS GPKDGHHRDH PLGGVHPMEL    740
Gene 216a  GAHLQRC--- ---------S WGCRRDPACS GPKDGHHRDH PLGGVHPMEL    699 mGene216   -QSSVSQT-- ---------- ---------- HSMNSY--GL YAELILSIGT    696
Gene 216c  GPTATGQPWP LAPGSPADHI HNIYPPPFLP DFENSHEPSS HPEKPLPAVS    833
Gene 216b  GPTATGQPWP L--------- ---------- DFENSHEPSS HPEKPLPAVS    771
Gene 216a  GPTATGQPWP L--------- ---------- DFENSHEPSS HPEKPLPAVS    730 mGene216   PEP- -DHV-V- SR- -LP                                     707
Gene 216c  PDPQADQVQM PRSCLW                                       849
Gene 216b  PDPQADQVQM PRSCLW                                       787
Gene 216a  PDPQADQVQM PRSCLW                                       746
```

FIG. 12B

>Mouse 216 homologue genomic DNA sequence
CACAATATATACACATGGTAAGTGTATTAGCAAAATGGCTTTCTATGTAATATAAATAAG
ATAAAAAAACAAACAAACAAAAAACAAAACCAGAAATACCAGCACTTCAGAGTACCCCAC
TCCCAACCCCTGCCCAGTGTAGCTGCTAACTTCACTAATCAAGTTAATTTAAAAATCAAA
TATAATACCACAGATTTTATTTTTCCTGTGTTTCTGCTTTATACAAATGGTATCATATTT
TAAACATGAGAACATTGTGAGATGACTAGCCAGTGTCTGTCTGTCTGTCTCTCTCAGATA
TTTATTTATTTATTTCATGTATGTAGGTACACTGTCACTGTCTTCAGACACACCAGAAGA
GGACATTGGATCCCATTACAGATGGTTGTGAGCCACCATGTGGTTGCTGAGAATTGAACT
CAGGACCTCTGGAAGAGTAGTCAGTGCTCTTAACCACTGGGCCATCTTTCCAGTCCTGAC
CAGTGTCTCTTAATGGTGAAATATTCTTCCCTTGGCCCTAGCATTTTATCCTTGGGCATT
TTCTCAGGAAAAATGAAGGCGCGTGTCACCCTGAGATTTGTTACTAGGATGTTCATAACA
GTGCTACCCATCAGCCAGGAACTGAAAACAATAAATGCTCGGCAGCAGGGGAATGACCGA
GTAGACAGAGCTACGCCCACACAGCTATGAGAGCTGTGCCTACAGCTGAGTGTGGTTCTC
AGACGGTCAGTGGGAGGGGCTGGCAGCGATGGCTGCCTGTGGCAGTTACATGTCCTACCG
CTCTATTAAAGGAGCTAACAAAGGCAACCTTAAGGAAGGAAACATTTATTTTGGGTCACG
GTTAGTAGGCACAGTCTCAGAGTGGTTGGAAAGATGGCAGCAAGTGTCTCTAGCTGAGGG
GGCAGGAGTGGGAGGCCCTGGTCACTTTGTGTCGGCGAGGAAGCAGACAGAGAGGTGGGG
GTGCCGTTTGCTTCTTACTTTCCTCTTCCTACCCAGTCCAGGATGACAGAACATCAGGTA
TTGCCACCCACATTTGGAGTGGGTCTTCTGGTCTCTGTTAAAACTCTCTGGAAACACCCT
CACTGACCTGATGTGCCCGGAACAAGGTGATTCTCAGCCCAAGCAAGTCACAGCGAAGAC
CAAGGACAGGTATAGTTAAGGAATGGGATAGAAGTCAATACACAGCCACTGGTGGGCAAA
AGGGATGGGCGGGAGCACAATGGAGATTCGAGAGCCAGGGAAGTGAGCAGGTTCACTTTG
TGAAAATCTCACATTTCTGAATCTATATTTTGGAAAGAAAACTTAATTTAAAAAAATCTG
CCACTTTTCCTACGCCTTGTGCTGTGTATCGACATGGGAGGATACCTTGAGGCCAGGAGA
CTGAGATCAGCCTGAGCAACACAATAAAACCTCATTTCTTACAAAACAGAACAAATTGGG
TGTGGAGGTGCACGCCTTTAATCCCAGCACCCAGGGAGCAGAGCCAATCACCCTTGTAAC
CATCTCAAATTCAGACCCAGGGGCTGTCTAGCGGCAGAAGAGTCCATGGAACACTGTGAC
CATAGTCATACAATTGGAAACTACTTATCGACAAGAATAAATGGCCATAGGTAATAGGCA
ATAGGTTGGGTAAAACTCACAAATTGGGAAAATACAACCCATACTCCAGACAAGGGCCAA
TCGCCTTTAAACATAGAGGTCCTTTAAACTGTTAAAAGAAGGACCAACCACTCACTAGAA
AAATGAGCTACACATGAATATGTTACTATATTTAAAAAAAAAAAAAACCTGTGTCTAAAA
CAGCAGCTTATGTAAGAAATTGGTAGTAGTGGCTTTCTGTGGGGAAGGAGTACCCAAAGG
ATGGAGACTAAAGGAAGACTCTCCTAAGCATTTTATACCTTCTCCCTTGTTTGCTTTGTT
GTAGTGGTGGTGGTTGTTTTTGATTCTTTTTTGTTTGGTTGGTTTTGGTTTTTTTCAAGA
CAGTGTTTCTTTGTGGAGCCCTGGTTGTCCTGGAACTCACTCAGGCTGCCCTTGAACTCA
GAGATTCTCCTGCCTCTGGGCTTAAAGGTGTACCTCACCACTGTCAGGCTTGGGTTTGTT
TTTGAGACGGGGTCTTGCTGTGTAGCTCCAGCTGCCTCTGAAGTGCTAGAATTACAGACA
TGAACTACAGATATCTCCCAGTCTCCTCTCATTCTCCCTCCCTGCCCCCTTTGTATACAC
ATTCACCTGTGTGTGCATGTGTGACTCACTCTGAGTTCTTCCAGTGTTACTCTCCATCAG
ATTTTTTGAGATAGGGTCTCTTACTGAACCTGGACCTCAAACATTTGCCTGTCTCTGTCC
AGTCCAACACTTGGCTTACAAGTTTGTGCAATGGTTCTGGCTTTCTCTGATTGCTGGAGA
CTTGAACTCAAGAACCAACGCAGGTCCTTTACTTACTAAGCCTTCTCCTTGATGACACCC
CTCACCCCACTGCCACACACCAGGTCTCCAGGCTGATCTCACACTTTTTCCATATAGGAC
TTTGAACTTGTCTTTTGCCTCTCTGCTGGGATACAGGTGTGTGCTGCTACACCCAATTTA
TGGGATGCTGGGGATGGAACTCAGGGCCCCAATCTTGTATCAACTGAGGTGCGCTCGCTC
TCTCGCTCTCATTCTCTCTCTCTCTCTCTCTCTCTCTCTCTCTCTCTCTCTCTCTCTCCC
CCCTCCTTCCCTTCCCTCTCTCTTCCATGAGACTTCTTTCTATATTGCACAGGCTAGCTA
TCTTGAGTGTCCTGTCTCGATCCAATTGCCTGACCTATCATACTGGTTTCTGTTTTTGG
TTTTGGTTTTTTCGAGACTGGGTTTCTCTGTGTAGCCCTGGCTGTCCTGGAACTCACTTT
GTAGACCAGGCTGGCCTCGAACTCAGAAATCCGCCTGCCTCTGCCTCCCGAGTGCTGGGA
TTAAAGGCGTGCACCACCACGCCTTTAATCCCAGCATTTGATGTTCGAATCGTATAAATG
TTTTTTCTTCTGCCGTTGGAACTTTTACATTCCATATTCTCAGAACGAAATTATTAATCA
TCTTATTTCAAAGTTAAATCTCTTGCTATCCGAAATCATACCAAGTGTACGAAGTGATCT
TTTCAACACGAAAGCAATGTCCTTAAAATTTGGGAAAGGGTCCCTCATGCCTGGGGTCT
GTGGTATAGAACAATTCTGTCCTGGCCATCGCTGTTCCTCTGCCCTGTGCCCACCACTGC
ATTGCCTTTACCAGGAACCACAGACTTCAGCAACGCGGCCACCACAAGACCCCTAGGTAC

FIG. 18A

```
CCAGATGCATCTCAGCTGCAGTGGGACAGCTTCACTGCTGTGGGACACTAGGTGCAGGTA
GACAGATCCTGGGTAGAAAGGAGAATCCAGATGTCACTAGGGAGACTGCGACCAGAGATG
TGTGCTAGGCAGACAGAGCAGCTGTGGGGATCACTTAGCTAGTGCCTCTATTCAGCACCA
GAGAGGTTCTCTAAGAACCTTCCCGGACTTTCCAGCCCATCAGCCATCCCTTGGCCAGCG
TGGATAGGATTGTTGCAGATAACGCCAGGGAGGGTCATCCTGGCTCCCGCAGCGCGACAT
CCTGTTTTGCGGGCCAGGGTAGGGCCACACTCCTGCGCTCCTGTGAGGTGGCGCGAGGCC
CGCTGAGGGCGGGAGGAGGCGGCCCCCTCTAGCCGGGGTGGAGCCAACAGCACAGCAAGA
GTGAGAGGGAAAGGCACTCCCAGCCATGGGCTCGAGGTGCGGGAGACCCGGGGGGTCTCC
GGTGCTGCTATTGCTGCCGCTGTTGCTGCCCTCGTGTCCGCTGCGGAGCGCTCGGATGTT
TCCAGGTGAGGATACAGGCGGCGGGGGGGGGGGGGGCGGCTCTAGGGCAGGGTGAAG
TGGTGGTGGTCATGGGTTCCAGTGCAACTACAGAACATAGAGTTCCCGACCCTCGGCTAC
CTGGCCAGGACAGGATGTGGGAAGGGTCTGTGCTCCTGGTAAGGGTGGCCCTGGAGCAGA
CTTGCCCACACTTACTTAGCAAAGCAAATAGGCAACACTACCCTTTCCTCAGTGCTGCCC
AGCTCTGTCCGGAAGCTTCTGCACTTCCAAACTGCCAGGCCAGAGTGTCTCCCTGCTCCT
GGAAGGACCTGGGGTCCTTGGAGTCCTGGTCTGCCCACAGGCCTAGCTGTCTCATTCGGC
TCGTCCTCTTCTCATGCTGGGTCTGGGCAGTGTGTATGGTGTTTATACAGTTGCCTTATG
TGGCAGTTCTTCAAACAGGGGTGTCTGCCTAGCCGTGCCTGGGCTACCACTTTCTCTTC
CTACTGTAACCTCTCCTTACTCCGGGACGACAGGGCTCTTAGCATCTCCAAGCCTGTAGG
GTGAATCTCCAAACTCCACATAGCAAGCACTAGGCTGGCCAGAAGGCAGAAGGACCACCG
GGGAGGAGGCAGTAAGGGCTGAGGGCTGGATATTGGGCAGTCTGGAAACCACCCCATATC
TGTTGACTGCTGCTTCCGTAAGGCTTCTGAGGGGGCTGACTGACAGCTGTATTGCCTTTA
GCCTGCGGATAGTTAATGGTGAGGAGAGAGAGCCTCTGTGTTTCCTAATGCAGACTGGCT
TCCTCAGTTTCCACTTTAGTCCACCGGACTCCTAGCTTGCCTCCTTCCTTGTCTTGCAGG
GCTGCACAGAGAACACTCACACCTGAATCCTTATCCTGCACCCTTGGTAATCCGAGGCCA
GCAAGACTTGGTTCTCCATACTCAGTTAAGCCTTCTCTTGGCGGAGAGATCTTTAACCTC
TCAGGAAGGCTTCTCTGTCCTTCCTTCTCCTCCTCTCCCTTCTCTCTCTTCAGCCTCCAT
TCCAAAGCCACACTTGCACATCCCCACTTGCACATGGCTCACTAATTACGAAGCACATGT
GACTTAAGGACGAGGTTCCTGGAGCTGCTGCTATTTCAGATTTTGAAAATGTATATGAG
CGTTTGCCTGCACATGCATCTGTGTACCGCGGAGGTACCAGGAAAACCTGGGGCCGGA
AGAGAGAGGCGGATCCCCTGGAGCTGGGGTTACAGATAGTTATGAGGCACCATGTGGGTG
CTGAGAACTGAACCCGGTCCTCAGGAAGAACAGCGAGTGCTCTCAATCCCCGATCCACCT
CTCCAGCTCCCATTCCAGAATCTTGATGTCTGGGATCTAGGGAGGCGGTGGAACAAGGAG
CTGGGATGACCCAGGAAGGGCTGAGCCAACAGAGCTCTCCACTCAGGCAAGGCCAGAGCT
GGAGTGGCTGGGGTTTCTATGTTTTTTCCTTTTTTTTCTGTAACCTGTGCCAACTGGA
AGATGCAGCGGCAGAGGGATAAGTGGGCTTGCTGCTATCTCTGCAGGAGCTTGGCTCCTG
CAGGATAGGTCCTGTGAGTGTTTCTGGACCAGATAGGAGATGGGGAGGTAGGAACATTC
CTGAAGAACATTCCAACACCGTCTGAGTAATGCTTGGCTCCGATTCTCTTCCTGGAGCCC
CTTGGAAACGCCTGGCCCAGGATCACTGAGCCTCTGAACCCTAGCTCCTTCAGGTTCTGG
GCCAGGTCCGTCAGAGTCCCAACACCAGCATCAACCCTAATGGGAGTCAGGAGCTGTGGG
ACAGACATTTGGTGGCTGTCTTACTCAGATGGCAAAGGAGGCCTCCAAACACCTCCCTCA
CCATAAAGGCATCTACTACCCAGTCTAAAAATACCCAAGGCTGCCTCCTTCTTCCCAGCC
CCTCTGCGCTGGGGTCTGGGCTTCTTCCCGGGACCTCTGACCTCAAACCAGCTCTCTAAG
CTCTGGCCGCTTCAAATTCCCCAATGGGATGGTTCCTGGTGCCTCGGTTTCTCTTTTGC
CACCTCCCTGGTTGCTTCTCCATTTAGGGGATGCCCCATGAATACCAAATCCTGGAAGTG
CTACACATGGAGTCCAGCTTTCAGGACCCTCCTTCCCCGATGGCTTCCTGCTCCTAACT
GCAATTTAACACTATTCTCTGCTTTCACCCCAGGAAATGCCCATGGAGAGCTAGTCACT
CCCCACTGGATCCTGGAGGGCAGACTCTGGCTCAAGGTCACCCTGGAGGAGCCGGTAAGT
ATCCGTTATCCTGTCCTTATTAGGGGCCCTAGGTCTCCCGCTCTCTGTCCTTTCCCCCAA
ATGCAGCGTGACAGTTTTTCTGGGGTTCTCAGAACCAAATCACTGTACCGTTAAGCCACT
CCCTGTTGGGTGGGTGGGACAAAGAGACATCTAGATGGCGTGAGGCTGCACACATGGAAG
TCATTTTGGGCTTCCTCCCTCCCACCCCCTTCTATTCCTGGCCCTAACCCTCTTCTCCAT
GGGGGAACATTCAGGCCATGCCCACTCAACTAAGCAAAGATGAGTTCATAGTTTGGGGCC
TAAAGCCTTTCAGGAGAGCTCTGTGTGTGTGTGTGTGTGTGTGTCTGTGTGTGTGT
GTGTGTGTATTCTGTTCTGTTTTGTTTTGATTGAGACAGGGTCTTGCTATGTAGCTCT
GGGGGGCTTCAAGTCATGAGCCATCATGCCAGCCACAGGAGATTTTAAAAGAAGGACAC
CAAAATGTCCTCTTTGGCCGTGTTTATGGGGAACATGTGACTCCGTGGACATGCTGCTGT
CCTGTAACCTCAGCTTCCATGGCTGGAAGCCACCTGGGACAAGGAAGCTGTGGGCCATTC
```

FIG. 18B

```
TCCTCCTGTCCCCAGATGTATTCTCACTCTGGTTTGCTTCTCCAGAGCCCTGCTCAGCCT
CCTCCTAACTTCTGCTCATTGTGTTCCCCCAGAAGAGCCATGTGTGCCTTCACTGCTTCG
CTGCCCATGGGGAGGCCGGCACTGATCCGCCTGGCTTACAGAGAGGCAAGCGAGCCCCAC
AGAGCTTGTAAAGTTGCTCATGCTTGAATAGTTCATTGGGCCTAGAAACCTGAGGCTCCG
TGGGACCTAAGGGCTTCAGATGATTGGCTGCCTCCCCTTCTTTCCTATAACTACTCAGGC
TGGAGAGAGTTCAATTCTGTACCTCCTGACAGAGGGCAGCCCCACTGTCCAAACCTAGAG
TGTTGCAACAGTGAGGATGCATTCCCAGAAACCTAAACCTTCCAAGTCAGGGCCTTCACT
GGGGTCCCCCAGACTTCTAGGACTTCTCTCAACCAAGCAAAGATGGCTTGTGGACATGCA
CGGGTTCCCCTGATGGTGGCCTCTCTCCTTGCCTGGCTCGGTCTGTGAGAGAATCCCAGG
GGGACTCTGCTCTGCGTTAGGAAGCCTGTGAGGCCAGGCCAGGAAGAGCTTTGGCAGGGT
GTGTGTATTTCACAAACAGGGTTGTACTGCAGGATGGGGATGGTGCACAAAGGGGGAGGG
AGACCCTGGAGCAGAAGTAAAGGCAGCAAGGGCCGCAGAGGGAAGGGACCTTCCACTGGG
GCTACTGCCTTTCTCCCAGAGCAGACATTTTCCCATAAAGCAAGAGGCACTCCAACCATA
TAAGCTCATGTTTGGGCCCTTGTGGAGCCTGTGGCTGGGGAAGTGAGGGCCATCTTCTCT
ACACCTGCTGCAGAAGGGCCCTGAAAGATTCTTGGCCAGGGTCCCAGCCCAGTGCATTTT
GGGATAAAAAGGGAAAGCCATCGTGGGTGGGGAAAACATTTAAAAAAAAAAATACAGCAGC
CTCCCCTGGAATCTCTTGGGCTAGTTCCAGTTCTGGCTTCTAGCCAGGCTAAGTGGACTA
GCCTGAGAGAGACCAAGTCAGTGAGAGAGGAGAGGTGGCTAGAGGGCCAAGGCCAGCCCT
TCTGACATCTAGCTAAGAGAGTCAACACTTTTAGGGAGCCAAAGTTGGGTTTCATGTTT
ACTTCATGAGTTCAGTTATGAGGCCAGCTCAGAGGAATTTCAGAGGATCGGGCAGTTTGT
CAGAACTGAAGGTGGAGGAAAAAGTTTGGGTTCTCTCAGGAATGAGGGAAAGGCAGCAAG
ATGGAGAGATGTGCAACCAGGAGCTGTGGATGCAGCTGGGTGATTTGGTGCTTGCTTGGC
ATGTGCAAGGCCCTGGGTTTGATCTATAGCACCCACAGCAAACTAGCAAGCAAGCAAACA
AGCATACAAACAAACAGAAGCAAGGTTGCAGGTAGTACAAGAGATGGCCAAAGCTGTAG
CCCACCCAATGACCCACATCACCCTCAGTGCCCACTGCCTCCTGCTTTTCCTGCCTTTTC
ATGGGGCTCCTGACTATGGCCATAGCATATGTCCATAGCAGACATAACAACATATGCCAG
GCAACGTAGCAACTGCTATGTCCGTATATGGTGGTTATGCATCTTTAAGGGTCCGTTGTC
ACAAACACAAGCACTGAGAACATCTCTAAGTTACAACTCCCACACATATCCACTCCCTGC
AATGCGAGAGCCAGCTGTTCCTATGAGCTTTCTCACTAGGCAGCTCTACATCCTACCGGT
TCCTGGGCAGCCAGGTGGCCTTGGGGCCTAGTGTGTCACTGCGTTCCTTCTCGGTCAGAT
CTTGAAGCCTGACTCGGTGCTGGTGGCTTTAGAGGCTGAAGGCCAGGATCTCCTGCTTGA
ACTGGAGAAGAAGCAGTGAGTACCAGCGGGGGGGTTGCTGAAGTCCAGACAAAGACCCTC
TCTGGAGAGGATCAGTGCTTTCTGGGAGGGGGTTGGGGGCTGGGTGGGAAGCAGCAGTGG
GAGTGACAGGGAGAGTGGCGGATGTACTTGGGGCTACAGTGGACTGAACCCAACTGTAGG
AAGTACATACCTGGTCATCTCATACCCTGGAGCAGCTGGATGGGCGGCTCCCCGCTGGAG
AAGAGTGAGCACCAGAACAGACATTGACTGATACCTTAATTCAAAGGGAATTCTTAGGCA
AAGGGAACTTCCACAGATGGCAGAAGAAAAAGCTGCGAAGGTCAAATCCAATGGTGACAG
TTCATCTGGTCTACCTGGAATGCCTCCATCTGCGTGGAAGAGAACAGAGACATCTGGTCT
ACCTGGAATGCCTCCATCTGCGTGGAAGGGAACAGAGAGGAGAGGGCTGGGGTGGGGGC
TTCCCAGTGGGGCCGATCGAAGAGGGCATCTTAGTGCTAAAGATCTTGGATGGACCTAAA
GAGTCAAAGAACGGGAGGTGGTAAAGGAGAAACACAGTGTCGAAGGAGTGCAGAGGGTAA
GCAAGATGGAGGCGTGGAACTGCAGACTCCACCACCAACCACACCACTCGCTCATGTCTG
CTTTCTTACGGACATTGCAGAAGGCACTCATTCATTTATTCTCTCCATGGAATCAGACA
GACTGGGAACAAACTGCAAACACCACGCCAAACCACAGTTCCTGACAGTGCCACATCCCT
TCCTACTAAACGGTCTTGTACATGTGTGCACACATTGAACGTTAGCATGTATGAGTGCAG
CCAGCAAAGCAGCAGAGTTGTAATGTGTGTAAGGATGGCTGGCCGTACAACAGCCTGGGT
TTTTGATGGAGGACAATGTGAATTTGGAGTCAGGATTTTCTGTAAGGAAGAGCAATTGAA
GTCAGGCATGGAGGTAGAGGCCTGTAAGTCCGGCTCCTCTGGGCAGGAGAACACAGAGTC
AAGTCAGGGACTGCCTGAGTTATAAAGAATGAGTTCAAGACCAGCCTAGGCAACTTAGCA
AAATCCAGTCTCAAAATATAAAGGAGTGAGGAAGAGGGAAAGAGAAAAAGAGGGAGAAGG
AGAAGGAGGAAAAGAAAAGAAAGAAGGAAAGAAAGAAAGAGAAGGAAGGAAGAAAGGAAG
GAAGGAAGATAAAGAAAGAGAGAGAGACAGACAGACAGAAAGAAAGACAGAAGACAGAAA
GAAAGACAGAAAGAAAGAAAGAAAGGCAGAAAAGCAGCTATTTATTTATGGTTGCAATGT
TCCTGGTGGGGACAGGGAAGAAGCCTGAAAATGGAAACATTACTGATAGAGTCTAGCTCC
AGGTAAAGGGACCCTTCCCCGGGTGGCTGAACAGAAGCAGCTACAGGCAGGTGGAAGTCG
GAAGTACGCATCACTGAGGGACAGATGGAGACATGAGATCTAGCAGTCTGAGGAGAACTG
GAGGGCCTGGGGTCCGCTCAGCAAAGGCAGGAGTACCCTGGCCCTACTTGGCCTCTCTGA
```

FIG. 18C

```
GGTAGTATCTCCTGGCACACACACACACACACACACACACACACACACACACACACAC
ACCTGCCTGCAGCAGGCTCCACAGCACCAAAGGTCCCCAGCCTGTCCTTCTGGGTGCTTC
CCACACTTCCCATCCCCTTGACTAACCCACCTCAGGACTCGCTCCAGACCTTTGTCTTCT
TTTGCCTGAGGTTTTCTCTTTGAGGCACAGTGTCTCCTTTCTCTCTGACACACTGAATG
CCTCCGCTAGCACTCAGGGAGGAGAGCTGGAAGCAAGCGGCAGGATGCAGGTCTAAATCC
AGTGACTCCTAACCCTCCCCCTTTCCAGCAAGCTTCTGGCCCCAGGATACACAGAAACCC
ACTACAGGCCAGATGGGCATCCGGTAGTGCTGTCCCCCAACCACACGGTGAGACACTTTC
ATGGGATCTGAGAACATGGGGAGGGTGCAGCCTCAATGCCTACCCTGTCCTGTTTTGCAT
TCCTAAGGAGGTTGTAGTCTGCCTTCAGGCCCCACTTCCTCCTTGTCCCACCAACTTGAG
CTCCTACTCAGATGTGGGTATGAGCCTCTTCCTCTCTAGGATCATTGCCAATATCACGGG
CGTGTGAGGGGCTTCCGGGAATCCTGGGTGGTTCTCAGCACCTGCTCTGGGATGAGGTAA
GGCGTTGGGGGAGAGGGCCTGGGGCTGCGGCAGAGGTGAGCGCTTCCTGTTCACACATCC
TTGCTATCCACTGCACTCTAGTGGCCTTATTGTGCTCAGCAGCAAAGTCAGCTATTATCT
GCAACCTCGGACTCCTGGGGATACCAAAGACTTCCCAACCCACGAGATCTTCCGGATGGA
GCAGTTGTTCACCTGGAGAGGGGTCCAGAGAGACAAGAACTCCCAATACAAAGCAGGAAT
GGCCAGTCTTCCTCATGTCCCCAGAGCCGGGTAAGGGGTACAGACTAGAGTGGGACTGG
TCCTTCAAAGCAGAGGACACAGGAATGCGGGTCCTGGACGGGGTCTCCCTGTTTTAATTC
AGAGGCTGAAGAATCAAGTTTGAGCAGAAGTTTAACTATCCCCTCCCCTAGCCCGGGGGG
ATCACGGTGTGTGGCCAAGGATTCGGTCAAGCAGCCTGCCCCTCACCATTTGCTCCTCCC
AGGTGAGGCGAGAGGCGCGCAGGAGTCCCAGGTACCTGGAACTGTACATAGTGGCTGACC
ACACCCTGGTGAGGAGAGACCTAAGAGGTCTGCTGGGTGGGGGACTGCTCAGCACCGTT
ATGACCAGGGACCTCTCTGCCTTCTCAGTTCTTGCTTCAGCATCAGAACTTGAACCACAC
GAGACAGCGCCTCCTGGAGGTTGCCAATTGCGTGGACCAGGTTGGATGATTAGGCGCTG
AAGGTTGGGAGTGAGGCAGTTGAAAAGCTCTGGTGAGTGCCTGGTTCCTGGCTTCAGCAG
GTCTCTCCCTCAGATTCTCAGGACTCTGGATATACAGTTGGTGTTGACCGGGCTGGAAGT
GTGGACCGAGCAGGATCTCAGTCGCATCACTCAGGACGCAAACGAAACGCTCTGGGCTTT
CCTACAGTGGCGCCGCGGGTGTGGGCCAGGAGACCACACGACTCCACACAACTGCTCAC
GTGGGTGCCATTTACACACACACACACACACACACACACACACACACACACACACACA
CACCCCGGTTGCGGGATGTCCTTATTTCCAACTCCACCCAGTCACGCCCTGCTCCATCAT
CCTTAGGGGCCGCACCTTCCAGGGTACCACGGTGGGCCTGGCACCTGTGGAGGGCATATG
CCGCGCGGAGAGCTCCGGAGGTGTGAGCACAGTAAGCTCTGCTGGGGACCTAGGAGGAGA
GAGGTTTGGGTAGGGTTTGTGGTCCTCAGTGAAACCCGGCTCCTCAGGACCACTCGGAAC
TCCCCATCGGCACAGCAGCCACCATGGCCCACGAGATAGGCCACAGCCTGGGCCTCCACC
ATGATCCCGAGGGCTGCTGCGTGCAGGCCGATGCAGAGCAAGGAGGCTGCGTCATGGAGG
CAGCCACAGGGTACGCAAAGAAGGTCGTTGTTACCGGACCTAGACAAAGCGACTGCGTAT
CTTTGGTTACCCCTCAGTTCCCTCTTTAGTAAAGATAACAGCCTGCTAATAGGGCCTCGG
TGGGAAAGATGCTGATAAGGTGGAGTCTCAGAATGACTGCGGGACTAGGGTACTCCACTC
TGATCCTTGGTCCTCCTTGGGGCCCGGACTGCCCGATTTTAGCGTCACAGCCTCCTGTCT
CCAGTTCCTAGGCTCCTCTCTCTCTCGATTGCTCGCTTAGCTTAGAAAGAAACAGCACAT
CTTGAGGGCTGTGTGGCTAACCTCAGGGCCCAGAGTGCAGAAGTAGCCTGAGCTTAGGAG
GTGGCTCCAGCACCCGAGATGGTCCCCACACCACCAATGACATCCATCTTCCATCTGCAG
GCACCCTTTCCCGCGCGTCTTCAGCGCCTGCAGCCGCCGCCAGCTGCGCACCTTCTTCCG
CAAAGGGGGCGGTCCTTGCCTCTCCAACACCTCGGCGCCGGGGCTCCTGGTGCTGCCCAG
CCGCTGCGGAAACGGCTTCTTGGAAGCAGGAGAAGAGTGCGACTGCGGTTCTGGCCAGGT
CAGATCGTCATCTTCGTCCCTGGGGTTCAAGGCTAACCCATGCTCCAGCCTTTCCCAGG
TCTAGCTTGCTCCACCATCACGTGTTCTGTTCTCTCCTTTCTGACTTCAGAAGTGCCCAG
ACCCCTGCTGCTTTGCCCACAATTGCTCCCTGCGTGCGGGGCTCAATGTGCCCACGGTG
ATTGCTGTGCGAGGTGCCTGGTGAGGATACTGGGGAGCGCCCTGTACATCTTAGCTGGGC
TGGGACTTCTAGTCCCTTTTCTGAGTGTGAGTTTGACCCAGTGTATGGGTTCACGTAGCA
CTCCCTCGGGCTTTCAGCAAAGATCTCTCTGCTTTCCCTTAATGGGTCTCTGGTGTAGTT
AAAGTCCGCGGGCACGCCTTGTCGTCCTGCTGCGACTGACTGCGATCTCCCCGAGTTCTG
CACCGGCACCTCCCCGTATTGCCCGCAGATGTTTACCTACTGGATGGCTCACCCTGCGC
TGAGGGTCGCGGCTATTGCCTAGACGGCTGGTGTCCCACGCTGGAGCAGCAGTGCCAGCA
GCTATGGGGCCTGGTGAGACCGCACGCTGGTCCTGGTGCCCTGACCAATACTAAAACCT
GCGGTTTTCTACTGAGGGCAAGCTCCACCCGTGGAACTGAGGCCCGAGCTGCCCGCTTCT
TACTCCCCCTCCCCCCAGGGTCCAAGCCGGCCCCAGAGCCATGTTTCCAGCAGATGAACT
CCATGGGGAATTCGCAAGGGAACTGTGGCCAGGACCACAAGGGTAGCTTCCTGCCTTGTG
```

FIG. 18D

```
CTCAGAGGTGAGGTGTGATGCTGAGGGTCTGCAGCTGTAAAGTAGGGCGGAGCATGCGGA
GGGAACACTCCAAGTTGTTGACCACCTTCCACTTCCTCCCCAGGGACGCTCTGTGTGGGA
AACTGCTGTGCCAGGGAGGGGAGCCGAACCCACTAGTGCCGCACATAGTGACTATGGACT
CCACAATTCTCCTAGAGGGCCGCGAAGTGGTTTGCCGAGGGGCCTTTGTGCTCCCAGATA
GTCACCTGGACCAGCTTGACTTGGGTCTGGTAGAGCCAGGCACCGGCTGTGGACCTAGAA
TGGTGAGCCCTGCCCACCCAACCCCTCCTGGTTATTGAGTCCTCCATGCCAAAGTGTTCT
CCTCACTGCCCAGTGGGCACAATGCCCATAGGTGTGCCAGGACAGGCACTGTCAGAATGC
TACCTCCCAGGAGCTGGAACGTTGCTTGACTGCCTGCCATAACGGTGGGGTGAGTAGCCT
AAGGGGTCAGGGTGACCTTGGAGGTCCTTGCTACCTGGTGACTTTTCTATCCTCATCTTA
GGTTTGCAATAGCAATCGTAACTGTCACTGTGCTGCTGGCTGGGCTCCACCCTTCTGTGA
CAAGCCTGGCTTGGGTGGTAGCGTGGATAGTGGCCCTGCACAGTCTGCAAGTATCCCAAT
GGGGTGGGGGCAGGCAGGAACCACCTGGGCAGTAGCCTGCTTGAGACTCAGCACCCCTGC
CCTCCACAGACCGAGATGCCTTCCCCTTGGCCATGCTCCTCAGCTTCCTGCTGCCTCTGC
TCCCTTGGGCTTGCCTAGCCTGGTGCTACTACCAGCTCCCAACATTCTTGTCATCGAAGG
GACTGTGCTGCAGGAGGGACCCCCTATGGAATAGGTAGGTTCGGTGCTCAGGTCTCTCTT
CCTGAGCCTGCCCCCATGGCTCCTGCTTCTCAGAACTCTTCAGGGCTTTGTAGAGTGAGA
GGCTACAGGGAGCTGGGCTTTAGGAAGCTAGATGGGATCCTTATTCTCTAGATGTAGTG
AGAGCTCCCAGGCTGTGGGAAGAAGTCCGTGGTGTGTATCACTGCCCTGACCAGCACTTG
GTGGTGTGGTCCTTTCCATGGGCTTCCCTTGATTTTTTGTTTTATGTTTTTGTTGTTG
TTGGTTTTTTTCTGCTTTAAAGAAATTCAACACAGCCTGTGCTCCGCTTTGTCCTGAAGA
CGACTCTAGCTTCCTTGTCTCAATATCAGCCATCTCCCATGGCCTTTGCCCTAATTACTC
CCTTCAGGTCCCTCGGTGCTAGCCAAGGACCCCTTTGTGCTCCCTATAAACTGGCCAGCT
ATAGTGTTGCTCTTTCTGTGCCAGGACTCTGTGCCTCTGTCCCCTGTAGATCACAGTGCT
GTAAACCCAATTTTCTGGCAGGCAGAAATGCCACCTGATAGCACACATTATCTACCGAGG
GCAGCCTCCTCACTAGGCCCCTCGGGCAAGTCAGGCACATTATGTCCCTGTCTGAACTTG
GAAGTGTTCTAGACCAATTGAGGGAAGGGCAGGGTTGGGTTGGAGATGTGACTAGAGGGC
ACCTCAGGCCAGAAACAGCACCAGCAGGCCCCAGGAGCCAGTGAGACGGTCTGGGGAAAG
CCAGGTAGTGCCTGGGGGTGGGGCGGTGTCTGCAGACAGGGAAACAGGTGGAGTGACA
GTTGGGAGGGGGCACTTCAGAGGGGTGGCAGCTGCACACCGTTATCGGGATAGGGTGTCA
AGGACAGTGGGAATATCTGGATGAACCATCCAAAGAAATGGCAAGGTCTGTGAGAAAGGT
CCCGGCAGTTCAGAGTCTAGACTGGCAGAGCACGGCTAAACGGAGCATGGGAAGGCACAG
TTCCCACCAAGGGAGACATCTCTGCACTTCAGCTCTAGGTGGGCCCTCGGTGACGCCTAC
ATCTAGACTGAGTGGGGGCTGGAGTGGAGTCACCTCGGGAGAAAGGATGTCCACAGCCCT
GGAGGCCCTGGGACATAAGTGAGGTCTGGACATCTTAAGGACAGAACAGGAATGTGGAAT
TCGAAGCTTGAGTGGAATGGAGAAGCAATCCCCCTTTGTCTCATACACGGTCACTTTCCA
ACCTTCTGAACTCTTATCTGGTCTGTCACTGGCCCTGCAGAGACATACCCCTGGGCAGT
GTGCATCCGGTGGAGTTTGGCTCCATCATCACTGGAGAGCCCTCGCCCCCTCGTAAGTGT
GCCCCTTGGGACATGGAGAGGGAAGCAAGGGGTGGGTGCTTGCCATCTGCCTCCTTCTAA
ATGCTCTCCTTAACACACCTTCAATCCTCTGCCCTGCTCAGCCCCATGGACCTCTTGCCA
ACAGCGTTCGCACCCTCCATCTCTTGACTTGCTCTCAGACCCTGCGAACTCTGAGCTTAC
CTAAGAACTACCCTCTGAAGCAGCCTGGTCTACAGATTGAGTTCCAGACCTGCCCTATCC
CTATGGTATGGAAGCACCCTGAGGACCTCCTGTTGCCCAGTCACCTACCTCTGTCTCAGT
TTGTTGTCCCCTCCTCAGATTTACAGGCTTGCATCAATAAAGAAATGAGACATGGCCTC
AGAGAAGCTGTTGTCATAGAGACCATGATGCTGGAAGCCCTAGGGGCAGGGAAGGGAGAC
ACTGTGGTTCTTCTTGGGTCCTTATAGAGGGAGGACAAATGTGCCCTGCCATGTGACTTG
CAGTCCTCAGTTTCTCAGACGCACTCTTATAATTCCTATGGCTGTATGCTGAGCTCTTA
CTCAGCATAGGAACCCCAGAGCCCGATCATGTTGTATCCCGCCTGCCCTGAGAGCTGTGC
TATTCTGAAATGTTAGAATGTATCTAATAACAATAAATCACAAGTTATATCAGTGTTGT
TGGCTGTGACCTGTTAAAAGGGTCTAAGTTGTTTATTAAAAAGATATGGAGATGGATTAC
TGAGAAAGAAATTAGAAACAACATCTGGACAGTGGAGGAGCCAGCACTGGGGAGGAAAGG
GCAGACAGATCTCTGAGTTCAAGGCCAGCCTGGTCTACAGATTGAGTTCCAGGATAGCTA
GGGCCACACAGAGGAAACCCTGTTTTGAAAACCAAACAGTCAAATAATAAAAACAAACTT
AGTAGCACCTTGTACAGACAGAGAGAAAGGTTCCCAGGAGAGCTCAGACCCCAGCACCAG
AGGTGGCAAGGCAGAGTCTCAAAGCCCAGGTGGCAAAAGTGGGATCTGTTAGCATAAACC
CAAAGGGCGCGTGGGACAGGCAGGGAGTACCCTTTGATGCAAGCTCACTCTGGTGAGGGC
CCCTCACCCCTGGATGTCTGTTAGCAAGGGAATCAGTCAGTGTCTCAGTCTGTTAACATC
TGTGAGAGGGGAAAGGCTGCTGCAGACATGGCCTGAGCAGCATCTGGATTCGAACATTTG
```

FIG. 18E

```
CACTTTAGGGCCTGGCCCCTGGGTGGGGCACTCGCCATTCATTGCCTTTACGACA
GCTGTGAGAGAGAGGTTGCTGCAAGTGTGTATGGCTGGGTTAGCTCGAGCCCACCAGGCA
ATCATGATTTCCCTCGACATCTAGTCATTAACAAACACAGGTTCTTTTACTACAATTTTA
ACTACCAATATTAACTAATAATGTGTATAAAATATATAACACAGTACACATATATAAGTA
CATAGATGTTAGTACATATAAATATTATATATATATATAATTGTAATTAATATTACTT
AATTTTATTTTATCATTTGATATTATTTTACTGTTAGTTATAACAATGTGCATAATATAT
GTGTAATATAAAATATAATTTTATTATTTAATATTATTATATAAATTTAATTAATATTAA
TTATACCTATATATTTAGTACATATACATAGGTTACAGAATGGCTACAAAAGTGCCAGGA
GCCATCAAGGAGAAGCTAAAAGCCAGCAAGTGATCTTCCTGAGACGGTTCTGCCATGGAC
TGTACAATTAGTGATGGATTTGCTTCTGTAGGCAAGGACGAGGAGATTTCATTTTAGGAA
AGATTCCTGCTATTAATATGCTTTTCCTGGTATTATTAAATATATATAACAATCACTAGG
TATTAGCCCACCGTTTTGAACAGAATGTTCTGCAGAACAATGAAGATGTACTCTCTTGTA
ATGATGCTATATAGACAAATAGATTATTTCTTTTTTAAAAAAGAAAAAAGAGCCGGGCGA
TGGTGGCACATGCCTTTAATCCCAGCACTTGGGAGGCAGAGGCAGGCAGATTTCTGAGTT
CAAGGCCAGCCTGGACTACAGAGTGAGTTCCAGGACAGCCAGGGCTACTCAGAGAAACTC
TGTCTTGGAAAAAAAAAAGAGGAAGAAAGAAAAAAGATTTATTTATTTATTTTATACAT
ATGAGTACACCATCAGACACACAAGAAGAGGGCACCAGACCCCATTACAGATGGTTGTGA
GCCACCATGTGGTTGCTGGGAATTGAACTCAGGACCTCTGGAAGAACAGTTGGTGCTCTT
AACCCCTGAGCCATCTCTCCAGCCCAAATAGATGATTTCTTAATTCTTAAGGATGATCCT
ATAAGAATTCCTAAACTTACATTAGTAATTATTAAGCTCTTTTACAATAGGACTTCTATT
AAGTCTTCTAATATGAAAACTTCAATAAGAACTCTGCCAGTCTTCAAGTGTCATGAGT
TAGTTGCTTCTGAGATAGCAAGTAGGCATCAACAACTTAGAGCACATTCTAGGAGGTTGT
AAAACCATTAACCAGTGGTCTTAAAAAGGGAACTAACAATAGGCTATAGGTGCAAGGACA
GAAGATAAAATATTGACTAGGTTTATCAATACAAAATTTACCCACAAAAGTTATGTTTTT
GACTTTTCATAAAAACTCTTTATGAACCTGTAGAACTGGTGAAAGATGACGAATGCTTAG
CCAGATAATTACTCCTAATAGATATGCATGTGAATATTCTGTGCTGTAAACTTATTTATG
TTTGAACTTCCAGTGAACTTTTGTTTAAAAAAGGGGGGGGGTTGAAAAAGCCATGTGATC
TATTCTCCTAGAAAGGGTACAGAAGACTAAGAAAGATTACATTGGAGATGTAACCTTGGA
GAGAAAGCTTTGGGAGCAAGAGCATAGAGAGCAAGGCCATTGTGGCATCAGAGCAGGAGG
AGAGAGCAAGATTAGAAGGAGATGCAGAGTGGAATAACTTAGAAACTATAAGGCAACATA
AAAAATTAAGAGAGCCATATGCAGAATGCAGAGGGAAAGAGAAAAAAAAAAAAAAAAGA
AGCTGCAGGGAGAGCAGAAGGAGCAGGCAGGCTTCTCCTGACCATGGGGTAGAACAGGGC
TTTTCTTAATACCAAGGCAGGCTTAGTCTTAAGGATAATAAAGCTTTTCTTTCTTACAGA
CTTGGTTTTAATTCATTTAGCAATAAAAGTGTAAAAGTGTTTTCTTTCCCTATGCAATAA
AGATTGGAGCTTATTTTTCAGCCAGAATGAGTGAGTTCTCTCTGCAACGGTGCTTGGTCT
TTTGCTTCATATACACACATAAGTGTGTGTGTGCGCGCATGCGTGTGTGTGTGTGTGTGT
GTGTGTGTGTGTAAGTGTGCAATTATCAGATGGCATGGAAGCTGGGCTCAATTGGTTC
AAATGGGGACTTGTGAGGGTATATGCATGAATCTGTATATGAATTCATGTGAGCTTATAT
ATATTTGCTTGTGTAAAAGTTTTTCCTTCTGTGAGTGTGACTCTCTTCTCCTGGTTCAAT
AGAGGTTTATTGCTTCAAACTTCCCCCTAGCCTGACAGTCGAGAGGCATCTGGACAAGAG
AGAAAAGGCTCTAGCCATTAATCCTTTTCTTAGATCCATTTTCTTAGAGAACTTTCTTAG
GAAACTGTTTAGAGAGAACATAGAAACAGGCTGAAATCACTTGTCAAACTGTCCCCTTTT
CTTCCTAAGGACTTCTACTAGCAGACTGGGAGTTAGAGCTGCACAGTCCCTGAGGAGATA
GAACAAAGGCTGCTTTACTGAATCCCCCTGCTGTTTTAAGATGAGGTTCTAAAGGAGATTG
CAGTTTCTGACCCCCAAAAGGAACTCAGGCAGGTCAGCTACAGTATCAAAGTGACTTAAA
CTTAAGATAGGGATATGTTTTATTATTAAACAGCTACCCTAAATATCTCATAAGATCAAG
CTTACCCCGGTGCACTTCCCCCTCTGTTGCCTCAAGAGGAACCAAGCAGAAAGAACCGC
CAGGGCTGGCTCCTGGCACAAATGGGTTAAAGATGTTGTAGCATGGGAAATGAAGAGAT
GGCTCAGCTATTAAGAGAATATCTTACTCTTCCAGAGGACCAGTGTTCAATTCCCAGCAA
ACATATCAGGTGCCACACCATCACTTGTAGCTCCAGCTGCAGATCTGCTACATCTGGCCT
CCATAGGCACCCACACACAGGTGGCACCCACAATTAAAAAAATAAGATAAATCTAAAACA
GCAAAGTTAAAGCATGAGCTGAAACTAGTAAAGTGCTTGTGTGGCATAGACCAAGACCTG
GGTTTGGTCCCTACCTGTTAGAAATAGTCTCAGTATCACACAAAGGAACACCCAAGCGAA
GCAAAAGCTCCCAGCAAGACAAAACTACAGTCTTCATTGAGAGTGTGCACGCTGAAGACC
GAGCACACTGGGTGCAAAATGTACTTGGATTCTGTTTGCTTGTTTTGTTCCAGACAGGGT
TTCTCTGCATAACAGCCTTGGCTGTCCCTGAAATTCACTGTGTAGACCAGGCTGGCCTCA
AACCCTCAGAGATCCGTTCACCCACGCTTATCTAGGCTTCAGTCTCACCCTGTGAGATGG
```

FIG. 18F

```
CCTGAAAGTTGTTAGAACCGCGCGGGATCTATTTCTGACAGACTGGCTGGCATCTTTTCC
TTCTCTCAGCATGAGATTCCTGGGGCGTTCCCATTTCAGCATCAAGCATGGTAGCAGAGT
TGGAACCTGAGGGCTGAGGGCTCAGACTCAGACCATAAACTGGAAGCAGAGAGAACTGGA
GATTGTGGGAGGCTTTGAAACCTCAGCTCCTGCCCCAGCAAATACCTTCCAGCAAGGCCA
CACCTCTTAAACCTCCCCAAACAGGGTCACCAACTGGGGACCTAATATTCAAATGCCCAC
AAATATGGGAGACATGACATCCAAACCGCCAGGACAGGTGTATACCTCCATGCTTGGTTT
CCGTAGTAAGAAACACTAAACATTAGCCTTTCCTAATAAACACTGATATAAAGCCCTGCT
ATTCTCGATGTTTTCCTCTGTTCTGCTCCTCCTTCTCCACCTGCTTCTCTGTTCTCTGA
CCTCTTCTGTGTCACAGATAGCCCTGCCATGTCCATCTGCCAGCCATGTTCTGTCTACTT
GCCTCTCTCTGCTCTGGACTCTTCTAGATGCCTCTGGCTGTTCTTTCTCATATCTACA
ATAAAAACCTGGCCCTTAATCATACCACAGAGATATCGAGTCTTCTTTATACAAATTTTC
TTGTAGCTCTCTTAAAGGGAGATTAAATAAACAGGCTGAGCACACAGGAGGATCATGGCA
TATTGACTTGCTTGTGAGGTTCAGCAGATGTTCAGGCTCTTTGAATGAAAGAGATACTTT
CATAAAATTCTATCATACACACAACAGCTAAAGACTTGCATGGGAAAATACTGGTGAGTA
GGCCATGTCCAGGTTACTAATAGCCTCTGCACAGGGAGAGCCCAACTGTGGAGAATAGGC
CAAGGACAGGCCGATAATCGCCTTATTTAGATCTGTTCTTTAAGATGTGTGTGTGTGT
GTGTGTGTCTGTGTGTGTGTCTGTGTGTGTGGTTTATGTATATGAGTACACTGT
AGCTGTCTTCAGACACACAGAAGAGGGCATCACACCCCATTACAGATGGTTGTGAGCCAC
CACATGGTTGCTGAGAATTGAACTCAGGACCTCTGGAAGAACAGTTAGCTCTTAACCATT
GTACCATCTCTTCAGCCCTTCCTTATATTTGTATTTTAAATAGCTTAAAAAAGAAAAAGA
AACCATGAATGTGAAAATTAGCATAAACTTTAGTGTTCAGAAATAGATTTTTTTTGGAAC
ACAGCCAGGTTCTTTCTTGTGTTGACTGTGTGAGGGCATTCTGGGAAACAGGGTGTGGCC
TGGGAAGCTGTGAAGGTGTACTTCTAGTTCCTTCTGGCCCTCCTGCAGACAGTGCAAGCC
CCACAGTACACTGCTGCATGTCTGGGGAGGTTGTTCCAGCTGCTGAACAAGTTCTTGTGG
AACACTGTCACCCTGCCCTGGGGTCATAATCATGACACTGCTGCTCCTCAATGTTTGAAG
GAAAATCACCCTTAGTCTCAATGCTGTATAAATAAACCCTCTATAAAATCAAAAGGCCGC
ATTCCATAGGATGAAACACGCGGGGAACATTTTCTTCCATGCCCAGGCCTTCTCTTCCTG
GCAGGGCTCCAACATGTCCTGGTCTGCCTGCCCTGACGCCAGGCTACGGCTGGCTGACTC
CTTATCAGGCACGTAGCCCTCCTTGGTCCTGGTTCTACCAGTCCCCAAGCCTAGTCCCAG
GTCAATGCACAGATTCAGCCCCTGTAATAGTAATCTTGGGGGAGGGGGCGTTCTATGTCC
CTTTTTGCTCCCAAATAACTGCAGAGTGTTTCTATACCCACTCGAGCCGTAAAGATACAG
AGACCTGGCATTTTTATTAACAAGCTATTAGAGTGTGTACTCTAATATCCGGGCAGATTC
TTATCTATCCTAACCCAATTAGACTACCTACTACCCAACCAAATGCCCTGGTACTTGCCC
TCTGGTCTTGCCCTGCTTCACTCTGGTCTATGTATGTTCTCATGGCTGTTTCTCATGGC
GAATCTTCCTGGTCTCTCCACGTGGTTTCTCCACACCGTCTCCTCCTCCTGGTCCTTATC
TACTCTCTGGTCTCCTTTGGGACCCCATGACTGGGATTGGAAGTCCCTCCCTATCTCTTC
TGCTCAGCTAATTGGCTGACCAGCTCTTTTATTAACCAATCAGAGGTGATGGAAAACAAT
GTTTACACAACATTGAGATCGGGAGATGGCTATCTTCCAGACTGCAACCAGATGTCTGCG
GTAAAGAAGTCAGCATCTGAACAACAGTGCACAAAACCATCCCCCAACAAGCCCACTCTG
GCCTGCCCTGCCCTGCCCTGCCCTGCCCCTCCACACCTGCTCAGCTCTTCCAGAAGGAA
GAGAGTTTGGTTTCCAGCAACCAGCCTTCCGAGAGCTGGTGCCCTTCTCTGGCCTCGGGG
TAACATGCATACATGCCCCATAAAATCTGCTTTACAATGCTGTCTTAATCTGACCAGAAG
AAAATGTAAGACTAACTCAGTAGAAATAGTCCAGGAAATAACTAGTGAGAATTCTTATGA
AAAATGGGGATAAGGTGAAGGAGAGTTTAAACATCCAGGGGAAGTTGGGACGGGCTTCCT
```

FIG. 18G

>Mouse 216 homologue aa sequence
MGSRCGRPGGSPVLLLLPLLLPSCPLRSARMFPASIPKPHLHIPTCTWLTNYEAHVTLRT
RFLELLLFQILKMYMSVLPAHASVYRGGNAHGELVTPHWILEGRLWLKVTLEEPILKPDS
VLVALEAEGQDLLLELEKKHKLLAPGYTETHYRPDGHPVVLSPNHTDHCQYHGRVRGFRE
SWVVLSTCSGMSGLIVLSSKVSYYLQPRTPGDTKDFPTHEIFRMEQLFTWRGVQRDKNSQ
YKAGMASLPHVPQSRVRREARRSPRYLELYIVADHTLVSPSDSQDSGYTVGVDRAGSVDR
AGSQSHHSGRKRNALGFPTVAPRGVGQETTRLHTTAHDHSELPIGTAATMAHEIGHSLGL
HHDPEGCCVQADAEQGGCVMEAATGHPFPRVFSACSRRQLRTFFRKGGGPCLSNTSAPGL
LVLPSRCGNGFLEAGEECDCGSGQLKSAGTPCRPAATDCDLPEFCTGTSPYCPADVYLLD
GSPCAEGRGYCLDGWCPTLEQQCQQLWGPGSKPAPEPCFQQMNSMGNSQGNCGQDHKGSF
LPCAQRDALCGKLLCQGGEPNPLVPHIVTMDSTILLEGREVVCRGAFVLPDSHLDQLDLG
LVEPGTGCGPRMPHGPLANSVRTLHLLTCSQTLRTLSLPKNYPLKQPGLQIEFQTCPIPM
REDKCALPCDLQSSVSQTHSYNSYGLYAELLLSIGTPEPDHVVSRLP

FIG. 19

>Gene 216 genomic DNA sequence
CCAAAAGCGAACACACCCAGATCAAGAAATAGACCATCCTACAGTCCCCCCTTACACTCT
GTACCAGTTGCAGCCCCCACAAGGGTAACTACTGTCTTGACTTCGAACACCATAGATTTG
ATTTGCCTGTTTTAAACTTTACATAAGTAGAATCACAGAGTGTGTACAATGACTTTGGA
AAACTGTTTGACAATATCTATTAAAGCTAAAATACCCTTGCCCTATGAACCTGAAATTCC
ACCCACCTTGCCAAGGGACAAAAAGTTCCCCTCTAAATGCACCAGGCTGTCAGGGATGAA
GCGTTGGCTTTGGGGCCCCCATTCACACACATGACCTTTTCTGGGGCACCCAAGCATCAG
CCTGTCGTCACCAGGTGCCACCCTGGCGATCTCTGAAGGCTGGAGTCGGAGTGCCTCCCT
CAGACATCCTGTTCTGCGTCACTCCTTGGGAGAAGTCGTGTTTACAGATGGTGGGTGTCA
CCCATGCCAAGCACTTCTAAGGGTTAATGCTCACTGGTTTGCCTGGTTCCCAGGACATTT
CCTGATGCCCTCTGGAGGGTGACGCCAACAAGCCAGTGGAGAAGCCATCTTTCCCAGGT
GCTGTCAGGCGCCCCGGAGCTGCTCGGTGCATCCTAGGATCCCTCTTCCTCAGCTTTGG
TTTGATGGCCTCATCTCCTCCCCTGCAACCTCAAAATGTAAATAAACCCTTTCTCAGAGA
CTTCGGCAGAAAATTCCTCTGACCTGCACTTGGACACAGCTCATCTGGGTTTGGGAGGTG
TCAACTGTGTAAGGATGACTCTGATCCCCATGTGGCTTTTCGACTGTGTCCCTCTACAG
TCAGTTATTAGCACTGACTGTGCTAGGAAGTGAGCAACACACATATTCCCAGACCACATG
GAGCTCAGGAGCTTGGGGAGAGAGACAGGGAAGTGGACGACTACAGGGCCTTCTGAAACG
TGTTGCAGGGAGAAGTGTCAGTCAGGGGATGCTAACCTGGCTTTGGGTAAGGGACAGCCT
CTGAATGACAGGACATTAAAGCCATGGCCTGCAGTTTAAGTAGGAGTTGGCCAGTTCGAG
GTAAGAATACCAGTAAGCAAGAACGCCAGAGTAGCTCCTCGAGCTGCCTTCTGTACCTGA
CATCCACACTGAAGCCAGCCCCTCTGTGTTCAGCCTTGCTTTACTGAAGAGGTGTCGCTG
AGGGGCTGCTCTGGGGTGCTGCTCTGCTTTCCTGTCCCCAACTTGTTCTGAGCTCGAGCC
ACCTCCATACTGGTGCTCCTGGTTCTCAGGCCTTTGAACTCAAACTGAATCACACCACTG
GCTTTCCTCGTTCTCCAGCTTGCAGATGGCAGATTCGGGAACTTTTTGGCCTCCATAATC
ACGTGAGCCAATTGCTATAATAAATATCTCTCTCCCTCTTTCTTCCTCTCTCTCTCTCTG
TGCAAATATAGTTCCAATTATAAGAGCCCCTAACTGGAAAATAACCCTATGGTGCACTGG
TGAGTAGAGAAACTGTGGTTCCCTCAAACCACCGAACACTATTCAGCAATACGAAGGAAC
AAACTATTGATATGCAAAATAGTGTAAATGAATCTCAAAAACATCGGAAAGAGGGAAGGA
AGCCAGACACAGAAGAGTGCATGCCGCATGATTCCATTTATATGAAATTCTAGAACAGGC
AAAACTTATCTATAGACAGAGAACAACAGATCAGTGGCTGTCTGGGGTTGGGAGTGGGA
AGTTTGGCTGGAAGGGCACAGGGCTCTTTCTGTGAGTGAGGGAATGTGTCTGCATTATAG
TGATGCTTATGTAGTTATATACACTTATCGAAACTCATCTTACTGGCCACTTAAAATAAG
TGCATTTTATTGTGTGTAAATTATACCTTAATGAAGTTGATTTGAAAATCCAAAGTAGTA
ATAATAAGTAATAATCTCGTAGCTGGACAGCTGTGGTGACTCACTCCTGTAATTCCAGCG
ATTTGAGAAGCTGAGGCAGGAGGATCACTTAAGATCAGGAGTTCTTTTTATTTTTATTTT
TATTTTTTGAGACGGAGTTTCGCTCTTGTTGCCCAGGCTGGAGTGCAATGGCATGATCTC
GGCTCGCTGCAACCTCCACCTTCTGAGTTCAAGCGATTTTCCTGCCTCAGCCTCCCAAGT
AGCTGGAACTACAGGCGCTCACCACCATGCCCGGCTAATTTTGTATTTTTAGTAGAGAT
GGGGTTTCACCATGTTGGCCAGACTGGTCTTGAACTCCTGACCTCCAGTGATCTGCCCGC
CTCGGCCTCCCAAAGTGCTGGGATTACAGGCATGAGACACTGCGCCTGGCCAAGACCAGG
AGTTTGAGACCAGCCTGGGAACAAAGTGAGACCCCTGTCTACAGAAAAATTAAAAATT
TTAGCTGGGCCTGGTGCCGTGTGCCTGTAGTTCCAGCTACTCAGGAGGCTGAGGTGGGAG
GATACCTTGAGCCCAGGATTTCAAGGCTGCAATGAGGCATGATCAGGCCACTGTCCTCTA
GCGTGGGTGACAGAGTGAGACCCTGTCTCTAAATAATAATCATAAGAACAACAAGGACCC
TCTAAACGCACTGATATCTAAGGTGTATTAAGCGACCAAAAAAAAAAGAAAATCAAAGT
GCAGAAAACGTTAATAAGAGAAAAAAATATGTCTGTATTGTCTTGAGTGTGAAAAAATA
ATCTAAAAGCCTATGAAAGAAACTAATCATATTGGTTTCCTGTTGGTGAGGAGGGCTAAG
AGCACGGAGACTTTTCCCTATGCTTTCTGTACTTTTGATTTTGAGATATGTGAATGTAG
GTTTCTCTCACTGCTCGAACTTTCACTAACCAAATTACTACATTCCAAATTCTCAAAAAC
AAATAGATTTACTTAAAAGTAGGCTGGGTGCGGTGTCTCACGCCTGTAATTCCAGCGCTT
TGGGAGGCCGAGGCGGGCAGATCACCTGAGGTCGGGAGTTCGAGACCAGCCTGACCAACA
TGGAGAAACCCCATCTCTACTAAAAATACAAAATTAGCCAGGCGTGGTGGCGAATGCCTG

FIG. 20A

```
TAATGCCAGCTACTCGGGAGGCTGAGGCAGAAGAATCACTTGAATCTGGGAGGCAGAGGT
TGCAGTGAGCCCAGATCATGCCATTGCACTCCAGTCTGGGTAACAAGAGAGAAACTCTGT
CTCAAAAAAAAAAAAAAAAAAAAAGATTTGCTTAAAAGTTAACATCTCCGGCTGGGCGCG
GTGGCTCATGCCTGTAATCCCAGCGCTTTGAGAGGCCGAGGCGGGTGGATCACGAGATCA
GGAGATTGAGACCATCCTGGCCAAAATGGTGAAACCTCGTCTCTGCTAAAAATACAAAAG
TTAGCTGGGGGTGGTAGCGCGCGCCTGTAGTCCCAGCTACTCGGGAGGCTGAGGCAGGAG
AATCGCTTGAACCAGGGAGTCGGAGGTTGCAGTGAGCCAAGATCGCGCCGCTGCACTCCA
GCCTGGCGACAGAGGGAGACTCCATCTCAAAAAAAAAAAAAAAAAAAAAGTTAACATCTC
ATCCAAATTTGCACCGAGTAGGAAAACAAAAGTTTAAAACATGAAACAGATGTTACTGAG
GCCGAAAGGGTCTCCCAGGCCTGGGAGTCTGCAGCTTTTATGCAATTCTGCCCTCTGGCC
ACCGCCAGGGAAGAAAGGTTGTCTCCGTCTGCTGCATCGCCTTTGCCCAGCAATGAAGCC
CCCAAGACAGCGGCAGCCGGTTGCCTGAACCTTCCTATCCTTGGGGGCACCCAGTGCAGG
TGGATGACCCGACTCAACCTCCGCCAGGGCACCCTCGGGGCAGGACGGGTAGCAAGGAGG
GGACAGAGATCGGCCCCAGGAGACCACGGAAGATCGCGCTCCTGGGGCCAACTTCAGCAG
CGAGAGGCGGCCTTTGCCCACCGCCTCATCCACCACGCCGCGGTCCTCCAAGAACCTTC
CCAGCGGTTCTCTCCTCCTCTCAGGAGTAGAGGCCCTCTGAGACCGACGGGGAGGGACGG
CTCGGGCCGGTCATCCGAGGGGCCGCACGGATTCCCTCCTCCGCCCAGCTCCACCCCCTC
GAGGGGCGGCGGTCCGGGAGTGGCGACCCGGCTCCCCCATGGCGCGCGCCGTCGGGGCCC
CTGGCCAGGCTCCGAGCGGGTTGGCGGGGAGGGGAGCGGGAGCGAGGGCGGGCGGTGG
GAGGTGGGGCGGGAAGGTCCGAAGGCGGCGGCCTGAGGCTGCACCGGGCACGGGTCGGC
CGCAATCCAGCCTGGGCGGAGCCGGAGTTGCGAGCCGCTGCCTAGAGGCCGAGGAGCTCA
CAGCTATGGGCTGGAGGCCCCGGAGAGCTCGGGGACCCCGTTGCTGCTGCTGCTACTAC
TGCTGCTGCTCTGGCCAGTGCCAGGCGCCGGGGTGCTTCAAGGTGAGGACGCGGGCGGGG
TGCGCCCTGAGGGGCAGGCTAGGCGCGGTGGTGGTGGCGGGGATGGGTTCTGCTCAGAGC
TCGGGTCAGCGCGCGGAGGGTCTCACGGCCCCGGCACCATACGGCCAGTAGGTCAGGGCG
TGGGGACTCTTTGGGGGGGTCTCCGTGGGACCTGCCCAGGGACGCTCAAGTGTGCTTGGG
CTGGCCCCGGGCCCGGACTTGCCCACACTGCCCGGCTGCCACTCCGCTGGCAAAGCAGAG
GGCATGGCTCCCTCCCCCTCGGGGACAGCCCAGCCCCCAGCCCCCAGCCCATAGCCGTAG
CCCCCTCTGCCTGGATTCTCGCTCTCACAACCAGCTTCCATCCGCAGGCCACCGTGTGAC
CCGCTCCTGCTCCTCCACCCCTTAGGACTCAGCGGGGCTCCATCCTCTAGGAAGCCCCCA
TGCCCAAGAGTCCCCCAGAGTCCCTGCTTTGCTCTCAGGCTGCAGAACTAGCTGTGGCCT
CCACCCTGCTCACCCCTCGTCCCTCCTCCCAGGGCAGCAGGGCAGTGTGTATGTTGTTTA
TATTGTTGCCTTGTTTGGTGAGATAGAGAAGGGCCTCTCCAGATAGAAGGTGTCTGTTTA
GCAGTGCTCTGGAAAGACTGCAGCTGTCTCCTCGGGGTAACCCCTCCAAACAAAGATGTT
AAGATGGGGCTGGAACAACCTCTGCAAGCGGGTGGGAGGATTAGCCAGTCCTGCACAGCA
AGTGCCTGGCCGGGAACAGGGAGGGCAACCAGGGAGGGGGCATGCGGGGCTGGGCTGTGC
TATGCAGACTGGGCGGTGGCTTCCACAGCACTGTGTGGGACCAAACAGGTACAGGGGCC
TGGTCTGTTCTGGCCCCAGGGGAGGGCCCCAGGCGGTCCACTGCTCCCTCCCTCTGAGC
CCTATCCTGGGGTCAGGGGAGGTGATGGGACCCTGGGAGAGGGCGTCTATGTGCCCAA
TACCAGCCTGGCTCCCTCGGGTTCCACCCCATTCACCCGGTCACCGGAGCTCCAGCTCC
AGCTCCAGCTCTGCCCCTCTCTCCCTCATTGGGGTCAGGGTGCCCGTGGCCAGCACGTGC
GCGCAAGGCCATGTGGACAGCACCCACACACCACACTGCACCCACACCACACCTGTGCCC
GGGCCCACCCTACCTCTTCCCCAAACCCTTAGAGGCCTAGGAGCAGCAAAGCTTGGTTCT
CTACTCTCAGTTAAGTGCTCTCTGGGCTGAGAGACCTCCCCTCCTTCCCCTCCCCACAT
CCACTCAGAGCCCTCCCTGCACTGGCCCTCTAGCCTCCTTTCCAAGGTGGCAGACTCCT
CTCGGCCCTCATCTGCCTGATGGCAATTCACTCATCCAATCAAGGAGGGCTTCTTGGAGG
AAGGGTCTTTGATGTTTGTAGTCTGGGAGAGAAGGTGGAGGAGAAAAAGGGAGTTGGGGT
GGCCTAGCAGGAGCTGAGTCACTTCCACAGGCAGCCATCAGCCCAGCAGGACTGAGGCCA
GGGCTGCGTGGAGGGGGAGGCTGTCTGTTCTGGGAGCTGGGACTGGGTACCGGGGAAG
GAGGGCTGCTGCAGGCTCTGGGTGCCTGGGGCCTGGCTCCTGCAGGGCGGGCCTGTGAGA
GTGGTTGGGGCCAGTGGAGGGGCTGGGAGCATTCCAGGGGAACATTCCAGGCGCCCTCTG
```

FIG. 20B

```
AGTAATGCTTGGCTCTGGGATTCCTCCTAGAGCCCCCTTAGGCACACCCGGCCAGGGAGC
ACCAAGGCTCCGTCCGGAAGCGTCCCCTCCCCTTGAAGAGATGAGGAGGGGCCTTCTGGG
CCAGGGTACCAAAACCCTGCCACCAGGACAGAGTCCCCGAGGGAGCTCTGGGCAAGGTGG
ACCTCGCAAGGCAACATCTGGCTGTTGTTTTCTCAGATGATGGGGGGGCACAAGTGTC
CTCTCTTCGTACATCTCTCACCCTAAAGGCATCTGCTGCCCATCTAAAAATCCCTAAGGC
TGCCGCGCTCTTTCCTTCCCTCTGCACTGGCGGCCTTGGCCTCTTCCTTGTGATCGCCG
AGCCCAAGCCTGCCCCCCGACAAAGGTCAGGGGACTCCCGTGTCCCCAGCTGAGCTGTCC
CTTTCCAGCCTTCTCTTTTCCTCCTCCTTGATAGCTCCTCAGATCCAAGGATGCCCACGG
GCGTCCCTCCTTCTCCAGGCTGAGCCCACGCGTGTTGAAGGTGAAGTCTGCCCCAAAAGG
CCTCCAGTGCCTCCCTGGGGATGTCCTCTACCCCCCTCCCTCTGCTTTGTCCCATGCCCC
TGTGTTCCTCAGGTCCCCCTCACCCTGTGCTCTGTCTTTACTCCAGGACATATCCCTGGG
CAGCCAGTCACCCCGCACTGGGTCCTGGATGGACAACCCTGGCGCACCGTCAGCCTGGAG
GAGCCGGTCAGTGCCATGTCTCCCGCCCTCCACAGGGGCCCTGAACCTCCCAGCCCTTT
TGTCTCTCCCTACATTACAGCTTCTAGTTTTGCTGGGGTCCCCAGAACCACCAAGTCACT
ACTCCTATAGGCCCCTGCCTCCCTGCCCCTCAAGTGGGCAGAAGAAGGCACTGGGGTTT
GGACATCTGGATCTCGTGAGCCCGCACACATGAAGTCATTTCAGCTTTCTCCACCCCAC
CTCCCTCTTTCCCTCCCTCCCTGGATGATCTGGGCCACCCCCACCCCCACCAGGCAGAAA
TGGGTCCAGAGTTTGTGGGTCCTGAAGCTTTTCAGGAGCCTCTAAAAAAAAAAAAAAAAA
AAAAAGCACCAAAAGAAAACCTTTTGCAAAGTTGACCAGAACATGTGACCCTGTGGACA
CACTGCTGTCCCTCTCAGGGCCCTGCCACGAAGGCCTGAACCTTCAGCCTCACTGGCTCC
TGTGGAATCCACTTCTGGTATGGGGGGGCAGTGGTCACTCTCCTGATGTCCCCCAGATG
TAAGACCACCCCATGTGCTTCTTCTGCAGGACGCTCTGCCCCAGCCTCTTCCCAATCCCG
CTCTTCACACGCTTCCAGAATAACCATGCCCCATCTGTTTGTGCCATAATATCTGTGCTG
CAAACTAAGAGGGCAGTAGCCTTGATATGCTCATTTTACAGAGGGGCAAACGGAAGCCCA
GAGAGCTTGGGGAAATTGTCCATGGTCACACAGCTCTTTAGGCTGGGAGCCTGAGACCCA
CTAAGGTCTGAACGATTTTAAACCATTGGCTACACCCTGCCCCTCCTAGAGAGCCCTCT
TTGTTTGGAATTTTCAGCCCTACTGTCCAAATCCAGCAAGAGGGAAGGCAGGGGAGCATT
GCCATGAAGGCTGAGAGGCCCCAGAGACCCAGCAGCTCCCAACCCAGGGCCCTCACTGG
GATCCCCTAGGCCCATAAGGCCCCCATTCCACTGGTCAAGCACGGCACTGGCCTGAGCTT
TGAGATTGCCCTCCCCATCCCCAGGAGGGGAAGGCTGGACACACACTGGGGTCACTCTGC
CTCTGGGCCTCCCTGTCTGTCTGGCCTGGGCTGTGACCAAGAGGAGAGCCCCAAAGGGGC
TCTGCTTCCCCCACCGGTGGGCCCCTGCCCCCAGGAAGCCTGCCAAGATGGTACAGAAGA
AAGAGTAGAGGCTAGGTATCCCCTCCAAAAGGCAGGAAACACTCACATTTCAAGATGAGG
GGTATATATCAAGGGGCAGGGTACCAGGAGGGCAAGAGTAAAGATAGCAGGGGCTGCAGA
GGAACAGGGACCTCGAGTATGGCCTTTTCCCGGTGCAGACCTTTCCCCAATAAAGCAAG
TGGCATTCCAGCCTCATGAGCTCATGCTGGAGGCCTTGTGGGGCCTGTGGCCAGGGAGGC
AAGGACCATCTGCTCCCCACTTGCGAAGGAAGAACTCCCTCCAAAGACTCTGAGACCCTT
GGACAGGGCCCCAGGCCAGTGCATTTTGGAGAAAAGGAGTCGGGGGTTAAACATTCCGA
AGGCGCAGCAGCCTCCCAGGAAGCTCCTGGGCCGGCTCCAACTCTGGGCCCCAGCCAGG
CTGAGTGGACAAGGGGGAAGTGGGGTGTTCCCACAGGGTGGGAGACGCCAAGAGGGTGGG
GGAAGGAGAGAGGGCTGGCCGTCCAAGCCAGCCTCCTGACACCTAGCTGAGAGCCAGTGT
GCTCTCTTGGCTGGAATGGCGTCCATGTTTACTTCGTGGGTCCAGTGAAGCAGGTGTCGG
AGCCGGAGGGACGGGGCTGCTGGAGGCCCAGGAAAACTTTGGAAGAGGGAGCAGTTTGC
CAAAATTGGAAGTGGAGGAGTCAAATTTGAATTCTATAGGAAATGAGCAGCAGCTCATTT
GGAACCAAGCCTCAGGTAGCAGAGGCTCTGAGGAGGCCCTGACCATGGCTACCCGATGCC
CCCATAATGTCCTCAGCACCCTCTGTCTTCCCCTGCTTTTGATGCCCCTTCTGGGCATG
AAAGAAGAGGGCGGGGCCAGGGAGGGGCACCTTTCTGGGACCTCTGGTCTCTAGGGAGG
ATGCTGGTGTGCCTGGCAGGCTGTGCCAACGCCCTTCCAAGTGGCTGTTGTCAGGACTGC
AAACATCCTGAGTTTGGGAACATCTTTGTATGTTCTCACCTCCTCCACGCCCTCCATAGT
ATGTGGGGGGTCCTGCTGACTCCCCAGCCCACGTTCTCCCAAGAACTTCCTCCCCAGCC
GGCTCCACAGGCCACCTACTCCCTGGCAGGCAGGAGGCCTGGAGGCCACCATCTCAGCTC
CACACTCTTTCTTGCCCAGGTCTCGAAGCCAGACATGGGCTGGTGGCCCTGGAGGCTGA
```

FIG. 20C

```
AGGCCAGGAGCTCCTGCTTGAGCTGGAGAAGAACCAGTGAGTGCCAGGCTGGGGTAGGGC
TGGGAGGAGGGGATCAGTGTTGGGGGGCAGGGACTGACACAGATCTGTGCGGGTGGCTGG
ATGGGCAGAGGACCCCAGAGAGGGTGCAGATGACAGGGAGAGTCACGCAGGCCTGTGGTT
GGCTCCCTGGAGGCTGAAGAGGACCGCTGAGGCTGTCAGCCCCGCTGTGGGGCACCTCCG
CCCTCCCAACCCCAGGAGCGGCTTGTTAGCTCCCTGCTGGCGATGAGTGAGCACCACCTA
GTGGACATTTGCAAGATATGCTGAGTCTAAAGAAATCCTAGAGGGAAAAGATGAGCCGGC
ACCCCAGGCTAAGGGAATGGCAGGGACCAAGATGCGGTGGCTTTGGGAGGCCGAGGCGGG
CGGCTCACCTGAGGTCAGGAGTTTGAGACCAGCCTTGCCAACATGGTGAAACCCCGTCTC
TACTAAAAATACAAAAAATTAGCCAGGCGTGGTGGCGGCGCCTGTAATCCCAGCTACTTA
GGGGGCTGAGACGGGAGAATCGCTTGAACCCCGGAGGTAGAGGTTGTGGTGAGCCAAGAT
CACACCACTGCACCACTCCGGCCTGGGCAAAGAGTGAGACTCCGTCTCAAAAAAAGAGAA
AAAAAGAAAAGAAAAAAAAAAGAAAGAAAGAAAAAGAAAAAGATGCAGTGGCTAC
ACTTGGGGGCAGCAGTTTGTCTGACCTGCCTGGAAGGTCTCCATCTACAGGGAGGGGAGC
AGGGGGGAATGAATTTGGAGAGTCCCAGGAGGCCAGATCACAGAAGGCCATTTTGGTGC
TCAGTGTCCTGGACCATCCAGAGCCAAAGATTTTGAGCTGGGGAAGGGACAGGCAGACCT
GTGCTCAGGAAGGTGCCTTGGGCTGGGTGGGGTGGGTGTCCGGGCTGGAGCGCAGGCTCT
TAAAACCACCCAGATTATGTTATCAGTATATATCACCTACTGAGTGCTTGACCGCAGGCG
CTGTTCTGAGCACTTGACACGTATTTTATTCTCCCTCGTGGAGTCGGATGGACAGGGAAC
AAACTCTAGTTCCACTGTGCCCAACCATATTTTCCCGACGTCCCTACCCTTTCAATGGGG
TGGTCACATCACCTACCTCCTAGGGTGGCGGGTGTGTGGGGCAGGGGTAGGGGCAGA
GCTGGGGCAGGTGGTGGAATGCCTGGGAGGGGGGAAGCAGCCATCATTAGCGGGTGGTCT
GGAGGTAATGAGGCCAAGGTGAGGTTGGGTTAAGGATTTTCTTTAAAGAAGACAGATTGA
CTTATGATTGATCCATCCGTGTGGGAAAGATCCTGTTGAGATGGAGCCTGAAGATGGAAT
CATTACCGGAGTGGGTGTGGAGAAGGCAGGGAGGGTGGAAGCAGCGTGGGCAGGTGGCGA
TTCTGTTTTCTCTGGAGGCAGGGGGTGAGCATCAATCACTGAAGGACAGGTGGGAGGTAT
GTGGGGTCTAGAAGTCTGAGGAAAATATTTCAAGGATCTAGGGCAGGTGGGGCAAGAGG
GTCGACCAGATGCCCAACAAAGGAGGGCAGCAGGCAGGGAACTGGGGGAGGTCACCGCA
TTTCCCCAACTCCAAGTCCCATTCTTCGGCAGTGTCTCCTGACTCCTCCCCTCCCGATCC
TGTGGATCCTGCTGCCTGCTGCAGGTCCCTGGGAACCACAAACTCTTCCCCTATTCCCA
CTCCTCCCCGGCGTCCTCCCTGGTGCTTCCCATATTCACATCTCCCACAACTAAGCCATC
ACCAAGGCTCCTTCCTCTAGCCCCAAGAGTTTCTGATCTGAGCAAGTCACCATTGCTCCT
GTCCCTTCCCTAAGACACACTGTGAGTGTCTCACTCATAAAGCTGCTCCATTAGCATTTA
GGGAGGAAGGCTGGGAGACATCCTGGAGGAGGCAGGAGGAAGCTGAATTCAGTGTTCCCT
GTAACACCCCTCTCAGCAGGCTGCTGGCCCCAGGATACATAGAAACCCACTACGGCCCA
GATGGGCAGCCAGTGGTGCTGGCCCCAACCACACGGTGAGATGCTTCCATGGGCTCTGG
GATGCACCGCCAGAGGTACCCCCCACCATTCCTACCCTACTCCTCCTTGCATTCCTAA
GGGGCGGTTGGAGCCAGCCCTACCACACCCTCCCTCTTGCCCCTCTTGCTCCAGCCCTG
GCTGAGATTTGGGGCTGGCCCCTTCCTCCCTAGGATCATTGCCACTACCAAGGGCGAGTA
AGGGGCTTCCCCGACTCCTGGGTAGTCCTCTGCACCTGCTCTGGGATGAGGTGAGCTCTG
GGAGAGGAGGCTGGGCCTGGGATGGGGAAAGAGCTCCCTCACACCCGCTCCTACCCCTCT
GCACCCTAGTGGCCTGATCACCCTCAGCAGGAATGCCAGCTATTATCTGCGTCCCTGGCC
ACCCCGGGGCTCCAAGGACTTCTCAACCCACGAGATCTTTCGGATGGAGCAGCTGCTCAC
CTGGAAAGGAACCTGTGGCCACAGGGATCCTGGGAACAAAGCGGGCATGACCAGCCTTCC
TGGTGGTCCCCAGAGCAGGGTCAGGGGCATCGATCGGATGGGAGTGGGAATGCTGTATCT
ATAGCCCTCCAAATCAGAAGAGACAGGAATTCACAGGCCTCGAGTCCCAGTATTTTTATT
GAAGTCTGAAGAAACAAGTTCCAGAAACATGTTAAACTTCCTTCTGGGAGCTGGGGTTG
GGGGTCAGGGCTCAAGCCCAGCAGCTTCCACTCAGGGTCCCCATTTGCACCTCCGCAGGG
CAGGCGAGAAGCGCGCAGGACCCGGAAGTACCTGGAACTGTACATTGTGGCAGACCACAC
CCTGGTGAGGAGAGACCCCAGGGGTTGGCGGGTCAGGGATGGGGCCAGCTCAGCCCCTC
AAGCCACCGGGATTTCTGCCTTCCCAGTTCTTGACTCGGCACCGAAACTTGAACCACACC
AAACAGCGTCTCCTGGAAGTCGCCAACTACGTGGACCAGGTTGGGGGCGGCGGGGAGAGA
```

FIG. 20D

```
GCGGTGATGGGGGTGGCGGCGGCAGGACAGGCAGGTGCTGGTGGGGTTTGGGGAAGAGGA
AGGGCGCCCCACGAAGGACCACCGGCGCGATGGGGCGCCCTGTCCCGGCTTCAGCCCCGC
CTCGCCCTCAGCTTCTCAGGACTCTGGACATTCAGGTGGCGCTGACCGGCCTGGAGGTGT
GGACCGAGCGGGACCGCAGCCGCGTCACGCAGGACGCCAACGCCACGCTCTGGGCCTTCC
TGCAGTGGCGCCGGGGCTGTGGGCGCAGCGGCCCCACGACTCCGCGCAGCTGCTCACGT
GGGTGCCTCTGACCCGGACGCGGGTCCCGGGTGGGGCGGCCTCACCTCCCGGCCCCGCCT
GGTCACGCCGCGCTCCGCCCCCAGGGGCCGCGCCTTCCAGGGCGCCACAGTGGGCCTGGC
GCCCGTCGAGGGCATGTGCCGCGCCGAGAGCTCGGGAGGCGTGAGCACGGTGAGCCCCGC
GGGCGGGGGCGAGGGAGAGACAGGAGGCTCTACGGCCGCAGTGACCGCCCTCCCACGGCC
CCCCAGGACCACTCGGAGCTCCCCATCGGCGCCGCAGCCACCATGGCCCATGAGATCGGC
CACAGCCTCGGCCTCAGCCACGACCCCGACGGCTGCTGCGTGGAGGCTGCGGCCGAGTCC
GGAGGCTGCGTCATGGCTGCGGCCACCGGGTACGCGGGTGGGGGTCGGGGCTGCGGCGG
GGCGGCTAGTCCTGGGACTTCCTCCGCTGCGTTTCTTTGGTCGTCCCTCAGTTTCCTCT
TCTGTAAAATGGGGATAATGATCATAGTGTCCGCTTCAGGGTGGTTTATGAGGCTTAAAG
GGAAGAAGCTCAGGCAAAGTGGATTCTCAACGGTATGAAGATTATTTTCCGAGTAACCTG
GCGAGGTTACTCCTACACCGGGAGGAGCACCGTCGGGTCGCGATTCCACCTTGGGTCCCG
GGCTGCTCACTATTGGGGCCGCATCGTCCCTGTCCCGCTTGTTGTGACTTTGCGCGG
GTTACTTCCCTCTCTGGGCTCTGCGCGTCTGGCGGCTGTAGCCAAGCCCAGGGGTGGGG
ATCAGAGAAGCGCGGGGGTTGGGGGACTGTCCCTCCATGCCCAATGCCCTCCCCGTGCCG
GTAGGCACCCGTTTCCGCGCGTGTTCAGCGCCTGCAGCCGCCGCCAGCTGCGCGCCTTCT
TCCGCAAGGGGGGCGGCGCTTGCCTCTCCAATGCCCCGGACCCCGGACTCCCGGTGCCGC
CGGCGCTCTGCGGGAACGGCTTCGTGGAAGCGGGCGAGGAGTGTGACTGCGGCCCTGGCC
AGGTTAAGTCGGCTCGCCCGGCCCCCACTTGCCCTCTCCGCTCAGGTCTGGGGCGCTGCG
CCCTCACCTGGGCCCTTCTTGCCTTTCTGGTCCCAGGAGTGCCGCGACCTCTGCTGCTTT
GCTCACAACTGCTCGCTGCGCCCGGGGCCCAGTGCGCCCACGGGGACTGCTGCGTGCGC
TGCCTGGTGAGGGCATGGAAGGTTCAGGGTGAGGGTTTCGGGGAGCTTGGGAGCCGGCCT
GTTGGCCTTAGTTAATTGGTGCCCTCAGGTTCCCCGTTGGGTGCTGGGCTTGGGTAGGC
CTGGCTCCCCAGCTCCGAGCCGCGCTCTCGGCATGGACCTCTCACTGCACGTGGCCTCT
CTCTGCCTTCCCCACCACCCGTCACCTGCGCAGCTGAAGCCGGCTGGAGCGCTGTGCCGC
CAGGCCATGGGTGACTGTGACCTCCCTGAGTTTTGCACGGGCACCTCCTCCCACTGTCCC
CCAGACGTTTACCTACTGGACGGCTCACCCTGTGCCAGGGGCAGTGGCTACTGCTGGGAT
GGCGCATGTCCCACGCTGGAGCAGCAGTGCCAGCAGCTCTGGGGGCCTGGTGAGAGGACA
CGAGCACCCTTGCACCCTGCCCCCCATCCTCTGGTGGGGCCAGTTTTCTACTGTGGGGAA
GATGGGCAGGGGAAACTGAGGCCCGCTGAGCGCAGCCCCTCTCCGAGCTGCCCCAGCCT
GGCCCATGCTTCCTCAGGCTCCCACCCAGCTCCCGAGGCCTGTTTCCAGGTGGTGAACTC
TGCGGGAGATGCTCATGGAAACTGCGGCCAGGACAGCGAGGGCCACTTCCTGCCCTGTGC
AGGGAGGTAGGGAGTGGAGCTGAGTGGAGGGAGCAGAAGCTATGAGTGGGTTTGGGGAA
GGGGGGTACTGCAGCTGTTGACCCCCTCTACTTCCTCCCCAGGGATGCCCTGTGTGGGA
AGCTGCAGTGCCAGGGTGGAAAGCCCAGCCTGCTCGCACCGCACATGGTGCCAGTGGACT
CTACCGTTCACCTAGATGGCCAGGAAGTGACTTGTCGGGGAGCCTTGGCACTCCCCAGTG
CCCAGCTGGACCTGCTTGGCCTGGGCCTGGTAGAGCCAGGCACCCAGTGTGGACCTAGAA
TGGTGAGCTCTGCCCACCCGACCCCTCCTTGCCGTTTGAATCCCGCAGGCCAGTGTCCCC
CTCACTGCCTGGTGCACTGCCCGTAGGTGTGCCAGAGCAGGCGCTGCAGGAAGAATGCCT
TCCAGGAGCTTCAGCGCTGCCTGACTGCCTGCCACAGCCACGGGGTGAGAGCCCGAGGAG
TGGGGGTGACCTTGGGGTTCCTAATCCTACGTGACCCTCCTCTTCTCTTCTCTGCAGGTT
TGCAATAGCAACCATAACTGCCACTGTGCTCCAGGCTGGGCTCCACCCTTCTGTGACAAG
CCAGGCTTTGGTGGCAGCATGGACAGTGGCCCTGTGCAGGCTGAAAGTATGCCAGTGGGG
GGCATGTGGGCAGGAGCTGGGGTGGTGCACCTGCTCAGGACTCAGCGCCCCTTCCCCCAA
TCCCCGCAGACCATGACACCTTCCTGCTGGCCATGCTCCTCAGCGTCCTGCTGCCTCTGC
TCCCAGGGGCCGGCCTGGCCTGGTGTTGCTACCGACTCCCAGGAGCCCATCTGCAGCGAT
GCAGCTGGGGCTGCAGAAGGGACCCTGCGTGCAGTGGGTAGGCTCCGAGCGCCTGCTTCC
```

FIG. 20E

```
TGAGCCTACTCCTGCGGTTCCCCTCCTCAGAGCTCTGCTGGGGCTGTGGGAGCTGGGGCA
GGCCCTCAGCCTTGCCCCAGGTGCAGAGAGCAGCCCCAGAGGCCATGGAAAGAAGTAGC
TTTGAACAGGAGGTTCCAGTGGCCTCCCAGTCAAGCGAGGGGGTGGATCCCTGCCCCACC
ACCAGCACCGCAAGGCATGGCCCTCTACCTCCCAGTACAGCTCCTCTTGTCCACTCTCCT
GCTTCTCCCACCAGCTGGCTGCCTCACCCTTGACTTCGCCCTGTTTTTCCCTGGCTCAGA
TTGCAGTCCCTGTACCATGCTGCCCCGGAGGCCTGTCCAGCCTCTGTCTCACCAGTTTT
CGGCCCTTTGCCACTTCCTCTGCACAAATCACCTCTGTCACCCCCTTGAAGTTCCCAAAT
GCTGGGCCCAGCACATCTTTTCACTCCATACCACTGGTCAGCTGCGGTGCTGGCTGCCCC
TGTGCCAGGGCCCTGCCTTAACCCAGTTCTCTGTGACCTGGGTGGTGGCGGAGTGGGGAG
TCACATAATACTAAGCATGGCTGTCCTAGGACTCACCCTGCACCAGGGCCCTAGGCAGGG
CAGGCACTCTGTGGCCATGTCTGACATAGCCTGGTCTTGGGAGTGCTCCGGGCAAGCCAA
GGGAGATGGCATGATTTGGGCCAGAGATGGGGGCAGAGGGCATAACAGACAGGGGCAGGG
CACCACCTGGGCCCCGGGTGGCAGCTAAGAGGACCCTGACAAAGCGAGTTGTGATTGAGG
GTCTGTGGGCAGAGGAGCAAGGTGGCCAGAGCCTGGCGTGTCAGCACGGAGGGGCGCTG
CAGAGGGTGGCGGCTGCTTCTCATCCCCAGGCGGGAGTCTCAGGGCAGGGGAGAATGTTT
TGAAGGAACATCACAGGAAATGACAAGGCCTTGGGGGATGGGATGGGACAGTCAAAGAT
GGCTTGGAATCATCAAGGGCAGCAGGGCACCCAGGGGCAAGGAGAGCAGACATAGCTGCC
GAAGGGGCGGACATCCAAGGTTCTTTGGAAGCTGAGCGATGCCAGCATCTGGAGAGTGCC
AGGCTGCTGGGTGGTGTCAGAGCCTGGAGGAAATGTTAGGACTAGAGAGAGGAGGTGCCA
GCCGAGGGCATGAGGCTCACTTGGAGCCTGGATCCCAAGGCTCCCCTGAAGAGGGAGCAG
GAAGGGAGCTGAGAGGGTGACTTGGAGCAGATGGGTGCCCCAAGAAACTCAGTAAACGCA
GAACTCCCTGGGCTGGACACCATGCTGCGGGGAGGCAATAACCCACTCAGGATCACTGTG
CCAACCTCCTGGACTCTTATCACGTTGCTCAGCCCCAAAGATGGCCCACACAGGGACCAC
CCCCTGGGCGGCGTTCACCCCATGGAGTTGGGCCCCACAGCCACTGGACAGCCCTGGCCC
CTGGGTGAGTGAGGCACCAGGGGGAGGTGGAGAGGGAAGGGAGAAGGGAAGGGCTCATGC
CTCCTGCCTCCTTCCAGATGGGCAGCACCCAGTCACCTTGAGTCCCCTATGCCCCTCCCC
AGCCCCAGGGTCTCCTGCTGACCATATTCACAACATTTACCCTCCACCATTTCTCCCAGA
CCCTGAGAACTCTCATGAGCCCAGCAGCCACCCTGAGAAGCCTCTGCCAGCAGTCTCGCC
TGACCCCAAGGTAGGCAGGGACCTGGATTCAAAGCCTCCCCCTCTCATCGCCCACCCTC
CCACCTCTCCCACCCCTCAGTTTGCTGCCCCTAATCAGGTTTCTGGGCTCAGGTTATTA
TGGAAATGAGTTTATGACCTCTTGGTTATCATGGAGACCAGGATGCTGGAAGCCCCTGGG
CTGGGGAGGGAGAAGCTGTGGCTTTTCCTGGATCACTGGTCCTCACTGAGTGAGGATGGG
CTCTCTGCCACACAGCTTGCAGCCTGGGGCCCCAGTCCTTAGGGGACAACATATCCTCCT
CATTCTCAGCAGATCAAGTCCAGATGCCAAGATCCTGCCTCTGGTGAGAGGTAGCTCCTA
AAATGAACAGATTTAAAGACAGGTGGCCACTGACAGCCACTCCAGGAACTTGAACTGCAG
GGGCAGAGCCAGTGAATCACCGGACCTCCAGCACCTGCAGGCAGCTTGGAAGTTTCTTCC
CCGAGTGGAGCTTCGACCCACCCACTCCAGGAACCCAGAGCCACACTAGAAGTTCCTGAG
GGCTGGAGAACACTGCTGGGCACACTCTCCAGCTCAATAAACCATCAGTCCCAGAAGCAA
AGGTCACACAGCCCTGACCTCCCTCACCAGTGGAGGCTGGGTAGTGCTGGCCATCCCAA
AAGGGCTCTGTCCTGGGAGTCTGGTGTGTCTCCTACATGCAATTTCCACGGACCCAGCTC
TGTGGAGGGCATGACTGCTGGCCAGAAGCTAGTGGTCCTGGGCCCTATGGTTCGACTGA
GTCCACACTCCCCTGGAGCCTGGCTGGCCTCTGCAAACAAACATAATTTTGGGGACCTTC
CTTCCTGTTTCTTCCCACCCTGTCTTCTCCCTAGGTGGTTCCTGAGCCCCACCCCCAA
TCCCAGTGCTACACCTGAGGTTCTGGAGCTCAGAATCTGACAGCCTCTCCCCATTCTGT
GTGTGTCGGGGGACAGAGGGAACCATTTAAGAAAAGATACCAAAGTAGAAGTCAAAGA
AAGACATGTTGGCTATAGGCGTGGTGGCTCATGCCTATAATCCCAGCACTTTGGGAAGCT
GGGGTAGGAGGATCACCAGAGGCCAGGAGGTCCACACCAGCCTGGGCAACACAGCAAGAC
ACCGCATCTACAGAAAAATTTTAAAATTAGCTGGGCGTGGTGGTGTGTACCTGTAGGCCT
AGCTGCTCAGGAGGCTGAAGCAGGAGGATCACTTGAGCCTGAGTTCAACACTGCAGTGAG
CTATGGTGGCACCACTGCACTCCAGCCTGGGTGACAGAGCAAGACCCTGTCTCTAAAATA
AATTTTAAAAGACATATTACACTTGGACCTTGGTTAGTCTTTTCTGTATGTAAATTCAA
```

FIG. 20F

```
CCCATGGGGTGCCCTGAGGACCACACGGGGTGGTGGTTGGCGGGGTGGTGGTTGGTGGGG
TGGTGGCTGACGGGGTGGTGGCTGGCAGGCCGAGCCTAGATGGCAGCCAGAGCCCCAGGC
ATGTGTCTGGGCACAGGACGGTGTTGCCTAGTTTGAACACCCTCTTTGCTCTGTCACTCC
TGCCTCCCTTGGGCGTTCACATTCTCCCATTGCTTCATGCAAGAGCTGCTGAGTGGCCTA
TATCAGCCAGCTGTTGCCGCATAACAAAACCATCCCAAAACTGAGTGCAGGGAGGCAACT
TCACCTCGGGCTCCACTCCACAAGCCCAAGGGGCCAGGTGAGAGTGCTCTCTAAAGCCCC
CTCCTGCCTCAGTTGTAGTTGCAAAATTTTAATTTATGAAGGTGACTGATGACACAGAGG
CCAATGCTGTTGAAATAAGTTATTACTCACAGTTTCCCACCATGCAGGGCCACAGTGGGG
AGGCACTAGGTTTGGTCCAGGGACAGAATCAGGAGCGAGTGGAAGGCACAGGCCACAGCC
CACAGTGCCGTTTCCACTGGGGAGGCAAGGCAGGCCAGGGGAAGAGGGTAGGATTGGCAT
TTTGAATCATTCTGGTGGGGTTTGGGGCGTGGGGTTGGGCTCTAATTGTCTGGGTAGGTG
CCTGGCCCTGAGCTGGTTTAGGGCAGGGGAAATACTGGTTTCGTATGTGAGAGTTCCTTG
AAGGGGGTGGTTGGTGTATGGACTCAAGACTGGTCGGTTTGCATATGAAAGGCATGAGTT
GTTTCTGATCTCCAGGAATCAAGCAGTTTCTCTCCAGCCAACAAGCCCCCACCCCGAGAT
GTTAAACCATCATAAAATAGAGAATCTAAGGCCAGGCATGGTGGCTCACGCCTGTAATCC
CAGCACTTTGGGAGGCCAAGGCGGGAGGATCATTTGAGGTCAGAAGTTCGAGACCAGCCT
GGCCAATGTGGTGAAACCCCATCTCTACTAAAAATACAAAAATTAGCCCGGTGTGGTGGC
ACGTGCCTATAATCCCAGCTACTCGGGAGGCTGCGGCAGGAGAATTGTTTGAACATGGGA
GGTGGAGGTTGCAGTGAGCTGAGATCGTGCCACTGCACTCCAGCCTGGGCAACAAGAGCA
AGACTCCGTCTCAAAAAAAAAAAAAAAAAAAGAGAGACTCTAAAAATACACGTTAATAT
ACCTCCCCCGCTCTTACCCTTCAGGAGGGGGTGTCTAGACCCCGCGGGACTCCAGCTACA
AGGGACCCTGGGGAGGCCAACTCTGCCCTCTTGGCTAATCCCCAAGACTGCCCAGCACCC
CCTCCACCCCTTCTCCATTCAGTGGCGAACCCTGGGGAGGCCACGTGGGAAGGAAAGAGG
GCTCTAAGAGGGGAGGCCCCAGACTGGGGGAGAGGCCTGTCTGGAGCCCAGGATCACCTG
GCTGTGCTGCAGAACTGGAGAAGAGAAGCTCAGCAGAAAGGAGCTGGCATGGGGCCAACA
GCAGAAAAGCAGGAGGCACGCAGAAGTGACTGGGAAGCAGGAGGGTAGGCATGGACCCTG
AGGCTGAGCAGGAGGTACTGAGGGGCAGAGTGGACGCTGAGCTGGGGGTAGCGAGCGAGC
CCAGCTCAGCTGTGACGCCCTCTGTTTGGCCACCCAACTACCAGCTACTTGGGCTGCCCC
GGGAGGAACTGGGCTTCCTCTGACATTCTGTGGCCTGCGGCCATCTGTCACACCTTCTTC
TCTCTCTGCCCCTCCCTTGACTTGTGGCACCCACAGACAGGTGGGAGAGTGTACCTGCCC
TGTGTGGTCAGAGCTTGGTTTTGAGTTTCCTTCCCTCACCCCTCTTTCCTCCCACACGCC
AAAACACAAGAGGATGTGTCAGAGGCCTGTGAACCAGAGCAACTCCATCCTGAATAGGGG
CTGAGCAAAATAAGGCTGAGACCTACTGGGCTGCGTTTCCAGACAGTTACAGCATTCTGC
GTCACAGGATGAGATAGGAGATACAGGTCATAAAGACCTTGCTGATAAAATAGTTTGCAG
TAGGCCAGGCGCGGTAGCTCACGCCTGTAATCCCAGCACT
```

FIG. 20G

SEQUENCE LISTING

<160> NUMBER OF SEQ ID NOS: 170

<210> SEQ ID NO 1
<211> LENGTH: 3271
<212> TYPE: DNA
<213> ORGANISM: Homo sapiens
<220> FEATURE:
<221> NAME/KEY: CDS
<222> LOCATION: (1)..(2241)

<400> SEQUENCE: 1

| | | | | | | | | | | | | | | | | |
|---|---|---|---|---|---|---|---|---|---|---|---|---|---|---|---|---|
| atg | ggc | tgg | agg | ccc | cgg | aga | gct | cgg | ggg | acc | ccg | ttg | ctg | ctg | ctg | 48 |
| Met | Gly | Trp | Arg | Pro | Arg | Arg | Ala | Arg | Gly | Thr | Pro | Leu | Leu | Leu | Leu | |
| 1 | | | | 5 | | | | | 10 | | | | | 15 | | |

| cta | cta | ctg | ctg | ctg | ctc | tgg | cca | gtg | cca | ggc | gcc | ggg | gtg | ctt | caa | 96 |
|---|---|---|---|---|---|---|---|---|---|---|---|---|---|---|---|---|
| Leu | Leu | Leu | Leu | Leu | Leu | Trp | Pro | Val | Pro | Gly | Ala | Gly | Val | Leu | Gln | |
| | | | | 20 | | | | | 25 | | | | | 30 | | |

| gga | cat | atc | cct | ggg | cag | cca | gtc | acc | ccg | cac | tgg | gtc | ctg | gat | gga | 144 |
|---|---|---|---|---|---|---|---|---|---|---|---|---|---|---|---|---|
| Gly | His | Ile | Pro | Gly | Gln | Pro | Val | Thr | Pro | His | Trp | Val | Leu | Asp | Gly | |
| | | 35 | | | | | 40 | | | | | 45 | | | | |

| caa | ccc | tgg | cgc | acc | gtc | agc | ctg | gag | gag | ccg | gtc | tcg | aag | cca | gac | 192 |
|---|---|---|---|---|---|---|---|---|---|---|---|---|---|---|---|---|
| Gln | Pro | Trp | Arg | Thr | Val | Ser | Leu | Glu | Glu | Pro | Val | Ser | Lys | Pro | Asp | |
| 50 | | | | | 55 | | | | | 60 | | | | | | |

| atg | ggg | ctg | gtg | gcc | ctg | gag | gct | gaa | ggc | cag | gag | ctc | ctg | ctt | gag | 240 |
|---|---|---|---|---|---|---|---|---|---|---|---|---|---|---|---|---|
| Met | Gly | Leu | Val | Ala | Leu | Glu | Ala | Glu | Gly | Gln | Glu | Leu | Leu | Leu | Glu | |
| 65 | | | | | 70 | | | | | 75 | | | | | 80 | |

| ctg | gag | aag | aac | cac | agg | ctg | ctg | gcc | cca | gga | tac | ata | gaa | acc | cac | 288 |
|---|---|---|---|---|---|---|---|---|---|---|---|---|---|---|---|---|
| Leu | Glu | Lys | Asn | His | Arg | Leu | Leu | Ala | Pro | Gly | Tyr | Ile | Glu | Thr | His | |
| | | | | 85 | | | | | 90 | | | | | 95 | | |

| tac | ggc | cca | gat | ggg | cag | cca | gtg | gtg | ctg | gcc | ccc | aac | cac | acg | gat | 336 |
|---|---|---|---|---|---|---|---|---|---|---|---|---|---|---|---|---|
| Tyr | Gly | Pro | Asp | Gly | Gln | Pro | Val | Val | Leu | Ala | Pro | Asn | His | Thr | Asp | |
| | | | 100 | | | | | 105 | | | | | 110 | | | |

| cat | tgc | cac | tac | caa | ggg | cga | gta | agg | ggc | ttc | ccc | gac | tcc | tgg | gta | 384 |
|---|---|---|---|---|---|---|---|---|---|---|---|---|---|---|---|---|
| His | Cys | His | Tyr | Gln | Gly | Arg | Val | Arg | Gly | Phe | Pro | Asp | Ser | Trp | Val | |
| | | | 115 | | | | | 120 | | | | | 125 | | | |

| gtc | ctc | tgc | acc | tgc | tct | ggg | atg | agt | ggc | ctg | atc | acc | ctc | agc | agg | 432 |
|---|---|---|---|---|---|---|---|---|---|---|---|---|---|---|---|---|
| Val | Leu | Cys | Thr | Cys | Ser | Gly | Met | Ser | Gly | Leu | Ile | Thr | Leu | Ser | Arg | |
| | | 130 | | | | | 135 | | | | | 140 | | | | |

| aat | gcc | agc | tat | tat | ctg | cgt | ccc | tgg | cca | ccc | cgg | ggc | tcc | aag | gac | 480 |
|---|---|---|---|---|---|---|---|---|---|---|---|---|---|---|---|---|
| Asn | Ala | Ser | Tyr | Tyr | Leu | Arg | Pro | Trp | Pro | Pro | Arg | Gly | Ser | Lys | Asp | |
| 145 | | | | | 150 | | | | | 155 | | | | | 160 | |

| ttc | tca | acc | cac | gag | atc | ttt | cgg | atg | gag | cag | ctg | ctc | acc | tgg | aaa | 528 |
|---|---|---|---|---|---|---|---|---|---|---|---|---|---|---|---|---|
| Phe | Ser | Thr | His | Glu | Ile | Phe | Arg | Met | Glu | Gln | Leu | Leu | Thr | Trp | Lys | |
| | | | | 165 | | | | | 170 | | | | | 175 | | |

| gga | acc | tgt | ggc | cac | agg | gat | cct | ggg | aac | aaa | gcg | ggc | atg | acc | agc | 576 |
|---|---|---|---|---|---|---|---|---|---|---|---|---|---|---|---|---|
| Gly | Thr | Cys | Gly | His | Arg | Asp | Pro | Gly | Asn | Lys | Ala | Gly | Met | Thr | Ser | |
| | | | 180 | | | | | 185 | | | | | 190 | | | |

| ctt | cct | ggt | ggt | ccc | cag | agc | agg | ggc | agg | cga | gaa | gcg | cgc | agg | acc | 624 |
|---|---|---|---|---|---|---|---|---|---|---|---|---|---|---|---|---|
| Leu | Pro | Gly | Gly | Pro | Gln | Ser | Arg | Gly | Arg | Arg | Glu | Ala | Arg | Arg | Thr | |
| | | 195 | | | | | 200 | | | | | 205 | | | | |

| cgg | aag | tac | ctg | gaa | ctg | tac | att | gtg | gca | gac | cac | acc | ctg | ttc | ttg | 672 |
|---|---|---|---|---|---|---|---|---|---|---|---|---|---|---|---|---|
| Arg | Lys | Tyr | Leu | Glu | Leu | Tyr | Ile | Val | Ala | Asp | His | Thr | Leu | Phe | Leu | |
| | 210 | | | | | 215 | | | | | 220 | | | | | |

| act | cgg | cac | cga | aac | ttg | aac | cac | acc | aaa | cag | cgt | ctc | ctg | gaa | gtc | 720 |
|---|---|---|---|---|---|---|---|---|---|---|---|---|---|---|---|---|
| Thr | Arg | His | Arg | Asn | Leu | Asn | His | Thr | Lys | Gln | Arg | Leu | Leu | Glu | Val | |
| 225 | | | | | 230 | | | | | 235 | | | | | 240 | |

| gcc | aac | tac | gtg | gac | cag | ctt | ctc | agg | act | ctg | gac | att | cag | gtg | gcg | 768 |
|---|---|---|---|---|---|---|---|---|---|---|---|---|---|---|---|---|
| Ala | Asn | Tyr | Val | Asp | Gln | Leu | Leu | Arg | Thr | Leu | Asp | Ile | Gln | Val | Ala | |
| | | | 245 | | | | | 250 | | | | | 255 | | | |

| ctg | acc | ggc | ctg | gag | gtg | tgg | acc | gag | cgg | gac | cgc | agc | cgc | gtc | acg | 816 |

-continued

```
Leu Thr Gly Leu Glu Val Trp Thr Glu Arg Asp Arg Ser Arg Val Thr
            260                 265                 270 cag gac gcc aac gcc acg ctc tgg gcc ttc ctg cag tgg cgc cgg ggg       864
Gln Asp Ala Asn Ala Thr Leu Trp Ala Phe Leu Gln Trp Arg Arg Gly
            275                 280                 285 ctg tgg gcg cag cgg ccc cac gac tcc gcg cag ctg ctc acg ggc cgc       912
Leu Trp Ala Gln Arg Pro His Asp Ser Ala Gln Leu Leu Thr Gly Arg
    290                 295                 300 gcc ttc cag ggc gcc aca gtg ggc ctg gcg ccc gtc gag ggc atg tgc       960
Ala Phe Gln Gly Ala Thr Val Gly Leu Ala Pro Val Glu Gly Met Cys
305                 310                 315                 320 cgc gcc gag agc tcg gga ggc gtg agc acg gac cac tcg gag ctc ccc      1008
Arg Ala Glu Ser Ser Gly Gly Val Ser Thr Asp His Ser Glu Leu Pro
                325                 330                 335 atc ggc gcc gca gcc acc atg gcc cat gag atc ggc cac agc ctc ggc      1056
Ile Gly Ala Ala Ala Thr Met Ala His Glu Ile Gly His Ser Leu Gly
            340                 345                 350 ctc agc cac gac ccc gac ggc tgc tgc gtg gag gct gcg gcc gag tcc      1104
Leu Ser His Asp Pro Asp Gly Cys Cys Val Glu Ala Ala Ala Glu Ser
        355                 360                 365 gga ggc tgc gtc atg gct gcg gcc acc ggg cac ccg ttt ccg cgc gtg      1152
Gly Gly Cys Val Met Ala Ala Ala Thr Gly His Pro Phe Pro Arg Val
370                 375                 380 ttc agc gcc tgc agc cgc cgc cag ctg cgc gcc ttc ttc cgc aag ggg      1200
Phe Ser Ala Cys Ser Arg Arg Gln Leu Arg Ala Phe Phe Arg Lys Gly
385                 390                 395                 400 ggc ggc gct tgc ctc tcc aat gcc ccg gac ccc gga ctc ccg gtg ccg      1248
Gly Gly Ala Cys Leu Ser Asn Ala Pro Asp Pro Gly Leu Pro Val Pro
                405                 410                 415 ccg gcg ctc tgc ggg aac ggc ttc gtg gaa gcg ggc gag gag tgt gac      1296
Pro Ala Leu Cys Gly Asn Gly Phe Val Glu Ala Gly Glu Glu Cys Asp
            420                 425                 430 tgc ggc cct ggc cag gag tgc cgc gac ctc tgc tgc ttt gct cac aac      1344
Cys Gly Pro Gly Gln Glu Cys Arg Asp Leu Cys Cys Phe Ala His Asn
        435                 440                 445 tgc tcg ctg cgc ccg ggg gcc cag tgc gcc cac ggg gac tgc tgc gtg      1392
Cys Ser Leu Arg Pro Gly Ala Gln Cys Ala His Gly Asp Cys Cys Val
    450                 455                 460 cgc tgc ctg ctg aag ccg gct gga gcg ctg tgc cgc cag gcc atg ggt      1440
Arg Cys Leu Leu Lys Pro Ala Gly Ala Leu Cys Arg Gln Ala Met Gly
465                 470                 475                 480 gac tgt gac ctc cct gag ttt tgc acg ggc acc tcc tcc cac tgt ccc      1488
Asp Cys Asp Leu Pro Glu Phe Cys Thr Gly Thr Ser Ser His Cys Pro
                485                 490                 495 cca gac gtt tac cta ctg gac ggc tca ccc tgt gcc agg ggc agt ggc      1536
Pro Asp Val Tyr Leu Leu Asp Gly Ser Pro Cys Ala Arg Gly Ser Gly
            500                 505                 510 tac tgc tgg gat ggc gca tgt ccc acg ctg gag cag cag tgc cag cag      1584
Tyr Cys Trp Asp Gly Ala Cys Pro Thr Leu Glu Gln Gln Cys Gln Gln
        515                 520                 525 ctc tgg ggg cct gat ggc cag gaa gtg act tgt cgg gga gcc ttg gca      1632
Leu Trp Gly Pro Asp Gly Gln Glu Val Thr Cys Arg Gly Ala Leu Ala
    530                 535                 540 ctc ccc agt gcc cag ctg gac ctg ctt ggc ctg ggc ctg gta gag cca      1680
Leu Pro Ser Ala Gln Leu Asp Leu Leu Gly Leu Gly Leu Val Glu Pro
545                 550                 555                 560 ggc acc cag tgt gga cct aga atg gtg tgc cag agc agg cgc tgc agg      1728
Gly Thr Gln Cys Gly Pro Arg Met Val Cys Gln Ser Arg Arg Cys Arg
                565                 570                 575 aag aat gcc ttc cag gag ctt cag cgc tgc ctg act gcc tgc cac agc      1776
```

```
                    Lys Asn Ala Phe Gln Glu Leu Gln Arg Cys Leu Thr Ala Cys His Ser
                                580                 585                 590 cac ggg gtt tgc aat agc aac cat aac tgc cac tgt gct cca ggc tgg                1824
His Gly Val Cys Asn Ser Asn His Asn Cys His Cys Ala Pro Gly Trp
            595                 600                 605 gct cca ccc ttc tgt gac aag cca ggc ttt ggt ggc agc atg gac agt                1872
Ala Pro Pro Phe Cys Asp Lys Pro Gly Phe Gly Gly Ser Met Asp Ser
        610                 615                 620 ggc cct gtg cag gct gaa aac cat gac acc ttc ctg ctg gcc atg ctc                1920
Gly Pro Val Gln Ala Glu Asn His Asp Thr Phe Leu Leu Ala Met Leu
625                 630                 635                 640 ctc agc gtc ctg ctg cct ctg ctc cca ggg gcc ggc ctg gcc tgg tgt                1968
Leu Ser Val Leu Leu Pro Leu Leu Pro Gly Ala Gly Leu Ala Trp Cys
                645                 650                 655 tgc tac cga ctc cca gga gcc cat ctg cag cga tgc agc tgg ggc tgc                2016
Cys Tyr Arg Leu Pro Gly Ala His Leu Gln Arg Cys Ser Trp Gly Cys
            660                 665                 670 aga agg gac cct gcg tgc agt ggc ccc aaa gat ggc cca cac agg gac                2064
Arg Arg Asp Pro Ala Cys Ser Gly Pro Lys Asp Gly Pro His Arg Asp
        675                 680                 685 cac ccc ctg ggc ggc gtt cac ccc atg gag ttg ggc ccc aca gcc act                2112
His Pro Leu Gly Gly Val His Pro Met Glu Leu Gly Pro Thr Ala Thr
690                 695                 700 gga cag ccc tgg ccc ctg gac cct gag aac tct cat gag ccc agc agc                2160
Gly Gln Pro Trp Pro Leu Asp Pro Glu Asn Ser His Glu Pro Ser Ser
705                 710                 715                 720 cac cct gag aag cct ctg cca gca gtc tcg cct gac ccc caa gca gat                2208
His Pro Glu Lys Pro Leu Pro Ala Val Ser Pro Asp Pro Gln Ala Asp
                725                 730                 735 caa gtc cag atg cca aga tcc tgc ctc tgg tga gaggtagctc ctaaaatgaa              2261
Gln Val Gln Met Pro Arg Ser Cys Leu Trp
            740                 745 cagatttaaa gacaggtggc cactgacagc cactccagga acttgaactg caggggcaga             2321
gccagtgaat caccggacct ccagcacctg caggcagctt ggaagtttct tccccgagtg             2381
gagcttcgac ccacccactc caggaaccca gagccacatt agaagttcct gagggctgga             2441
gaacactgct gggcacactc tccagctcaa taaaccatca gtcccagaag caaaggtcac             2501
acagcccctg acctccctca ccagtggagg ctgggtagtg ctggccatcc caaaagggct             2561
ctgtcctggg agtctggtgt gtctcctaca tgcaatttcc acggacccag ctctgtggag             2621
ggcatgactg ctggccagaa gctagtggtc ctggggccct atggttcgac tgagtccaca             2681
ctcccctgca gcctgctgg cctctgcaaa caaacataat tttggggacc ttccttcctg              2741
tttcttccca ccctgtcttc tccctaggt ggttcctgag ccccaccc caatcccagt                2801 gctacacctg aggttctgga gctcagaatc tgacagcctc tcccccattc tgtgtgtgtc             2861 gggggacag agggaaccat ttaagaaaag ataccaaagt agaagtcaaa agaaagacat              2921
gttggctata ggcgtggtgg ctcatgccta taatcccagc actttgggaa gccggggtag             2981
gaggatcacc agaggccagg aggtccacac cagcctgggc aacacagcaa gacaccgcat             3041
ctacagaaaa attttaaaat tagctgggcg tggtggtgtg tacctgtagg cctagctgct             3101
caggaggctg aagcaggagg atcacttgag cctgagttca acactgcagt gagctatggt             3161
ggcaccactg cactccagcc tgggtgacag agcaagaccc tgtctctaaa ataaatttta             3221
aaaagacata ttaaaaaaaa aaaaaaaaaa aaaaaaaaaa aaaaaaaaa                         3271

<210> SEQ ID NO 2
```

```
<211> LENGTH: 3390
<212> TYPE: DNA
<213> ORGANISM: Homo sapiens
<220> FEATURE:
<221> NAME/KEY: CDS
<222> LOCATION: (1)..(2364)

<400> SEQUENCE: 2 atg ggc tgg agg ccc cgg aga gct cgg ggg acc ccg ttg ctg ctg ctg        48
Met Gly Trp Arg Pro Arg Arg Ala Arg Gly Thr Pro Leu Leu Leu Leu
 1               5                  10                  15 cta cta ctg ctg ctg ctc tgg cca gtc cca ggc gcc ggg gtg ctt caa        96
Leu Leu Leu Leu Leu Leu Trp Pro Val Pro Gly Ala Gly Val Leu Gln
            20                  25                  30 gga cat atc cct ggg cag cca gtc acc ccg cac tgg gtc ctg gat gga       144
Gly His Ile Pro Gly Gln Pro Val Thr Pro His Trp Val Leu Asp Gly
        35                  40                  45 caa ccc tgg cgc acc gtc agc ctg gag gag ccg gtc tcg aag cca gac       192
Gln Pro Trp Arg Thr Val Ser Leu Glu Glu Pro Val Ser Lys Pro Asp
 50                  55                  60 atg ggg ctg gtg gcc ctg gag gct gaa ggc cag gag ctc ctg ctt gag       240
Met Gly Leu Val Ala Leu Glu Ala Glu Gly Gln Glu Leu Leu Leu Glu
 65                  70                  75                  80 ctg gag aag aac cac agg ctg ctg gcc cca gga tac ata gaa acc cac       288
Leu Glu Lys Asn His Arg Leu Leu Ala Pro Gly Tyr Ile Glu Thr His
                 85                  90                  95 tac ggc cca gat ggg cag cca gtg gtg ctg gcc ccc aac cac acg gat       336
Tyr Gly Pro Asp Gly Gln Pro Val Val Leu Ala Pro Asn His Thr Asp
            100                 105                 110 cat tgc cac tac caa ggg cga gta agg ggc ttc ccc gac tcc tgg gta       384
His Cys His Tyr Gln Gly Arg Val Arg Gly Phe Pro Asp Ser Trp Val
        115                 120                 125 gtc ctc tgc acc tgc tct ggg atg agt ggc ctg atc acc ctc agc agg       432
Val Leu Cys Thr Cys Ser Gly Met Ser Gly Leu Ile Thr Leu Ser Arg
    130                 135                 140 aat gcc agc tat tat ctg cgt ccc tgg cca ccc cgg ggc tcc aag gac       480
Asn Ala Ser Tyr Tyr Leu Arg Pro Trp Pro Pro Arg Gly Ser Lys Asp
145                 150                 155                 160 ttc tca acc cac gag atc ttt cgg atg gag cag ctg ctc acc tgg aaa       528
Phe Ser Thr His Glu Ile Phe Arg Met Glu Gln Leu Leu Thr Trp Lys
                165                 170                 175 gga acc tgt ggc cac agg gat cct ggg aac aaa gcg ggc atg acc agc       576
Gly Thr Cys Gly His Arg Asp Pro Gly Asn Lys Ala Gly Met Thr Ser
            180                 185                 190 ctt cct ggt ggt ccc cag agc agg ggc agg cga gaa gcg cgc agg acc       624
Leu Pro Gly Gly Pro Gln Ser Arg Gly Arg Arg Glu Ala Arg Arg Thr
        195                 200                 205 cgg aag tac ctg gaa ctg tac att gtg gca gac cac acc ctg ttc ttg       672
Arg Lys Tyr Leu Glu Leu Tyr Ile Val Ala Asp His Thr Leu Phe Leu
    210                 215                 220 act cgg cac cga aac ttg aac cac acc aaa cag cgt ctc ctg gaa gtc       720
Thr Arg His Arg Asn Leu Asn His Thr Lys Gln Arg Leu Leu Glu Val
225                 230                 235                 240 gcc aac tac gtg gac cag ctt ctc agg act ctg gac att cag gtg gcg       768
Ala Asn Tyr Val Asp Gln Leu Leu Arg Thr Leu Asp Ile Gln Val Ala
                245                 250                 255 ctg acc ggc ctg gag gtg tgg acc gag cgg gac cgc agc cgc gtc acg       816
Leu Thr Gly Leu Glu Val Trp Thr Glu Arg Asp Arg Ser Arg Val Thr
            260                 265                 270 cag gac gcc aac gcc acg ctc tgg gcc ttc ctg cag tgg cgc cgg ggg       864
Gln Asp Ala Asn Ala Thr Leu Trp Ala Phe Leu Gln Trp Arg Arg Gly
        275                 280                 285
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 275 |     |     |     |     | 280 |     |     |     |     | 285 |     |     |     |      |
| ctg | tgg | gcg | cag | cgg | ccc | cac | gac | tcc | gcg | cag | ctg | ctc | acg | ggc | cgc | 912  |
| Leu | Trp | Ala | Gln | Arg | Pro | His | Asp | Ser | Ala | Gln | Leu | Leu | Thr | Gly | Arg |      |
|     | 290 |     |     |     |     | 295 |     |     |     |     | 300 |     |     |     |     |      |
| gcc | ttc | cag | ggc | gcc | aca | gtg | ggc | ctg | gcg | ccc | gtc | gag | ggc | atg | tgc | 960  |
| Ala | Phe | Gln | Gly | Ala | Thr | Val | Gly | Leu | Ala | Pro | Val | Glu | Gly | Met | Cys |      |
| 305 |     |     |     |     | 310 |     |     |     |     | 315 |     |     |     |     | 320 |      |
| cgc | gcc | gag | agc | tcg | gga | ggc | gtg | agc | acg | gac | cac | tcg | gag | ctc | ccc | 1008 |
| Arg | Ala | Glu | Ser | Ser | Gly | Gly | Val | Ser | Thr | Asp | His | Ser | Glu | Leu | Pro |      |
|     |     |     |     | 325 |     |     |     |     | 330 |     |     |     |     | 335 |     |      |
| atc | ggc | gcc | gca | gcc | acc | atg | gcc | cat | gag | atc | ggc | cac | agc | ctc | ggc | 1056 |
| Ile | Gly | Ala | Ala | Ala | Thr | Met | Ala | His | Glu | Ile | Gly | His | Ser | Leu | Gly |      |
|     |     |     | 340 |     |     |     |     | 345 |     |     |     |     | 350 |     |     |      |
| ctc | agc | cac | gac | ccc | gac | ggc | tgc | tgc | gtg | gag | gct | gcg | gcc | gag | tcc | 1104 |
| Leu | Ser | His | Asp | Pro | Asp | Gly | Cys | Cys | Val | Glu | Ala | Ala | Ala | Glu | Ser |      |
|     |     | 355 |     |     |     |     | 360 |     |     |     |     | 365 |     |     |     |      |
| gga | ggc | tgc | gtc | atg | gct | gcg | gcc | acc | ggg | cac | ccg | ttt | ccg | cgc | gtg | 1152 |
| Gly | Gly | Cys | Val | Met | Ala | Ala | Ala | Thr | Gly | His | Pro | Phe | Pro | Arg | Val |      |
|     | 370 |     |     |     |     | 375 |     |     |     |     | 380 |     |     |     |     |      |
| ttc | agc | gcc | tgc | agc | cgc | cgc | cag | ctg | cgc | gcc | ttc | ttc | cgc | aag | ggg | 1200 |
| Phe | Ser | Ala | Cys | Ser | Arg | Arg | Gln | Leu | Arg | Ala | Phe | Phe | Arg | Lys | Gly |      |
| 385 |     |     |     |     | 390 |     |     |     |     | 395 |     |     |     |     | 400 |      |
| ggc | ggc | gct | tgc | ctc | tcc | aat | gcc | ccg | gac | ccc | gga | ctc | ccg | gtg | ccg | 1248 |
| Gly | Gly | Ala | Cys | Leu | Ser | Asn | Ala | Pro | Asp | Pro | Gly | Leu | Pro | Val | Pro |      |
|     |     |     |     | 405 |     |     |     |     | 410 |     |     |     |     | 415 |     |      |
| ccg | gcg | ctc | tgc | ggg | aac | ggc | ttc | gtg | gaa | gcg | ggc | gag | gag | tgt | gac | 1296 |
| Pro | Ala | Leu | Cys | Gly | Asn | Gly | Phe | Val | Glu | Ala | Gly | Glu | Glu | Cys | Asp |      |
|     |     |     | 420 |     |     |     |     | 425 |     |     |     |     | 430 |     |     |      |
| tgc | ggc | cct | ggc | cag | gag | tgc | cgc | gac | ctc | tgc | tgc | ttt | gct | cac | aac | 1344 |
| Cys | Gly | Pro | Gly | Gln | Glu | Cys | Arg | Asp | Leu | Cys | Cys | Phe | Ala | His | Asn |      |
|     |     | 435 |     |     |     |     | 440 |     |     |     |     | 445 |     |     |     |      |
| tgc | tcg | ctg | cgc | ccg | ggg | gcc | cag | tgc | gcc | cac | ggg | gac | tgc | tgc | gtg | 1392 |
| Cys | Ser | Leu | Arg | Pro | Gly | Ala | Gln | Cys | Ala | His | Gly | Asp | Cys | Cys | Val |      |
|     | 450 |     |     |     |     | 455 |     |     |     |     | 460 |     |     |     |     |      |
| cgc | tgc | ctg | ctg | aag | ccg | gct | gga | gcg | ctg | tgc | cgc | cag | gcc | atg | ggt | 1440 |
| Arg | Cys | Leu | Leu | Lys | Pro | Ala | Gly | Ala | Leu | Cys | Arg | Gln | Ala | Met | Gly |      |
| 465 |     |     |     |     | 470 |     |     |     |     | 475 |     |     |     |     | 480 |      |
| gac | tgt | gac | ctc | cct | gag | ttt | tgc | acg | ggc | acc | tcc | tcc | cac | tgt | ccc | 1488 |
| Asp | Cys | Asp | Leu | Pro | Glu | Phe | Cys | Thr | Gly | Thr | Ser | Ser | His | Cys | Pro |      |
|     |     |     |     | 485 |     |     |     |     | 490 |     |     |     |     | 495 |     |      |
| cca | gac | gtt | tac | cta | ctg | gac | ggc | tca | ccc | tgt | gcc | agg | ggc | agt | ggc | 1536 |
| Pro | Asp | Val | Tyr | Leu | Leu | Asp | Gly | Ser | Pro | Cys | Ala | Arg | Gly | Ser | Gly |      |
|     |     |     | 500 |     |     |     |     | 505 |     |     |     |     | 510 |     |     |      |
| tac | tgc | tgg | gat | ggc | gca | tgt | ccc | acg | ctg | gag | cag | cag | tgc | cag | cag | 1584 |
| Tyr | Cys | Trp | Asp | Gly | Ala | Cys | Pro | Thr | Leu | Glu | Gln | Gln | Cys | Gln | Gln |      |
|     |     | 515 |     |     |     |     | 520 |     |     |     |     | 525 |     |     |     |      |
| ctc | tgg | ggg | cct | ggc | tcc | cac | cca | gct | ccc | gag | gcc | tgt | ttc | cag | gtg | 1632 |
| Leu | Trp | Gly | Pro | Gly | Ser | His | Pro | Ala | Pro | Glu | Ala | Cys | Phe | Gln | Val |      |
|     | 530 |     |     |     |     | 535 |     |     |     |     | 540 |     |     |     |     |      |
| gtg | aac | tct | gcg | gga | gat | gct | cat | gga | aac | tgc | ggc | cag | gac | agc | gag | 1680 |
| Val | Asn | Ser | Ala | Gly | Asp | Ala | His | Gly | Asn | Cys | Gly | Gln | Asp | Ser | Glu |      |
| 545 |     |     |     |     | 550 |     |     |     |     | 555 |     |     |     |     | 560 |      |
| ggc | cac | ttc | ctg | ccc | tgt | gca | ggg | agg | gat | gcc | ctg | tgt | ggg | aag | ctg | 1728 |
| Gly | His | Phe | Leu | Pro | Cys | Ala | Gly | Arg | Asp | Ala | Leu | Cys | Gly | Lys | Leu |      |
|     |     |     |     | 565 |     |     |     |     | 570 |     |     |     |     | 575 |     |      |
| cag | tgc | cag | ggt | gga | aag | ccc | agc | ctg | ctc | gca | ccg | cac | atg | gtg | cca | 1776 |
| Gln | Cys | Gln | Gly | Gly | Lys | Pro | Ser | Leu | Leu | Ala | Pro | His | Met | Val | Pro |      |
|     |     |     | 580 |     |     |     |     | 585 |     |     |     |     | 590 |     |     |      |
| gtg | gac | tct | acc | gtt | cac | cta | gat | ggc | cag | gaa | gtg | act | tgt | cgg | gga | 1824 |

-continued

| | | | | | | | | | | | | |
|---|---|---|---|---|---|---|---|---|---|---|---|---|
| Val | Asp | Ser | Thr | Val | His | Leu | Asp | Gly | Gln | Glu | Val | Thr | Cys | Arg | Gly |
| | | 595 | | | | 600 | | | | | 605 | | | |

```
gcc ttg gca ctc ccc agt gcc cag ctg gac ctg ctt ggc ctg ggc ctg      1872
Ala Leu Ala Leu Pro Ser Ala Gln Leu Asp Leu Leu Gly Leu Gly Leu
    610                 615                 620 gta gag cca ggc acc cag tgt gga cct aga atg gtt tgc aat agc aac      1920
Val Glu Pro Gly Thr Gln Cys Gly Pro Arg Met Val Cys Asn Ser Asn
625                 630                 635                 640 cat aac tgc cac tgt gct cca ggc tgg gct cca ccc ttc tgt gac aag      1968
His Asn Cys His Cys Ala Pro Gly Trp Ala Pro Pro Phe Cys Asp Lys
                645                 650                 655 cca ggc ttt ggt ggc agc atg gac agt ggc cct gtg cag gct gaa aac      2016
Pro Gly Phe Gly Gly Ser Met Asp Ser Gly Pro Val Gln Ala Glu Asn
            660                 665                 670 cat gac acc ttc ctg ctg gcc atg ctc ctc agc gtc ctg ctg cct ctg      2064
His Asp Thr Phe Leu Leu Ala Met Leu Leu Ser Val Leu Leu Pro Leu
        675                 680                 685 ctc cca ggg gcc ggc ctg gcc tgg tgt tgc tac cga ctc cca gga gcc      2112
Leu Pro Gly Ala Gly Leu Ala Trp Cys Cys Tyr Arg Leu Pro Gly Ala
    690                 695                 700 cat ctg cag cga tgc agc tgg ggc tgc aga agg gac cct gcg tgc agt      2160
His Leu Gln Arg Cys Ser Trp Gly Cys Arg Arg Asp Pro Ala Cys Ser
705                 710                 715                 720 ggc ccc aaa gat ggc cca cac agg gac cac ccc ctg ggc ggc gtt cac      2208
Gly Pro Lys Asp Gly Pro His Arg Asp His Pro Leu Gly Gly Val His
                725                 730                 735 ccc atg gag ttg ggc ccc aca gcc act gga cag ccc tgg ccc ctg gac      2256
Pro Met Glu Leu Gly Pro Thr Ala Thr Gly Gln Pro Trp Pro Leu Asp
            740                 745                 750 cct gag aac tct cat gag ccc agc agc cac cct gag aag cct ctg cca      2304
Pro Glu Asn Ser His Glu Pro Ser Ser His Pro Glu Lys Pro Leu Pro
        755                 760                 765 gca gtc tcg cct gac ccc caa gca gat caa gtc cag atg cca aga tcc      2352
Ala Val Ser Pro Asp Pro Gln Ala Asp Gln Val Gln Met Pro Arg Ser
770                 775                 780 tgc ctc tgg tga gaggtagctc taaaatgaa cagatttaaa gacaggtggc           2404
Cys Leu Trp
785 cactgacagc cactccagga acttgaactg caggggcaga gccagtgaat caccggacct   2464 ccagcacctg caggcagctt ggaagtttct tccccgagtg gagcttcgac ccacccactc   2524 caggaaccca gagccacatt agaagttcct gagggctgga gaacactgct gggcacactc   2584 tccagctcaa taaccatca gtcccagaag caaaggtcac acagcccctg acctccctca    2644 ccagtggagg ctgggtagtg ctggccatcc caaaagggct ctgtcctggg agtctggtgt   2704 gtctcctaca tgcaatttcc acggacccag ctctgtggag ggcatgactg ctggccagaa   2764 gctagtggtc ctggggccct atggttcgac tgagtccaca ctcccctgca gcctggctgg   2824 cctctgcaaa caaacataat tttggggacc ttccttcctg tttcttccca ccctgtcttc   2884 tcccctaggt ggttcctgag cccccacccc caatcccagt gctacacctg aggttctgga   2944 gctcagaatc tgacagcctc tcccccattc tgtgtgtgtc gggggacag agggaaccat    3004 ttaagaaaag ataccaaagt agaagtcaaa agaaagacat gttggctata ggcgtggtgg   3064 ctcatgccta taatcccagc actttgggaa gccggggtag gaggatcacc agaggccagg   3124 aggtccacac cagcctgggc aacacagcaa gacaccgcat ctacagaaaa attttaaaat   3184 tagctgggcg tggtggtgtg tacctgtagg cctagctgct caggaggctg aagcaggagg   3244
```

-continued

```
atcacttgag cctgagttca acactgcagt gagctatggt ggcaccactg cactccagcc    3304
tgggtgacag agcaagaccc tgtctctaaa ataaatttta aaaagacata ttaaaaaaaa    3364
aaaaaaaaaa aaaaaaaaaa aaaaa                                          3390

<210> SEQ ID NO 3
<211> LENGTH: 3582
<212> TYPE: DNA
<213> ORGANISM: Homo sapiens
<220> FEATURE:
<221> NAME/KEY: CDS
<222> LOCATION: (1)..(2550)

<400> SEQUENCE: 3 atg ggc tgg agg ccc cgg aga gct cgg ggg acc ccg ttg ctg ctg ctg    48
Met Gly Trp Arg Pro Arg Arg Ala Arg Gly Thr Pro Leu Leu Leu Leu
 1               5                  10                  15 cta cta ctg ctg ctg ctc tgg cca gtg cca ggc gcc ggg gtg ctt caa    96
Leu Leu Leu Leu Leu Leu Trp Pro Val Pro Gly Ala Gly Val Leu Gln
             20                  25                  30 ggt gag gac gcg ggc ggg gtc ccc ctc acc ctg tgc tct gtc ttt act   144
Gly Glu Asp Ala Gly Gly Val Pro Leu Thr Leu Cys Ser Val Phe Thr
         35                  40                  45 cca gga cat atc cct ggg cag cca gtc acc ccg cac tgg gtc ctg gat   192
Pro Gly His Ile Pro Gly Gln Pro Val Thr Pro His Trp Val Leu Asp
     50                  55                  60 gga caa ccc tgg cgc acc gtc agc ctg gag gag ccg gtc tcg aag cca   240
Gly Gln Pro Trp Arg Thr Val Ser Leu Glu Glu Pro Val Ser Lys Pro
 65                  70                  75                  80 gac atg ggg ctg gtg gcc ctg gag gct gaa ggc cag gag ctc ctg ctt   288
Asp Met Gly Leu Val Ala Leu Glu Ala Glu Gly Gln Glu Leu Leu Leu
                 85                  90                  95 gag ctg gag aag aac cac agg ctg ctg gcc cca gga tac ata gaa acc   336
Glu Leu Glu Lys Asn His Arg Leu Leu Ala Pro Gly Tyr Ile Glu Thr
            100                 105                 110 cac tac ggc cca gat ggg cag cca gtg gtg ctg gcc ccc aac cac acg   384
His Tyr Gly Pro Asp Gly Gln Pro Val Val Leu Ala Pro Asn His Thr
        115                 120                 125 gat cat tgc cac tac caa ggg cga gta agg ggc ttc ccc gac tcc tgg   432
Asp His Cys His Tyr Gln Gly Arg Val Arg Gly Phe Pro Asp Ser Trp
    130                 135                 140 gta gtc ctc tgc acc tgc tct ggg atg agt ggc ctg atc acc ctc agc   480
Val Val Leu Cys Thr Cys Ser Gly Met Ser Gly Leu Ile Thr Leu Ser
145                 150                 155                 160 agg aat gcc agc tat tat ctg cgt ccc tgg cca ccc cgg ggc tcc aag   528
Arg Asn Ala Ser Tyr Tyr Leu Arg Pro Trp Pro Pro Arg Gly Ser Lys
                165                 170                 175 gac ttc tca acc cac gag atc ttt cgg atg gag cag ctg ctc acc tgg   576
Asp Phe Ser Thr His Glu Ile Phe Arg Met Glu Gln Leu Leu Thr Trp
            180                 185                 190 aaa gga acc tgt ggc cac agg gat cct ggg aac aaa gcg ggc atg acc   624
Lys Gly Thr Cys Gly His Arg Asp Pro Gly Asn Lys Ala Gly Met Thr
        195                 200                 205 agc ctt cct ggt ggt ccc cag agc agg ggc agg cga gaa gcg cgc agg   672
Ser Leu Pro Gly Gly Pro Gln Ser Arg Gly Arg Arg Glu Ala Arg Arg
    210                 215                 220 acc cgg aag tac ctg gaa ctg tac att gtg gca gac cac acc ctg ttc   720
Thr Arg Lys Tyr Leu Glu Leu Tyr Ile Val Ala Asp His Thr Leu Phe
225                 230                 235                 240 ttg act cgg cac cga aac ttg aac cac acc aaa cag cgt ctc ctg gaa   768
Leu Thr Arg His Arg Asn Leu Asn His Thr Lys Gln Arg Leu Leu Glu
```

-continued

```
                        245                      250                       255
gtc gcc aac tac gtg gac cag ctt ctc agg act ctg gac att cag gtg                816
Val Ala Asn Tyr Val Asp Gln Leu Leu Arg Thr Leu Asp Ile Gln Val
            260                      265                      270 gcg ctg acc ggc ctg gag gtg tgg acc gag cgg gac cgc agc cgc gtc                864
Ala Leu Thr Gly Leu Glu Val Trp Thr Glu Arg Asp Arg Ser Arg Val
                275                      280                      285 acg cag gac gcc aac gcc acg ctc tgg gcc ttc ctg cag tgg cgc cgg                912
Thr Gln Asp Ala Asn Ala Thr Leu Trp Ala Phe Leu Gln Trp Arg Arg
    290                      295                      300 ggg ctg tgg gcg cag cgg ccc cac gac tcc gcg cag ctg ctc acg ggc                960
Gly Leu Trp Ala Gln Arg Pro His Asp Ser Ala Gln Leu Leu Thr Gly
305                      310                      315                      320 cgc gcc ttc cag ggc gcc aca gtg ggc ctg gcg ccc gtc gag ggc atg               1008
Arg Ala Phe Gln Gly Ala Thr Val Gly Leu Ala Pro Val Glu Gly Met
                325                      330                      335 tgc cgc gcc gag agc tcg gga ggc gtg agc acg gac cac tcg gag ctc               1056
Cys Arg Ala Glu Ser Ser Gly Gly Val Ser Thr Asp His Ser Glu Leu
            340                      345                      350 ccc atc ggc gcc gca gcc acc atg gcc cat gag atc ggc cac agc ctc               1104
Pro Ile Gly Ala Ala Ala Thr Met Ala His Glu Ile Gly His Ser Leu
        355                      360                      365 ggc ctc agc cac gac ccc gac ggc tgc tgc gtg gag gct gcg gcc gag               1152
Gly Leu Ser His Asp Pro Asp Gly Cys Cys Val Glu Ala Ala Ala Glu
370                      375                      380 tcc gga ggc tgc gtc atg gct gcg gcc acc ggg cac ccg ttt ccg cgc               1200
Ser Gly Gly Cys Val Met Ala Ala Ala Thr Gly His Pro Phe Pro Arg
385                      390                      395                      400 gtg ttc agc gcc tgc agc cgc cgc cag ctg cgc gcc ttc ttc cgc aag               1248
Val Phe Ser Ala Cys Ser Arg Arg Gln Leu Arg Ala Phe Phe Arg Lys
                405                      410                      415 ggg ggc ggc gct tgc ctc tcc aat gcc ccg gac ccc gga ctc ccg gtg               1296
Gly Gly Gly Ala Cys Leu Ser Asn Ala Pro Asp Pro Gly Leu Pro Val
            420                      425                      430 ccg ccg gcg ctc tgc ggg aac ggc ttc gtg gaa gcg ggc gag gag tgt               1344
Pro Pro Ala Leu Cys Gly Asn Gly Phe Val Glu Ala Gly Glu Glu Cys
        435                      440                      445 gac tgc ggc cct ggc cag gag tgc cgc gac ctc tgc tgc ttt gct cac               1392
Asp Cys Gly Pro Gly Gln Glu Cys Arg Asp Leu Cys Cys Phe Ala His
    450                      455                      460 aac tgc tcg ctg cgc ccg ggg gcc cag tgc gcc cac ggg gac tgc tgc               1440
Asn Cys Ser Leu Arg Pro Gly Ala Gln Cys Ala His Gly Asp Cys Cys
465                      470                      475                      480 gtg cgc tgc ctg ctg aag ccg gct gga gcg ctg tgc cgc cag gcc atg               1488
Val Arg Cys Leu Leu Lys Pro Ala Gly Ala Leu Cys Arg Gln Ala Met
                485                      490                      495 ggt gac tgt gac ctc cct gag ttt tgc acg ggc acc tcc tcc cac tgt               1536
Gly Asp Cys Asp Leu Pro Glu Phe Cys Thr Gly Thr Ser Ser His Cys
            500                      505                      510 ccc cca gac gtt tac cta ctg gac ggc tca ccc tgt gcc agg ggc agt               1584
Pro Pro Asp Val Tyr Leu Leu Asp Gly Ser Pro Cys Ala Arg Gly Ser
        515                      520                      525 ggc tac tgc tgg gat ggc gca tgt ccc acg ctg gag cag cag tgc cag               1632
Gly Tyr Cys Trp Asp Gly Ala Cys Pro Thr Leu Glu Gln Gln Cys Gln
    530                      535                      540 cag ctc tgg ggg cct ggc tcc cac cca gct ccc gag gcc tgt ttc cag               1680
Gln Leu Trp Gly Pro Gly Ser His Pro Ala Pro Glu Ala Cys Phe Gln
545                      550                      555                      560 gtg gtg aac tct gcg gga gat gct cat gga aac tgc ggc cag gac agc               1728
```

```
                                                            -continued

Val Val Asn Ser Ala Gly Asp Ala His Gly Asn Cys Gly Gln Asp Ser
            565                 570                 575 gag ggc cac ttc ctg ccc tgt gca ggg agg gat gcc ctg tgt ggg aag   1776
Glu Gly His Phe Leu Pro Cys Ala Gly Arg Asp Ala Leu Cys Gly Lys
            580                 585                 590 ctg cag tgc cag ggt gga aag ccc agc ctg ctc gca ccg cac atg gtg   1824
Leu Gln Cys Gln Gly Gly Lys Pro Ser Leu Leu Ala Pro His Met Val
            595                 600                 605 cca gtg gac tct acc gtt cac cta gat ggc cag gaa gtg act tgt cgg   1872
Pro Val Asp Ser Thr Val His Leu Asp Gly Gln Glu Val Thr Cys Arg
    610                 615                 620 gga gcc ttg gca ctc ccc agt gcc cag ctg gac ctg ctt ggc ctg ggc   1920
Gly Ala Leu Ala Leu Pro Ser Ala Gln Leu Asp Leu Leu Gly Leu Gly
625                 630                 635                 640 ctg gta gag cca ggc acc cag tgt gga cct aga atg gtg tgc cag agc   1968
Leu Val Glu Pro Gly Thr Gln Cys Gly Pro Arg Met Val Cys Gln Ser
                645                 650                 655 agg cgc tgc agg aag aat gcc ttc cag gag ctt cag cgc tgc ctg act   2016
Arg Arg Cys Arg Lys Asn Ala Phe Gln Glu Leu Gln Arg Cys Leu Thr
            660                 665                 670 gcc tgc cac agc cac ggg gtt tgc aat agc aac cat aac tgc cac tgt   2064
Ala Cys His Ser His Gly Val Cys Asn Ser Asn His Asn Cys His Cys
            675                 680                 685 gct cca ggc tgg gct cca ccc ttc tgt gac aag cca ggc ttt ggt ggc   2112
Ala Pro Gly Trp Ala Pro Pro Phe Cys Asp Lys Pro Gly Phe Gly Gly
            690                 695                 700 agc atg gac agt ggc cct gtg cag gct gaa aac cat gac acc ttc ctg   2160
Ser Met Asp Ser Gly Pro Val Gln Ala Glu Asn His Asp Thr Phe Leu
705                 710                 715                 720 ctg gcc atg ctc ctc agc gtc ctg ctg cct ctc cca ggg gcc ggc       2208
Leu Ala Met Leu Leu Ser Val Leu Leu Pro Leu Leu Pro Gly Ala Gly
                725                 730                 735 ctg gcc tgg tgt tgc tac cga ctc cca gga gcc cat ctg cag cga tgc   2256
Leu Ala Trp Cys Cys Tyr Arg Leu Pro Gly Ala His Leu Gln Arg Cys
            740                 745                 750 agc tgg ggc tgc aga agg gac cct gcg tgc agt ggc ccc aaa gat ggc   2304
Ser Trp Gly Cys Arg Arg Asp Pro Ala Cys Ser Gly Pro Lys Asp Gly
            755                 760                 765 cca cac agg gac cac ccc ctg ggc ggc gtt cac ccc atg gag ttg ggc   2352
Pro His Arg Asp His Pro Leu Gly Gly Val His Pro Met Glu Leu Gly
770                 775                 780 ccc aca gcc act gga cag ccc tgg ccc ctg gcc cca ggg tct cct gct   2400
Pro Thr Ala Thr Gly Gln Pro Trp Pro Leu Ala Pro Gly Ser Pro Ala
785                 790                 795                 800 gac cat att cac aac att tac cct cca cca ttt ctc cca gac cct gag   2448
Asp His Ile His Asn Ile Tyr Pro Pro Pro Phe Leu Pro Asp Pro Glu
                805                 810                 815 aac tct cat gag ccc agc agc cac cct gag aag cct ctg cca gca gtc   2496
Asn Ser His Glu Pro Ser Ser His Pro Glu Lys Pro Leu Pro Ala Val
            820                 825                 830 tcg cct gac ccc caa gca gat caa gtc cag atg cca aga tcc tgc ctc   2544
Ser Pro Asp Pro Gln Ala Asp Gln Val Gln Met Pro Arg Ser Cys Leu
            835                 840                 845 tgg tga gaggtagctc ctaaaatgaa cagatttaaa gacaggtggc cactgacagc   2600
Trp cactccagga acttgaactg caggggcaga gccagtgaat caccggacct ccagcacctg  2660
caggcagctt ggaagtttct tccccgagtg gagcttcgac ccaccactc caggaaccca   2720 gagccacact agaagttcct gagggctgga gaacactgct gggcacactc tccagctcaa  2780
```

-continued

```
taaaccatca gtcccagaag caaaggtcac acagcccctg acctccctca ccagtggagg    2840
ctgggtagtg ctggccatcc caaaagggct ctgtcctggg agtctggtgt gtctcctaca    2900
tgcaatttcc acggacccag ctctgtggag ggcatgactg ctggccagaa gctagtggtc    2960
ctggggccct atggttcgac tgagtccaca ctccctgsa gcctggctgg cctctgcaaa     3020
caaacataat tttggggacc ttccttcctg tttcttccca ccctgtcttc tccctaggt     3080 ggttcctgag ccccaccccc aatcccagt gctacacctg aggttctgga gctcagaatc     3140
tgacagcctc tccccattc tgtgtgtgtc ggggggacag agggaaccat ttaagaaaag     3200
ataccaaagt agaagtcaaa agaaagacat gttggctata ggcgtggtgg ctcatgccta    3260
taatcccagc actttgggaa gcyggggtag gaggatcacc agaggccags aggtccacac    3320
cagcctgggc aacacagcaa gacaccgcat ctacaraaaa attttaaaat tagctgggcg    3380
tggtggtgtg tacctgtagg cctagctgct caggaggctg aagcaggagg atcacttgag    3440
cctgagttca acactgcagt gagctatggt ggcaccactg cactccagcc tgggtgacag    3500
agcaagaccc tgtctctaaa ataaatttta aaaagacata ttaaaaaaaa aaaaaaaaa    3560 aaaaaaaaaa aaaaaaaaaa aa                                            3582
```

<210> SEQ ID NO 4
<211> LENGTH: 746
<212> TYPE: PRT
<213> ORGANISM: Homo sapiens

<400> SEQUENCE: 4

```
Met Gly Trp Arg Pro Arg Arg Ala Arg Gly Thr Pro Leu Leu Leu
  1               5                  10                  15

Leu Leu Leu Leu Leu Trp Pro Val Pro Gly Ala Gly Val Leu Gln
                 20                  25                  30

Gly His Ile Pro Gly Gln Pro Val Thr Pro His Trp Val Leu Asp Gly
             35                  40                  45

Gln Pro Trp Arg Thr Val Ser Leu Glu Glu Pro Val Ser Lys Pro Asp
         50                  55                  60

Met Gly Leu Val Ala Leu Glu Ala Glu Gly Gln Glu Leu Leu Leu Glu
  65                  70                  75                  80

Leu Glu Lys Asn His Arg Leu Leu Ala Pro Gly Tyr Ile Glu Thr His
                 85                  90                  95

Tyr Gly Pro Asp Gly Gln Pro Val Val Leu Ala Pro Asn His Thr Asp
                100                 105                 110

His Cys His Tyr Gln Gly Arg Val Arg Gly Phe Pro Asp Ser Trp Val
            115                 120                 125

Val Leu Cys Thr Cys Ser Gly Met Ser Gly Leu Ile Thr Leu Ser Arg
        130                 135                 140

Asn Ala Ser Tyr Tyr Leu Arg Pro Trp Pro Arg Gly Ser Lys Asp
145                 150                 155                 160

Phe Ser Thr His Glu Ile Phe Arg Met Glu Gln Leu Leu Thr Trp Lys
                165                 170                 175

Gly Thr Cys Gly His Arg Asp Pro Gly Asn Lys Ala Gly Met Thr Ser
            180                 185                 190

Leu Pro Gly Gly Pro Gln Ser Arg Gly Arg Arg Glu Ala Arg Arg Thr
        195                 200                 205

Arg Lys Tyr Leu Glu Leu Tyr Ile Val Ala Asp His Thr Leu Phe Leu
    210                 215                 220
```

-continued

```
Thr Arg His Arg Asn Leu Asn His Thr Lys Gln Arg Leu Leu Glu Val
225                 230                 235                 240

Ala Asn Tyr Val Asp Gln Leu Leu Arg Thr Leu Asp Ile Gln Val Ala
            245                 250                 255

Leu Thr Gly Leu Glu Val Trp Thr Glu Arg Asp Arg Ser Arg Val Thr
        260                 265                 270

Gln Asp Ala Asn Ala Thr Leu Trp Ala Phe Leu Gln Trp Arg Arg Gly
    275                 280                 285

Leu Trp Ala Gln Arg Pro His Asp Ser Ala Gln Leu Leu Thr Gly Arg
290                 295                 300

Ala Phe Gln Gly Ala Thr Val Gly Leu Ala Pro Val Glu Gly Met Cys
305                 310                 315                 320

Arg Ala Glu Ser Ser Gly Gly Val Ser Thr Asp His Ser Glu Leu Pro
                325                 330                 335

Ile Gly Ala Ala Ala Thr Met Ala His Glu Ile Gly His Ser Leu Gly
            340                 345                 350

Leu Ser His Asp Pro Asp Gly Cys Cys Val Glu Ala Ala Glu Ser
        355                 360                 365

Gly Gly Cys Val Met Ala Ala Thr Gly His Pro Phe Pro Arg Val
370                 375                 380

Phe Ser Ala Cys Ser Arg Arg Gln Leu Arg Ala Phe Arg Lys Gly
385                 390                 395                 400

Gly Gly Ala Cys Leu Ser Asn Ala Pro Asp Pro Gly Leu Pro Val Pro
            405                 410                 415

Pro Ala Leu Cys Gly Asn Gly Phe Val Glu Ala Gly Glu Glu Cys Asp
        420                 425                 430

Cys Gly Pro Gly Gln Glu Cys Arg Asp Leu Cys Cys Phe Ala His Asn
    435                 440                 445

Cys Ser Leu Arg Pro Gly Ala Gln Cys Ala His Gly Asp Cys Cys Val
450                 455                 460

Arg Cys Leu Leu Lys Pro Ala Gly Ala Leu Cys Arg Gln Ala Met Gly
465                 470                 475                 480

Asp Cys Asp Leu Pro Glu Phe Cys Thr Gly Thr Ser His Cys Pro
            485                 490                 495

Pro Asp Val Tyr Leu Leu Asp Gly Ser Pro Cys Ala Arg Gly Ser Gly
        500                 505                 510

Tyr Cys Trp Asp Gly Ala Cys Pro Thr Leu Glu Gln Gln Cys Gln Gln
    515                 520                 525

Leu Trp Gly Pro Asp Gly Gln Glu Val Thr Cys Arg Gly Ala Leu Ala
530                 535                 540

Leu Pro Ser Ala Gln Leu Asp Leu Leu Gly Leu Gly Leu Val Glu Pro
545                 550                 555                 560

Gly Thr Gln Cys Gly Pro Arg Met Val Cys Gln Ser Arg Arg Cys Arg
                565                 570                 575

Lys Asn Ala Phe Gln Glu Leu Gln Arg Cys Leu Thr Ala Cys His Ser
            580                 585                 590

His Gly Val Cys Asn Ser Asn His Asn Cys His Cys Ala Pro Gly Trp
        595                 600                 605

Ala Pro Pro Phe Cys Asp Lys Pro Gly Phe Gly Gly Ser Met Asp Ser
    610                 615                 620

Gly Pro Val Gln Ala Glu Asn His Asp Thr Phe Leu Leu Ala Met Leu
625                 630                 635                 640

Leu Ser Val Leu Leu Pro Leu Leu Pro Gly Ala Gly Leu Ala Trp Cys
```

```
                    645                 650                 655
Cys Tyr Arg Leu Pro Gly Ala His Leu Gln Arg Cys Ser Trp Gly Cys
            660                 665                 670
Arg Arg Asp Pro Ala Cys Ser Gly Pro Lys Asp Gly Pro His Arg Asp
            675                 680                 685
His Pro Leu Gly Gly Val His Pro Met Glu Leu Gly Pro Thr Ala Thr
            690                 695                 700
Gly Gln Pro Trp Pro Leu Asp Pro Glu Asn Ser His Glu Pro Ser Ser
705                 710                 715                 720
His Pro Glu Lys Pro Leu Pro Ala Val Ser Pro Asp Pro Gln Ala Asp
                725                 730                 735
Gln Val Gln Met Pro Arg Ser Cys Leu Trp
            740                 745

<210> SEQ ID NO 5
<211> LENGTH: 787
<212> TYPE: PRT
<213> ORGANISM: Homo sapiens

<400> SEQUENCE: 5

Met Gly Trp Arg Pro Arg Arg Ala Arg Gly Thr Pro Leu Leu Leu Leu
1               5                   10                  15
Leu Leu Leu Leu Leu Leu Trp Pro Val Pro Gly Ala Gly Val Leu Gln
                20                  25                  30
Gly His Ile Pro Gly Gln Pro Val Thr Pro His Trp Val Leu Asp Gly
            35                  40                  45
Gln Pro Trp Arg Thr Val Ser Leu Glu Glu Pro Val Ser Lys Pro Asp
        50                  55                  60
Met Gly Leu Val Ala Leu Glu Ala Glu Gly Gln Leu Leu Leu Glu
65                  70                  75                  80
Leu Glu Lys Asn His Arg Leu Leu Ala Pro Gly Tyr Ile Glu Thr His
                85                  90                  95
Tyr Gly Pro Asp Gly Gln Pro Val Val Leu Ala Pro Asn His Thr Asp
                100                 105                 110
His Cys His Tyr Gln Gly Arg Val Arg Gly Phe Pro Asp Ser Trp Val
            115                 120                 125
Val Leu Cys Thr Cys Ser Gly Met Ser Gly Leu Ile Thr Leu Ser Arg
        130                 135                 140
Asn Ala Ser Tyr Tyr Leu Arg Pro Trp Pro Arg Gly Ser Lys Asp
145                 150                 155                 160
Phe Ser Thr His Glu Ile Phe Arg Met Glu Gln Leu Leu Thr Trp Lys
                165                 170                 175
Gly Thr Cys Gly His Arg Asp Pro Gly Asn Lys Ala Gly Met Thr Ser
                180                 185                 190
Leu Pro Gly Gly Pro Gln Ser Arg Gly Arg Glu Ala Arg Arg Thr
            195                 200                 205
Arg Lys Tyr Leu Glu Leu Tyr Ile Val Ala Asp His Thr Leu Phe Leu
        210                 215                 220
Thr Arg His Arg Asn Leu Asn His Thr Lys Gln Arg Leu Leu Glu Val
225                 230                 235                 240
Ala Asn Tyr Val Asp Gln Leu Leu Arg Thr Leu Asp Ile Gln Val Ala
                245                 250                 255
Leu Thr Gly Leu Glu Val Trp Thr Glu Arg Asp Arg Ser Arg Val Thr
                260                 265                 270
```

-continued

```
Gln Asp Ala Asn Ala Thr Leu Trp Ala Phe Leu Gln Trp Arg Arg Gly
        275                 280                 285

Leu Trp Ala Gln Arg Pro His Asp Ser Ala Gln Leu Leu Thr Gly Arg
    290                 295                 300

Ala Phe Gln Gly Ala Thr Val Gly Leu Ala Pro Val Glu Gly Met Cys
305                 310                 315                 320

Arg Ala Glu Ser Ser Gly Gly Val Ser Thr Asp His Ser Glu Leu Pro
                325                 330                 335

Ile Gly Ala Ala Ala Thr Met Ala His Glu Ile Gly His Ser Leu Gly
            340                 345                 350

Leu Ser His Asp Pro Asp Gly Cys Cys Val Glu Ala Ala Glu Ser
        355                 360                 365

Gly Gly Cys Val Met Ala Ala Thr Gly His Pro Phe Pro Arg Val
    370                 375                 380

Phe Ser Ala Cys Ser Arg Arg Gln Leu Arg Ala Phe Phe Arg Lys Gly
385                 390                 395                 400

Gly Gly Ala Cys Leu Ser Asn Ala Pro Asp Pro Gly Leu Pro Val Pro
                405                 410                 415

Pro Ala Leu Cys Gly Asn Gly Phe Val Glu Ala Gly Glu Glu Cys Asp
            420                 425                 430

Cys Gly Pro Gly Gln Glu Cys Arg Asp Leu Cys Cys Phe Ala His Asn
        435                 440                 445

Cys Ser Leu Arg Pro Gly Ala Gln Cys Ala His Gly Asp Cys Cys Val
        450                 455                 460

Arg Cys Leu Leu Lys Pro Ala Gly Ala Leu Cys Arg Gln Ala Met Gly
465                 470                 475                 480

Asp Cys Asp Leu Pro Glu Phe Cys Thr Gly Thr Ser Ser His Cys Pro
                485                 490                 495

Pro Asp Val Tyr Leu Leu Asp Gly Ser Pro Cys Ala Arg Gly Ser Gly
            500                 505                 510

Tyr Cys Trp Asp Gly Ala Cys Pro Thr Leu Glu Gln Gln Cys Gln Gln
        515                 520                 525

Leu Trp Gly Pro Gly Ser His Pro Ala Pro Glu Ala Cys Phe Gln Val
    530                 535                 540

Val Asn Ser Ala Gly Asp Ala His Gly Asn Cys Gly Gln Asp Ser Glu
545                 550                 555                 560

Gly His Phe Leu Pro Cys Ala Gly Arg Asp Ala Leu Cys Gly Lys Leu
                565                 570                 575

Gln Cys Gln Gly Gly Lys Pro Ser Leu Leu Ala Pro His Met Val Pro
            580                 585                 590

Val Asp Ser Thr Val His Leu Asp Gly Gln Glu Val Thr Cys Arg Gly
        595                 600                 605

Ala Leu Ala Leu Pro Ser Ala Gln Leu Asp Leu Leu Gly Leu Gly Leu
    610                 615                 620

Val Glu Pro Gly Thr Gln Cys Gly Pro Arg Met Val Cys Asn Ser Asn
625                 630                 635                 640

His Asn Cys His Cys Ala Pro Gly Trp Ala Pro Pro Phe Cys Asp Lys
                645                 650                 655

Pro Gly Phe Gly Gly Ser Met Asp Ser Gly Pro Val Gln Ala Glu Asn
            660                 665                 670

His Asp Thr Phe Leu Leu Ala Met Leu Leu Ser Val Leu Leu Pro Leu
        675                 680                 685

Leu Pro Gly Ala Gly Leu Ala Trp Cys Cys Tyr Arg Leu Pro Gly Ala
```

```
                690                  695                   700
His Leu Gln Arg Cys Ser Trp Gly Cys Arg Arg Asp Pro Ala Cys Ser
705                 710                 715                 720

Gly Pro Lys Asp Gly Pro His Arg Asp His Pro Leu Gly Gly Val His
                725                 730                 735

Pro Met Glu Leu Gly Pro Thr Ala Thr Gly Gln Pro Trp Pro Leu Asp
            740                 745                 750

Pro Glu Asn Ser His Glu Pro Ser His Pro Glu Lys Pro Leu Pro
            755                 760                 765

Ala Val Ser Pro Asp Pro Gln Ala Asp Gln Val Gln Met Pro Arg Ser
770                 775                 780

Cys Leu Trp
785

<210> SEQ ID NO 6
<211> LENGTH: 849
<212> TYPE: PRT
<213> ORGANISM: Homo sapiens

<400> SEQUENCE: 6

Met Gly Trp Arg Pro Arg Arg Ala Arg Gly Thr Pro Leu Leu Leu Leu
1               5                   10                  15

Leu Leu Leu Leu Leu Trp Pro Val Pro Gly Ala Gly Val Leu Gln
            20                  25                  30

Gly Glu Asp Ala Gly Gly Val Pro Leu Thr Leu Cys Ser Val Phe Thr
            35                  40                  45

Pro Gly His Ile Pro Gly Gln Pro Val Thr Pro His Trp Val Leu Asp
        50                  55                  60

Gly Gln Pro Trp Arg Thr Val Ser Leu Glu Glu Pro Val Ser Lys Pro
65                  70                  75                  80

Asp Met Gly Leu Val Ala Leu Glu Ala Gly Gln Glu Leu Leu Leu
                85                  90                  95

Glu Leu Glu Lys Asn His Arg Leu Leu Ala Pro Gly Tyr Ile Glu Thr
            100                 105                 110

His Tyr Gly Pro Asp Gly Gln Pro Val Val Leu Ala Pro Asn His Thr
        115                 120                 125

Asp His Cys His Tyr Gln Gly Arg Val Arg Gly Phe Pro Asp Ser Trp
130                 135                 140

Val Val Leu Cys Thr Cys Ser Gly Met Ser Gly Leu Ile Thr Leu Ser
145                 150                 155                 160

Arg Asn Ala Ser Tyr Tyr Leu Arg Pro Trp Pro Pro Arg Gly Ser Lys
                165                 170                 175

Asp Phe Ser Thr His Glu Ile Phe Arg Met Glu Gln Leu Leu Thr Trp
            180                 185                 190

Lys Gly Thr Cys Gly His Arg Asp Pro Gly Asn Lys Ala Gly Met Thr
        195                 200                 205

Ser Leu Pro Gly Gly Pro Gln Ser Arg Gly Arg Glu Ala Arg Arg
        210                 215                 220

Thr Arg Lys Tyr Leu Glu Leu Tyr Ile Val Ala Asp His Thr Leu Phe
225                 230                 235                 240

Leu Thr Arg His Arg Asn Leu Asn His Thr Lys Gln Arg Leu Leu Glu
                245                 250                 255

Val Ala Asn Tyr Val Asp Gln Leu Leu Arg Thr Leu Asp Ile Gln Val
            260                 265                 270
```

```
Ala Leu Thr Gly Leu Glu Val Trp Thr Glu Arg Asp Arg Ser Arg Val
            275                 280                 285

Thr Gln Asp Ala Asn Ala Thr Leu Trp Ala Phe Leu Gln Trp Arg Arg
            290                 295                 300

Gly Leu Trp Ala Gln Arg Pro His Asp Ser Ala Gln Leu Leu Thr Gly
305                 310                 315                 320

Arg Ala Phe Gln Gly Ala Thr Val Gly Leu Ala Pro Val Glu Gly Met
            325                 330                 335

Cys Arg Ala Glu Ser Ser Gly Gly Val Ser Thr Asp His Ser Glu Leu
            340                 345                 350

Pro Ile Gly Ala Ala Ala Thr Met Ala His Glu Ile Gly His Ser Leu
            355                 360                 365

Gly Leu Ser His Asp Pro Asp Gly Cys Cys Val Glu Ala Ala Ala Glu
            370                 375                 380

Ser Gly Gly Cys Val Met Ala Ala Ala Thr Gly His Pro Phe Pro Arg
385                 390                 395                 400

Val Phe Ser Ala Cys Ser Arg Arg Gln Leu Arg Ala Phe Phe Arg Lys
            405                 410                 415

Gly Gly Gly Ala Cys Leu Ser Asn Ala Pro Asp Pro Gly Leu Pro Val
            420                 425                 430

Pro Pro Ala Leu Cys Gly Asn Gly Phe Val Glu Ala Gly Glu Glu Cys
            435                 440                 445

Asp Cys Gly Pro Gly Gln Glu Cys Arg Asp Leu Cys Cys Phe Ala His
450                 455                 460

Asn Cys Ser Leu Arg Pro Gly Ala Gln Cys Ala His Gly Asp Cys Cys
465                 470                 475                 480

Val Arg Cys Leu Leu Lys Pro Ala Gly Ala Leu Cys Arg Gln Ala Met
            485                 490                 495

Gly Asp Cys Asp Leu Pro Glu Phe Cys Thr Gly Thr Ser Ser His Cys
            500                 505                 510

Pro Pro Asp Val Tyr Leu Leu Asp Gly Ser Pro Cys Ala Arg Gly Ser
            515                 520                 525

Gly Tyr Cys Trp Asp Gly Ala Cys Pro Thr Leu Glu Gln Gln Cys Gln
530                 535                 540

Gln Leu Trp Gly Pro Gly Ser His Pro Ala Pro Glu Ala Cys Phe Gln
545                 550                 555                 560

Val Val Asn Ser Ala Gly Asp Ala His Gly Asn Cys Gly Gln Asp Ser
            565                 570                 575

Glu Gly His Phe Leu Pro Cys Ala Gly Arg Asp Ala Leu Cys Gly Lys
            580                 585                 590

Leu Gln Cys Gln Gly Gly Lys Pro Ser Leu Leu Ala Pro His Met Val
            595                 600                 605

Pro Val Asp Ser Thr Val His Leu Asp Gly Gln Glu Val Thr Cys Arg
            610                 615                 620

Gly Ala Leu Ala Leu Pro Ser Ala Gln Leu Asp Leu Leu Gly Leu Gly
625                 630                 635                 640

Leu Val Glu Pro Gly Thr Gln Cys Gly Pro Arg Met Val Cys Gln Ser
            645                 650                 655

Arg Arg Cys Arg Lys Asn Ala Phe Gln Glu Leu Gln Arg Cys Leu Thr
            660                 665                 670

Ala Cys His Ser His Gly Val Cys Asn Ser Asn His Asn Cys His Cys
            675                 680                 685

Ala Pro Gly Trp Ala Pro Pro Phe Cys Asp Lys Pro Gly Phe Gly Gly
```

```
                  690                 695                 700
Ser Met Asp Ser Gly Pro Val Gln Ala Glu Asn His Asp Thr Phe Leu
705                 710                 715                 720

Leu Ala Met Leu Leu Ser Val Leu Leu Pro Leu Pro Gly Ala Gly
                725                 730                 735

Leu Ala Trp Cys Cys Tyr Arg Leu Pro Gly Ala His Leu Gln Arg Cys
                740                 745                 750

Ser Trp Gly Cys Arg Arg Asp Pro Ala Cys Ser Gly Pro Lys Asp Gly
        755                 760                 765

Pro His Arg Asp His Pro Leu Gly Gly Val His Pro Met Glu Leu Gly
        770                 775                 780

Pro Thr Ala Thr Gly Gln Pro Trp Pro Leu Ala Pro Gly Ser Pro Ala
785                 790                 795                 800

Asp His Ile His Asn Ile Tyr Pro Pro Phe Leu Pro Asp Pro Glu
                805                 810                 815

Asn Ser His Glu Pro Ser Ser His Pro Glu Lys Pro Leu Pro Ala Val
                820                 825                 830

Ser Pro Asp Pro Gln Ala Asp Gln Val Gln Met Pro Arg Ser Cys Leu
        835                 840                 845

Trp

<210> SEQ ID NO 7
<211> LENGTH: 17000
<212> TYPE: DNA
<213> ORGANISM: Homo sapiens

<400> SEQUENCE: 7
tccatctcaa aaaaaaaaa aaaaaaaag ttaacatctc atccaaattt gcaccgagta      60
ggaaaacaaa agtttaaaac atgaaacaga tgttactgag gccgaaaggg tctcccaggc    120
ctgggagtct gcagctttta tgcaattctg ccctctggcc accgccaggg aagaaaggtt    180
gtctccgtct gctgcatcgc ctttgcccag caatgaagcc cccaagacag cggcagccgg    240
ttgcctgaac cttcctatcc ttgggggcac ccagtgcagg tggatgaccc gactcaacct    300
ccgccagggc accctcgggg caggacgggt agcaaggagg ggacagagat cggccccagg    360
agaccacgga agatcgcgct cctggggcca acttcagcag cgagaggcgg cctttgccca    420
ccgcctcatc ccaccacgcc gcggtcctcc aagaaccttc ccagcggttc tctcctcctc    480
tcaggagtag aggccctctg agaccgacgg ggagggacgg ctcgggccgg tcatccgagg    540
ggccgcacgg attccctcct ccgcccagct ccacccctc gagggcggc ggtccgggag     600 tggcgacccg gctcccccat ggcgcgcgcc gtcgggccc ctggccaggc tccgagcggg     660
gttggcgggg aggggaggcg ggagcgaggg cgggcggtgg gaggtgggg cgggaaggtc     720 cgaaggcggc ggcctgaggc tgcaccgggc acgggtcggc cgcaatccag cctgggcgga    780
gccggagttg cgagccgctg cctagaggcc gaggagctca cagctatggg ctggaggccc    840
cggagagctc gggggacccc gttgctgctg ctgctactac tgctgctgct ctggccagtg    900
ccaggcgccg gggtgcttca aggtgaggac gcgggcgggg tgcgccctga ggggcaggct    960
aggcgcggtg gtggtggcgg ggatggggttc tgctcagagc tcgggtcagc gcgcggaggg   1020
tctcacggcc ccggcaccat acggccagta ggtcagggcg tggggactct ttggggggt    1080 ctccgtggga cctgcccagg gacgctcaag tgtgcttggg ctggcccggg ccccggactt    1140
gcccacactg cccggctgcc actccgctgg caaagcagag ggcatggctc cctcccctc    1200
```

-continued

```
gggacagcc cagcccccag ccccagccc atagccgtag cccctctgc ctggattctc    1260 gctctcacaa ccagcttcca tccgcaggcc accgtgtgac ccgctcctgc tcctccaccc    1320
cttaggactc agcggggctc catcctctag aagcccccca tgcccaagag tcccccagag    1380
tccctgcttt gctctcaggc tgcagaacta gctgtggcct ccaccctgct caccctcgt    1440 ccctcctccc agggcagcag ggcagtgtgt atgttgttta tattgttgcc ttgtttggtg    1500
agatagagaa gggcctctcc agatagaagg tgtctgttta gcagtgctct ggaaagactg    1560
cagctgtctc ctcggggtaa cccctccaaa caaagatgtt aagatgggc tggaacaacc    1620 tctgcaagcg ggtgggagga ttagccagtc ctgcacagca agtgcctggc cgggaacagg    1680
gagggcaacc agggaggggg catgcggggc tgggctgtgc tatgcagact gggcggtggc    1740
ttccacagca ctgtgtgggg accaaacagg tacagggcc tggtctgttc tggccccagg    1800
ggagggcccc aggcggtcca ctgctccctc ccctctgagc cctatcctgg ggtcagggga    1860
ggtgatggga cccctgggag aggggcgtct atgtgcccaa taccagcctg gctccctcgg    1920
gttccacccc cattcacccg gtcaccggag ctccagctcc agctccagct ctgcccctct    1980
ctccctcatt ggggtcaggg tgcccgtggc cagcacgtgc gcgcaaggcc atgtggacag    2040
cacccacaca ccacactgca cccacaccac acctgtgccc gggcccaccc tacctcttcc    2100 ccaaacccctt agaggcctag agcagcaaa gcttggttct ctactctcag ttaagtgctc    2160
tctgggctga gagacctccc ctccttcccc tcccccacat ccactcagag ccctccctgc    2220 actgcccct ctagcctcct ttccaaggtg gcagactcct ctcggccctc atctgcctga    2280
tggcaattca ctcatccaat caaggagggc ttcttggagg aagggtcttt gatgtttgta    2340
gtctgggaga gaaggtggag gagaaaaaag gagttggggt ggcctagcag gagctgagtc    2400
acttccacag gcagccatca gcccagcagg actgaggcca gggctgcgtg gagggggag    2460 gctgtctgtt ctgggagctg ggactgggta ccggggaag gagggctgct gcaggctctg    2520
ggtgcctggg gcctggctcc tgcagggcgg gcctgtgaga gtggttgggg ccagtggagg    2580
ggctgggagc attccagggg aacattccag gcgccctctg agtaatgctt ggctctggga    2640
ttcctcctag agccccctta ggcacacccg gccagggagc accaaggctc cgtccggaag    2700
cgtcccctcc ccttgaagag atgaggaggg gccttctggg ccagggtacc aaaaccctgc    2760
caccaggaca gagtccccga gggagctctg ggcaaggtgg acctcgcaag gcaacatctg    2820
gctgttgttt ttctcagatg atggggggg cacaagtgtc ctctcttcgt acatctctca    2880
ccctaaaggc atctgctgcc catctaaaaa tccctaaggc tgccgcgctc tttccttccc    2940
ctctgcactg gcggccttgg cctcttcctt gtgatcgccg agcccaagcc tgccccccga    3000
caaaggtcag gggactcccg tgtccccagc tgagctgtcc cttccagcc ttctcttttc    3060 ctcctccttg atagctcctc agatccaagg atgcccacgg gcgtccctcc ttctccaggc    3120
tgagcccacg cgtgttgaag gtgaagtctg cccaaaagg cctccagtgc ctccctgggg    3180
atgtcctcta cccccctccc tctgctttgt cccatgcccc tgtgttcctc aggtcccct    3240 caccctgtgc tctgtctta ctccaggaca tatccctggg cagccagtca cccgcactg    3300 ggtcctggat ggacaaccct ggcgcaccgt cagcctggag gagccggtca gtgccatgtc    3360
tccccgccct ccacagggc cctgaacctc ccagccctt tgtctctccc tacattacag    3420
cttctagttt tgctgggtc cccagaacca ccaagtcact actcctatag gcccctgcct    3480
cccctgcccc tcaagtgggc agaagaaggc actgggttt ggacatctgg atctcgtgag    3540
cccgcacaca tggaagtcat ttcagctttc tccaccccac ctccctcttt ccctccctcc    3600
```

-continued

```
ctggatgatc tgggccaccc ccaccccac caggcagaaa tgggtccaga gtttgtgggt    3660
cctgaagctt ttcaggagcc tctaaaaaaa aaaaaaaaa aaaaagcacc aaaaagaaaa    3720
ccttttgcaa agttgaccag aacatgtgac cctgtggaca cactgctgtc cctctcaggg    3780
ccctgccacg aaggcctgaa ccttcagcct cactggctcc tgtggaatcc acttctggta    3840 tgggggggc agtggtcact ctcctgatgt cccccagatg taagaccacc ccatgtgctt    3900
cttctgcagg acgctctgcc ccagcctctt cccaatcccg ctcttcacac gcttccagaa    3960
taaccatgcc ccatctgttt gtgccataat atctgtgctg caaactaaga gggcagtagc    4020
cttgatatgc tcattttaca gaggggcaaa cggaagccca gagagcttgg ggaaattgtc    4080
catggtcaca cagctctttta ggctgggagc ctgagaccca ctaaggtctg aacgatttta    4140
aaccattggc tacacccctg cccctcctag agagccctct ttgtttggaa ttttcagccc    4200
tactgtccaa atccagcaag agggaaggca ggggagcatt gccatgaagg ctgagaggcc    4260
cccagagacc cagcagctcc caacccaggg ccctcactgg gatcccctag cccataagg    4320 cccccattcc actggtcaag cacggcactg gcctgagctt tgagattgcc ctccccatcc    4380
ccaggagggg aaggctggac acacactggg gtcactctgc ctctgggcct ccctgtctgt    4440
ctggcctggg ctgtgaccaa gaggagagcc ccaaagggc tctgcttccc ccaccggtgg    4500
gcccctgccc ccaggaagcc tgccaagatg gtacagaaga aagagtagag gctaggtatc    4560
ccctccaaaa ggcaggaaac actcacattt caagatgagg ggtatatatc aaggggcagg    4620
gtaccaggag ggcaagagta aagatagcag gggctgcaga ggaacaggga cctcgagtat    4680 ggccttttc ccggtgcaga cctttcccca ataaagcaag tggcattcca gcctcatgag    4740
ctcatgctgg aggccttgtg gggcctgtgg ccagggaggc aaggaccatc tgctccccac    4800
ttgcgaagga agaactccct ccaaagactc tgagaccctt ggacagggcc ccaggccagt    4860
gcatttttgg agaaaaggag tcgggggtta acattccga aggcgcagca gcctcccagg    4920
aagctcctgg gccggctcca actctgggcc cccagccagg ctgagtggac aaggggggaag    4980 tggggtgttc ccacagggtg ggagacgcca agagggtggg ggaaggagag agggctggcc    5040
gtccaagcca gcctcctgac acctagctga gagccagtgt gctctcttgg ctggaatggc    5100
gtccatgttt acttcgtggg tccagtgaag caggtgtcgg agccggaggg acggggggctg    5160 ctggaggccc aggaaaactt tggaagaggg agcagtttgc caaaattgga agtggaggag    5220
tcaaatttga attctatagg aaatgagcag cagctcattt ggaaccaagc ctcaggtagc    5280
agaggctctg aggaggccct gaccatggct acccgatgcc cccataatgt cctcagcacc    5340
cctctgtctt ccctgctttt tgatgcccct tctgggcatg aaagaagagg gcggggccag    5400
ggagggggca cctttctggg acctctggtc tctagggagg atgctggtgt gcctggcagg    5460
ctgtgccaac gcccttccaa gtggctgttg tcaggactga aaacatcctg agtttgggaa    5520
catctttgta tgttctcacc tcctccacgc cctccatagt atgtggggg tcctgctgac    5580 tccccagccc acgttctccc caagaacttc ctccccagcc ggctccacag gccacctact    5640
ccctggcagg caggaggcct ggaggccacc atctcagctc cacactcttt cttgcccagg    5700
tctcgaagcc agacatgggg ctggtggccc tggaggctga aggccaggag ctcctgcttg    5760
agctggagaa gaaccagtga gtgccaggct ggggtagggc tgggaggagg ggatcagtgt    5820 tgggggggcag ggactgacac agatctgtgc gggtggctgg atgggcagag gaccccagag    5880
agggtgcaga tgacagggag agtcacgcag gcctgtggtt ggctccctgg aggctgaaga    5940
```

```
ggaccgctga ggctgtcagc cccgctgtgg ggcacctccg ccctcccaac cccaggagcg   6000
gcttgttagc tccctgctgg cgatgagtga gcaccaccta gtggacattt gcaagatatg   6060
ctgagtctaa agaaatccta gagggaaaag atgagccggc accccaggct aagggaatgg   6120
cagggaccaa gatgcggtgg ctttgggagg ccgaggcggg cggctcacct gaggtcagga   6180
gtttgagacc agccttgcca acatggtgaa acccgtctc tactaaaaat acaaaaaatt   6240
agccaggcgt ggtggcggcg cctgtaatcc cagctactta gggggctgag acgggagaat   6300
cgcttgaacc ccgaggtag aggttgtggt gagccaagat cacaccactg caccactccg   6360
gcctgggcaa agagtgagac tccgtctcaa aaaagagaa aaaaagaaa aagaaaaaaa   6420 aaaagaaaga aaagaaaaaa gaaaagatg cagtggctac acttgggggc agcagtttgt   6480
ctgacctgcc tggaaggtct ccatctacag ggaggggagc agggggaat gaatttggag   6540 agtcccagga gggccagatc acagaaggcc attttggtgc tcagtgtcct ggaccatcca   6600
gagccaaaga ttttgagctg gggaagggac aggcagacct gtgctcagga aggtgccttg   6660
ggctgggtgg ggtgggtgtc cgggctggag cgcaggctct taaaaccacc cagattatgt   6720
tatcagtata tatcacctac tgagtgcttg accgcaggcg ctgttctgag cacttgacac   6780
gtattttatt ctccctcgtg gagtcggatg gacaggggaac aaactctagt tccactgtgc   6840
ccaaccatat tttcccgacg tccctaccct ttcaatgggg tggtcacatc acctacctcc   6900
tagggtggcg ggtgtgtgtg gggcagggggt agggggcaga gctggggcag gtggtggaat   6960
gcctgggagg ggggaagcag ccatcattag cgggtggtct ggaggtaatg aggccaaggt   7020
gaggttgggt taaggatttt ctttaaagaa gacagattga cttatgattg atccatccgt   7080
gtgggaaaga tcctgttgag atggagcctg aagatggaat cattaccgga gtgggtgtgg   7140
agaaggcagg gagggtggaa gcagcgtggg caggtggcga ttctgttttc tctggaggca   7200
gggggtgagc atcaatcact gaaggacagg tgggaggtat gtgggtcta gaagtctgag   7260 gaaaatattt caaggatcta gggcaggtgg gggcaagagg gtcgaccaga tgcccaacaa   7320
aggagggcag caggcagggg aactggggga ggtcaccgca tttccccaac tccaagtccc   7380
attcttcggc agtgtctcct gactcctccc ctcccgatcc tgtggatcct gctgcctgct   7440
gcaggtcccc tggaaccac aaactcttcc cctattccca ctcctcccg gcgtcctccc   7500 tggtgcttcc catattcaca tctcccacaa ctaagccatc accaaggctc cttcctctag   7560
ccccaagagt ttctgatctg agcaagtcac cattgctcct gtcccttccc taagacacac   7620
tgtgagtgtc tcactcataa agctgctcca ttagcattta gggaggaagg ctgggagaca   7680
tcctggagga ggcaggagga agctgaattc agtgttccct gtaacacccc ctctcagcag   7740
gctgctggcc ccaggataca tagaaaccca ctacggccca gatgggcagc cagtggtgct   7800
ggcccccaac cacacggtga gatgcttcca tgggctctgg gatgcaccgc cagaggtacc   7860
cccccaccat tcctaccct actcctcctt gcattcctaa ggggcggttg gagccagccc   7920
ctaccacacc ctccctcttg cccctcttgc tccagccctg gctgagattt ggggctggcc   7980
ccttcctccc taggatcatt gccactacca agggcgagta aggggcttcc ccgactcctg   8040
ggtagtcctc tgcacctgct ctgggatgag gtgagtctg ggagaggagg ctgggcctgg   8100
gatggggaaa gagctccctc acaccgctc ctacccctct gcaccctagt ggcctgatca   8160
ccctcagcag gaatgccagc tattatctgc gtccctggcc accccggggc tccaaggact   8220
tctcaaccca cgagatcttt cggatggagc agctgctcac ctggaaagga acctgtggcc   8280
acagggatcc tgggaacaaa gcgggcatga ccagccttcc tggtggtccc cagagcaggg   8340
```

```
tcagggcat cgatcggatg ggagtgggaa tgctgtatct atagccctcc aaatcagaag    8400
agacaggaat tcacaggcct cgagtcccag tattttatt gaagtctgaa gaaacaagtt    8460
ccagaaaaca tgttaaactt ccttctggga gctggggttg ggggtcaggg ctcaagccca    8520
gcagcttcca ctcagggtcc ccatttgcac ctccgcaggg caggcgagaa gcgcgcagga    8580
cccggaagta cctggaactg tacattgtgg cagaccacac cctggtgagg agagacccca    8640
ggggttggcg gggtcaggga tggggccagc tcagcccctc aagccaccgg gatttctgcc    8700
ttcccagttc ttgactcggc accgaaactt gaaccacacc aaacagcgtc tcctggaagt    8760
cgccaactac gtggaccagg ttggggggcgg cggggagaga gcggtgatgg gggtggcggc    8820
ggcaggacag gcaggtgctg gtggggtttg gggaagagga agggcgcccc acgaaggacc    8880
accggcgcga tggggcgccc tgtcccggct tcagccccgc ctcgccctca gcttctcagg    8940
actctggaca ttcaggtggc gctgaccggc ctggaggtgt ggaccgagcg ggaccgcagc    9000
cgcgtcacgc aggacgccaa cgccacgctc tgggccttcc tgcagtggcg ccggggggctg    9060 tgggcgcagc ggccccacga ctccgcgcag ctgctcacgt gggtgcctct gacccggacg    9120
cgggtcccgg gtggggcggc ctcacctccc ggccccgcct ggtcacgccg cgctccgccc    9180
ccaggggccg cgccttccag ggcgccacag tgggcctggc cccgtcgag ggcatgtgcc    9240 gcgccgagag ctcgggaggc gtgagcacgg tgagccccgc gggcggggc gagggagaga    9300 caggaggctc tacggccgca gtgaccgccc tcccacggcc cccaggacc actcggagct    9360 ccccatcggc gccgcagcca ccatggccca tgagatcggc cacagcctcg gcctcagcca    9420
cgaccccgac ggctgctgcg tggaggctgc ggccgagtcc ggaggctgcg tcatggctgc    9480
ggccaccggg tacgcgggtg gggtcggg gctgcggcgg ggcggctagt cctggggact    9540
tcctccgctg cgtttctttg gtcgtccctc agtttcctct tctgtaaaat ggggataatg    9600
atcatagtgt ccgcttcagg gtggtttatg aggcttaaag ggagaagct caggcaaagt    9660 ggattctcaa cggtatgaag attattttcc gagtaacctg gcgaggttac tcctacaccg    9720
ggaggagcac cgtcgggtcg cgattccacc ttgggtcccg ggctgctcac tattggggcc    9780
gcatcgtccc ctgtcccgct tgttgtgtga ctttgcgcgg gttacttccc ctctctgggc    9840
tctgcgcgtc tggcggctgt agccaagccc aggggtggg atcagagaag cgcggggtt    9900 gggggactgt ccctccatgc ccaatgccct cccgtgccg gtaggcaccc gtttccgcgc    9960
gtgttcagcg cctgcagccg ccgccagctg cgcgccttct ccgcaagggg gggcggcgct   10020
tgcctctcca atgccccgga ccccggactc ccggtgccgc cggcgctctg cgggaacggc   10080
ttcgtggaag cgggcgagga gtgtgactgc ggccctggcc aggttaagtc ggctcgcccg   10140
gcccccactt gccctctccg ctcaggtctg gggcgctgcg ccctcacctg ggcccttctt   10200
gcctttctgg tcccaggagt gccgcgacct ctgctgcttt gctcacaact gctcgctgcg   10260 cccggggggcc cagtgcgccc acggggactg ctgcgtgcgc tgcctggtga gggcatggaa   10320
ggttcagggt gagggtttcg gggagcttgg gagccggcct gttggcccta gttaattggt   10380
gccctcaggt tccccgttg ggtgctgggc ttgggtaggc ctggctcccc cagctccgag   10440
ccgcgctctc ggcatggacc tctcactgca cgtggcctct ctctgccttc ccaccaccc   10500 gtcacctgcg cagctgaagc cggctggagc gctgtgccgc caggccatgg gtgactgtga   10560
cctccctgag ttttgcacgg gcacctcctc ccactgtccc ccagacgttt acctactgga   10620
cggctcaccc tgtgccaggg gcagtggcta ctgctgggat ggcgcatgtc ccacgctgga   10680
```

-continued

| | |
|---|---|
| gcagcagtgc cagcagctct gggggcctgg tgagaggaca cgagcaccct tgcaccctgc | 10740 |
| cccccatcct ctggtggggc cagttttcta ctgtggggaa gatgggcagg ggaaactgag | 10800 |
| gcccgctgag cgcagcccct ctccgagctg ccccagcct ggcccatgct tcctcaggct | 10860 |
| cccacccagc tcccgaggcc tgtttccagg tggtgaactc tgcgggagat gctcatggaa | 10920 |
| actgcggcca ggacagcgag ggccacttcc tgccctgtgc agggaggtag ggagtggagc | 10980 |
| tgagtggagg gagcagaagc tatggagtgg gtttgggaa gggggtact gcagctgttg | 11040 |
| accccctct acttcctccc cagggatgcc ctgtgtggga agctgcagtg ccagggtgga | 11100 |
| aagcccagcc tgctcgcacc gcacatggtg ccagtggact ctaccgttca cctagatggc | 11160 |
| caggaagtga cttgtcgggg agccttggca ctccccagtg cccagctgga cctgcttggc | 11220 |
| ctgggcctgg tagagccagg cacccagtgt ggacctagaa tggtgagctc tgcccacccg | 11280 |
| acccctcctt gccgtttgaa tcccgcaggc cagtgtcccc ctcactgcct ggtgcactgc | 11340 |
| ccgtaggtgt gccagagcag gcgctgcagg aagaatgcct tccaggagct tcagcgctgc | 11400 |
| ctgactgcct gccacagcca cggggtgaga gcccgaggag tggggtgac cttgggttc | 11460 |
| ctaatcctac gtgaccctcc tcttctcttc tctgcaggtt tgcaatagca accataactg | 11520 |
| ccactgtgct ccaggctggg ctccacccct ctgtgacaag ccaggctttg gtggcagcat | 11580 |
| ggacagtggc cctgtgcagg ctgaaagtat gccagtgggg gcatgtggg caggagctgg | 11640 |
| ggtggtgcac ctgctcagga ctcagcgccc cttccccaa tccccgcaga ccatgacacc | 11700 |
| ttcctgctgg ccatgctcct cagcgtcctg ctgcctctgc tcccagggc cggcctggcc | 11760 |
| tggtgttgct accgactccc aggagcccat ctgcagcgat gcagctgggg ctgcagaagg | 11820 |
| gaccctgcgt gcagtgggta ggctccgagc gcctgcttcc tgagcctact cctgcggttc | 11880 |
| ccctcctcag agctctgctg gggctgtggg agctggggca ggccctcagc cttgccccca | 11940 |
| ggtgcagaga gcagccccag aggccatgga aagaagtagc tttgaacagg aggttccagt | 12000 |
| ggcctcccag tcaagcgagg gggtggatcc ctgcccacc accagcaccg caaggcatgg | 12060 |
| ccctctacct cccagtacag ctcctcttgt ccactctcct gcttctccca ccagctggct | 12120 |
| gcctcaccct tgacttcgcc ctgttttttcc ctggctcaga ttgcagtccc tgtaccatgc | 12180 |
| tgccccgga ggcctgtcca gcctctgtct caccagtttt cggccttttg ccacttcctc | 12240 |
| tgcacaaatc acctctgtca cccccttgaa gttcccaaat gctgggccca gcacatcttt | 12300 |
| tcactccata ccactggtca gctgcggtgc tggctgcccc tgtgccaggg ccctgcctta | 12360 |
| acccagttct ctgtgacctg ggtggtggcg gagtggggag tcacataata ctaagcatgg | 12420 |
| ctgtcctagg actcaccctg caccagggcc ctaggcaggg caggcactct gtggccatgt | 12480 |
| ctgacatagc ctggtcttgg gagtgctccg ggcaagccaa gggagatggc atgatttggg | 12540 |
| ccagagatgg gggcagaggg cataacagac aggggcaggg caccacctgg gccccgggtg | 12600 |
| gcagctaaga ggaccctgac aaagcgagtt gtgattgagg gtctgtgggc agaggagcaa | 12660 |
| ggtggccaga gcctggcgtg tcagcacgga gggggcgctg cagagggtgg cggctgcttc | 12720 |
| tcatccccag gcgggagtct cagggcaggg gagaatgttt tgaaggaaca tcacaggaaa | 12780 |
| tgacaaggcc ttgggggatg ggatgggac agtcaaagat ggcttggaat catcaagggc | 12840 |
| agcagggcac ccagggcaa ggagagcaga catagctgcc gaaggggcgg acatccaagg | 12900 |
| ttctttggaa gctgagcgat gccagcatct ggagagtgcc aggctgctgg gtggtgtcag | 12960 |
| agcctggagg aaatgttagg actagagaga ggaggtgcca gccgagggca tgaggctcac | 13020 |
| ttggagcctg gatcccaagg ctcccctgaa gagggagcag gaagggagct gagagggtga | 13080 |

```
cttggagcag atgggtgccc caagaaactc agtaaacgca gaactccctg ggctggacac    13140
catgctgcgg ggaggcaata acccactcag gatcactgtg ccaacctcct ggactcttat    13200
cacgttgctc agccccaaag atggcccaca cagggaccac cccctgggcg gcgttcaccc    13260
catggagttg ggccccacag ccactggaca gccctggccc ctgggtgagt gaggcaccag    13320
ggggaggtgg agagggaagg gagaagggaa gggctcatgc ctcctgcctc cttccagatg    13380
ggcagcaccc agtcaccttg agtcccctat gcccctcccc agcccagggg tctcctgctg    13440
accatattca caacatttac cctccaccat ttctcccaga ccctgagaac tctcatgagc    13500
ccagcagcca ccctgagaag cctctgccag cagtctcgcc tgaccccaa ggtaggcagg     13560 gacctggatt caaagcctcc ccctctcatc gcccaccctc ccacctctcc caccctcag    13620 tttgctgccc cctaatcagg tttctgggct caggttatta tggaaatgag tttatgacct    13680
cttggttatc atgagaccca ggatgctgga agcccctggg ctggggaggg agaagctgtg    13740
gcttttcctg gatcactggt cctcactgag tgaggatggg ctctctgcca cacagcttgc    13800
agcctggggc cccagtcctt agggacaac atatcctcct cattctcagc agatcaagtc     13860
cagatgccaa gatcctgcct ctggtgagag gtagctccta aaatgaacag atttaaagac    13920
aggtggccac tgacagccac tccaggaact tgaactgcag gggcagagcc agtgaatcac    13980
cggacctcca gcacctgcag gcagcttgga agtttcttcc ccgagtggag cttcgaccca    14040
cccactccag gaacccagag ccacactaga agttcctgag ggctgagaa cactgctggg    14100 cacactctcc agctcaataa accatcagtc ccagaagcaa aggtcacaca gccctgacc     14160 tccctcacca gtggaggctg ggtagtgctg gccatcccaa aagggctctg tcctgggagt    14220
ctggtgtgtc tcctacatgc aatttccacg gacccagctc tgtggagggc atgactgctg    14280
gccagaagct agtggtcctg gggccctatg gttcgactga gtccacactc ccctggagcc    14340
tggctggcct ctgcaaacaa acataatttt ggggaccttc cttcctgttt cttcccaccc    14400
tgtcttctcc cctaggtggt tcctgagccc ccaccccaa tcccagtgct acacctgagg     14460
ttctggagct cagaatctga cagcctctcc cccattctgt gtgtgtcggg gggacagagg    14520
gaaccattta agaaaagata ccaaagtaga agtcaaaaga aagacatgtt ggctataggc    14580
gtggtggctc atgcctataa tcccagcact ttgggaagct ggggtaggag gatcaccaga    14640
ggccaggagg tccacaccag cctgggcaac acagcaagac accgcatcta cagaaaaatt    14700
ttaaaattag ctgggcgtgg tggtgtgtac ctgtaggcct agctgctcag gaggctgaag    14760
caggaggatc acttgagcct gagttcaaca ctgcagtgag ctatggtggc accactgcac    14820
tccagcctgg gtgacagagc aagaccctgt ctctaaaata aattttaaaa agacatatta    14880
cacttggacc ttggttagtc ttttctgtat gtaaattcaa cccatggggt gccctgagga    14940
ccacacgggg tggtggttgg cggggtggtg gttggtgggg tggtggctga cggggtggtg    15000
gctggcaggc cgagcctaga tggcagccag agcccaggc atgtgtctgg gcacaggacg     15060
gtgttgccta gtttgaacac cctctttgct ctgtcactcc tgcctccctt gggcgttcac    15120
attctcccat tgcttcatgc aagagctgct gagtggccta tatcagccag ctgttgccgc    15180
ataacaaaac catcccaaaa ctgagtgcag ggaggcaact tcacctcggg ctccactcca    15240
caagcccaag gggccaggtg agagtgctct ctaaagcccc ctcctgcctc agttgtagtt    15300
gcaaaatttt aatttatgaa ggtgactgat gacacagagg ccaatgctgt tgaaataagt    15360
tattactcac agtttcccac catgcagggc cacagtgggg aggcactagg tttggtccag    15420
ggacagaatc aggagcgagt ggaaggcaca ggccacagcc cacagtgccg tttccactgg    15480
```

```
ggaggcaagg caggccaggg gaagagggta ggattggcat tttgaatcat tctggtgggg    15540
tttggggcgt ggggttgggc tctaattgtc tgggtaggtg cctggccctg agctggttta    15600
gggcagggga aatactggtt tcgtatgtga gagttccttg aagggggtgg ttggtgtatg    15660
gactcaagac tggtcggttt gcatatgaaa ggcatgagtt gtttctgatc tccaggaatc    15720
aagcagtttc tctccagcca acaagccccc accccgagat gttaaaccat cataaaatag    15780
agaatctaag gccaggcatg gtggctcacg cctgtaatcc cagcactttg ggaggccaag    15840
gcgggaggat catttgaggt cagaagttcg agaccagcct ggccaatgtg gtgaaacccc    15900
atctctacta aaaatacaaa aattagcccg gtgtggtggc acgtgcctat aatcccagct    15960
actcgggagg ctgcggcagg agaattgttt gaacatggga ggtggaggtt gcagtgagct    16020
gagatcgtgc cactgcactc cagcctgggc aacaagagca agactccgtc tcaaaaaaaa    16080 aaaaaaaaa aagagagact ctaaaaatac acgttaatat acctcccccg ctcttaccct    16140
tcaggagggg gtgtctagac cccgcgggac tccagctaca agggaccctg ggaggccaa    16200 ctctgccctc ttggctaatc cccaagactg cccagcaccc cctccacccc ttctccattc    16260
agtggcgaac cctggggagg ccacgtggga aggaaagagg gctctaagag gggaggcccc    16320
agactggggg agaggcctgt ctggagccca ggatcacctg gctgtgctgc agaactggag    16380
aagagaagct cagcagaaag gagctggcat ggggccaaca gcagaaaagc aggaggcacg    16440
cagaagtgac tggaagcag gagggtaggc atggaccctg aggctgagca ggaggtactg    16500
aggggcagag tggacgctga gctgggggta gcgagcgagc ccagctcagc tgtgacgccc    16560 tctgttggc cacccaacta ccagctactt gggctgcccc gggaggaact gggcttcctc    16620
tgacattctg tggcctgcgg ccatctgtca caccttcttc tctctctgcc cctcccttga    16680
cttgtggcac ccacagacag gtgggagagt gtacctgccc tgtgtggtca gagcttggtt    16740
ttgagtttcc ttccctcacc cctctttcct cccacacgcc aaaacacaag aggatgtgtc    16800
agaggcctgt gaaccagagc aactccatcc tgaataggg ctgagcaaaa taaggctgag    16860
acctactggg ctgcgtttcc agacagttac agcattctgc gtcacaggat gagataggag    16920
atacaggtca taaagacctt gctgataaaa tagtttgcag taggccaggc gcggtagctc    16980
acgcctgtaa tcccagcact                                                17000
```

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
aactcttgaa atgagaagcg tg                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 9
aatatcatgc accatgaccc ac                                              22

<210> SEQ ID NO 10

```
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
tggagtaagt attgtaaact at                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
ggagcttatc ctggattatc ta                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
agagccacac atccatgtcc tg                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 13
aagccactct gtgaattgcc at                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 14
gagtagtcgt agtaccagat gg                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 15
gtctggcaat ggagcatgaa aa                                              22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 16
```

```
attagagcac atgaaggaaa gg                                              22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 17
acactgcttt gggggacagg ct                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
cacgacgcca cagagccagc tc                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 19
aaccaccacg gattcacgct tc                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 20
ataaccagat ggctgtgggt ca                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 21
atccccgcaa tgaaatagtt ta                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 22
gttgagagcc cacttagata at                                              22

<210> SEQ ID NO 23
<211> LENGTH: 22
<212> TYPE: DNA
```

```
<213> ORGANISM: Artificial Sequence
<220> FEATURE:
<223> OTHER INFORMATION: Description of Artificial Sequence: Primer

<400> SEQUENCE: 23
gcattggggg aagccaggac at                                              22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 24
gccactagga ggcaatggca at                                              22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 25
cgacggcatc acggccatct gg                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 26
tccaggctca ttcattttca tg                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 27
tgacatcaac ttctcctttc ct                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 28
agttgcagag acctagcctg tc                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 29
tctgggagag gacggagctg gc                                              22
```

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 30
tgtaggacta tattgctc                                           18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 31
cgacatttag gtgacact                                           18

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      linker adapter

<400> SEQUENCE: 32
gtcttcacca cggggg                                             15

<210> SEQ ID NO 33
<211> LENGTH: 11
<212> TYPE: DNA
<213> ORGANISM: Artificial Sequence
<220> FEATURE:
<223> OTHER INFORMATION: Description of Artificial Sequence: Synthetic
      linker adapter

<400> SEQUENCE: 33
gtggtgaaga c                                                  11

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 34
ctcgagaatt ctggatcctc                                         20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 35
ttgaggatcc agaattctcg ag                                      22

<210> SEQ ID NO 36

```
<211> LENGTH: 21
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 36
tgtatgcgaa ttcgctgcgc g                                              21

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 37
ttcgcgcagc gaattcgcat aca                                            23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 38
cctacggaat tctcactcag c                                              21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 39
ttgctgagtg agaattccgt agg                                            23

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 40
gaatccgaat tcctggtcag c                                              21

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 41
ttgctgacca ggaattcgga ttc                                            23

<210> SEQ ID NO 42
<211> LENGTH: 32
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42
cuacuacuac uactcgagaa ttctggatcc tc                                    32

<210> SEQ ID NO 43
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
cuacuacuac uatgtatgcg aattcgctgc gcg                                   33

<210> SEQ ID NO 44
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44
cuacuacuac uacctacgga attctcactc agc                                   33

<210> SEQ ID NO 45
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 45
cuacuacuac uagaatccga attcctggtc agc                                   33

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Met Ala His Glu Ile Gly His Ser Leu Gly Leu Ser His Asp Pro
  1               5                  10                  15

Asp

<210> SEQ ID NO 47
```

```
<211> LENGTH: 55
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Cys Phe Ala His Asn Cys Ser Leu Arg Pro Gly Ala Gln Cys Ala
  1               5                  10                  15

His Gly Asp Cys Cys Val Arg Cys Leu Leu Lys Pro Ala Gly Ala Leu
             20                  25                  30

Cys Arg Gln Ala Met Gly Asp Cys Asp Leu Pro Glu Phe Cys Thr Gly
         35                  40                  45

Thr Ser Ser His Cys Pro Pro
         50                  55

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Met Ala His Glu Ile Gly His Ser Leu Gly
  1               5                  10

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 49
tcacagctat gggctggag                                                19

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 50
ctgcctagag gccgagga                                                 18

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 51
cccctgtgtt cctcaggtc                                                19

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 52
gctccacact ctttcttgcc                                                20

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 53
aggcaggagg aagctgaat                                                 19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 54
cctacccctc tgcaccta                                                  19

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 55
aacttccttc tgggagctgg                                                20

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 56
caagccaccg ggatttct                                                  18

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 57
cacaccctgg tgaggagaga                                                20

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 58
ccacgaagga ccaccg                                                    16

<210> SEQ ID NO 59
<211> LENGTH: 17
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 59
gtgggtgcct ctgaccc                                                    17

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 60
cacgtgggtg cctctgac                                                   18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 61
ctcacgtggg tgcctctg                                                   18

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 62
agagacagga ggctctacgg                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 63
agagacagga ggctctacgg                                                 20

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 64
ctctacggcc gcagtgac                                                   18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 65
```

-continued gtccctccat gcccaatg                                              18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 66
caggttaagt cggctcgc                                              18

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 67
ctctctctgc cttccccac                                             19

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 68
tctactgtgg ggaagatggg                                            20

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 69
cccctctact tcctcccca                                             19

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 70
gaccttgggg ttcctaatcc                                            20

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 71
gtgcacctgc tcaggactc                                             19

<210> SEQ ID NO 72
<211> LENGTH: 19
<212> TYPE: DNA
<213> ORGANISM: Artificial Sequence

```
<220> FEATURE:
<223> OTHER INFORMATION: Description of Artificial Sequence: Primer

<400> SEQUENCE: 72
gtgcacctgc tcaggactc                                                19

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 73
cctggactct tatcacgttg c                                             21

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 74
ttaccctcca ccatttctcc                                               20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 75
ttcctggatc actggtcctc                                               20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 76
gagctctgag cagaacccat                                               20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 77
agctctgagc agaacccatc                                               20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 78
agtgacttgg tggttctggg                                               20
```

```
<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 79
tgtcatctgc accctctctg                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 80
aagagggagg gtgtggtagg                                              20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 81
atacagcatt cccactccca                                              20

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 82
gaaggcagaa atcccggt                                                18

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 83
cccttcctct tccccaaac                                               19

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 84
caccagcacc tgcctgtc                                                18

<210> SEQ ID NO 85
<211> LENGTH: 17
<212> TYPE: DNA
<213> ORGANISM: Artificial Sequence
<220> FEATURE:
<223> OTHER INFORMATION: Description of Artificial Sequence: Primer
```

<400> SEQUENCE: 85
gggtcagagg cacccac                          17

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 86
agagcctcct gtctctccct                       20

<210> SEQ ID NO 87
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 87
gggtcagagg cacccac                          17

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 88
gccgtagagc ctcctgtct                        19

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 89
aagtccccag gactagccg                        19

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 90
gaaactgagg gacgaccaaa                       20

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 91
gacgaccaaa gaaacgcag                        19

<210> SEQ ID NO 92

```
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 92
tgagcggaga gggcaagt                                                18

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 93
aaaccctcac cctgaacctt                                              20

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 94
aagggtgctc gtgtcctct                                               19

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 95
ccactcagct ccactcccta                                              20

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 96
ggattcaaac ggcaaggag                                               19

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 97
gctgagtcct gagcaggtg                                               19

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 98
```
gcaggagtag gctcaggaag                                          20

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 99
gaaccgcagg agtaggctc                                           19

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 100
atatggtcag caggagaccc                                          20

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 101
gcatcctggt ctccatgata a                                        21

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 102
cggtgattca ctggctctg                                           19

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 103
cctctcagga gtagaggccc                                          20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 104
agcggttctc tcctcctctc                                          20

<210> SEQ ID NO 105
<211> LENGTH: 18
<212> TYPE: DNA

```
<213> ORGANISM: Artificial Sequence
<220> FEATURE:
<223> OTHER INFORMATION: Description of Artificial Sequence: Primer

<400> SEQUENCE: 105
gcacggattc cctcctcc                                              18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 106
tccctggtgc ttcccata                                              18

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 107
ccactaccaa gggcgagtaa                                            20

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 108
cctcttgccc ctcttgct                                              18

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 109
ggcctcgagt cccagtattt                                            20

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 110
tcgccctcag cttctcag                                              18

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 111
tcacgtgggt gcctctga                                              18
```

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 112
gggttacttc ccctctctgg                                        20

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 113
cctgtcccgc ttgttgtgt                                         19

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 114
cgggctgctc actattgg                                          18

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 115
gcgaggttac tcctacaccg                                        20

<210> SEQ ID NO 116
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 116
tccaggtggt gaactctgc                                         19

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 117
gaccttgggg ttcctaatcc                                        20

<210> SEQ ID NO 118
<211> LENGTH: 20
<212> TYPE: DNA
<213> ORGANISM: Artificial Sequence
<220> FEATURE:

<223> OTHER INFORMATION: Description of Artificial Sequence: Primer

<400> SEQUENCE: 118
agagggtgac ttggagcaga                                              20

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 119
ccaagcacac ttgagcgtc                                               19

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 120
agccatgccc tctgcttt                                                18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 121
agccatgccc tctgcttt                                                18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 122
gagggagctc tttcccca                                                18

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 123
agttccaggt acttccgggt                                              20

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 124
aaccccagct cccagaag                                                18

```
<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 125
actgcaggaa ggcccagag                                                      19

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 126
tgagggacga ccaaagaaac                                                     20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 127
caaagtcaca caacaagcgg                                                     20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 128
gaacctgagg gcaccaatta                                                     20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 129
acgtgcagtg agaggtccat                                                     20

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 130
gagaggtcca tgccgaga                                                       18

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Primer
```

<400> SEQUENCE: 131
aaggttcagg gtgagggttt                                                       20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 132
ctggagcaca gtggcagtta                                                       20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 133
tgtactggga ggtagagggc                                                       20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 134
ccagaaacct gattaggggg                                                       20

<210> SEQ ID NO 135
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 135
gtgcttccca tattcacatc tcccacaact aagccatcac                                 40

<210> SEQ ID NO 136
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 136
gtgcttccca tattcacacc tcccacaact aagccatcac                                 40

<210> SEQ ID NO 137
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 137
aactaagcca tcaccaaggc tccttcctct agccccaag                                  39

<210> SEQ ID NO 138
<211> LENGTH: 39

```
<212> TYPE: DNA
<213> ORGANISM: Artificial Sequence
<220> FEATURE:
<223> OTHER INFORMATION: Description of Artificial Sequence: Primer

<400> SEQUENCE: 138
aactaagcca tcaccaagcc tccttcctct agccccaag                              39

<210> SEQ ID NO 139
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 139
ggatacatag aaacccacta cggcccagat gggcagcca                              39

<210> SEQ ID NO 140
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 140
ggatacatag aaacccacca cggcccagat gggcagcca                              39

<210> SEQ ID NO 141
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 141
ctgctcacct ggaaaggaac ctgtggccac agggatcct                              39

<210> SEQ ID NO 142
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 142
ctgctcacct ggaaaggagc ctgtggccac agggatcct                              39

<210> SEQ ID NO 143
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 143
ctccaaatca gaagagacag gaattcacag gcctcgagt                              39

<210> SEQ ID NO 144
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 144
```

-continued ctccaaatca gaagagacgg gaattcacag gcctcgagt          39

<210> SEQ ID NO 145
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 145
cctgcagtgg cgccgggggc tgtgggcgca gcggcccca          39

<210> SEQ ID NO 146
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 146
cctgcagtgg cgccggggac tgtgggcgca gcggcccca          39

<210> SEQ ID NO 147
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 147
ccctctctgg gctctgcgcg tctggcggct gtagccaag          39

<210> SEQ ID NO 148
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 148
ccctctctgg gctctgcgca tctggcggct gtagccaag          39

<210> SEQ ID NO 149
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 149
gagaagcgcg ggggttgggg gactgtccct ccatgccca          39

<210> SEQ ID NO 150
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 150
gagaagcgcg ggggttggag gactgtccct ccatgccca          39

<210> SEQ ID NO 151
<211> LENGTH: 39
<212> TYPE: DNA
<213> ORGANISM: Artificial Sequence

```
<220> FEATURE:
<223> OTHER INFORMATION: Description of Artificial Sequence: Primer

<400> SEQUENCE: 151
agccgccgcc agctgcgcgc cttcttccgc aaggggggc                              39

<210> SEQ ID NO 152
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 152
agccgccgcc agctgcgcgt cttcttccgc aagggggc                               39

<210> SEQ ID NO 153
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 153
gttcagggtg agggtttcgg ggagcttggg agccggcct                              39

<210> SEQ ID NO 154
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 154
gttcagggtg agggtttcgt ggagcttggg agccggcct                              39

<210> SEQ ID NO 155
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 155
tgagctctgc ccacccgacc cctccttgcc gtttgaatcc                             40

<210> SEQ ID NO 156
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 156
tgagctctgc ccacccgact cctccttgcc gtttgaatcc                             40

<210> SEQ ID NO 157
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 157
gctggccatg ctcctcagcg tcctgctgcc tctgctccca                             40
```

```
<210> SEQ ID NO 158
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 158
gctggccatg ctcctcagca tcctgctgcc tctgctccca                          40

<210> SEQ ID NO 159
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 159
tcctgctgcc tctgctccca ggggccggcc tggcctggtg                          40

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 160
tcctgctgcc tctgctccca ggcgccggcc tggcctggtg                          40

<210> SEQ ID NO 161
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 161
gtggcctccc agtcaagcga gggggtggat ccctgcccc                           39

<210> SEQ ID NO 162
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 162
gtggcctccc agtcaagcgt gggggtggat ccctgcccc                           39

<210> SEQ ID NO 163
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 163
ctgggcggcg ttcaccccat ggagttgggc cccacagcc                           39

<210> SEQ ID NO 164
<211> LENGTH: 39
<212> TYPE: DNA
<213> ORGANISM: Artificial Sequence
<220> FEATURE:
<223> OTHER INFORMATION: Description of Artificial Sequence: Primer
```

```
<400> SEQUENCE: 164
ctgggcggcg ttcaccccac ggagttgggc cccacagcc                    39

<210> SEQ ID NO 165
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 165
agttgggccc cacagccact ggacagccct ggcccctgg                    39

<210> SEQ ID NO 166
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 166
agttgggccc cacagccact ggacagtcct ggcccctgg                    39

<210> SEQ ID NO 167
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 167
gggctcatgc ctcctgcctc cttccagatg ggcagcaccc                   40

<210> SEQ ID NO 168
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 168
gggctcatgc ctcctgcctt cttccagatg ggcagcaccc                   40

<210> SEQ ID NO 169
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 169
tatgcccctc cccagcccca gggtctcctg ctgaccatat                   40

<210> SEQ ID NO 170
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 170
tatgcccctc cccagcccca ggggctcctg ctgaccatat                   40
```

HUMAN GENE RELATING TO RESPIRATORY DISEASES AND OBESITY

RELATED APPLICATIONS

This application claims the benefit of U.S. Provisional Application Serial No. 60/129,391, filed Apr. 13, 1999, the entire teachings of which are incorporated herein by reference.

FIELD OF THE INVENTION

The present invention relates generally to isolated nucleic acids and the classification of the same. The invention more particularly relates to a novel gene and novel nucleic acids related to asthma and other respiratory diseases and the classification and therapeutic and diagnostic uses of this gene.

BACKGROUND

Mouse chromosome 2 has been linked to a variety of disorders including airway hyperesponsiveness and obesity (DeSanctis et al., *Nature Genetics*, 11: 150–154 (1995)); (Nagle et al., *Nature*, 398: 148–152 (1999)). This region of the mouse genome is homologous to portions of human chromosome 20 including 20p13-p12. Although human chromosome 20p13-12p has been linked to a variety of genetic disorders including diabetes insipidus, neurohypophyseal, congenital endothelial dystrophy of cornea, insomnia, neurodegeneration with brain iron accumulation 1 (Hallervorden-Spatz syndrome), fibrodysplasia ossificans progressiva, alagille syndrome, hydrometrocolpos (McKusick-Kaufman syndrome), Creutzfeldt-Jakob disease and Gerstmann-Straussler disease (See National Center for Biotechnology Information: http://www.ncbi.nlm.nih.gov/omim/), the genes affecting these disorders have yet to be discovered. There is a need in the art for identifying specific genes for such disorders because they are also associated with obesity, lung disease, particularly, inflammatory lung disease phenotypes such as Chronic Obstructive Lung Disease (COPD), Adult Respiratory Distress Syndrome (ARDS), and asthma. Identification and characterization of such genetic compositions will make possible the development of effective diagnostics and therapeutic means to treat lung related disorders.

SUMMARY OF THE INVENTION

This invention relates to Gene 216 located on chromosome 20p13-p12. Nucleic acids comprising all or a part of, or complementary fragments of Gene 216 and cDNA are described in various embodiments. Vectors and host cells containing the nucleic acids herein described are also included in this invention. These nucleic acids can be used in therapeutic applications for a multitude of diseases either through the overexpression of a recombinant nucleic acid comprising all or a portion of a Gene 216 gene, or by the use of these oligonucleotides and genes to modulate the expression of an endogenous gene or the activity of an endogenous gene product. Examples of therapeutic approaches include anti-sense inhibition of gene expression, gene therapy, monoclonal antibodies that specifically bind to the gene products, and the like. In vitro expression of the recombinant gene products can also be obtained.

Diagnostic methods are also described which utilize all or part of the nucleic acids of this invention. Such nucleic acids can be used, for example, as part of diagnostic methods to identify Gene 216 nucleic acids to screen for a predisposition to various genetic diseases. In addition, nucleic acids described herein can be used to identify chromosomal abnormalities within chromosomal regions 20p13-p12.

Further, this invention identifies various single nucleotide polymorphisms (SNPs) within several of the nucleic acids described herein. These polymorphisms also comprise changes to the polypeptides of the present invention. The SNPs, together with the wild-type alleles can be used to prepare specific probes for detection of various disease states in an individual. Thus, in one embodiment, this invention provides a method of detecting chromosome abnormalities on chromosome 20p13-p12.

Proteins, polypeptides, and peptides encoded by all or a part of the nucleic acids comprising Gene 216 are included in this invention. Such amino acid sequences are useful for diagnostic and therapeutic purposes. Further, antibodies can be raised against all or a part of these amino acid sequences for specific diagnostic and therapeutic methods requiring such antibodies. These antibodies can be polyclonal, monoclonal, or antibody fragments.

In a further embodiment, vectors and host cells containing vectors which comprise all or a portion of the nucleic acid sequences of this invention can be constructed for nucleic acid preparations, including anti-sense, and/or for expression of encoded proteins and polypeptides. Such host cells can be prokaryotic or eukaryotic cells.

Still another embodiment of the invention comprises a method of identifying a protein which is a candidate for being involved in asthma (a "candidate protein"). Candidate proteins are identified by a process comprising identifying a protein in a first individual having the asthma phenotype; (ii) identifying a protein in a second individual not having the asthma phenotype; comparing the protein of the first individual to the protein of the second individual, wherein (a) the protein that is present in the second individual but not the first individual is the candidate protein or (b) the protein that is present in a higher amount in the second individual than in the first individual is the candidate protein or (c) the protein that is present in a lower amount in the second individual than in the first individual is the candidate protein.

This invention also includes nonhuman transgenic animals containing one or more of the nucleic acids of this invention for screening and other purposes. Further, knockout nonhuman transgenic animals can be produced wherein one or more endogenous genes or portions of such genes corresponding to the nucleic acids of this invention are replaced by marker genes or are deleted.

BRIEF DESCRIPTION OF THE FIGURES

FIG. 1 shows the plot of multipoint LOD score against the map location of the markers along chromosome 20.

FIG. 2A–2B depict the BAC/STS content contig map 20p13-p12 containing BAC RPCI 11-1098L22.

FIGS. 3A–3F depict the partial nucleotide and amino acid sequence of Gene 216a.

FIGS. 4A–4F depict the partial nucleotide and amino acid sequence of Gene 216b.

FIGS. 5A–5G depict the partial nucleotide and amino acid sequence of Gene 216c.

FIGS. 7A–7B depict the nucleotide sequence of the predicted exons of Gene 216a.

FIGS. 8A–8B depict the nucleotide sequence of the predicted exons of Gene 216b.

FIGS. 9A–9B depict the nucleotide sequence of the predicted exons of Gene 216c.

FIGS. 11A–D show a comparison of Gene 216a, Gene 216b, and Gene 216c and the ADAM family of genes.

FIGS. 12A–12B show a comparison of Gene 216a-protein, Gene 216b-protein and Gene 216c-protein and the mouse homolog of Gene 216.

FIGS. 18A–18G depict the nucleotide sequence of the mouse homolog of Gene 216.

FIG. 19 depicts the amino acid sequence of the mouse homolog of Gene 216.

FIGS. 20A–20G depict the genomic sequence of Gene 216.

DETAILED DESCRIPTION OF THE INVENTION

Figure 6:
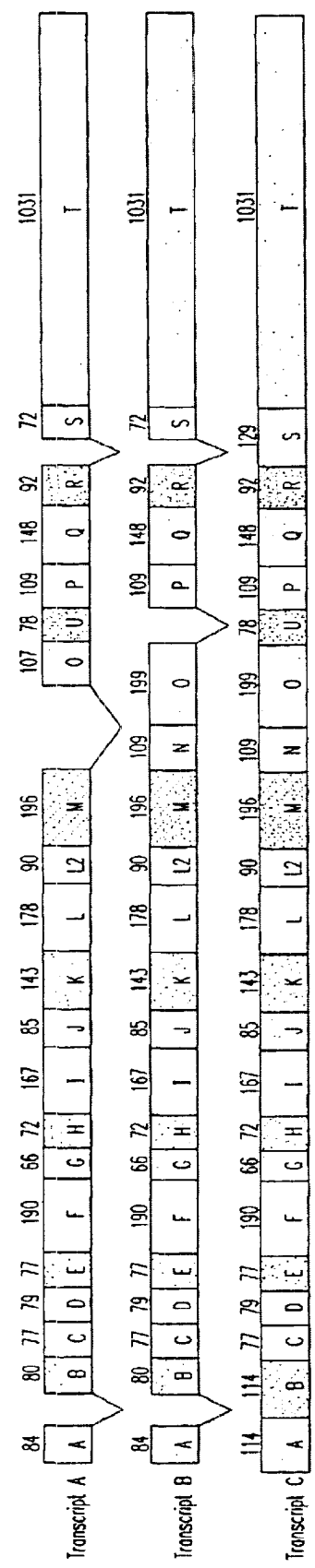
FIG. 6 shows a schematic view of the exons of Gene 216a, 216b and 216c.

The present invention relates to Gene 216 nucleic acids comprising genomic DNA within BAC RPCI_1098L22, the corresponding cDNA sequences, RNA, fragments of the genomic, cDNA, or RNA nucleic acids comprising 20, 40, 60, 100, 200, 500 or more contiguous nucleotides, and the complements thereof. Closely related variants are also included as part of this invention, as well as recombinant nucleic acids comprising at least 50, 60, 70, 80, or 90% of the nucleic acids described above which would be identical to a Gene 216 nucleic acids except for one or a few substitutions, deletions, or additions.

Further, the nucleic acids of this invention include the adjacent chromosomal regions of Gene 216 required for accurate expression of the respective gene. In a preferred embodiment, the present invention is directed to at least 15 contiguous nucleotides of the nucleic acid sequence of any of SEQ ID NO:1–SEQ ID NO:3. More particularly, embodiments of this invention include the BAC clone containing segments of Gene 216 including RPCI_1098L22. A preferred embodiment is the nucleotide sequence of the BAC clones consisting of SEQ ID NO:7 (FIGS. 20A–20G).

This invention further relates to methods using isolated and/or recombinant nucleic acids (DNA or RNA) that are characterized by their ability to hybridize to (a) a nucleic acid encoding a protein or polypeptide, such as a nucleic acid having any of the sequences of SEQ ID NO:1–SEQ ID NO:3 or (b) a portion of the foregoing (erg., a portion comprising the minimum nucleotides of the Gene 216 nucleic acid code a functional Gene 216 protein or the minimum number to inhibit an endogenous Gene 216; or by their ability.to encode a polypeptide having the amino acid sequence of SEQ ID NO:4–SEQ ID NO:6, or to encode functional equivalents thereof; e.g., a polypeptide which when incorporated into a cell, has all or part of the activity of a Gene 216 protein, or by both characteristics. A functional equivalent of a Gene 216 protein, therefore, would have a similar amino acid sequence (at least 65% sequence identity) and similar characteristics to, or perform in substantially the same way as Gene 216 protein. A nucleic acid which hybridizes to a nucleic acid encoding a Gene 216 protein or polypeptide, such as SEQ ID NO:1–SEQ ID NO:3 can be double- or single-stranded. Hybridization to DNA such as DNA having the sequence SEQ ID NO:1–SEQ ID NO:3 includes hybridization to the strand shown or its complementary strand.

In one embodiment, the percent amino acid sequence similarity between a Gene 216 polypeptide such as SEQ ID NO:4–SEQ ID NO:6, and functional equivalents thereof is at least about 50%. In a preferred embodiment, the percent amino acid sequence similarity between such a Gene 216 polypeptide and its functional equivalents is at least about 65%. More preferably, the percent amino acid sequence similarity between a Gene 216 polypeptide and its functional equivalents is at least about 75%, and still more preferably, at least about 80%.

To determine percent nucleotide or amino acid sequence similarity, sequences can be compared to publicly available sequence databases (National Center for Biotechnology Information, National Library of Medicine, 38A, 8N905, 8600 Rockville Pike, Bethesda, Md. 20894; www.ncbi.nlm.nih.gov) using the blastn2 algorithm (Altsch, *Nucl. Acids Res.*, 25:3389–3402 (1997)). The parameters for a typical search are: E=0.05, v=50, B=50 (where E is the expected probability score cutoff, V is the number of database entries returned in the reporting of the results, and B is the number of sequence alignments returned in the reporting of the results (Altsch et al, *J. Mol. Biol.*, 215:403–410 (1990)).

Isolated and/or recombinant nucleic acids meeting these criteria comprise nucleic acids having sequences identical to sequences of naturally occurring Gene 216 genes such as Gene 216a, Gene 216b, Gene 216c, and portions thereof, or variants of the naturally occurring genes. Such variants include mutants differing by the addition, deletion or substitution of one or more nucleotides, modified nucleic acids in which one or more nucleotides are modified (e.g., DNA or RNA analogs), and mutants comprising one or more modified nucleotides including repeated fragments.

Such nucleic acids, including DNA or RNA, can be detected and isolated by hybridization under high stringency conditions or moderate stringency conditions, for example, which are chosen so as to not permit the hybridization of nucleic acids having non-complementary sequences. "Stringency conditions" for hybridizations is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

High stringency hybridization procedures (1) employ low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) employ during hybridization 50% (vol/vol) formamide with 5×Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5×SSC at 42° C.; or (3) employ hybridization with 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

By varying hybridization conditions from a level of stringency at which no hybridization occurs to a level at which hybridization is first observed, conditions which will allow a given sequence to hybridize with the most similar sequences in the sample can be determined. Preferably the hybridizing sequences will have 60–70% sequence identity, more preferably 70–85% sequence identity, and even more preferably 90–100% sequence identity.

Exemplary conditions are described in Krause, M. H. and S. A. Aaronson (1991) *Methods in Enzymology*, 200:546–556. Also, see especially page 2.10.11 in *Current Protocols in Molecular Biology* (supra), which describes how to determine washing conditions for moderate or low stringency conditions. Washing is the step in which conditions are usually set so as to determine a minimum level of complementarity of the hybrids. Generally, from the lowest temperature at which only homologous hybridization occurs, a 1% mismatch between hybridizing nucleic acids results in a 1° C. decrease in the melting temperature $T_m$, for any chosen SSC concentration. Generally, doubling the concentration of SSC results in an increase in $T_m$ of ~17° C. Using these guidelines, the washing temperature can be determined empirically for moderate or low stringency, depending on the level of mismatch sought.

Isolated and/or recombinant nucleic acids that are characterized by their ability to hybridize to (a) a nucleic acid encoding a Gene 216 polypeptide, such as the nucleic acids depicted as SEQ ID NO:1–SEQ ID NO:3, b) the complement, (c) or a portion of (a) or (b) (e.g. under high or moderate-stringency conditions), may further encode a protein or polypeptide having at least one function characteristic of a Gene 216 polypeptide, such as proteolysis, adhesion, fusion, and intracellular activity, or binding of antibodies that also bind to non-recombinant Gene 216 protein or polypeptide. The catalytic or binding function of a protein or polypeptide encoded by the hybridizing nucleic acid may be detected by standard enzymatic assays for activity or binding (e.g., assays which measure the binding of a transit peptide or a precursor, or other components of the translocation machinery). Enzymatic assays, complementation tests, or other suitable methods can also be used in procedures for the identification and/or isolation of nucleic acids which encode a polypeptide such as a polypeptide of the amino acid sequences SEQ ID NO:4–SEQ ID NO:6, or a functional equivalent of this polypeptide. The antigenic properties of proteins or polypeptides encoded by hybridizing nucleic acids can be determined by immunological methods employing antibodies that bind to a Gene 216 polypeptide such as immunoblot, immunoprecipitation and radioimmunoassay. PCR methodology, including RAGE (Rapid Amplification of Genomic DNA Ends), can also be used to screen for and detect the presence of nucleic acids which encode Gene 216-like proteins and polypeptides, and to assist in cloning such nucleic acids from genomic DNA. PCR methods for these purposes can be found in Innis, M. A., et al. (1990) *PCR Protocols: A Guide to Methods and Applications*, Academic Press, Inc., San Diego, Calif., incorporated herein by reference.

It is understood that, as a result of the degeneracy of the genetic code, many nucleic acid sequences are possible which encode a Gene 216-like protein or polypeptide. Some of these will have little homology to the nucleotide sequences of any known or naturally-occurring Gene 216-like gene but can be used to produce the proteins and polypeptides of this invention by selection of combinations of nucleotide triplets based on codon choices. Such variants, while not hybridizable to a naturally-occurring Gene 216 gene, are contemplated within this invention.

The nucleic acids described herein are used in the methods of the present invention for production of proteins or polypeptides, through incorporation into cells, tissues, or organisms. In one embodiment, DNA containing all or part of the coding sequence for a Gene 216 polypeptide, or DNA which hybridizes to DNA having the sequence SEQ ID NO:1–SEQ ID NO:3, is incorporated into a vector for expression of the encoded polypeptide in suitable host cells. The encoded polypeptide consisting of Gene 216, or its functional equivalent is capable of normal activity, such as proteolysis, adhesion, fusion, and intracellular activity. The term "vector" as used herein refers to a nucleic acid molecule capable of replicating another nucleic acid to which it has been linked. A vector, for example, can be a plasmid.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated", as used herein, refers to nucleic or amino acid sequences that are at least 60% free, preferably 75% free, and most preferably 90% free from other components with which they are naturally associated. "Isolated" nucleic acids (polynucleotides) include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial replication, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event. Portions of the isolated nucleic acids which code for polypeptides having a certain function can be identified and isolated by, for example, the method of Jasin, M., et al., U.S. Pat. No. 4,952,501.

A further embodiment of the invention is antisense nucleic acids or oligonucleotides which are complementary, in whole or in part, to a target molecule comprising a sense strand, and can hybridize with the target molecule. The target can be DNA, or its RNA counterpart (i.e., wherein T residues of the DNA are U residues in the RNA counterpart).

When introduced into a cell, antisense nucleic acids or oligonucleotides can inhibit the expression of the gene encoded by the sense strand or the mRNA transcribed from the sense strand. Antisense nucleic acids can be produced by standard techniques. See, for example, Shewmaker, et al., U.S. Pat. No. 5,107,065.

In a particular embodiment, an antisense nucleic acid or oligonucleotide is wholly or partially complementary to and can hybridize with a target nucleic acid (either DNA or RNA), wherein the target nucleic acid can hybridize to a nucleic acid having the sequence of the complement of the strand in SEQ ID NO:1–SEQ ID NO:3. For example, an antisense nucleic acid or oligonucleotide can be complementary to a target nucleic acid having the sequence shown as the strand of the open reading frame of SEQ ID NO:1–SEQ ID NO:3 or nucleic acid encoding a functional equivalent of Gene 216, or to a portion of these nucleic acids sufficient to allow hybridization. A portion, for example a sequence of 16 nucleotides, could be sufficient to inhibit expression of the protein. Or, an antisense nucleic acid or oligonucleotide, complementary to 5' or 3' untranslated regions, or overlapping the translation initiation codon (5' untranslated and translated regions), of the Gene 216 gene, or a gene encoding a functional equivalent can also be effective. In another embodiment, the antisense nucleic acid is wholly or partially complementary to and can hybridize with a target nucleic acid which encodes a Gene 216 polypeptide.

In addition to the antisense nucleic acids of the invention, oligonucleotides can be constructed which will bind to duplex nucleic acid either in the gene or the DNA:RNA complex of transcription, to form a stable triple helix-containing or triplex nucleic acid to inhibit transcription and/or expression of a gene encoding Gene 216, or its functional equivalent (Frank-Kamenetskii, M. D. and Mirkin, S. M. (1995) *Ann. Rev. Biochem.* 64:65–95.) Such oligonucleotides of the invention are constructed using the base-pairing rules of triple helix formation and the nucleotide sequence of the gene or mRNA for Gene 216. These oligonucleotides can block Gene 216 -type activity in a number of ways, including prevention of transcription of the Gene 216 gene or by binding to mRNA as it is transcribed by the gene.

The invention also relates to proteins or polypeptides encoded by the novel nucleic acids described herein. The proteins and polypeptides of this invention can be isolated and/or recombinant. Proteins or polypeptides referred to herein as "isolated" are proteins or polypeptides purified to a state beyond that in which they exist in cells. In a preferred embodiment, they are at least 10% pure; i.e., most preferably they are substantially purified to 80 or 90% purity. "Isolated" proteins or polypeptides include proteins or polypeptides obtained by methods described infra, similar methods or other suitable methods, and include essentially pure proteins or polypeptides, proteins or polypeptides produced by chemical synthesis or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of a Gene 216 protein or polypeptide, for example, proteolysis, adhesion, fusion, and intracellular activity in the case of Gene 216 analogs, and/or antigenic function (e.g., binding of antibodies that also bind to naturally occurring Gene 216 polypeptide). As such, these proteins are referred to as analogs, and include, for example, naturally occurring Gene 216, variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues. The variant can have "conservative" changes, wherein a substituted amino acid has similar structural or chemical properties, e.g., replacement of leucine with isoleucine. More infrequently, a variant can have "nonconservative" changes, e.g., replacement of a glycine with a tryptophan. Guidance in determining which amino acid residues can be substituted, inserted, or deleted without abolishing biological or immunological activity can be found using computer programs well known in the art, for example, DNASTAR software (DNASTAR, Inc., Madison, Wis. 53715 U.S.A.).

A "portion" as used herein with regard to a protein or polypeptide, refers to fragments of that protein or polypeptide. The fragments can range in size from 5 amino acid residues to all but one residue of the entire protein sequence. Thus, a portion or fragment can be at least 5, 5–50, 50–100, 100–200, 200–400, 400–800, or more consecutive amino acid residues of a Gene 216 protein or polypeptide, for example, SEQ ID NO:4–SEQ ID NO:6, or a variant thereof.

The invention also relates to isolated, synthesized and/or recombinant portions or fragments of a Gene 216 protein or polypeptide as described above. Polypeptide fragments of the enzyme can be made which have full or partial function on their own, or which when mixed together (though fully, partially, or nonfunctional alone), spontaneously assemble with one or more other polypeptides to reconstitute a functional protein having at least one functional characteristic of a Gene 216 protein of this invention.

The invention also concerns the use of the nucleotide sequence of the nucleic acids of this invention to identify DNA probes for Gene 216 genes, PCR primers to amplify Gene 216 genes, nucleotide polymorphisms in Gene 216 genes, and regulatory elements of the Gene 216 genes.

Gene 216 was isolated by narrowly defining the region of chromosome 20p13-p12 which was associated with airway hyperresponsiveness, asthma and atopy. Gene 216 is also important in other diseases such as obesity and thus, there was a need to identify and isolate the gene.

To aid in the understanding of the specification and claims, the following definitions are provided.

"Disorder region" refers to a portion of the human chromosome 20 bounded by the markers D20S502 and D20S851. A "disorder-associated" nucleic acid or polypeptide sequence "derived from" refers to a nucleic acid sequence that maps to region 20p13-p12 and polypeptides encoded therein. For nucleic acid sequences, this encompasses sequences that are homologous or complementary to the sequence, as well as "sequence-conservative variants" and "function-conservative variants." For polypeptide sequences, this encompasses "function-conservative variants." Included are naturally-occurring mutations causative of respiratory diseases or obesity, such as but not limited to mutations which cause inappropriate expression (e.g., lack of expression, over-expression, expression in an inappropriate tissue type). "Sequence-conservative" variants are those in which a change of one or more nucleotides in a given codon position results in no alteration in the amino acid encoded at that position. "Function-conservative" variants are those in which a change in one or more nucleotides in a given codon position results in a polypeptide sequence in which a given amino acid residue in a polypeptide has been changed without substantially altering the overall conformation and function of the native polypeptide, including, but not limited to, replacement of an amino acid with one having similar physico-chemical properties (such as, for example, acidic, basic, hydrophobic, and the like). "Function-conservative" variants also include analogs of a given polypeptide and any polypeptides that have the ability to elicit antibodies specific to a designated polypeptide.

"Nucleic acid or "polynucleotide" as used herein refers to purine-and pyrimidine-containing polymers of any length, either polyribonucleotides or polydeoxyribonucleotide or mixed polyribo-polydeoxyribo nucleotides. This includes single-and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" of a nucleic acid sequence as used herein refers to the "antisense" sequence that participates in Watson-Crick base-pairing with the original sequence.

A "probe" refers to a nucleic acid or oligonucleotide that forms a hybrid structure with a sequence in a target region due to complementarily of at least one sequence in the probe with a sequence in the target region.

Nucleic acids are "hybridizable" to each other when at least one strand of nucleic acid can anneal to another nucleic acid strand under defined stringency conditions. As is well known in the art, stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarily, variables well known in the art.

An "immunogenic component", is a moiety that is capable of eliciting a humoral and/or cellular immune response in a host animal.

An "antigenic component" is a moiety that binds to its specific antibody with sufficiently high affinity to form a detectable antigen-antibody complex.

A "sample" as used herein refers to a biological sample, such as, for example, tissue or fluid isolated from an individual (including without limitation plasma, serum, cerebrospinal fluid, lymph, tears, saliva, milk, pus, and tissue exudates and secretions) or from in vitro cell culture constituents, as well as samples obtained from eg., a laboratory procedure.

"Gene" refers to a DNA sequence that encodes through its template or messenger RNA a sequence of amino acids characteristic of a specific peptide, polypeptide or protein. The term "gene" as used herein with reference to genomic DNA includes intervening, non-coding regions, as well as regulatory regions, and can include 5' and 3' ends.

"Gene sequence" refers to a DNA molecule, including both a DNA molecule which contains a non-transcribed or non-translated sequence. The term is also intended to include any combination of gene(s), gene fragment(s), non-transcribed sequence(s) or non-translated sequence(s) which are present on the same DNA molecule.

A gene sequence is "wild-type" if such sequence is usually found in individuals unaffected by the disease or condition of interest. However, environmental factors and other genes can also play an important role in the ultimate determination of the disease. In the context of complex diseases involving multiple genes ("oligogenic disease"), the "wild type" or normal sequence can also be associated with a measurable risk or susceptibility, receiving its reference status based on its frequency in the general population.

A gene sequence is a "mutant" sequence if it differs from the wild-type sequence. In some cases, the individual carrying such gene has increased susceptibility toward the disease or condition of interest. In other cases, the "mutant" sequence might also refer to a sequence that decreases the susceptibilty toward a disease or condition of interest, and thus acting in a protective manner. Also a gene is a "mutant" gene if too much ("overexpressed") or too little ("underexpressed") of such gene is expressed in the tissues in which such gene is normally expressed, thereby causing the disease or condition of interest.

A gene sequence is a "variant" sequence if it is substantially similar in structure to either the entire gene or to a fragment of the gene. Both wild-type genes and mutant genes have variant sequences.

The sequences of the present invention may be derived from a variety of sources including DNA, cDNA, synthetic DNA, synthetic RNA or combinations thereof. Such sequences may comprise genomic DNA which may or may not include naturally occurring introns. Moreover, such genomic DNA may be obtained in association with promoter regions or poly (A) sequences. The sequences, genomic DNA or cDNA may be obtained in any of several ways. Genomic DNA can be extracted and purified from suitable cells by means well known in the art. Alternatively, mRNA can be isolated from a cell and used to produce cDNA by reverse transcription or other means.

"cDNA" refers to complementary or copy DNA produced from an RNA template by the action of RNA-dependent DNA polymerase (reverse transcriptase). Thus, a "cDNA clone" means a duplex DNA sequence complementary to an RNA molecule of interest, carried in a cloning vector or PCR amplified. This term includes genes from which the intervening sequences have been removed.

"Recombinant DNA" means a molecule that has been recombined by in vitro splicing/and includes cDNA or a genomic DNA sequence.

"Cloning" refers to the use of in vitro recombination techniques to insert a particular gene or other DNA sequence into a vector molecule. In order to successfully clone a desired gene, it is necessary to use methods for generating DNA fragments, for joining the fragments to vector molecules, for introducing the composite DNA molecule into a host cell in which it can replicate, and for selecting the clone having the target gene from amongst the recipient host cells.

"cDNA library" refers to a collection of recombinant DNA molecules containing cDNA inserts which together comprise the entire genome of an organism. Such a cDNA library can be prepared by methods known to one skilled in the art and described by, for example, Cowell and Austin, "cDNA Library Protocols," Methods in Molecular Biology (1997). Generally, RNA is first isolated from the cells of an organism from whose genome it is desired to clone a particular gene.

"Cloning vehicle" refers to a plasmid or phage DNA or other DNA sequence which is able to replicate in a host cell. The cloning vehicle is characterized by one or more endonuclease recognition sites at which such DNA sequences may be cut in a determinable fashion without loss of an essential biological function of the DNA, which may contain a marker suitable for use in the identification of transformed cells.

"Expression control sequence" refers to a sequence of nucleotides that control or regulate expression of structural genes when operably linked to those genes. These include, for example, the lac systems, the trp system, major operator and promoter regions of the phage lambda, the control region of fd coat protein and other sequences known to control the expression of genes in prokaryotic or eukaryotic cells. Expression control sequences will vary depending on whether the vector is designed to express the operably linked gene in a prokaryotic or eukaryotic host, and may contain transcriptional elements such as enhancer elements, termination sequences, tissue-specificity elements and/or translational initiation and termination sites.

"Expression vehicle" refers to a vehicle or vector similar to a cloning vehicle but which is capable of expressing a gene which has been cloned into it, after transformation into a host. The cloned gene is usually placed under the control of (i.e., operably linked to) an expression control sequence.

"Operably linked" means that the promoter controls the initiation of expression of the gene. A promoter is operably linked to a sequence of proximal DNA if upon introduction into a host cell the promoter determines the transcription of the proximal DNA sequence(s) into one or more species of RNA. A promoter is operably linked to a DNA sequence if the promoter is capable of initiating transcription of that DNA sequence.

"Host" includes prokaryotes and eukaryotes. The term includes an organism or cell that is the recipient of a replicable expression vehicle.

"Amplification of nucleic acids" refers to methods such as polymerase chain reaction (PCR), ligation amplification (or ligase chain reaction, LCR) and amplification methods based on the use of Q-beta replicase. These methods are well known in the art and described, for example, in U.S. Pat. Nos. 4,683,195 and 4,683,202. Reagents and hardware for conducting PCR are commercially available. Primers useful for amplifying sequences from the disorder region are preferably complementary to, and preferably hybridize specifically to, sequences in the 20p13-p12 region or in regions that flank a target region therein. Gene 216 generated by amplification may be sequenced directly. Alternatively, the amplified sequence(s) may be cloned prior to sequence analysis.

"Antibodies" refer to polyclonal and/or monoclonal antibodies and fragments thereof, and immunologic binding equivalents thereof, that can bind to asthma proteins and fragments thereof or to nucleic acid sequences from the 20p13-p12 region, particularly from the asthma locus or a portion thereof. The term antibody is used-both to refer to a homogeneous molecular entity, or a mixture such as a serum product made up of a plurality of different molecular entities. Proteins may be prepared synthetically in a protein synthesizer and coupled to a carrier molecule and injected over several months into rabbits. Rabbit sera is tested for immunoreactivity to the protein or fragment. Monoclonal antibodies may be made by injecting mice with the proteins, or fragments thereof. Monoclonal antibodies will be screened by ELISA and tested for specific immunoreactivity with protein or fragments thereof. (Harlow et al, *Antibodies: A Laboratory Manual*, Cold Spring Harbor Laboratory, Cold Spring Harbor, N.Y. (1988.) These antibodies will be useful assays as well as pharmaceuticals.

A nucleic acid or fragment thereof is "substantially homologous" or "substantially similar" to another if, when optimally aligned (with appropriate nucleotide insertions and/or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or similarity exists when a nucleic acid or fragment thereof will hybridize, under selective hybridization conditions, to another nucleic acid (or a complementary strand thereof). Selectivity of hybridization exists when hybridization which is substantially more selective than total lack of specificity occurs. Typically, selective hybridization will occur when there is at least about 55% homology over a stretch of at least about nine or more nucleotides, preferably at least about 65%, more preferably at least about 75%, and most preferably at least about 90%. (See, Kanehisa, 1984.) The length of homology comparison, as described, may be over longer stretches, and in certain embodiments will often be over a stretch of at least about 14 nucleotides, usually at least about 20 nucleotides, more usually at least about 24 nucleotides, typically at least about 28 nucleotides, more typically at least about 32 nucleotides, and preferably at least about 36 or more nucleotides.

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., *Molecular Cloning: A Laboratory Manual*, 2d Ed., Cold Spring Harbor Laboratory Press, Planview, N.Y. (1989); Kaufman, P. B., et al., Eds., *Handbook of Molecular and Cellular Methods in Biology and Medicine*, CRC Press, Boca Raton (1995); McPherson, M. J., Ed., *Directed Mutagenesis: A Practical Approach*, IRL Press, Oxford (1991); Jones, J., *Amino Acid and Peptide Synthesis*, Oxford Science Publications, Oxford (1992); Austen, B. M. and Westwood, O. M. R., *Protein Targeting and Secretion*, IRL Press, Oxford (1991); *DNA Cloning*, Volumes I and II (D. N Glover ed. 1985); *Oligonucleotide Synthesis* (M. J. Gait ed, 1984); *Nucleic Acid Hybridization* (B. D. Hames & S. J. Higgins eds. 1984); the series, *Methods in Enzymology* (Academic Press, Inc.), particularly Vol. 154 and Vol. 155 (Wu and Grossman, eds.); *PCR—A Practical Approach* (McPherson, Quirke, and Taylor, eds., 1991); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning; Gene Transfer Vectors for Mammalian Cells*, 1987 (J. H. Miller and M. P. Calos eds., Cold Spring Harbor Laboratory); Martin J. Bishop, ed., *Guide to Human Genome Computing*, 2d Edition, Academic Press, San Diego, Calif. (1998); and Leonard F. Peruski, Jr., and Anne Harwood Peruski, *The Internet and the New Biology: Tools for Genomic and Molecular Research*, American Society for Microbiology, Washington, D.C. (1997). Standard reference works setting forth the general principles of immunology include Sell, S., *Immunology, Immunopathology & Immunity*, 5th Ed., Appleton & Lange, Publ., Stamford, Conn. (1996); Male, D., et al., *Advanced Immunology*, 3d Ed., Times Mirror Int'l Publishers Ltd., Publ., London (1996); Stites, D. P., and Terr, A. I., *Basic and Clinical Immunology*, 7th Ed., Appleton & Lange, Publ., Norwalk, Conn. (1991); and Abbas, A. K., et al., *Cellular and Molecular Immunology*, W. B. Saunders Co., Publ., Philadelphia, Pa. (1991). Any suitable materials and/or methods known to those of skill can be utilized in carrying out the present invention; however, preferred materials and/or methods are described. Materials, reagents and the like to which reference is made in the following description and examples are obtainable from commercial sources, unless otherwise noted.

The nucleic acids of the invention may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The invention also provides vectors comprising the disorder-associated sequences or derivatives or fragments thereof and host cells for the production of purified proteins. A large number of vectors, including plasmid and fungal vectors, have been described for replication and/or expression in a variety of eukaryotic and prokaryotic hosts, and may be used for gene therapy as well as for simple cloning or protein expression.

Using the information provided in SEQ ID NO:1–SEQ ID NO:3, one skilled in the art will be able to clone and sequence all representative nucleic acids of interest, including nucleic acids encoding complete protein-coding sequences. It is to be understood that non-protein-coding sequences contained within SEQ ID NO:1–SEQ ID NO:3 and the genomic sequence of SEQ ID NO:7 (FIGS. 20A–20G) are also within the scope of the invention. Such sequences include, without limitation, sequences important for replication, recombination, transcription and translation. Non-limiting examples include promoters and regulatory binding sites involved in regulation of gene expression, and 5'- and 3'-untranslated sequences (e.g., ribosome-binding sites) that form part of mRNA molecules.

The nucleic acids of the present invention find use as primers and templates for the recombinant production of disorder-associated peptides or polypeptides, for chromosome and gene mapping, to provide antisense sequences, for tissue distribution studies, to locate and obtain full length genes, to identify and obtain homologous sequences (wild-type and mutants), and in diagnostic applications.

Polypeptides according to the invention are at least five or more residues in length. Preferably, the polypeptides comprise at least about 12, more preferably at least about 20 and most preferably at least about 30 such residues. Nucleic acids comprising protein-coding sequences can be used to direct the expression of asthma-associated polypeptides in intact cells or in cell-free translation systems. The known genetic code, tailored if desired for more efficient expression in a given- host organism, can be used to synthesize oligonucleotides encoding the desired amino acid sequences. The resulting oligonucleotides can be inserted into an appropriate vector and expressed in a compatible host organism.

The polypeptides of the present invention, including function-conservative variants, may be isolated from wild-type or mutant cells, or from heterologous organisms or cells (e.g., bacteria, fungi, yeast, insect, plant, and mammalian cells) in which an disorder-associated protein-coding sequence has been introduced and expressed. Furthermore, the polypeptides may be part of recombinant fusion proteins. The polypeptides can also, advantageously, be made using cell-free protein synthesis systems or by synthetic chemistry. Polypeptides may be chemically synthesized by commercially available automated procedures, including, without limitation, exclusive solid phase synthesis, partial solid phase methods, fragment condensation or classical solution synthesis.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the disorder-associated protein contains an additional sequence tag that facilitates purification. Alternatively, antibodies produced against an disorder-associated protein or against peptides derived therefrom can be used as purification reagents. Other purification methods are possible.

The present invention also encompasses derivatives and homologies of disorder-associated polypeptides. For some purposes, nucleic acid sequences encoding the peptides may be altered by substitutions, additions, or deletions that provide for functionally equivalent molecules, i.e., function-conservative variants.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

Both the naturally occurring and recombinant forms of the polypeptides of the invention can advantageously be used to screen compounds for binding activity. Many methods of screening for binding activity are known by those skilled in the art and may be used to practice the invention. Several methods of automated assays have been developed in recent years so as to permit screening of tens of thousands of compounds in a short period of time. Such high-throughput screening methods are particularly preferred. The use of high-throughput screening assays to test for inhibitors is greatly facilitated by the availability of large amounts of purified polypeptides, as provided by the invention. The polypeptides of the invention also find use as therapeutic agents as well as antigenic components to prepare antibodies.

The polypeptides of this invention find use as immunogenic components useful as antigens for preparing antibodies by standard methods. It is well known in the art that immunogenic epitopes generally contain at least about five amino acid residues, Ohno et al., 1985, *Proc. Natl. Acad. Sci. USA* 82:2945. Therefore, the immunogenic components of this invention will typically comprise at least five amino acid residues of the sequence of the complete polypeptide chains. Preferably, they will contain at least 7, and most preferably at least about 10 amino acid residues or more to ensure that they will be immunogenic. Whether a given component is immunogenic can readily be determined by routine experimentation Such immunogenic components can be produced by proteolytic cleavage of larger polypeptides or by chemical synthesis or recombinant technology and are thus not limited by proteolytic cleavage sites. The present invention thus encompasses antibodies that specifically recognize asthma- associated immunogenic components.

Antibodies according to the present invention include polyclonal and monoclonal antibodies. The antibodies may be elicited in an animal host by immunization with disorder-associated immunogenic components or may be formed by in vitro immunization (sensitization) of immune cells. The immunogenic components used to elicit the production of antibodies may be isolated from cells or chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies, chimeric antibodies, and univalent antibodies. Also included are Fab fragments, including $Fab^1$ and $Fab(ab)^2$ fragments of antibodies.

These antibodies, whether polyclonal or monoclonal, can be used, e.g., in an immobilized form bound to a solid support by well known methods, to purify the immunogenic components and disorder-associated polypeptides by immunoaffinity chromatography. Antibodies against the immunogenic components can also be used, unlabeled or labeled by standard methods, as the basis for immunoassays, i.e., as diagnostic reagents.

Hybridomas of the invention used to make monoclonal antibodies against the immunogenic components of the invention are produced by well-known techniques. Usually, the process involves the fusion of an immortalizing cell line with a B-lymphocyte that produces the desired antibody. Alternatively, non- fusion techniques for generating immortal antibody-producing cell lines are possible, and come within the purview of the present invention, e.g., virally-induced transformation, Casali et al., 1986, *Science* 234:476. Immortalizing cell lines are usually transformed mammalian cells, particularly myeloma cells of rodent, bovine, and human origin. Most frequently, rat or mouse myeloma cell lines are employed as a matter of convenience and availability.

Hybridomas are selected by standard procedures, such as HAT (hypoxanthine-aminopterin-thymidine) selection. From among these hybridomas, those secreting the desired antibody are selected by assaying their culture medium by standard immunoassays; such as Western blotting, ELISA (enzyme-linked immunosorbent assay), RtA (radioimmunoassay), or the like. Antibodies are recovered from the medium using standard protein purification techniques, Tijssen, 1985, *Practice and Theory of Enzyme Immunoassays*, Elsevier, Amsterdam.

I. LOCALIZATION OF AN ASTHMA LOCUS ON CHROMOSOME 20p13-p12 AND THE CHARACTERIZATION OF A CANDIDATE GENE WITHIN THE REGION

To identify genes in the region on 20p13-p12, a set of bacterial artificial chromosome(BAC) clones containing this chromosomal region was identified. The BAC clones served as a template for genomic DNA sequencing and serve as reagents for identifying coding sequences by direct cDNA selection. Genomic sequencing and direct cDNA selection were used to characterize DNA from 20p13-p12.

When a gene has been genetically localized to a specific chromosomal region, the genes in this region can be characterized at the molecular level by a series of steps that include: cloning of the entire region of DNA in a set of overlapping clones (physical mapping), characterization of genes encoded by these clones by a combination of direct cDNA selection, exon trapping and DNA sequencing (gene identification), and identification of mutations in these genes by comparative DNA sequencing of affected and unaffected members of the kindred and/or in unrelated affected individuals and unrelated unaffected controls(mutation analysis).

Physical mapping is accomplished by screening libraries of human DNA cloned in vectors that are propagated in a host such as *E. coli*, using hybridization or PCR assays from unique molecular landmarks in the chromosomal region of interest. To generate a physical map of the disorder region, a library of human DNA cloned in BACs was screened with a set overgo markers that had been previously mapped to chromosome 20p13-p12 by the efforts of the Human Genome Project. Overgos are unique molecular landmarks in the human genome that can be assayed by hybridization. Through the combined efforts of the Human Genome Project, the location of thousands of overgos on the twenty-two autosomes and two sex chromosomes has been determined. For a positional cloning effort, the physical map is tied to the genetic map because the markers used for genetic mapping can also be used as overgos for physical mapping. By screening a BAC library with a combination of overgos derived from genetic markers, genes, and random DNA fragments, a physical map comprised of overlapping clones representing all of the DNA in a chromosomal region of interest can be assembled.

BACs are cloning vectors for large (80 kilobase to 200 kilobase) segments of human or other DNA that are propagated in *E. coli*. To construct a physical map using BACs, a library of BAC clones is screened so that individual clones harboring the DNA sequence corresponding to a given overgo or set of overgos are identified. Throughout most of the human genome, the overgo markers are spaced approximately 20 to 50 kilobases apart, so that an individual BAC clone typically contains at least two overgo markers. In addition, the BAC libraries that were screened contain enough cloned DNA to cover the human genome twelve times over. Therefore, an individual overgo typically identifies more than one BAC clone. By screening a twelve-fold coverage BAC library with a series of overgo markers spaced approximately 50 kilobases apart, a physical map consisting of a series of overlapping contiguous BAC clones, i.e., BAC "contigs," can be assembled for any region of the human genome. This map is closely tied to the genetic map because many of the overgo markers used to prepare the physical map are also genetic markers.

When constructing a physical map, it often happens that there are gaps in the overgo map of the genome that result in the inability to identify BAC clones that are overlapping in a given location. Typically, the physical map is first constructed from a set of overgos identified through the publicly available literature and World Wide Web resources. The initial map consists of several separate BAC contigs that are separated by gaps of unknown molecular distance. To identify BAC clones that fill these gaps, it is necessary to develop new overgo markers from the ends of the clones on either side of the gap. This is done by sequencing the terminal 200 to 300 base pairs of the BACs flanking the gap, and developing a PCR or hybridization based assay. If the terminal sequences are demonstrated to be unique within the human genome, then the new overgo can be used to screen the BAC library to identify additional BACs that contain the DNA from the gap in the physical map. To assemble a BAC contig that covers a region the size of the disorder region (6,000,000 or more base pairs), it is necessary to develop new overgo markers from the ends of a number of clones.

After building a BAC contig, this set of overlapping clones serves as a template for identifying the genes encoded in the chromosomal region. Gene identification can be accomplished by many methods. Three methods are commonly used: (1) a set of BACs selected from the BAC contig to represent the entire chromosomal region can be sequenced, and computational methods can be used to identify all of the genes, (2) the BACs from the BAC contig can be used as a reagent to clone cDNAs corresponding to the genes encoded in the region by a method termed direct cDNA selection, or (3) the BACs from the BAC contig can be used to identify coding sequences by selecting for specific DNA sequence motifs in a procedure called exon trapping. The present invention includes Gene 216 identified by the first two methods.

To sequence the entire BAC contig representing the disorder region, a set of BACs can be chosen for subcloning into plasmid vectors and subsequent DNA sequencing of these subclones. Since the DNA cloned in the BACs represents genomic DNA, this sequencing is referred to as genomic sequencing to distinguish it from cDNA sequencing. To initiate the genomic sequencing for a chromosomal region of interest, several non-overlapping BAC clones are chosen. DNA for each BAC clone is prepared, and the clones are sheared into random small fragments which are subsequently cloned into standard plasmid vectors such as pUC18. The plasmid clones are then grown to propagate the smaller fragments, and these are the templates for sequencing. To ensure adequate coverage and sequence quality for the BAC DNA sequence, sufficient plasmid clones are sequenced to yield three-fold coverage of the BAC clone. For example, if the BAC is 100 kilobases long, then phagemids are sequenced to yield 300 kilobases of sequence. Since the BAC DNA was randomly sheared prior to cloning in the phagemid vector, the 300 kilobases of raw DNA sequence can be assembled by computational methods into overlapping DNA sequences termed sequence contigs. For the purposes of initial gene identification by computational methods, three-fold coverage of each BAC is sufficient to yield twenty to forty sequence contigs of 1000 base pairs to 20,000 base pairs.

The sequencing strategy employed in this invention was to initially sequence "seed" BACs from the BAC contig in the disorder region. The sequence of the "seed" BACs was then used to identify minimally overlapping BACs from the contig, and these were subsequently sequenced. In this manner, the entire candidate region can be sequenced, with several small sequence gaps left in each BAC. This sequence serves as the template for computational gene identification. One method for computational gene identification is to compare the sequence of BAC contig to publicly available databases of cDNA and genomic sequences, e.g. unigene, dbEST, genbank. These comparisons are typically done using the BLAST family of computer algorithms and programs (Altshul et al, *J. Mol. Biol.*, 215:403–410 (1990)). The BAC sequence can also be translated into protein sequence, and the protein sequence can be used to search publicly available protein databases, using a version of BLAST designed to analyze protein sequences (Altshul et al, *Nucl. Acids Res.*, 25:3389–3402 (1997)). Another method is to use computer algorithms such as MZEF (Zhang, *Proc. Natl. Acad. Sci.*, 94:565–568 (1997)), GRAIL (Uberbacher et al, *Methods Enzymol.*, 266:259–281 (1996)), and Genscan (Burge and Karlin, *J. Mol. Biol.*, 268:78–94) which predicts the location of exons in the sequence based on the presence of specific DNA sequence motifs that are common to all exons, as well as the presence of codon usage typical of human protein encoding sequences.

In addition to identifying genes by computational methods, genes were also identified by direct cDNA selection (Del Mastro and Lovett, *Methods in Molecular Biology*, Humana Press Inc., NJ (1996)). In direct cDNA selection, cDNA pools from tissues of interest are prepared, and BACs from the candidate region are used in a liquid hybridization assay to capture the cDNAs which base pair to coding regions in the BAC. In the methods described herein, the cDNA pools were created from several different tissues by random priming and oligo dT priming the first strand cDNA from polyA RNA, synthesizing the second strand cDNA by standard methods, and adding linkers to the ends of the cDNA fragments. The linkers are used to amplify the c-DNA pools BAC clones from the disorder region identified by screening the RPCI-11 BAC library (P. deJong, Russell Park Cancer Institute) were used as a template for initiating DNA synthesis to create a biotin labeled copy of BAC DNA. The biotin labelled copy of the BAC DNA is then denatured and incubated with an excess of the PCR amplified, linkered cDNA pools which have also been denatured. The BAC DNA and cDNA are allowed to anneal in solution, and heteroduplexes between the BAC and the cDNA are isolated using streptavidin coated magnetic beads. The cDNAs that are captured by the BAC are then amplified using primers complimentary to the linker sequences, and the hybridization/selection process is repeated for a second round. After two rounds of direct cDNA selection, the cDNA fragments are cloned, and a library of these direct selected fragments is created.

The cDNA clones isolated by direct selection are analyzed by two methods. Since a pool of BACs from the disorder region is used to provide the genomic target DNA sequence, the cDNAs must be mapped to BAC genomic clones to verify their chromosomal location. This is accomplished by arraying the cDNAs in microtiter dishes, and replicating their DNA in high density grids. Individual genomic clones known to map to the region are then hybridized to the grid to identify direct selected cDNAs mapping to that region. cDNA clones that are confirmed to correspond to individual BACs are sequenced. To determine whether the cDNA clones isolated by direct selection share sequence identity or similarity to previously identified genes, the DNA and protein coding sequences are compared to publicly available databases using the BLAST family of programs.

The combination of genomic DNA sequence and cDNA sequence provided by BAC sequencing and by direct cDNA selection yields an initial list of putative genes in the region. The genes in the region were all candidates for the asthma locus. To further characterize each gene, Northern blots were performed to determine the size of the transcript corresponding to each gene, and to determine which putative exons were transcribed together to make an individual gene. For Northern blot analysis of each gene, probes were prepared from direct selected cDNA clones or by PCR amplifying specific fragments from genomic DNA, cDNA or from the BAC encoding the putative gene of interest. The Northern blots gave information on the size of the transcript and the tissues in which it was expressed. For transcripts which were not highly expressed, it was sometimes necessary to perform a reverse transcription PCR assay using RNA from the tissues of interest as a template for the reaction.

Gene identification by computational methods and by direct cDNA selection provides unique information about the genes in a region of a chromosome. When genes are identified, then it is possible to examine different individuals for mutations in each gene. Variants in gene sequences between individuals can be inherited allelic differences or can arise from mutations in the individuals. Gene sequence variants are clinically important in that they can affect drug action on such gene. Most drugs elicit a safe response in only a fraction of individuals, and drugs are commonly administered to patients with no certainty that they will be safe and effective. Many important drugs are effective in only 30–40% of patients for whom the drug is prescribed, and virtually all drugs cause adverse events in some individuals. Identification of mutations in disorder genes in different individuals will enable a correlation between the safety and efficacy of drug therapies used to treat lung diseases and the genotypes of the treated individuals. This correlation enables health care providers to prescribe a drug regimen which is most appropriate for the individual patient rather than trying different drug regimens in turn until a successful drug is identified. Identification of variants in disorder genes will also have a benefit during the development of new drugs for the treatment of lung diseases, as the ability to correlate genetic variation with the efficacy of new candidate drugs will enhance lead optimization and increase the efficiency and success rate of new drug approvals.

A. FAMILY COLLECTION

A critical component of any disease gene search is the careful selection and phenotyping of family resources. The family collection utilized in this study consists of 421 Caucasian affected sibling ("sib") pairs families collected in the United States and the United Kingdom, as well as an additional 39 Caucasian families from the United Kingdom collected under different ascertainment criteria.

The affected sibling (or "sib") pair families in the United States collection were Caucasian families with two affected siblings that were identified through both private practice and community physicians. Advertising was also used to identify candidates. A total of 98 families were collected in Kansas, Nebraska, and Southern California. In the United Kingdom collection, 323 families were identified through physicians' registers in a region surrounding Southampton and including the Isle of Wight.

Families were included in the study if they met all of the following criteria: (1) the biological mother and biological father were Caucasian and agreed to participate in the study, (2) at least two biological siblings were alive, each with a current physician diagnosis of asthma, and 5 to 21 years of age, and (3) the two siblings were currently taking asthma medications on a regular basis. This included regular, intermittent use of inhaled or oral bronchodilators and regular use of cromolyn, theophylline, or steroids.

Families were excluded from the study if they met any one of the following criteria: (1) both parents were affected (i.e., with a current diagnosis of asthma, having asthma symptoms, or on asthma medications at the time of the study), or (2) any of the siblings to be included in the study was less than 5 years of age, or (3) any asthmatic family member to be included in the study was taking beta-blockers at the time of the study or (4) any family member had congenital or acquired pulmonary disease at birth (e.g. cystic fibrosis) history of serious cardiac disease (myocardial infarction) or any history of serious pulmonary disease (e.g. emphysema) or (5) pregnant.

An additional 39 families from the United Kingdom were utilized from an earlier collection effort with different ascertainment criteria. These families were recruited either: 1) without reference to asthma and atopy or 2) by having at least one family member or at least two family members affected with asthma. The randomly ascertained samples were identified from general practitioner registers in the Southampton area. For the families with affected members, the probands were recruited from hospital based clinics in Southampton. Seven pedigrees extended beyond a single nuclear family.

B. GENOME SCAN

In order to identify chromosomal regions linked to asthma, the inheritance pattern of alleles from genetic markers spanning the genome was assessed on the collected family resources. As described above, combining these results with the segregation of the asthma phenotype in these families allows the identification of genetic markers that are tightly linked to asthma, thus providing an indication of the location of genes predisposing affected individuals to asthma. The following discussion describes the protocol used to assess the genotypes of the collected population using genetic markers spanning the entire genome.

Genotypes of PCR amplified simple sequence microsatellite genetic linkage markers were determined using ABI model 377 Automated Sequencers. Microsatellite markers comprising a variation of a human linkage mapping panel as released from the Cooperative Human Linkage Center (CHLC), also known as the Weber lab screening set version 8, were obtained from Research Genetics Inc. (Huntsville, Ala.) in the fluorescent dye-conjugated form (Dubovsky et al., Hum. Mol. Genet. Mar; 4(3):449–452 (1995)).

Our variation of the Weber 8 screening set consists of 529 markers with an average spacing of 6.87 cM (autosomes only) and 6.98 cM (all chromosomes). Eighty-nine percent of the markers consist of either tri- or tetra-nucleotide microsatellites. In addition, there exist no gaps in chromosomal coverage greater than 17.5 cM.

Study subject genomic DNA (5 $\mu$l; 4.5 $\mu$g/$\mu$l) was amplified in a 10 $\mu$l PCR reaction using AmpliTaq Gold DNA polymerase (0.225 U) and containing the final reaction components: 1×PCR buffer (80 mM $(NH_4)_2SO_4$, 30 mM Tris-HCl (pH 8.8), 0.5% Tween-20), 200 $\mu$M each dATP, dCTP, dGTP and dTTP, 1.5–3.5 $\mu$M $MgCl_2$ and 250 $\mu$M forward and reverse PCR primers. PCR reactions were set up in 192 well plates (Costar) using a Tecan Genesis 150 robotic workstation equipped with a refrigerated deck. PCR reactions were overlaid with 20 $\mu$l mineral oil, and thermocycled on an MJ Research Tetrad DNA Engine equipped with four 192 well heads under the following conditions: 92° C. for 3 min, 6 cycles of 92° C. 30 sec, 56° C. 1 min, 72° C. 45 sec, followed by 20 cycles of 92° C. 30 sec, 55° C. 1 min, 72° C. 45 sec and a 6 min incubation at 72° C. PCR products of 8–12 microsatellite markers were subsequently pooled using a Tecan Genesis 200 robotic workstation into two 96 well microtitre plates (2.0 $\mu$l PCR product from TET and FAM labeled markers, 3.0 1 HEX labeled markers) and brought to a final volume of 25 $\mu$l with $H_2O$. 1.9 $\mu$l of pooled PCR product was transferred to a loading plate and combined with 3.0 $\mu$l loading buffer (loading buffer is 2.5 1 formamide/blue dextran (9.0 mg/ml), 0.5 $\mu$l GS-500 TAMRA labeled size standard, Perkin-Elmer/ABI division). Samples were denatured in the loading plate for 4 min at 95° C., placed on ice for 2 min, and electrophoresed in a 5% denaturing polyacrylamide gel (FMC on the ABI 377XL). Samples (0.8 $\mu$l) were loaded using an 8 channel Hamilton Syringe pipettor.

Each gel consisted of 62 study subjects and 2 control subjects (CEPH parents ID #1331-01 and 1331-02, Coriell Cell Repository, Camden, N.J.). Genotyping gels were scored in duplicate by investigators blind to patient identity and affection status using GENOTYPER analysis software V 1.1.12 (ABI Division, Perkin Elmer Corporation). Nuclear families were loaded onto the gel with the parents flanking the siblings to facilitate error detection. Data with allele peak amplitude less than 100, as detected by GENESCAN analysis software V 2.0.2 (ABI Division, Perkin Elmer Corporation), were either left unscored or rerun.

The final tables obtained from the Genotyper output for each gel analysed were imported into a Sybase Database. Allele calling (binning) was performed using the SYBASE version of the ABAS software (Ghosh et al, Genome Research 7:165–178 (1997)). Offsize bins were checked manually and incorrect calls were corrected or blanked. The binned alleles were then imported into the program MENDEL (Lange et al., Genetic Epidemiology, 5, 471(1988)) for inheritance checking using the USERM13 subroutine (Boehnke et al, AM. J. Hum. Genet. 48:22–25 (1991)). Non-inheritance was investigated by examining the genotyping traces and once all discrepancies were resolved, the subroutine USERM 13 was used to estimate allele frequencies.

C. LINKAGE ANALYSIS

Linkage analysis is possible because of the nature of inheritance of chromosomes from parents to offspring. During meiosis, the two parental homologs pair to guide their proper separation to daughter cells. While they are lined up and paired, the two homologs exchange pieces of the chromosomes, in an event called "crossing over" or "recombination." The resulting chromosomes contain parts that originate from both parental homologs. The closer together two sequences are on the chromosome, the less likely that a recombination event will occur between them, and the more closely linked they are. Data obtained from the different families are combined and analyzed together by a computer using statistical methods. The result is information indicating the evidence for linkage between the genetic markers used and a disease susceptibility locus. A recombination frequency of 1% is equivalent to approximately 1 map unit, a relationship that holds up to frequencies of about 20% or 20 cM. Furthermore, 1 centiMorgan (cM) is roughly equivalent to 1,000 kb of DNA.

The entire human genome is 3,300 cM long. In order to find an unknown disease gene within 5–10 cM of a marker locus, the whole human genome can be searched with roughly 330 informative marker loci spaced at approximately 10 cM intervals (Botstein et al, Am. J. Hum. Genet., 32:314–331 (1980)). The reliability of linkage results is established by using a number of statistical methods. The methods most commonly used for the detection by linkage analysis of oligogenes involved in the etiology of a complex trait are non-parametric or model-free methods which have been implemented into the computer programs MAPMAKER/SIBS (Kruglyak L & Lander ES, Am J Hum Genet 57:439–454, 1995) and GENEHUNTER (Kruglyak L et al., Am J Hum Genet 58:1347–1363,1996). Linkage analysis is performed by typing members of families with multiple affected individuals at a given marker locus and evaluating if the affected members (excluding parent-offspring pairs) share alleles at the marker locus that are identical by descent (IBD) more often than expected by chance alone. As a result of the rapid advances in mapping the human genome over the last few years, and concomitant improvements in computer methodology, it has become feasible to carry out linkage analyses using multi-point data. Multi-point analysis provides a simultaneous analysis of linkage between the trait and several linked genetic markers, when the recombination distance among the markers is known. A LOD score statistic is computed at multiple locations along a chromosome to measure the evidence that a susceptibility locus is located nearby. A LOD score is the logarithm base 10 of the ratio of the likelihood that a susceptibility locus exists at a given location to the likelihood that no susceptibility locus is located there. By convention, when testing a single marker, a total LOD score greater than +3.0 (that is, odds of linkage being 1,000 times greater than odds of no linkage) is considered to be significant evidence for linkage.

Multi-point analysis is advantageous for two reasons. First, the informativeness of the pedigrees is usually increased. Each pedigree has a certain amount of potential information, dependent on the number of parents heterozygous for the marker loci and the number of affected individuals in the family. However, few markers are sufficiently polymorphic as to be informative in all those individuals. If multiple markers are considered simultaneously, then the probability of an individual being heterozygous for at least one of the markers is greatly increased. Second, an indication of the position of the disease gene among the markers may be determined. This allows identification of flanking markers, and thus eventually allows identification of a small region in which the disease gene resides.

For the initial linkage analysis, the phenotype and asthma affection status were defined by a patient described above who answered the following questions in the affirmative: (i) have you ever had asthma, (ii) do you have a current physician's diagnosis of asthma, and (iii) are you currently taking asthma medications? Medications include inhaled or oral bronchodilators, cromolyn, theophylline or steroids.

The distribution of the number of genotyped affected siblings was as follows: 88.7% of the families had 2 siblings, 10.8% had 3 siblings and 0.4% had 4 siblings. Ninety six families were ascertained in the US and 345 in the UK.

Allele sharing methods, implemented in the MAPMAKER/SIBS(Kruglyak L & Lander ES, Am J. Hum Genet 57:439–454, 1995), were used on our sample of 462 nuclear with affected sibling pairs. Multipoint linkage analyses were performed using 23 polymorphic markers spanning a 95 cM region on both arms of chromosome 20. The map location and distances between markers were obtained from the genetic maps published by the Marshfield medical research foundation (http://www.marshmed.org/genetics/). Ambiguous order in the Marshfield map was resolved using the program MULTIMAP (Matise T C et al., Nature Genet 6:384–390, 1994).

FIG. 1 displays the multipoint LOD score against the map location of the markers along the chromosome 20. A Maximum LOD Score (MLS) of 2.9 was obtained at location 7.9 cM, 0.3 cM proximal to marker D20S906. A second MLS of 2.9 was obtained at marker D20S482 at location 12.1 cM. An excess sharing by descent (Identity By Descent, IBD=2) of 0.31 was observed at both maximum LOD scores. Table 1 lists the single and multipoint LOD scores at each marker.

TABLE 1

Chromosome 20 Linkage Analysis

| Marker | Distance | Single-point | Multipoint |
|---|---|---|---|
| D20S502 | 0.5 | 0.7 | 2.4 |
| D20S103 | 2.1 | 2.4 | 2.4 |
| D20S117 | 2.8 | 1.2 | 2.1 |

TABLE 1-continued

Chromosome 20 Linkage Analysis

| Marker | Distance | Single-point | Multipoint |
|---|---|---|---|
| GTC4ATG | 6.3 | 2.4 | 2.5 |
| GTC3CA | 6.6 | 1.3 | 2.8 |
| D20S906 | 7.6 | 2.9 | 2.9 |
| D20S842 | 9.0 | 1.3 | 2.4 |
| D20S193 | 9.5 | 2.5 | 2.4 |
| D20S181 | 9.5 | 1.8 | 2.6 |
| D20S889 | 11.2 | 1.6 | 2.6 |
| D20S482 | 12.1 | 1.9 | 2.9 |
| D20S849 | 14.0 | 0.8 | 2.0 |
| D20S835 | 15.1 | 0.5 | 1.8 |
| D20S448 | 18.8 | 1.4 | 1.4 |
| D20S602 | 21.2 | 1.1 | 1.1 |
| D20S851 | 24.7 | 1.0 | 0.8 |
| D20S604 | 32.9 | 0.0 | 0.1 |
| D20S470 | 39.3 | 0.0 | 0.1 |
| D20S477 | 47.5 | 0.0 | 0.0 |
| D20S478 | 54.1 | 0.0 | 0.0 |
| D20S481 | 62.3 | 0.0 | 0.0 |
| D20S480 | 79.9 | 0.0 | 0.0 |
| D20S171 | 95.7 | 0.4 | 0.1 |

D. PHYSICAL MAPPING

The linkage results for chromosome 20 described above were used to delineate a candidate region for a disorder-associated gene located on chromosome 20. Gene discovery efforts were thus initiated in a 25 cM interval from the 20p telomere (marker D20S502) to marker D20S851, representing a >98% confidence interval. All genes known to map to this interval were pursued as candidates. Intensive physical mapping (BAC contig construction) focused on a 90% confidence interval between markers D20S 103 and D20S916, a 15 cM interval. The discovery of novel genes using direct cDNA selection focused on a 95% confidence interval between markers D20S502 (20p telomere) and D20S916, a 17 cM region.

The following section describes details of the efforts to generate cloned coverage of the disorder gene region on chromosomes 20, i.e., construction of a BAC contig spanning the region. There are two primary reasons for this: 1) to provide genomic clones for DNA sequencing; analysis of this sequence provides information about the gene content of the region, and 2) to provide reagents for direct cDNA selection; this provides additional information about novel genes mapping to the interval. The physical map consists of an ordered set of molecular landmarks, and a set of bacterial artificial chromosome (BAC, Kim, U.-J., et al., (1996), *Genomics* 34, 213–218 and Shizuya, H., et al., (1992). *Proc.* *Natl. Acad. Sci. USA* 89, 8794–8797) clones that contain the disorder gene region from chromosome 20p13-p12.

FIG. 2 depicts the BAC/STS content contig map in 20p13-p12. Markers used to screen the RPCI-11BAC library (P. deJong—Roswell Park Cancer Institute) are shown in the top row. For markers that are present in GDB the same nomenclature has been used. BAC clones are shown below the markers as horizontal lines. In particular BAC 1098L22 is labeled. The location of the Gene 216 described herein is indicated at the top of the figure.

1. Map Integration. Various publicly available mapping resources were utilized to identify existing STS markers (Olson et al, (1989), *Science*, 245:1434–1435) in the 20p13-p12 region. Resources included the Genome Database (GDB, http://gdbwww.gdb.org/), Genethon (http://www.genethon.fr/genethon_en.html), Marshfield Center for Medical Genetics (http://www.marshmed.org/genetics/), the Whitehead Institute Genome Center (http://www-genome.wi.mit.edu/), GeneMap98, dbSTS and dbEST (NCBI, http://www.ncbi.nlm.nih.gov/), the Sanger Centre (http://www.sanger.ac.uk/), and the Stanford Human Genome Center (http://www-shgc.stanford.edu/). Maps were integrated manually to identify markers mapping to the disorder region. A list of the markers is provided in Table 1.

2. Marker Development. Sequences for existing STSs were obtained from the GDB, RHDB (http://www.ebi.ac.uk/RHdb/), or NCBI and were used to pick primer pairs (overgos, See Table 2) for BAC library screening. Novel markers were developed either from publicly available genomic sequences, proprietary cDNA sequences or from sequences derived from BAC insert ends (described below). Primers were chosen using a script that automatically performs vector and repetitive sequence masking using Crossmatch (P. Green, U. of Washington); subsequent primer picking was performed using a customized Filemaker Pro database. Primers for use in PCR-based clone confirmation or radiation hybrid mapping (described below) were chosen using the program Primer3 (Steve Rozen, Helen J. Skaletsky (1996, 1997); Primer3 is available at http://www-genome.wi.mit.edu/qenome software/other/primer3.html).

TABLE 2

| Overgo | Locus | DNA Type | Gene | Foward Primer | Reverse Primer |
|---|---|---|---|---|---|
| stSG24277 | | Genomic | | AACTCTTGAAATGAGAAGCGTG | CGGATTCACGCTTC |
| stSG408 | | EST | | AATATCATGCACCATGACCCAC | ATGGCTGTGGGTCA |
| A005O05 | | EST | Attractin (ATTN) | TGGAGTAAGTATTGTAAACTAT | AATGAAATAGTTTA |
| B849D17AL | | BACend | | GGAGCTTATCCTGGATTATCTA | CCCACTTAGATAAT |
| SN2 | | EST | Sialoadhesin (SN) | AGAGCCACACATCCATGTCCTG | GGGAAGCCAGGACAT |
| AFMb026xh5 | D20S867 | MSAT | | AAGCCACTCTGTGAATTGCCAT | GAGGCAATGGCAAT |
| SN1 | | EST | Sialoadhesin (SN) | GAGTAGTCGTAGTACCAGATGG | ATCACGGCCATCTGG |
| stsH22126 | | EST | | GTCTGGCAATGGAGCATGAAAA | TCATTCATTTTCATG |
| WI4876 | D20S752 | Genomic | | ATTAGAGCACATGAAGGAAAGG | ACTTCTCCTTTCCT |
| stSG30448 | | EST | | ACACTGCTTTGGGGGACAGGCT | AGACCTAGCCTGTC |
| WI18677 | | | EST | CACGACGCCACAGAGCCAGCTC | GAGGACGGAGCTGGC |

3. Radiation Hybrid (RH) Mapping. Radiation hybrid mapping was performed against the Genebridge4 panel (Gyapay, et al., (1996), *Hum. Mol. Genet.* 5:339–46) purchased from Research Genetics, in order to refine the chromosomal localization of genetic markers used in genotyping as well as to identify, confirm and refine localizations of markers from proprietary sequences. Standard PCR procedures were used for typing the RH panel with markers of interest. Briefly, 10 μl PCR reactions contained 25 μg DNA of each of the 93 Genebridge4 RH samples. PCR products were electrophoresed in 2% agarose gels (Sigma) containing 0.5 μg/ml ethidium bromide in 1×TBE at 150 volts for 45 min. The electrophoresis units used were the Model A3-1 systems from Owl Scientific Products. Typically, gels contained 10 tiers of lanes with 50 wells/tier. Molecular weight markers (100 bp ladder, GIBCO/BRL) were loaded at both ends of the gel. Images of the gels were captured with a Kodak DC40 CCD camera and processed with Kodak 1D software. The gel data were exported as tab delimited text files; names of the files included information about the panel screened, the gel image files and the marker screened. These data were automatically imported using a customized Perl script into Filemaker databases for data storage and analysis. The data were then automatically formatted and submitted to an internal server for linkage analysis to create a radiation hybrid map using RHMAPPER (Stein, L., Kruglyak, L., Slonim, D., and El Lander (1995); available from the Whitehead Institute/MIT Center for Genome Research, at http://www.genome.wi.mit.edu/ftp/pub/software/rhmapper/, and via anonymous ftp to ftp.genome.wi.mit.edu, in the directory/pub/software/rhmapper.)

4. BAC Library Screening. The protocol used for BAC library screening was based on the "overgo" method, originally developed by John McPherson at Washington University in St. Louis (http://www.tree.caltech.edu/protocols/overgo.html, and Cai, W-W., et al., (1998), *Genomics* 54:387–397). This method involves filling in the overhangs generated after annealing two primers, each 22 nucleotides in length, that overlap by 8 nucleotides. The resulting labeled 36 bp product is then used in hybridization-based screening of high density grids derived from the RPCI-11 BAC library (Pieter deJong, Roswell Park Cancer Institute, http://bacpac.med.buffalo.edu). Typically, 15 probes were pooled together in one hybridization of 12 filters (13.5 genome equivalents).

Stock solutions (2 μM) of combined complementary oligos were heated at 80° C. for 5 min, then placed at 37° C. for 10 min followed by storage on ice. Labeling reactions were set up as follows: 1.0 μl $H_2O$, 5 μl mixed oligos—2 μM each, 0.5 μl BSA (2 mg/ml), 2 μl OLB(-A, -C, -N6) Solution (see below), 0.5 μl $^{32}$P-dATP (3000 Ci/mmol), 0.5 μl $^{32}$P-dCTP (3000 Ci/mmol), 0.5 μl Klenow fragment (5 U/μl). The reaction was incubated at room temperature for 1 hr followed by removal of unincorporated nucleotides with Sephadex G50 spin columns.

OLB(-A, -C, -N6) Solution

Solution O—1.25 M Tris-HCL, pH 8, 125 M $MgCl_2$

Solution A—1 ml Solution O, 18 μl 2-mercaptoethanol, 5 μl 0.1M dTTP, 5 μl 0.1M dGTP Solution B—2M HEPES-NaOH, pH 6.6

Solution C—3 mM Tris-HCl, pH 7.4, 0.2 mM EDTA

Solutions A, B, and C were combined to a final ratio of 1:2.5:1.5, aliquots were stored at −20° C.

High density BAC library membranes were pre-wetted in 2×SSC at 58° C. Filters were then drained slightly and placed in hybridization solution (1% Bovine serum albumin, 1 mM EDTA—pH 8.0, 7% SDS, and 0.5 M sodium phosphate) pre-warmed to 58° C. and incubated at 58° C. for 2–4 hr. Typically, 6 filters were hybridized per container. Ten ml of pre-hybridization solution were removed, combined with the denatured overgo probes, and added back to the filters. Hybridization was performed overnight at 58° C. The hybridization solution was removed and filters were washed once in 2×SSC, 0.1% SDS, followed by a 30 minute wash in the same solution but at 58° C. Filters were then washed in 1.5×SSC, 01.% SDS at 58° C. for 30 min. 0.5×SSC, 0.1%SDS at 58° C. for 30 min and finally in 0.1×SSC, 0.1% SDS at 58° C. for 30 min. Filters were then wrapped in Saran Wrap and exposed to film overnight. To remove bound probe, filters were treated in 0.1×SSC, 0.1% SDS prewarmed to 95° C. and allowed to return to room temperature. Clone addresses were determined as described by instructions supplied by RPCI.

Recovery of clonal BAC cultures from the library involved streaking out a sample from the appropriate library well onto LB agar (Maniatis, T., Fritsch, E. F., and J. Sambrook, (1982) Molecular Cloning: A Laboratory Manual, Cold Spring Harbor Laboratory, Cold Spring Harbor, N.Y.) containing 12.5 μg/ml chloramphenicol (Sigma) and incubating overnight. A single colony and a portion of the initial streak quadrant were inoculated into 400 μl LB plus chloramphenicol in wells of a 96 well plate. Cultures were grown overnight at 37° C. For storage, 100 μl of 80% glycerol was added and the plates placed at ‖80° C. To determine the marker content of clones, aliquots of the 96 well plate cultures were transferred to the surface of nylon filters (GeneScreen Plus, NEN) placed on LB/chloramphenicol Petri plates. Colonies were grown overnight at 37° C. and colony lysis was performed as follows: Filters were placed on pools of 10% SDS for 3 min, 0.5 N NaOH, 1.5 M NaCl for 5 min, and 0.5 M Tris-HCl, pH 7.5, 1 M NaCl for 5 min. Filters were then air dried and washed free of debris in 2×SSC for 1 hr. The filters were air dried for at least 1 hr and DNA crosslinked linked to the membrane using standard conditions. Probe hybridization and filter washing were performed as described above for the primary library screening. Confirmed clones were stored in LB containing 15% glycerol.

In some cases polymerase chain reaction (PCR) was used to confirm the marker content of clones. PCR conditions for each primer pair were initially optimized with respect to $MgCl_2$ concentration. The standard buffer was 10 mM Tris-HCl (pH 8.3), 50 mM KCl, $MgCl_2$, 0.2 mM each dNTP, 0.2 μM each primer, 2.7 ng/μl human DNA, 0.25 units of AmpliTaq (Perkin Elmer) and $MgCl_2$ concentrations of 1.0 mM, 1.5 mM, 2.0 mM or 2.4 mM. Cycling conditions included an initial denaturation at 94° C. for 2 minutes followed by 40 cycles at 94° C. for 15 seconds, 55° C. for 25 seconds, and 72° C. for 25 seconds followed by a final extension at 72° C. for 3 minutes. Depending on the results from the initial round of optimization the conditions were further optimized if necessary. Variables included increasing the annealing temperature to 58° C. or 60° C., increasing the cycle number to 42 and the annealing and extension times to 30 seconds, and using AmpliTaqGold (Perkin Elmer).

5. BAC DNA Preparation. Several different types of DNA preparation methods were used for isolation of BAC DNA. The manual alkaline lysis miniprep protocol listed below (Maniatis, T., Fritsch, E. F., and J. Sambrook, (1982) Molecular Cloning: A Laboratory Manual, Cold Spring Harbor Laboratory, Cold Spring Harbor, N.Y.) was successfully used for most applications, i.e., restriction mapping, CHEF gel analysis and FISH mapping, but was not reproducibly successful in endsequencing. The Autogen protocol described below was used specifically for BAC DNA preparation for endsequencing purposes.

For manual alkaline lysis BAC minipreps, bacteria were grown in 15 ml Terrific Broth containing 12.5 μg/ml chloramphenicol in a 50 ml conical tube at 37° C. for 20 hrs with shaking at 300 rpm. The cultures were centrifuged in a Sorvall RT 6000 D at 3000 rpm (1800×g) at 4° C. for 15 min.

The supernatant was then aspirated as completely as possible. In some cases cell pellets were frozen at −20° C. at this step for up to 2 weeks. The pellet was then vortexed to homogenize the cells and minimize clumping. 250 μl of P1 solution (50 mM glucose, 15 mM Tris-HCl, pH 8, 10 mM EDTA, and 100 μg/ml RNase A) was added and the mixture pipeted up and down to mix. The mixture was then transferred to a 2 ml Eppendorf tube. 350 μl of P2 solution (0.2 N NaOH, 1% SDS) was then added, and the mixture mixed gently and incubated for 5 min at room temperature. 350 μl of P3 solution (3M KOAc, pH 5.5) was added and the mixture mixed gently until a white precipitate formed. The solution was incubated on ice for 5 min and then centrifuged at 4° C. in a microfuge for 10 min. The supernatant was transferred carefully (avoiding the white precipitate) to a fresh 2 ml Eppendorf tube, and 0.9 ml of isopropanol was added; the solution was mixed and left on ice for 5 min. The samples were centrifuged for 10 min, and the supernatant removed carefully. Pellets were washed in 70% ethanol and air dried for 5 min. Pellets were resuspended in 200 μl of TE8 (10 mM Tris-HCl, pH 8.0, 1.0 mM EDTA, pH 8.0), and RNase (Boehringer Mannheim) added to 100 μg/ml. Samples were incubated at 37° C. for 30 min, then precipitated by addition of $NH_4OAc$ to 0.5 M and 2 volumes of ethanol. Samples were centrifuged for 10 min, and the pellets washed with 70% ethanol followed by air drying and dissolving in 50 μl TE8. Typical yields for this DNA prep were 3–5 μg/15 ml bacterial culture. Ten to 15 μl were used for EcoRI restriction analysis; 5 μl was used for NotI digestion and clone insert sizing by CHEF gel electrophoresis.

Autogen 740 BAC DNA preparations for endsequencing were prepared by dispensing 3 ml of LB media containing 12.5 μg/ml of chloramphenicol into autoclaved Autogen tubes. A single tube was used for each clone. For inoculation, glycerol stocks were removed from −70° C. storage and placed on dry ice. A small portion of the glycerol stock was removed from the original tube with a sterile toothpick and transferred into the Autogen tube; the toothpick was left in the Autogen tube for at least two minutes before discarding. After inoculation the tubes were covered with tape making sure the seal was tight. When all samples were inoculated, the tube units were transferred into an Autogen rack holder and placed into a rotary shaker at 37° C. for 16–17 hours at 250 rpm. Following growth, standard conditions for BAC DNA preparation, as defined by the manufacturer, were used to program the Autogen. Samples were not dissolved in TE8 as part of the program—DNA pellets were left dry. When the program was complete the tubes were removed from the output tray and 30 μl of sterile distilled and deionized H20 was added directly to the bottom of the tube. The tubes were then gently shaken for 2–5 seconds and then covered with parafilm and incubated at room temperature for 1–3 hours. DNA samples were then transferred to an Eppendorf tube and used either directly for sequencing or stored at 4° C. for later use.

6. BAC Clone Characterization. DNA samples prepared either by manual alkaline lysis or the Autogen protocol were digested with EcoRI for analysis of restriction fragment sizes. These data were used to compare the extent of overlap among clones. Typically 1–2 μg were used for each reaction. Reaction mixtures included: 1×Buffer 2 (New England Biolabs), 0.1 mg/ml bovine serum albumin (New England Biolabs), 50 μg/ml RNase A (Boehringer Mannheim), and 20 units of EcoRI (New England Biolabs) in a final volume of 25 μl. Digestions were incubated at 37° C. for 4–6 hours. BAC DNA was also digested with NotI for estimation of insert size by CHEF gel analysis (see below). Reaction conditions were identical to those for EcoRI except that 20 units of NotI were used. Six μl of 6×Ficoll loading buffer containing bromphenol blue and xylene cyanol was added prior to electrophoresis.

EcoRI digests were analyzed on 0.6% agarose (Seakem, FMC Bioproducts) in 1×TBE containing 0.5 μg/ml ethidium bromide. Gels (20 cm×25 cm) were electrophoresed in a Model A4 electrophoresis unit (Owl Scientific) at 50 volts for 20–24 hrs. Molecular weight size markers included undigested lambda DNA, HindIII digested lambda DNA, and HaeIII digested X174 DNA. Molecular weight markers were heated at 65° C. for 2 min prior to loading the gel. Images were captured with a Kodak DC40 CCD camera and analyzed with Kodak 1D software.

NotI digests were analyzed on a CHEF DRII (BioRad) electrophoresis unit according to the manufacturer's recommendations. Briefly, 1% agarose gels (BioRad pulsed field grade) were prepared in 0.5×TBE, equilibrated for 30 min in the electrophoresis unit at 14° C., and electrophoresed at 6 volts/cm for 14 hrs with circulation. Switching times were ramped from 10 sec to 20 sec. Gels were stained after electrophoresis in 0.5 μg/ml ethidium bromide. Molecular weight markers included undigested lambda DNA, HindIII digested lambda DNA, lambda ladder PFG ladder, and low range PFG marker (all from New England Biolabs).

7. BAC Endsequencing. The sequence of BAC insert ends utilized DNA prepared by either of the two methods described above. The ends of BAC clones were sequenced for the purpose of filling gaps in the physical map and for gene discovery information. The following vector primers specific to the BAC vector pBACe3.6 were used to generate endsequence from BAC clones:

pBAC 5'-2 TGT AGG ACT ATA TTG CTC pBAC 3'-1 CGA CAT TTA GGT GAC ACT

The following sequencing protocol using ABI dye-terminator chemistry was used to set up sequencing reactions for 96 clones. The BigDye (Mix: Perkin Elmer/ABI BigDye) Terminator Ready Reaction Mix with AmpliTaq" FS, Part number 4303151, was used for sequencing with fluorescently labelled dideoxy nucleotides. A master sequencing mix was prepared for each primer reaction set including:

1600 μl of BigDye terminator mix (ABI)

800 μl of 5×CSA buffer (ABI)

800 μl of primer (either pBAC 5'-2 or pBAC 3'-1 at 3.2 μM)

The sequencing cocktail was vortexed to ensure it was well-mixed and 32 μl was aliquoted into each PCR tube. Eight μl of the Autogen DNA for each clone was transferred from the DNA source plate to a corresponding well of the PCR plate. The PCR plates were sealed tightly and centrifuged briefly to collect all the reagents. Cycling conditions were as follows:

95° C. for 5 minutes

95° C. for 30 seconds

50° C. for 20 seconds

65° C. for 4 minutes

Go to steps 2 through 4 above for an additional 74 times

4° C. forever

At the end of the sequencing reaction, the plates were removed from the thermocycler and centrifuged briefly. Centri.Sep 96 plates were then used according to manufacturer's recommendation to remove unincorporated nucleotides, salts and excess primers. Each sample was resuspended in 1.5 µl of loading dye of which 1.3 µl was loaded on ABI 377 Fluorescent Sequencers. The resulting endsequences were then used to develop markers to rescreen the BAC library for filling gaps and were also analyzed by BLAST searching for EST or gene content.

E. SUB-CLONING AND SEQUENCING OF BAC RPCI_1098L22 FROM 20p13-p12

The physical map of the chromosome 20 region provides the location of the BAC RPCI_1098L22 clone that contains Gene 216 (see FIG. 2). DNA sequencing of BAC, RPCI 11-1098L22 from the region has been completed. BAC RPCI 11-1098L22 DNA, (the "BAC DNA") was isolated according to one of two protocols: either a Qiagen purification (Qiagen, Inc., Chatsworth, Calif., per manufacturer's instructions) or a manual purification using a method which is a modification of the standard alkaline lysis/Cesium Chloride preparation of plasmid DNA (see e.g., Ausubel et al, (1997), *Current Protocols in Molecular Biology*, John Wiley & Sons). Briefly, for the manual protocol, cells were pelleted, resuspended in GTE (50 mM glucose, 25 mM Tris-Cl (pH 8), 10 mM EDTA) and lysozyme (50 mg/ml solution), followed by NaOH/SDS (1% SDS/0.2N NaOH) and then an ice-cold solution of 3M KOAc (pH 4.5–4.8). RnaseA was added to the filtered supernatant, followed by treatment with Proteinase K and 20% SDS. The DNA was then precipitated with isopropanol, dried and resuspended in TE (10 mM Tris, 1 mM EDTA (pH 8.0)). The BAC DNA was further purified by Cesium Chloride density gradient centrifugation (Ausubel et al, (1997), *Current Protocols in Molecular Biology*, John Wiley & Sons).

Following isolation, the BAC DNA was hydrodynamically sheared using HPLC (Hengen, et al., (1997), *Trends in Biochem. Sci.*, 22:273–274) to an insert size of 2000–3000 bp. After shearing, the DNA was concentrated and separated on a standard 1% agarose gel. A single fraction, corresponding to the approximate size, was excised from the gel and purified by electroelution (Sambrook et al, (1989), *Molecular Cloning: A Laboratory Manual*, Cold Spring Harbor Laboratory, Cold Spring, N.Y.).

The purified DNA fragments were then blunt-ended using T4 DNA polymerase. The healed DNA was then ligated to unique BstXI-linker adapters (5' GTCTTCACCACGGGG and 5' GTGGTGAAGAC in 100–1000 fold molar excess). These linkers are complimentary to the BstXI-cut pMPX vectors, while the overhang is not self-complimentary. Therefore, the linkers will not concatemerize nor will the cut-vector re-ligate to itself easily. The linker-adapted inserts were separated from unincorporated linkers on a 1% agarose gel and purified using GeneClean (BIO 101, Inc.). The linker-adapted insert was then ligated to a modified pBlueScript vector to construct a "shotgun" subclone library. The vector contains an out-of-frame lacZ gene at the cloning site which becomes in-frame in the event that an adapter-dimer is cloned, allowing these to be avoided by their blue color.

All subsequent steps were based on sequencing by ABI377 automated DNA sequencing methods. Only major modifications to the. protocols are highlighted. Briefly, the library was then transformed into DH5-competent cells (Gibco/BRL, DH5-transformation protocol). Quality was assessed by plating onto antibiotic plates containing ampicillin and IPTG/Xgal. The plates were incubated overnight at 37° C. Successful transformants were then used for plating of clones and picking for sequencing. The cultures were grown overnight at 37° C. DNA was purified using a silica bead DNA preparation (Ng et al, *Nucl. Acids Res.*, 24:5045–5047 (1996)) method. In this manner, 25 µg of DNA was obtained per clone.

These purified DNA samples were then sequenced using ABI dye-terminator chemistry. The ABI dye terminator sequence reads were run on ABI377 machines and the data were directly transferred to UNIX machines following lane tracking of the gels. All reads were assembled using PHRAP (P. Green, Abstracts of DOE Human Genome Program Contractor-Grantee Workshop V, January 1996, p. 157) with default parameters and quality scores. The assembly was done at 8-fold coverage and yielded 1 contig, BAC RPCI 11 -1098L22. SEQ ID NO:7 (FIGS. 20A–20G) comprises a portion of the BAC which includes the genomic sequence of Gene 216.

F. GENE IDENTIFICATION

Any gene or EST mapping to the interval based on public map data or proprietary map data was considered a candidate respiratory disease gene. Public map data were derived from several sources: the Genome Database (GDB, http://gdbwww.gdb.org/), the Whitehead Institute Genome Center (http://www-genome.wi.mit.edu/), GeneMap98, UniGene, OMIM, dbSTS and dbEST (NCBI, http://www.ncbi.nlm.nih.gov/), the Sanger Centre (http://www.sanger.ac.uk/), and the Stanford Human Genorie Center (http://www-shgc.stanford.edu/). Proprietary data was obtained from sequencing genomic DNA (cloned into BACs) or cDNAs (identified by direct selection, screening of cDNA libraries or full length sequencing of IMAGE Consortium (http://www-bio.11nl.gov/bbrp/image.html) cDNA clones).

1. Gene Identification from clustered DNA fragments. DNA sequences corresponding to gene fragments in public databases (Genbank and human dbEST) and proprietary cDNA sequences (IMAGE consortium and direct selected cDNAs) were masked for repetitive sequences and clustered using the PANGEA Systems (Oakland, Calif.) EST clustering tool. The clustered sequences were then subjected to computational analysis to identify regions bearing similarity to known genes. This protocol included the following steps:

i. The clustered sequences were compared to the publicly available Unigene database (National Center for Biotechnology Information, National Library of Medicine, 38A, 8N905, 8600 Rockville Pike, Bethesda, Md. 20894; www.ncbi.nlm.nih.gov) using the blastn2 algorithm (Altschul et al, *Nucl. Acids Res.*, 25:3389–3402 (1997)). The parameters for this search were: E=0.05, v=50, B=50 (where E is the expected probability score cutoff, V is the number of database entries returned in the reporting of the results, and B is the number of sequence alignments returned in the reporting of the results (Altschul et al, *J. Mol. Biol.*, 215:403–410 (1990)).

ii. The clustered sequences were compared to the Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, *Nucl. Acids. Res.*, 25:3389–3402 (1997)). The parameters for this search were E=0.05, V=50, B=50, where E, V, and B are defined as above.

iii. The clustered sequences were translated into protein for all six reading frames, and the protein sequences were compared to a non-redundant protein database compiled from Genpept Swissprot PIR (National Center for Biotechnology Information, National Library of Medicine, 38A, 8N905, 8600 Rockville Pike, Bethesda, Md. 20894; www.ncbi.nlm.nih.gov). The parameters for this search were E=0.05, V=50, B=50, where E, V, and B are defined as above.

iv. The clustered sequences were compared to BAC sequences (see below) using blastn2 (Altschul et al, *Nucl. Acids. Res.*, 25:3389–3402 (1997)). The parameters for this search were E=0.05, V=50, B=50, where E, V, and B are defined as above.

2. Gene Identification from BAC Genomic Sequence.

Following assembly of the BAC sequences into contigs, the contigs were subjected to computational analyses to identify coding regions and regions bearing DNA sequence similarity to known genes.

This protocol included the following steps:

i. Contigs were degapped. The sequence contigs often contain symbols (denoted by a period symbol) that represent locations where the individual ABI sequence reads have insertions or deletions. Prior to automated computational analysis of the contigs, the periods were removed. The original data were maintained for future reference.

ii. BAC vector sequences were "masked" within the sequence by using the program crossmatch (Phil Green, http:\\chimera.biotech.washington.edu\UWGC). Since the shotgun library construction detailed above left some BAC vector in the shotgun libraries, this program was used to compare the sequence of the BAC contigs to the BAC vector and to mask any vector sequence prior to subsequent steps. Masked sequence was marked by an "X" in the sequence files, and remained inert during subsequent analyses.

iii. *E. coli* sequences contaminating the BAC sequences were masked by comparing the BAC contigs to the entire *E. coli* DNA sequence.

iv. Repetitive elements known to be common in the human genome were masked using crossmatch. In this implementation of crossmatch, the BAC sequence is compared to a database of human repetitive elements (Jerzy Jerka, Genetic Information Research Institute, Palo Alto, Calif.). The masked repeats were marked by X and remained inert during subsequent analyses.

v. The location of exons within the sequence was predicted using the MZEF computer program (Zhang, *Proc. Natl. Acad. Sci.*, 94:565–568 (1997);(Burge and Karlin, *J. Mol. Biol.*, 268:78–94))

vi. The sequence was compared to the publicly available unigene database (National Center for Biotechnology Information, National Library of Medicine, 38A, 8N905, 8600 Rockville Pike, Bethesda, Md. 20894; www.ncbi.nlm.nih.gov) using the blastn2 algorithm (Altschul et al, *Nucl. Acids Res.*, 25:3389–3402 (1997)). The parameters for this search were: E=0.05, v=50, B=50 (where E is the expected probability score cutoff, V is the number of database entries returned in the reporting of the results, and B is the number of sequence alignments returned in the reporting of the results (Altschul et al, *J. Mol. Biol.*, 215:403–410 (1990)).

vii. The sequence was translated into protein for all six reading frames, and the protein sequences were compared to a non-redundant protein database compiled from Genpept Swissprot PIR (National Center for Biotechnology Information, National Library of Medicine, 38A, 8N905, 8600 Rockville Pike, Bethesda, Md. 20894; www.ncbi.nlm.nih.gov). The parameters for this search were E=0.05, V=50, B=50, where E, V, and B are defined as above.

viii. The BAC DNA sequence was compared to a database of clustered sequences using blastn2 (Altschul et al, *Nucl. Acids. Res.*, 25:3389–3402 (1997)). The parameters for this search were E=0.05, V=50, B=50, where E, V, and B are defined as above. The database of clustered sequences was prepared utilizing a proprietary clustering technology (Pangea Systems, Inc.) using cDNA clones derived from direct selection experiments (described below), human dbEST mapping to the 20p13-p12 region, proprietary cDNAs; Genbank genes and IMAGE consortium cDNA clones.

ix. The BAC sequence was compared to the sequences derived from the ends of BACs from the region on chromosomes 20 using blastn2 (Altschul et al, *Nucl. Acids. Res.*, 25:3389–3402 (1997)). The parameters for this search were E=0.05, V=50, B=50, where E, V, and B are defined as above.

x. The BAC sequence was compared to the Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al, *Nucl. Acids. Res.*, 25:3389–3402 (1997)). The parameters for this search were E=0.05, V=50, B=50, where E, V, and B are defined as above.

xi. The BAC sequence was compared to the STS division of Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al., 1997). The parameters for this search were E=0.05, V=50, B=50, where E, V, and B are defined as above.

xii. The BAC sequence was compared to the Expressed Sequence Tag (EST) Genbank database (National Center for Biotechnology Information, National Library of Medicine, 38A, 8N905, 8600 Rockville Pike, Bethesda, Md. 20894; www.ncbi.nlm.nih.gov) using blastn2 (Altschul et al., *Nucl. Acids. Res.*, 25:3389–3402 (1997)). The parameters for this search were E=0.05, V=50, B=50, where E, V, and B are defined as above.

3. Gene Identification in region 20p13-p12 by Direct cDNA Selection.

Direct cDNA selection is a powerful technique for the identification of genes mapping to a particular genomic interval. It involves hybridizing genomic DNA (in this case, BACs) from a region of interest to pools of cDNAs derived from various tissue sources. The procedure permits the rapid isolation of cDNAs without the need for tedious cDNA library screening approaches. The tissues used in this study included unstimulated Th2 cells, Th2 cells stimulated with TPA, bronchial smooth muscle cells, unstimulated Th0 cells, Th0 stimulated with anti CD3 and TPA, pulmonary artery endothelium cells, Lung microvascular endothelial cells, bronchial epithelium cells, normal and asthmatic lung, small airway epithelium cells and lung fibroblasts. These cell types are implicated in the pathophysiology of asthma and are expected to express genes involved in the asthmatic inflammatory response. In addition, RNA isolated from brain was used because it is generally thought that brain expresses a diverse array of genes.

Cytoplasmic RNA was isolated as described by Sambrook et al, Molecular Cloning: A Laboratory Manual, Cold Spring Harbor Laboratories, Cold Spring Harbor, N.Y., (1989). Approximately 400–600 μg of cytoplasmic RNA was isolated from 50 million cells.

Total RNA was isolated from normal and asthmatic lung tissue using TRIzol Reagents (Gibco BRL, Rockville, Md.) which are ready-to-use monophasic solutions of guanadinium isothiocyanate and phenol (Chomczynski, P. and Sacchi, N. (1987) Anal. Biochem., 162:156–159; Chomczynski, P., Bowers-Finn, R., and Sabatini, L. (1987) J. NIH Res. 6:83; Simms, D., Cizdiel, P. E., and Chomczynski, P. (1993) Focus 15:99; Chomczynski, P. (1993) BioTechniques 15:532). Five hundred milligrams of frozen tissue was crushed into a fine powder using a Bessman tissue pulverizer (Fisher Scientific). The TRIzol Reagents were mixed with the crushed tissue according to the manufacturer's recommendations to isolate total RNA.

To ascertain whether there was genomic DNA or heteronuclear RNA contamination within the RNA isolates, PCR and RT/PCR were performed, respectively. The PCR analysis was performed using primers (Research Genetics) that amplify STS markers from chromosomes 2 (D2S2358), 7 (D7S2776, D7S685), 10 (D10S228, D10S1755) and 20 (D20S905, D20S95). All PCR reactions were performed in a volume of 25 µl that contained 1 µl of RNA, 10 mM Tris-HCl (pH 8.3), 50 mM KCl, 1.5 mM MgCl2, 0.001% gelatin, 200 mM each dNTPs, 10 µM of each primer and 1 unit Taq DNA polymerase (Perkin Elmer). A Perkin Elmer 9600 was used to amplify the material under the following conditions: 30 seconds at 94° C., 30 seconds at 55° C. and 30 seconds at 72° C. for 30 cycles. The RT/PCR analysis was performed using the SuperScript One-Step RT-PCR System (Gibco-BRL, Rockville, Md.) according to the manufacturer's recommendations. All PCR and RT/PCR products were evaluated by electrophoresis on a 1% agarose gel.

Poly A+ RNA was prepared from the total RNA isolated from the human primary cells and lung tissues using Dynabeads Oligo(dT) according to the manufacturer's recommendations (Dynal, Lake Success, N.Y.). Approximately 4 µg of messenger RNA was isolated from 150 µg of total RNA for each cell type and tissue source. Total RNA isolated from brain tissue was purchased from Clontech (Palo Alto, Calif.) and poly A+ RNA was prepared from this material using the Dynabeads Oligo(dT) as described above.

Oligo dT and random primed cDNA pools were generated from the mRNA isolated from each cell type and tissue source. Briefly, 2.0 µg mRNA was mixed with oligo(dT) primer in one reaction, and 2.0 µg mRNA was mixed with random hexamers in another reaction, and converted to double stranded complementary DNA using the SuperScript Choice System for cDNA Synthesis (Gibco-BRL, Rockville, Md.) according to manufacturer's recommendations.

Four different paired phosphorylated cDNA linkers (Table 3) were annealed by mixing in a 1:1 ratio (10 µg each), incubating at 65° C. for 5 minutes and allowing to cool to room temperature for 30 minutes. The annealed linkers were ligated to the oligo(dT) and random primed cDNA pools from various tissue and cell sources (Table 3) according to manufacturer's instructions (Gibco-BRL, Rockville, Md.). The linker sequence provides a tag to identify which tissue from which that particular RNA was derived after sequencing the cDNAs.

TABLE 3

Sequence and tissue distribution of the paired linkers

| Paired linkers | Sequence | Cell/Tissue Type |
|---|---|---|
| OLIGO 3 | 5'CTC GAG AAT TCT GGA TCC TC3' | Th2/unstimulated(dT + rp) |
| OLIGO 4 | 5'TTG AGG ATC CAG AAT TCT CGA G3' | Th0/stimulated/anti CD3 (dT + rp) |
|  |  | Pulmonary artery endothelium cells (dT + rp) |
|  |  | Lung microvascular endothelial cells (dT + rp) |
|  |  | Bronchial epithelium cells (dT + rp) |
| OLIGO 5 | 5'TGT ATG CGA ATT CGC TGC GCG3' | Normal Lung (dT + rp) |
| OLIGO 6 | 5'TTC GCG CAG CGA ATT CGC ATA CA3' | Athmatic lung (dT + rp) |
|  |  | Th2/stimulated/TPA (dT + rp) |
|  |  | Bronchial smooth muscle cells (dT + rp) |
| OLIGO 9 | 5'CCT ACG GAA TTC TCA CTC AGC3' | Brain (dT + rp) |
| OLIGO 10 | 5'TTG CTG AGT GAG AAT TCC GTA GG3' | Th0/unstimulated (dT + rp) |
|  |  | Pulmonary artery smooth muscle cells (dT + rp) |
| OLIGO 11 | 5'GAA TCC GAA TTC CTG GTC AGC3' | Lung fibroblasts (dT + rp) |
| OLIGO 12 | 5'TTG CTG ACC AGG AAT TCG GAT TC3' | Th0/stimulated/TPA (dT + rp) |
|  |  | Small airway epithelium cells (dT + rp) |

The cDNA pools were evaluated for length distribution by PCR amplification using 1 µl of a 1:1, 1:10, and 1:100 dilution of the ligation reaction. All PCR reactions were performed in a volume of 25 µl which contained 1 µl of DNA, 10 mM Tris-HCl (pH 8.3), 50 mM KCl, 1.5 mM MgCl2, 0.001% gelatin, 200 mM each dNTPs, 10 µM of each primer and 1 unit Taq DNA polymerase (Perkin Elmer). A Perkin Elmer 9600 was used to amplify the material under the following conditions: 30 seconds at 94° C., 30 seconds at 55° C. and 2 minutes at 72° C. for 30 cycles. The length distribution of the amplified cDNA pools was evaluated by electrophoresis on a 1% agarose gel. The PCR reaction that gave the best representation of the random primed and oligo dT primed cDNA pools was scaled up so that ~2–3 µg of each cDNA pool was produced and this represented a 1xPCR reaction of the starting cDNA pools.

One microgram of BAC RPCI 1098L22 DNA that spanned Gene 216 was pooled in equimolar amounts and 1 µg of the isolated genomic DNA was labelled with biotin 16-UTP by nick translation in accordance with the manufacturer's instructions (Boehringer Marnheim). The incorporation of the biotin was monitored by standard methods (Del Mastro and Lovett, Methods in Molecular Biology, Humana Press Inc., NJ (1996)

a. Direct cDNA Selection for Region 20p13-p12.

Direct cDNA selection was performed using standard methods (Del Mastro and Lovett, Methods in Molecular Biology, Humana Press Inc., NJ (1996)). Briefly, 1 µg of each cDNA pool was placed into individual PCR tubes. A total of 30 direct selection experiments were arrayed into a PCR plate. Suppression of high copy repeats, ribosomal RNA and plasmid in the cDNA pools was performed to a Cot of 20. One hundred nanograms of biotinylated BAC DNA was mixed with the suppressed cDNAs and hybridized in solution to a Cot of 200. The biotinylated DNA and the cognate cDNAs were then captured on streptavidin-coated paramagnetic beads. The beads were washed and the primary selected cDNAs were eluted. The products from the first round of direct selection were PCR amplified using appropriate primers (shown in Table 3) and a second round of direct selection was then performed.

b. Cloning and Arraying of the Secondary Selected Material.

The random primed product of the second round of direct selection (the secondary selected material)from lung microvascular endothelial cells, Th0/unstimulated cells, lung fibroblast cells, Th2/unstimulated cells, pulmonary artery endothelium cells, normal lung, small airway epithelium cells, bronchial epithelium cells and Th0 cells stimulated with TPA, and oligo dT primed Th0 cells stimulated with TPA was PCR amplified with modified primers that were used during the two rounds of direct cDNA selection (See Table 4 below).

TABLE 4

Sequence of the 5 modified oligonucleotides used to amplify the secondary selected material prior to cloning into the pAMP10 vector.

| Modified Oligonucleotides | Sequence |
| --- | --- |
| OLIGO 3 | 5'CUA CUA CUA CUA CTC GAG AAT TCT GGA TCC TC3' |
| OLIGO 5 | 5'CUA CUA CUACUATGT ATG CGA ATT CGC TGC GCG3' |
| OLIGO 9 | 5'CUA CUA CUA CUA CCT ACG GAA TTC TCA CTC AGC3' |
| OLIGO 11 | 5'CUA CUA CUA CUA GAA TCC GAA TTC CTG GTC AGC3' |

The amplified material was cloned into the UDG vector pAMP10 (Gibco-BRL, Rockville, Md.) in accordance with the manufacturer's recommendations. Four hundred and eighty clones were picked from each transformed source and arrayed into five 96 well microtiter plate. Each selected cDNA library was stamped, in duplicate, in a high density format onto Hybond N+ nylon membrane (Amersham). The bacteria were grown overnight at 37° C., and the membranes were processed as recommended by the manufacturer.

To identify which of the clones represented the most common contaminants, such as high copy repeats and ribosomal RNA, a radiolabelled probe containing 1 µg of Cot1 DNA and 0.5 µg ribosomal DNA was hybridized at 65° C. to the high density filters (Sambrook et al, (1989)Molecular Cloning: A Laboratory Manual, Cold Spring Harbor Laboratories, Cold Spring Harbor, N.Y.). The filters were washed three times in buffer (0.1×SSC, 0.1%SDS) at 65° C. and were autoradiographed. Those cDNAs that showed duplicate signals were scored as background contaminants. The remainder of the clones were re-arrayed into 96 well microtiter plates. A total of one hundred and eleven 96 well microtiter plates containing 10638 secondary selected clones were sequenced: Three 96 well microtiter plates from all the random primed selections, except Th0 cells stimulated with TPA where only two plates were sequenced, and one 96 well microtiter plate from Th0 cells stimulated with TPA oligo dT selection. All cDNA clones were sequenced using M13 dye primer terminator cycle sequencing kits (Applied Biosystems), and the data collected by the ABI 377 automated fluorescence sequencer (Applied Biosystems).

Further background clones such as high copy repeats, ribosomal RNA, plasmid, mitochondrial, E. coli and yeast that were not identified in the hybridization process were removed from the dataset using in silico methods. This process yielded 787 cDNA clones for further analysis. These clones were clustered using Pangea System's EST Clustering Tool (Oakland, Calif.) and analyzed with BLASTN, X and FASTA programs. This software tool enables one to construct full length gene sequences by aligning the DNA fragments.

These direct selected clones were combined with the proprietary cDNA sequences, and sequences within the public domain (dbEST and Genbank) then clustered using the Pangea Systems EST Clustering Tool. These clustered sequences are known to those skilled in the art as consensus sequences assisted in extending the gene sequences disclosed herein.

c. Mapping Analysis.

Those BACs that were identified, and mapped to the region 20p13- p12 were used to determine which cDNA clones map back using standard hybridization methods as described by Sambrook et al, (1989) *Molecular Cloning: A Laboratory Manual*, Cold Spring Harbor Laboratories, Cold Spring Harbor, N.Y. The DNA from each BAC was isolated using Nucleobond AX columns as described by the manufacturer (Clontech, Palo Alto, Calif.) and hybridized at 65° C. to high density filters containing the sequenced cDNAs. Those cDNAs that showed duplicate signals were scored as mapping back to the genomic clone and to the region. These cDNAs were studied further as disorder associated gene(s).

Through mapping analysis, BAC RPCI 1098L22 was identified as containing Gene 216. This BAC sequence (SEQ ID NO:7, FIGS. 20A–20G) is genomic nucleotide sequence corresponding to the cDNA sequence of Gene 216 (SEQ ID NO:1–SEQ ID NO:3).

G. cDNA CLONING AND EXPRESSION ANALYSIS

1. Construction of cDNA libraries. Directionally cloned cDNA libraries from normal lung and bronchial epithelium were constructed using standard methods described previously (Soares et. al., 1994, Automated DNA Sequencing and Analysis, Adams, Fields and Venter, Eds., Academic Press, NY, pages 110–114). Total and cytoplasmic RNAs were extracted from tissue or cells by homogenizing the sample in the presence of Guanidinium Thiocyanate-Phenol-Chloroform extraction buffer (e.g. Chomczynski and Sacchi, Anal. Biochem., 162:156–159 (1987)) using a polytron homogenizer (Brinkman Instruments). PolyA+ RNA was isolated from total/cytoplasmic RNA using dynabeads-dT according to the manufacturer's recommendations (Dynal, Inc.). The ds cDNA synthesized was then ligated into the plasmid vector pBluescript II KS+ (Stratagene, La Jolla, Calif.), and the ligation mixture was transformed into *E. coli* host DH10B or DH12S by electroporation (Soares, 1994). Following overnight growth at 37° C., DNA was recovered from the *E. coli* colonies after scraping the plates by processing as directed for the Mega-prep kit (Qiagen, Chatsworth, Calif.). The quality of the cDNA libraries was estimated by counting a portion of the total number of primary transformants, determining the average insert size and the percentage of plasmids with no cDNA insert. Additional cDNA libraries (human total brain, heart, kidney, leukocyte, and fetal brain) were purchased from Life Technologies, Bethesda, Md.

cDNA libraries, both oligo (dT) and random hexamer-primed were used for isolating cDNA clones mapping within the disorder critical region. Four 10×10 arrays of each of the cDNA libraries were prepared as follows: the cDNA libraries were titered to $2.5 \times 10^6$ using primary transformants. The appropriate volume of frozen stock was used to inoculate 2 L of LB/ampicillin (100 μg/μl). 400 aliquots containing 4 ml of the inoculated liquid culture were generated. Each tube contained about 5000 cfu. The tubes were incubated at 30° C. overnight with shaking until an OD of 0.7–0.9 was obtained. Frozen stocks were prepared for each of the cultures by aliquotting 300 μl of culture and 100 μl of 80% glycerol. Stocks were frozen in a dry ice/ethanol bath and stored at −70° C. DNA was isolated from the remaining culture using the Qiagen (Chatsworth, Calif.) spin mini-prep it according to the manufacturer's instructions. The DNAs from the 400 cultures were pooled to make 80 column and row pools. Markers were designed to amplify putative exons from candidate genes. Once a standard PCR condition was identified and specific cDNA libraries were determined to contain cDNA clones of interest, the markers were used to screen the arrayed library. Positive addresses indicating the presence of cDNA clones were confirmed by a second PCR using the same markers.

Once a cDNA library was identified as likely to contain cDNA clones corresponding to a specific transcript of interest from the disorder critical region, it was used to isolate a clone or clones containing cDNA inserts. This was accomplished by a modification of the standard "colony screening" method (Sambrook et al, Molecular Cloning: A Laboratory Manual, Cold Spring Harbor Laboratory, Cold Spring Harbor N.Y. (1989)). Specifically, twenty 150 mm LB+ampicillin agar plates were spread with 20,000 colony forming units (cfu) of cDNA library and the colonies allowed to grow overnight at 37° C. Colonies were transferred to nylon filters (Hybond from Amersham, or equivalent) and duplicates prepared by pressing two filters together essentially as described (Sambrook et al, Molecular Cloning: A Laboratory Manual, Cold Spring Harbor Laboratory, Cold Spring Harbor N.Y. (1989)). The "master" plate was then incubated an additional 6–8 hrs to allow the colonies additional growth. The DNA from the bacterial colonies was then bound onto the nylon filters by treating the filters sequentially with denaturing solution (0.5 N NaOH, 1.5 M NaCl) for two minutes, neutralization solution (0.5 M Tris-Cl pH 8.0, 1.5 M NaCl) for two minutes (twice). The bacterial colonies were removed from the filters by washing in a solution of 2×SSC/2% SDS for one minute while rubbing with tissue paper. The filters were air dried and baked under vacuum at 80° C. for 1–2 hrs to cross link the DNA to the filters.

cDNA hybridization probes were prepared by random hexamer labelling (Fineberg and Vogelstein, Anal. Biochem., 132:6–13 (1983)) or by including gene-specific primers and no random hexamers in the reaction (for small fragments). The colony membranes were then pre-washed in 10 mM Tris-Ci pH 8.0, 1 M NaCl, 1 mM EDTA, 0.1% SDS for 30 minutes at 55° C. Following the pre-wash, the filters were pre-hybridized in >2 ml/filter of 6×SSC, 50% deionized formamide, 2% SDS, 5×Denhardt's solution, and 100 mg/ml denatured salmon sperm DNA, at 42° C. for 30 minutes. The filters were then transferred to hybridization solution (6×SSC, 2% SDS, 5×Denhardt's, 100 mg/ml denatured salmon sperm DNA) containing denatured a-32P-dCTP-labelled cDNA probe and incubated overnight at 42° C.

The following morning, the filters were washed under constant agitation in 2×SSC, 2% SDS at room temperature for 20 minutes, followed by two washes at 65° C. for 15 minutes each. A second wash was performed in 0.5×SSC, 0.5% SDS for 15 minutes at 65° C. Filters were then wrapped in plastic wrap and exposed to radiographic film. Individual colonies on plates were aligned with the autoradiograph and positive clones picked into a 1 ml solution of LB Broth containing ampicillin. After shaking at 37° C. for 1–2 hours, aliquots of the solution were plated on 150 mm plates for secondary screening. Secondary screening was identical to primary screening (above) except that it was performed on plates containing ~250 colonies so that individual colonies could be clearly identified. Positive cDNA clones were characterized by restriction endonuclease cleavage, PCR, and direct sequencing to confirm the sequence identity between the original probe and the isolated clone.

To obtain the full-length cDNA, novel sequence from the 5'-end of the clone was used to reprobe the library. This process is repeated until the length of the cDNA cloned matched that of the mRNA, estimated by Northern analysis.

Rapid Amplification of cDNA ends (RACE) was performed following the manufacturer's instructions using a Marathon cDNA Amplification Kit (Clontech, Palo Alto, Calif.) as a method for cloning the 5' and 3' ends of candidate genes. cDNA pools were prepared from total RNA by performing first strand synthesis, where a sample of total RNA sample was mixed with a modified oligo (dT) primer, heated to 70° C., cooled on ice and followed by the addition of: 5×first strand buffer, 10 mM dNTP mix, and AMV Reverse Transcriptase (20 U/μl). The reaction mixture was incubated at 42° C. for an hour and placed on ice. For second strand synthesis, the following components were added directly to the reaction tube: 5×second strand buffer, 10 mM dNTP mix, sterile water, 20×second strand enzyme cocktail and the reaction tube was incubated at 16° C. for 1.5 hours. T4 DNA Polymerase was added to the reaction tube and incubated at 16° C. for 45 minutes. The second-strand synthesis was terminated with the addition of an EDTA/Glycogen mix. The sample was subjected to a phenol/chloroform extraction and an ammonium acetate precipitation. The cDNA pools were checked for quality by analyzing on an agarose gel for size distribution. Marathon cDNA adapters were then ligated onto the cDNA ends. The specific adapters contained priming sites that allowed for amplification of either 5' or 3' ends, and varied depending on the orientation of the gene specific primer (GSP) that was chosen. An aliquot of the double stranded cDNA was added to the following reagents: 10 μM Marathon cDNA adapter, 5×DNA ligation buffer, T4 DNA ligase. The reaction was incubated at 16° C. overnight and heat inactivated to terminate the reaction. PCR was performed by the addition of the following to the diluted double stranded cDNA pool: 10×cDNA PCR reaction buffer, 10 μM dNTP mix, 10 μM GSP, 10 μM AP1 primer (kit), 50×Advantage cDNA Polymerase Mix. Thermal Cycling conditions were 94° C. for 30 seconds, 5 cycles of 94° C. for 5 seconds, 72° C. for 4 minutes, 5 cycles of 94° C. for 5 seconds, 70° C. for 4 minutes, 23 cycles of 94° C. for 5 seconds, 68° C. for 4 minutes. After the first round of PCR was performed using the GSP to extend to the end of the adapter to create the adapter primer binding site, exponential amplification of the specific cDNA of interest was performed. Usually, a second, nested PCR was performed to provide specificity. The RACE product was analyzed on an agarose gel. Following excision from the gel and purification (GeneClean, BIO 101), the RACE product was then cloned into pCTNR (General Contractor DNA Cloning System, 5'-3', Inc.) and sequenced to verify that the clone was specific to the gene of interest.

Figure 16A:
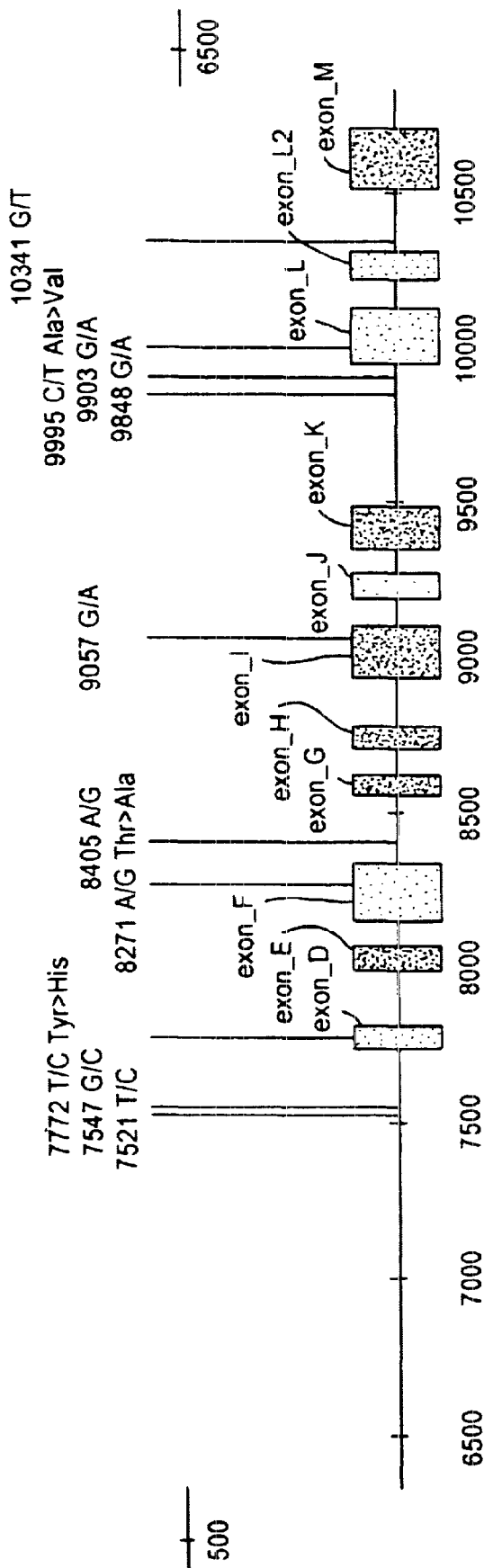
FIGS. 16A–16B show a view of Gene 216b and the corresponding single nucleotide polymorphic sites.
Figure 16B:
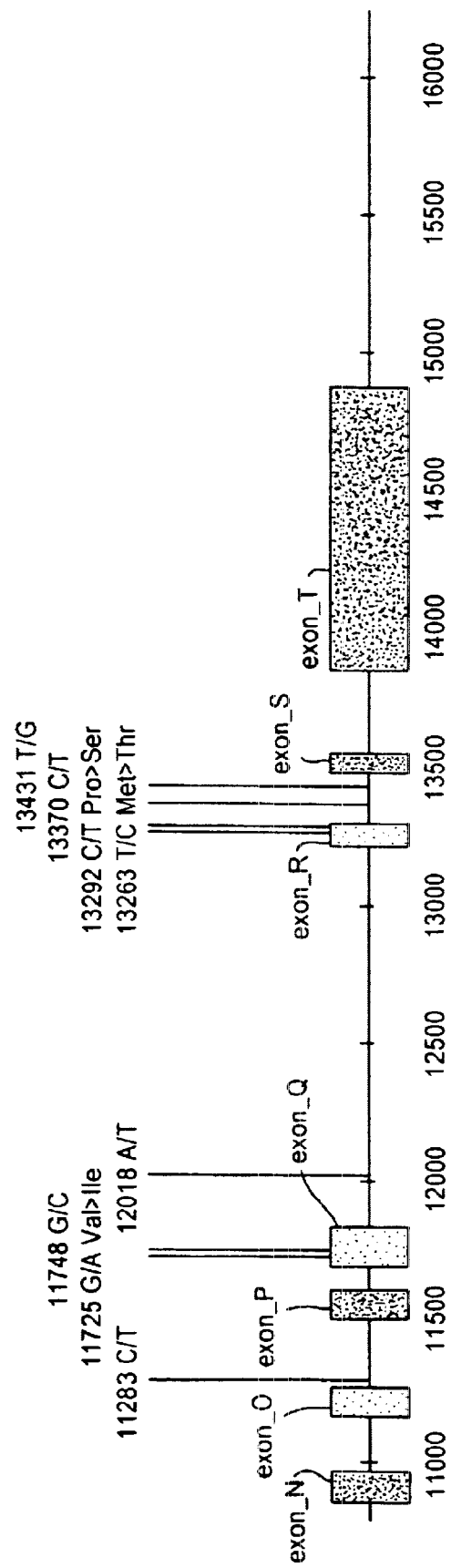
Figure 17A:
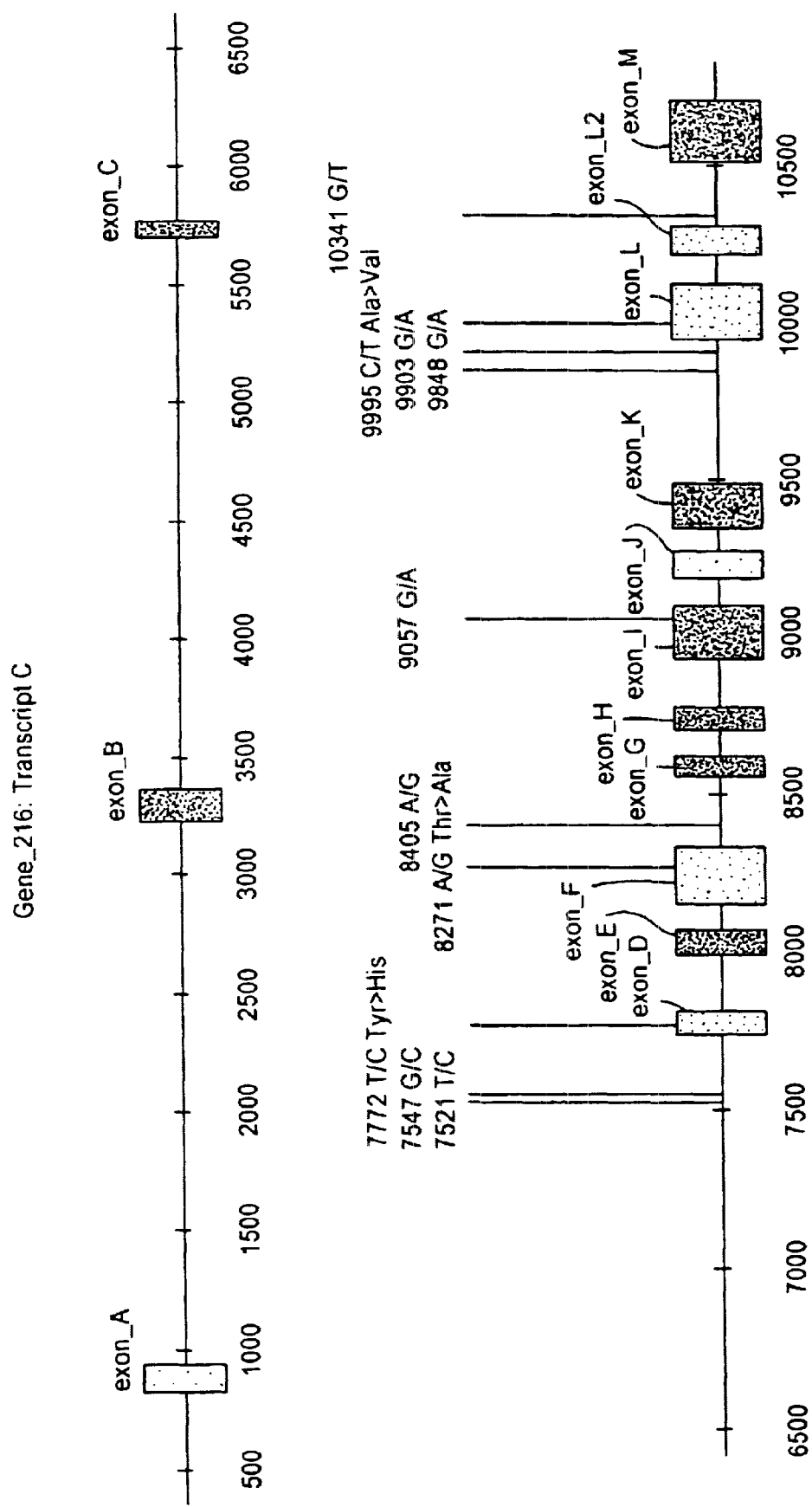
FIGS. 17A–17B show a view of Gene 216c and the corresponding single nucleotide polymorphic sites.
Figure 17B:
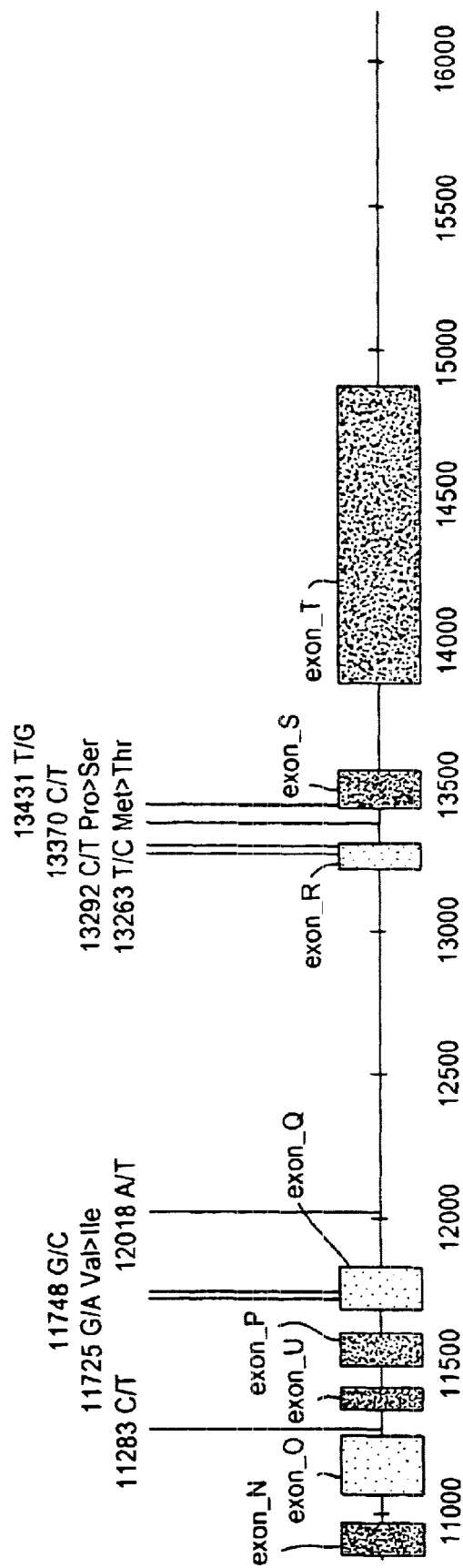

2. Expression Analysis. To characterize the expression of genes mapping to the 20p13-p12 region, a series of experiments were performed. First, oligonucleotide primers were designed for use in the polymerase chain reaction (PCR) so that portions of a cDNA, EST, or genomic DNA could be amplified from a pool of DNA molecules or RNA population (RT-PCR). The PCR primers were used in a reaction containing genomic DNA to verify that they generated a product of the predicted size (based on the genomic sequence). A critical piece of data that is required when characterizing novel genes is the length, in nucleotides, of the processed transcript or messenger RNA (mRNA). Those skilled in the art primarily determine the length of an mRNA by Northern analysis (Sambrook et al, Molecular Cloning: A Laboratory Manual, Cold Spring Harbor Laboratory, Cold Spring Harbor N.Y. (1989)). Probes were generated using one of the methods described below. Briefly, sequence verified IMAGE consortium cDNA clones were digested with appropriate restriction endonucleases to release the insert. The restriction digest was electrophoresed on an agarose gel and the bands containing the insert were excised. The gel piece containing the DNA insert was placed in a Spin-X (Corning Costar Corporation, Cambridge, MA) or Supelco spin column (Supelco Park, Pa.) and spun at high speed for 15 mins. The DNA was ethanol precipitated and resuspended in TE. Alternatively, PCR products obtained from genomic DNA or RT-PCR were also purified as described above. Inserts purified from IMAGE clones were random primer labelled (Feinberg and Vogelstein) to generate probes for hybridization. Probes from purified PCR products were generated by incorporation of a-$^{32}$P-dCTP in second round of PCR. Commercially available Multiple Tissue Northern blots (Clontech, Palo Alto, Calif.) were hybridized and washed under conditions recommended by the manufacturer. FIG. 16 depicts the Northern Analysis of Gene 216. As shown in the figure, various tissue sources showed expression of Gene 216.

3. RT-PCR. RT-PCR was used as an alternate method to Northern blotting to detect mRNAs with low levels of expression. Total RNA from multiple human tissues was purchased from Clontech (Palo Alto, Calif.) and genomic DNA was removed from the total RNA by DNaseI digestion. The "Superscript" Preamplification System for First strand cDNA synthesis" (Life Technologies, Gaithersburg, Md.) was used according to manufacturer's specifications with oligo(dT) or random hexamers to synthesize cDNA from the DNaseI treated total RNA. Gene specific primers were used to amplify the target cDNAs in a 30 $\mu$l PCR reaction containing 0.5 $\mu$l of first strand cDNA, 1 $\mu$l sense primer (10 $\mu$M), 1 $\mu$l antisense primer (10 $\mu$M), 3 $\mu$l dNTPs ( 2 mM), 1.2 $\mu$l MgCl$_2$ (25 mM), 3 $\mu$l 10×PCR buffer and 1 unit of Taq Polymerase (Perkin Elmer). The PCR reaction was initially denatured at 94° C. for 4 min, then 30 cycles of denaturation at 94° C. for 30 sec, annealing at 58° C. for 1 min and extension at 72° C. for 1 min, followed by a final extension at 72° C. for 7 min. PCR products were analyzed on agarose gels.

Three alternatively transcribed transcripts of Gene 216 were identified described as Gene 216a, isolated from lung cDNA library; Gene 216b, isolated from testes cDNA library; and 216c, predicted by Genscan (Burge and Karlin, *J. Mol. Biol.*, 268:78–94); and their corresponding cDNA sequence are shown in FIGS. 3A–F, 4A–4F and 5A–5G, respectively. FIG. 6 shows a schematic of the exons of Gene 216a, Gene 216b, and 216c. FIGS. 7A–7B, 8A–8B, and 9A–9B depict the predicted exon/intron structure of Gene 216a, Gene 216b, and 216c, respectively.

H. COMPUTATIONAL BIOLOGY ANALYSIS

Figure 10:
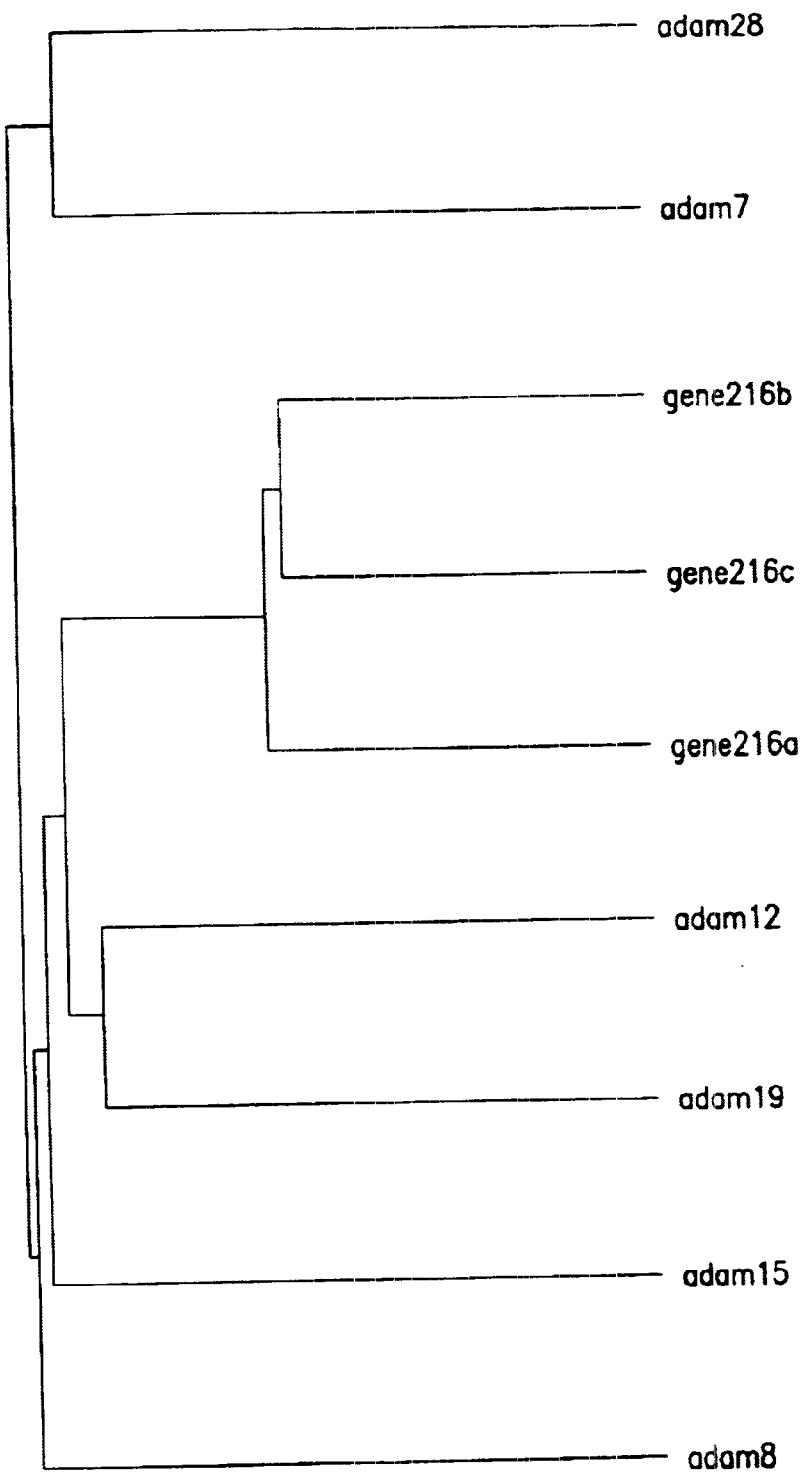
FIG. 10 depicts a Dendrogram of 19 human ADAMs and Gene 216a, Gene 216b, and Gene 216c.

Multiple protein alignment of 19 Human a disintegrin-like and metalloproteinase-containing protein (ADAMs) and Gene 216 was performed using the GCG program PILEUP (Wisconsin Package Version 9.1 Genetics Computer Group (GCG), 1997). The alignment was based on the full amino acid sequence of the 19 ADAMs and Gene 216, and utilized a gap creation penalty of 12 and a gap extension penalty of 4. The results of the alignment generated two outputs: a phylogenetic tree known as a dendogram that shows relatedness and evolutionary diversity of the genes to each other (FIG. 10); and an amino acid sequence alignment of those genes (FIGS. 11A–11D).

Multiple protein alignment of the predicted mouse homolog of Gene 216 and the alternately spliced variants, Gene 216a, Gene 216b and Gene 216c (FIGS. 12A–12B) was performed in GeneWorks version 2.3 (IntelliGenetics). The alignment was based on the full amino acid sequence of the predicted mouse gene and Gene 216, and utilized a gap creation penalty of 12 and a gap extension penalty of 4.

The Kyte-Doolittle hydrophobicity plot (FIG. 13) was utilized in GeneWorks version 2.3 (IntelliGenetics). This algorithm measures the hydrophobicity across a protein, thus providing an indication of the probable location of regions of Gene 216 that may interact with the lipid bilayer of the cell membrane. The black bar with the letter "A" indicates the signal peptide sequence. The transmembrane domain is located by the black bar with the letter "B."

I. GENE ANALYSIS AND POTENTIAL FUNCTION

The association of Gene 216 with asthma and other respiratory diseases is demonstrated as follows:

BLAST analysis against protein and nucleotide databases indicated that Gene 216 is likely to be a novel member of the ADAM gene family (Table 6). The ADAMs are zinc-dependent metalloproteinases, a growing gene family that currently contains 30 members. These genes have a complex domain organization that consists of a signal sequence, a propeptide, metalloprotease, disintegrin, cysteine-rich, and epidermal growth factor-like domains, a transmembrane region and a cytoplasmic tail. ADAMs have been implicated in many processes such as but not limited to, proteolysis in the secretory pathway and extracellular matrix, extra- and intra-cellular signaling, processing of plasma membrane proteins and procytokine conversion.

TABLE 6 shows the top five hits when Gene 216 was compared against NR protein database using BLAST.

| Hit | GenBank Locus | Description | Smallest Sum |
|---|---|---|---|
| 1 | U66003 | *Xenopus laevis* (ADAM 13) | 5.5e-166 |
| 2 | AF019887 | *Mus musculus* metalloprotease-disintegrin meltrin beta | 1.2e-139 |
| 3 | AF134707 | *Homo sapiens* disintegrin and metalloproteinase domain 19 (ADAM19) | 1.6e-139 |
| 4 | S60257 | Mouse mRNA for meltrin alpha | 1.8e-121 |
| 5 | AF023476 | *Homo sapiens* meltrin-L precursor (ADAM12) | 4.9e-119 |

Figure 14:
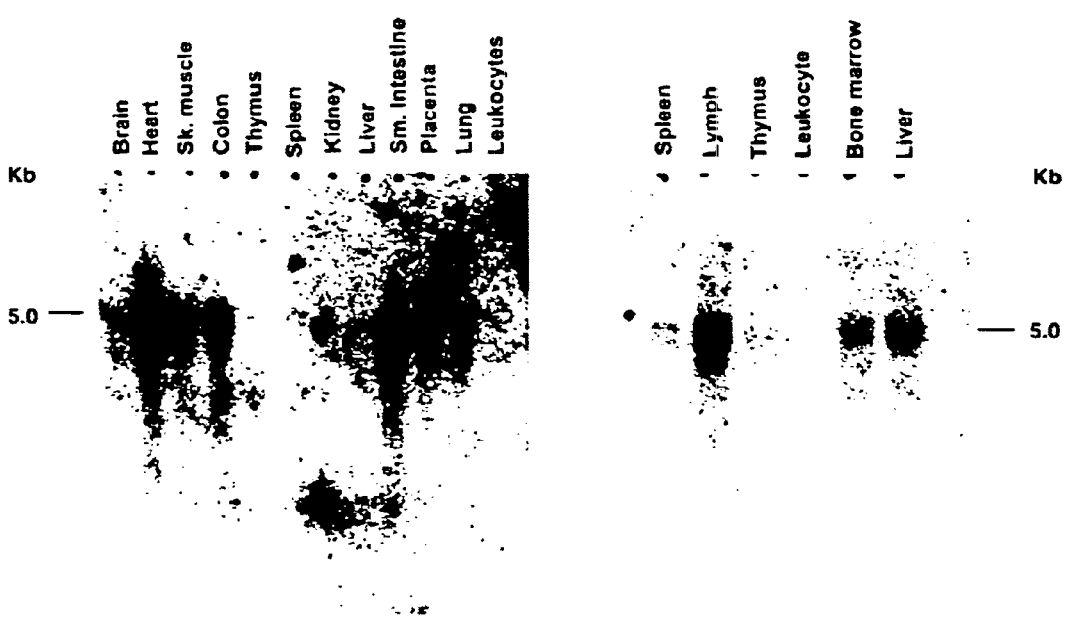
FIG. 14 shows a Northern Analysis of Gene 216.
Figure 15A:
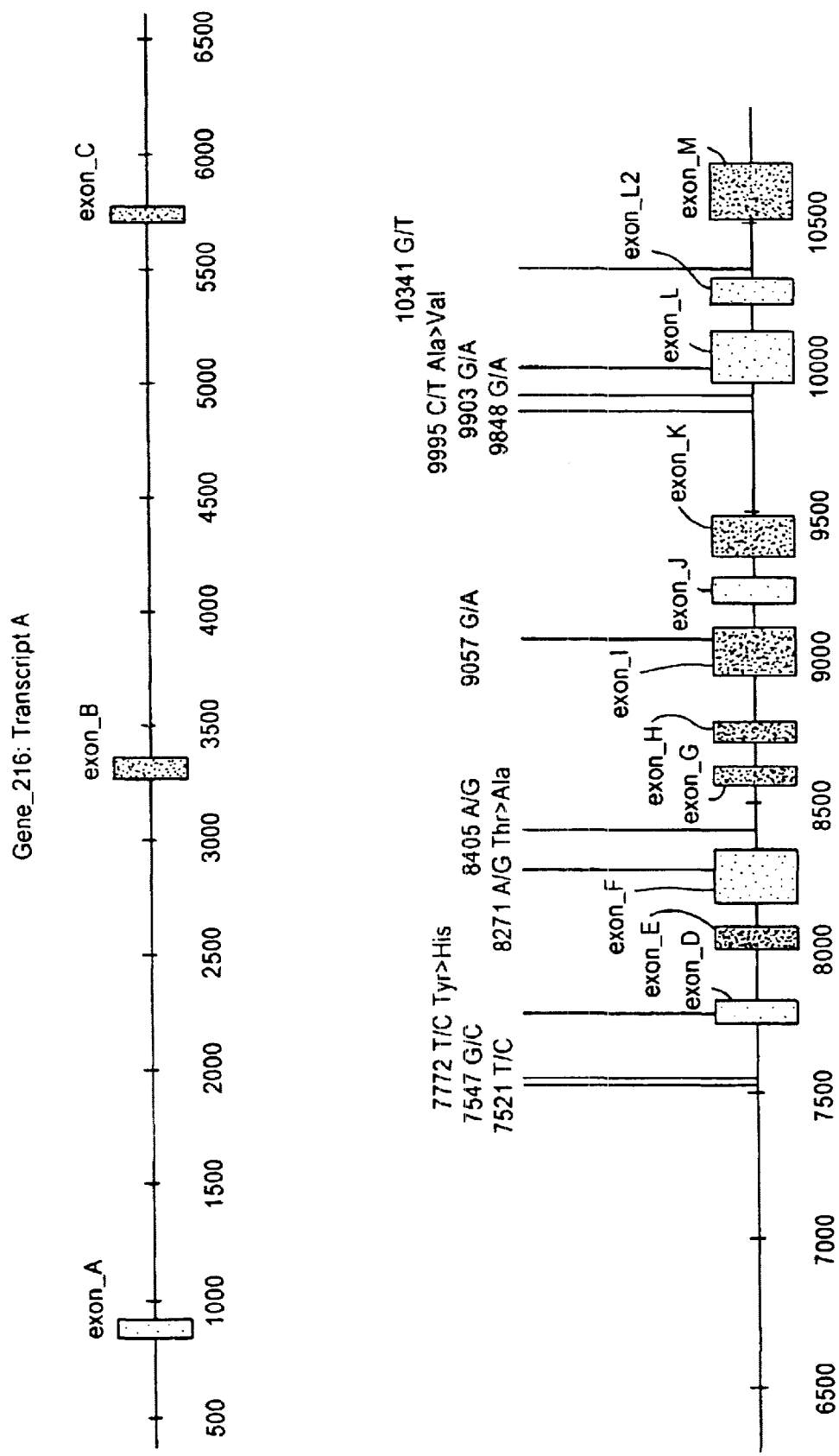
FIGS. 15A–15B show a view of Gene 216a and the corresponding single nucleotide polymorphic sites.
Figure 15B:
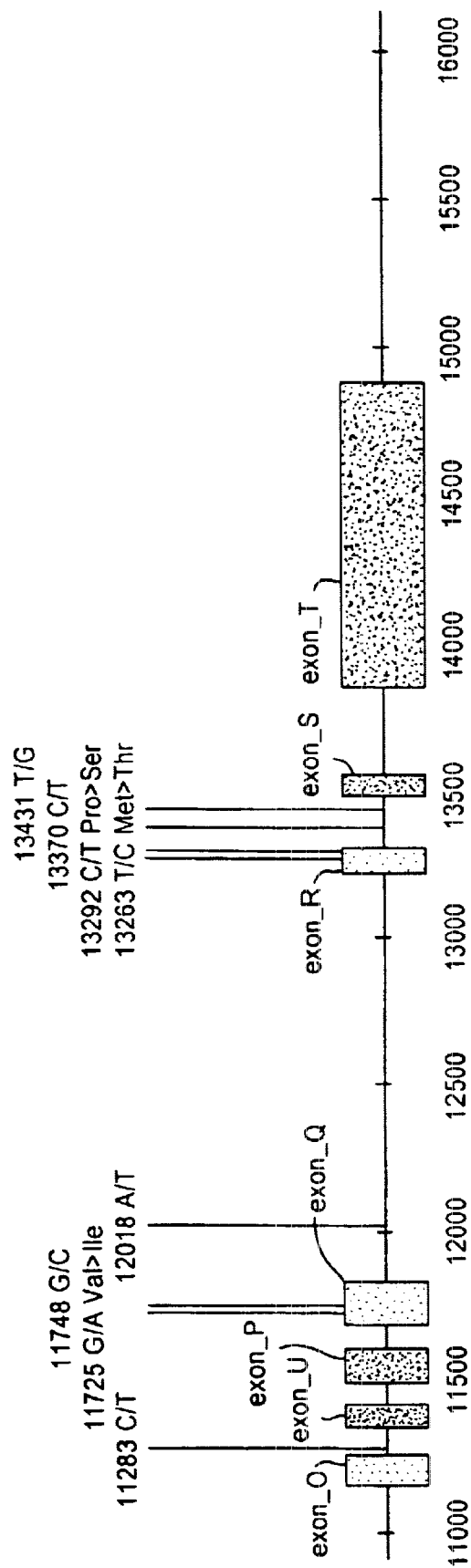

BAC RPCI-11__1098L22 (207 kb) maps to chromosome 20p13-p12 and contains the genetic marker D20S867 located 12.12 cM from the telomere of the p-arm of chromosome 20. Gene 216 spans 17 kb and maps within the BAC between nucleotides 91000 and 108000. The gene contains 21 exons (FIG. 6) and exhibits three probable alternatively spliced variants: Gene 216a, Gene 216b and Gene 216c (FIGS. 7A–7B, 8A–8B, and 9A–9B). Northern blot analysis of Gene 216 showed a 5.0 Kb transcript that was expressed in a wide variety of somatic tissues, including lung, brain, heart, skeletal muscle, colon, kidney, liver, small intestine, placenta, lymph, thymus and bone marrow (FIG. 14). The open reading frame (ORF) for Gene 216a is 2241 bp of the transcript and encodes 747 amino acids (FIGS. 3A–3F), for Gene 216b the ORF is 2364 bp of the transcript and encodes 788 amino acids (FIGS. 4A–4F) and for Gene 216c the ORF is 2550 bp of the transcript and encodes 850 amino acids (FIGS. 5A–5G).

The dendogram (FIG. 10) demonstrated that Gene 216 was probably most closely related to ADAM 12 and 19. The dendogram also indicated that 4 additional ADAMs were probably distantly related to Gene 216. Amino acid sequence alignment of these 6 ADAMs to Gene 216 (FIGS. 11A–11D) indicated regions of significant similarity that represented the domains which genes of this type possess. This alignment was determined by GCG (Wisconsin Package Version 9.1 Genetics Computer Group (GCG), 1997). The alignment was based on a gap creation penalty of 12 and gap extension penalty of 4. Arrows represent the likely position of the domains, boxed amino acid residues represent the consensus regions in Gene 216 with ADAMs and dashed boxed amino acids represents a putative $SH_3$ binding site.

Gene 216 contains a signal sequence (FIG. 13), which is also shared by most of the ADAMs (FIG. 11A). The presence of a signal sequence at the beginning of a protein helps to facilitate its transfer through the lipid bilayer.

The prodomain was identified through amino acid sequence alignment and by reference to publications describing ADAMs (Stone et al, *J. Prot. Chem.*, 18:447–465 (1999), Primakov and Myles, *TIG*, 16:83–87 (2000)). All ADAMs possess a prodomain that contains a conserved cysteine residue (FIG. 11A). This conserved cysteine is involved in formation of an intramolecular complex with a zinc ion bound to the catalytic domain. The interaction serves to block the active site and inhibits proteolysis. Upon conformational change or enzymatic cleavage of the prodomain the cysteine is dissociated from the active site and the ADAM is activated. This activation mechanism is called the "cysteine switch". The presence of the conserved domain suggests that Gene 216 has the ability to be activated by a conformational change or by unknown proteases.

All ADAMs also encode a highly conserved metalloprotease domain similar to the sequence (TMAHEIGHSLGLSHDPD) in Gene 216 (Table 7 and FIG. 11B). The 3 histidines (H) bind a zinc ion, the second glycine (G) allows a turn and the glutamic acid (E) is the catalytically active residue. This sequence is followed by a "Met turn", a structure that folds back and stabilizes the interaction with zinc. The presence of the metalloprotease domain and the "Met turn" suggests that Gene 216 has proteolytic activity.

TABLE 7 shows the top two hits when Gene 216 was compared against the motif database using Blimps. The disintegrin and metalloproteinase domains were identified.

| Description | Strength | Score | AA# | AA Sequence |
|---|---|---|---|---|
| Disintegrins proteins | 1950 | 1597 | 377 | CCfAhnCsLRPGAQCAh GdCCvRCllKpAGal CRqAMGDCDlPEfCT GTSshCPP |
| Zinc metallopeptidases | 1173 | 1276 | 276 | TMAHEIGHSLG |

The disintegrin domains of the ADAMs are purported to be ligands for integrins and other receptors. The presence of this domain in Gene 216 (Table 7 and FIGS. 11B–11C), suggests that it also has adhesion activity.

It is also probable that Gene 216 contains a cysteine rich and EGF-like domains as do other ADAM genes (FIG. 11C and Stone et al, *J. Prot. Chem.*, 18:447–465 (1999), Primakov and Myles, *TIG*, 16:83–87 (2000)).

Figure 13:
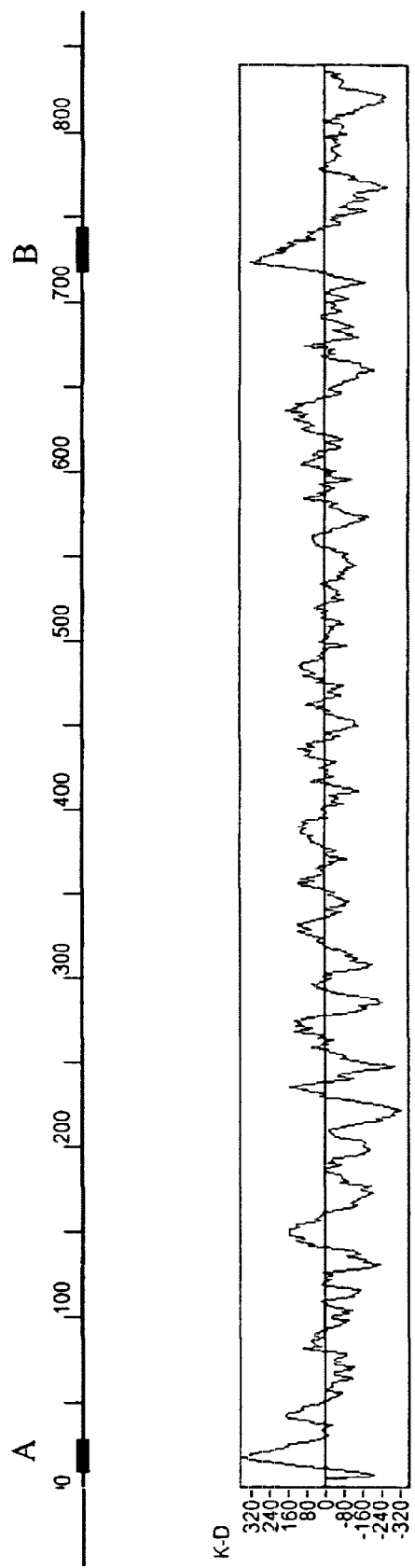
FIG. 13 depicts a hydrophobicity plot of Gene 216.

In ADAMs the presence of a transmembrane domain, as shown in Gene 216, serves to function as a membrane anchor (FIGS. 11C–11D and 13). The cytoplasmic tail and a putative SH3 binding site are also present in Gene 216 (FIG. 11D and Stone et al, *J. Prot. Chem.*, 18:447–465 (1999), Primakov and Myles, *TIG*, 16:83–87 (2000)). The transmembrane domain flanked by an EGF-like domain and a cytoplasmic tail is purported to play a role in signal transduction between the extracellular and intracellular space via cell-cell or cell-matrix interactions. Thus, Gene 216 is probably involved in signal transduction.

Gene 216 is most likely a novel member of the ADAM gene family which is part of a very large and relatively diverse superfamily called zinc-dependent metalloproteinases (Stone et al, *J. Prot. Chem.*, 18:447–465 (1999)). Interestingly, the proteolytic release of TNF-$\alpha$, an important proinflammatory cytokine in asthma, from the plasma membrane is catalyzed by TNF-$\alpha$ converting enzyme, a member of the ADAM gene family (TACE or ADAM-17). Excess of this protein can cause tissue damage leading to airway remodelling (Ohno et al, *Am. J. Cell Mol. Biol.*, 16:212–219 (1997)). ADAMs that can release soluble plasma membrane-anchored cytokines, growth factors, receptors, adhesion molecules and enzymes are called sheddases (Primakov and Myles, *TIG*, 16:83–87 (2000)). Currently these include ADAM 9 (sheds the heparin-binding EGF-like growth factor), ADAM 10 (sheds a soluble form of Delta, a Notch ligand) and ADAM 17 (sheds TNF-$\alpha$). The relationship and functional role of ADAMs to inflammatory responses suggests that Gene 216 is probably involved in the pathophysiology of asthma and other respiratory diseases.

In addition to respiratory diseases, Gene 216 is likely to be involved in obesity. Wilson et al. has shown that obesity may be linked to asthma (*Arch. Intern. Med.* 159: 2513–14 (1999)).

J. IDENTIFICATION OF THE MOUSE HOMOLOG TO GENE 216

The mouse homolog of Gene 216 was identified by BLAST analysis of the ORF of Gene 216a against mouse dbEST. The nucleotide sequence of the mouse homolog is depicted in FIGS. 18A–18G and the corresponding amino acid is depicted in FIG. 19. The results identified three mouse ESTs that were partially homologous to the human sequence but were not 100% homologous to any known mouse ADAM genes. The three mouse ESTs were 100% homologous to a partially sequenced mouse BAC (BAC389B9-accession number AF155960). This BAC maps to mouse chromosome 2 which is syntenic with the human chromosome 20p13. The 47 Kb sequence was analyzed for any potential genes using Genscan. The results identified a gene that possessed an ORF of 2124 bp which encoded 707 amino acids. The amino acid sequence was compared against the protein database by BLAST analysis and it was found to have homology to mouse and human ADAM genes. The 707 amino acid sequence was aligned against the amino acid sequences of Gene 216a, 216b and 216c. The results showed the mouse amino acid sequence to have >50% identity at the protein level (FIGS. 12A–12B). Shaded areas represent identical and similar proteins; i.e. conserved regions. This result demonstrated that the mouse sequence was indeed the murine homolog of the human Gene 216, a probable novel member of the ADAM family.

K. MUTATION ANALYSIS

A combination of fluorescent single stranded confirmation polymorphism (SSCP) analysis (ABI) and DNA sequencing was used to identify and determine precisely the nature of the variant at the nucleotide level. Genomic structure was elucidated for Gene 216. Through combination of exon-PCR with direct genomic sequencing of BAC DNA was utilized. cDNA sequence and predicted exons from Genscan was compared to genomic sequence to determine the precise exon-intron junctions. SSCP analysis was used to screen individual DNA for variants. Briefly, polymerase chain reaction (PCR) was used to generate templates from asthmatic individuals that showed increased sharing for the 20p13-p12 chromosomal region and contributed towards linkage. Non-asthmatic individuals were used as controls. Enzymatic amplification of Gene 216 was accomplished using PCR with oligonucleotides flanking each exon as well as the putative 5' region. The primers were chosen to amplify each exon as well as 15 or more base pairs within each intron on either side of the splice site. The forward and the reverse primers had two different dye colors to allow analysis of each strand and confirm variants independently. Standard PCR assays were utilized for each exon primer pair following optimization. Buffer and cycling conditions were specific to each primer set. The products were denatured using a formamide dye and electrophoresed on non-denaturing acrylamide gels with varying concentrations of glycerol (at least two different glycerol concentrations).

Comparative DNA sequencing was used to determine the sequence changes in Gene 216 in individuals found to be polymorphic by SSCP. Variants detected in the initial set of asthmatic and normal individuals were subject to fluorescent sequencing (ABI) using a standard protocol described by the manufacturer (Perkin Elmer, Palo Alto, Calif.) Sequence conserved variants were then re-examined in a larger set of asthmatic individuals and normal control/non-asthmatics to assess the frequency of the polymorphisms. Statistical analysis was performed to determine if the variant showed an increased prevalence in asthmatics as compared to non-asthmatics and hence was associated with the asthma phenotype.

Primers utilized in fluorescent SSCP experiments to screen coding and non-coding regions of Gene 216 for polymorphisms are provided in Table 8. Column one lists the gene targeted for mutation analysis. Column two lists the specific exon analyzed. Column three provides the GTC assigned primer name. Columns four and five list the forward primer sequence and-reverse primer sequence, respectively.

TABLE 8

| Gene | Exon | Assay Name | PrimerSequence | PrimerSequence |
|---|---|---|---|---|
| 216 | 216_A | 291_216_A_F_292_216_A_R | TCACAGCTATGGGCTGGAG | GAGCTCTGAGCAGAACCCAT |
| 216 | 216_A | 502_216_A_F_503_216_A_R | CTGCCTAGAGGCCGAGGA | AGCTCTGAGCAGAACCCATC |
| 216 | 216_B | 293_216_B_F_294_216_B_R | CCCCTGTGTTCCTCAGGTC | AGTGACTTGGTGGTTCTGGG |
| 216 | 216_C | 295_216_C_F_296_216_C_R | GCTCCACACTCTTTCTTGCC | TGTCATCTGCACCCTCTCTG |
| 216 | 216_D | 297_216_D_F_298_216_D_R | AGGCAGGAGGAAGCTGAAT | AAGAGGGAGGGTGTGGTAGG |
| 216 | 216_F | 299_216_F_F_300_216_F_R | CCTACCCCTCTGCACCCTA | ATACAGCATTCCCACTCCCA |
| 216 | 216_G | 301_216_G_F_302_216_G_R | AACTTCCTTCTGGGAGCTGG | GAAGGCAGAAATCCCGGT |
| 216 | 216_H | 303_216_H_F_304_216_H_R | CAAGCCACCGGGATTTCT | CCCTTCCTCTTCCCCAAAC |
| 216 | 216_H | 700_216_H_F_701_216_H_R | CACACCCTGGTGAGGAGAGA | CACCAGCACCTGCCTGTC |
| 216 | 216_I | 305_216_I_F_306_216_I_R | CCACGAAGGACCACCG | GGGTCAGAGGCACCCAC |
| 216 | 216_J | 307_216_J_F_308_216_J_R | GTGGGTGCCTCTGACCC | AGAGCCTCCTGTCTCTCCCT |
| 216 | 216_J | 703_216_J_F_734_216_J_R | CACGTGGGTGCCTCTGAC | GGGTCAGAGGCACCCAC |
| 216 | 216_J | 889_216_J_F_890_216_J_R | CTCACGTGGGTGCCTCTG | GCCGTAGAGCCTCCTGTCT |
| 216 | 216_K | 309_216_K_F_310_216_K_R | AGAGACAGGAGGCTCTACGG | AAGTCCCCAGGACTAGCCG |
| 216 | 216_K | 309_216_K_F_704_216_K_R | AGAGACAGGAGGCTCTACGG | GAAACTGAGGGACGACCAAA |
| 216 | 216_K | 891_216_K_F_892_216_K_R | CTCTACGGCCGCAGTGAC | GACGACCAAAGAAACGCAG |
| 216 | 216_L | 311_216_L_F_312_216_L_R | GTCCCTCCATGCCCAATG | TGAGCGGAGAGGGCAAGT |
| 216 | 216_L | 313_216_L_F_314_216_L_R | CAGGTTAAGTCGGCTCGC | AAACCCTCACCCTGAACCTT |
| 216 | 216_M | 315_216_M_F_316_216_M_R | CTCTCTCTGCCTTCCCCAC | AAGGGTGCTCGTGTCCTCT |
| 216 | 216_N | 317_216_N_F_318_216_N_R | TCTACTGTGGGGAAGATGGG | CCACTCAGCTCCACTCCCTA |
| 216 | 216_O | 319_216_O_F_320_216_O_R | CCCCTCTACTTCCTCCCCA | GGATTCAAACGGCAAGGAG |
| 216 | 216_P | 321_216_P_F_322_216_P_R | GACCTTGGGGTTCCTAATCC | GCTGAGTCCTGAGCAGGTG |
| 216 | 216_Q | 323_216_Q_F_324_216_Q_R | GTGCACCTGCTCAGGACTC | GCAGGAGTAGGCTCAGGAAG |
| 216 | 216_Q | 323_216_Q_F_504_216_Q_R | GTGCACCTGCTCAGGACTC | GAACCGCAGGAGTAGGCTC |
| 216 | 216_R | 325_216_R_F_326_216_R_R | CCTGGACTCTTATCACGTTGC | ATATGGTCAGCAGGAGACCC |
| 216 | 216_S | 327_216_S_F_328_216_S_R | TTACCCTCCACCATTTCTCC | GCATCCTGGTCTCCATGATAA |
| 216 | 216_T | 985_216_T_F_986_216_T_R | TTCCTGGATCACTGGTCCTC | CGGTGATTCACTGGCTCTG |

Primers utilized in DNA sequencing for purposes of confirming polymorphisms detected using fluorescent SSCP are provided in Table 9. Column one lists the specific exon sequenced. Column two provides the GTC assigned forward primer name and column three lists the forward primer sequence. Columns four and five lists the GTC assigned reverse primer name and the corresponding reverse primer sequence, respectively.

amino acid position of these polymorphisms are also underlined in FIGS. 3A–3F, 4A–4F and 5A–5G.

L. RESTRICTION FRAGMENT LENGTH POLYMORPHISM (RFLP ASSAY) AND ALLELE SPECIFIC OLIGONUCLEOTIDE ANALYSIS (ASO ASSAY)

To identify other individuals with the polymorphisms listed in Table 10, RPLP assay and ASA were performed.

TABLE 9

| Exon | Forward | ForwardSeq | ReverseName | ReverseSeq |
|---|---|---|---|---|
| 216_A | MDSeq_101_216_A_F | CCTCTCAGGAGTAGAGGCCC | MDSeq_101_216_A_R | CCAAGCACACTTGAGCGTC |
| 216_A | MDSeq_175_216_A_F | AGCGGTTCTCTCCTCCTCTC | MDSeq_175_216_A_R | AGCCATGCCCTCTGCTTT |
| 216_A | MDSeq_79_216_A_F | GCACGGATTCCCTCCTCC | MDSeq_79_216_A_R | AGCCATGCCCTCTGCTTT |
| 216_D | MDSeq_61_216_D_F | TCCCTGGTGCTTCCCATA | MDSeq_61_216_D_R | GAGGGAGCTCTTTCCCCA |
| 216_F | MDSeq_47_216_F_F | CCACTACCAAGGGCGAGTAA | MDSeq_47_216_F_R | AGTTCCAGGTACTTCCGGGT |
| 216_F | MDSeq_57_216_F_F | CCTCTTGCCCCTCTTGCT | MDSeq_57_216_F_R | AACCCCAGCTCCCAGAAG |
| 216_H | MDSeq_155_216_H_F | GGCCTCGAGTCCCAGTATTT | MDSeq_155_216_H_R | ACTGCAGGAAGGCCCAGAG |
| 216_J | MDSeq_181_216_J_F | TCGCCCTCAGCTTCTCAG | MDSeq_181_216_J_R | TGAGGGACGACCAAAGAAAC |
| 216_K | MDSeq_182_216_K_F | TCACGTGGGTGCCTCTGA | MDSeq_182_216_K_R | CAAAGTCACACAACAAGCGG |
| 216_L | MDSeq_106_216_L_F | GGGTTACTTCCCCTCTCTGG | MDSeq_106_216_L_R | GAACCTGAGGGCACCAATTA |
| 216_L | MDSeq_48_216_L_F | CCTGTCCCGCTTGTTGTGT | MDSeq_48_216_L_R | ACGTGCAGTGAGAGGTCCAT |
| 216_L | MDSeq_56_216_L_F | CGGGCTGCTCACTATTGG | MDSeq_56_216_L_R | GAGAGGTCCATGCCGAGA |
| 216_L | MDSeq_67_216_L_F | GCGAGGTTACTCCTACACCG | MDSeq_67_216_L_R | AAGGTTCAGGGTGAGGGTTT |
| 216_O | MDSeq_49_216_O_F | TCCAGGTGGTGAACTCTGC | MDSeq_49_216_O_R | CTGGAGCACAGTGGCAGTTA |
| 216_Q | MDSeq_96_216_Q_F | GACCTTGGGGTTCCTAATCC | MDSeq_96_216_Q_R | TGTACTGGGAGGTAGAGGGC |
| 216_R | MDSeq_50_216_R_F | AGAGGGTGACTTGGAGCAGA | MDSeq_50_216_R_R | CCAGAAACCTGATTAGGGGG |

Single nucleotide polymorphisms (SNPs) that were identified in Gene 216 are provided in Table 10. Column one contains the exon or intron in which the SNP was detected. Column two provides a reference sequence in which the SNP appears underlined. Column three lists the base change of the SNP. Column four details the location of the SNP as intronic or exonic. Column five describes the SNP location of the genomic BAC sequence of SEQ ID NO:7 (FIGS. 20A–20G).

1. RFLP Assay. The amplicon, containing the polymorphism, was PCR amplified using primers that were used to generate a fragment for sequencing (sequencing primers) or SSCP (SSCP primers). The appropriate population of individuals was PCR amplified in 96 well microtitre plates.

Enzymes were purchased from New England Biolabs (NEB). The restriction cocktail containing the appropriate enzyme for the particular polymorphism is added to the PCR

TABLE 10

| | | | | |
|---|---|---|---|---|
| D | GTGCTTCCCATATTCACATCTCCCACAACTAAGCCATCAC | T > C | Intron | 7521 |
| D | AACTAAGCCATCACCAAGGCTCCTTCCTCTAGCCCCAAG | G > C | Intron | 7547 |
| D | GGATACATAGAAACCCACTACGGCCCAGATGGGCAGCCA | T > C | Exon | 7772 |
| F | CTGCTCACCTGGAAAGGAACCTGTGGCCACAGGGATCCT | A > G | Exon | 8271 |
| F | CTCCAAATCAGAAGAGACAGGAATTCACAGGCCTCGAGT | A > G | Intron | 8405 |
| I | CCTGCAGTGGCGCCGGGGGCTGTGGGCGCAGCGGCCCA | G > A | Intron | 9057 |
| L | CCCTCTCTGGGCTCTGCGCGTCTGGCGGCTGTAGCCAAG | G > A | Intron | 9848 |
| L | GAGAAGCGCGGGGGTTGGGGGACTGTCCCTCCATGCCCA | G > A | Intron | 9903 |
| L | AGCCGCCGCCAGCTGCGCGCCTTCTTCCGCAAGGGGGGC | C > T | Exon | 9995 |
| L | GTTCAGGGTGAGGGTTTCGGGGAGCTTGGGAGCCGGCCT | G > T | Intron | 10341 |
| O | TGAGCTCTGCCCACCCGACCCCTCCTTGCCGTTTGAATCC | C > T | Intron | 11283 |
| Q | GCTGGCCATGCTCCTCAGCGTCCTGCTGCCTCTGCTCCCA | G > A | Exon | 11725 |
| Q | TCCTGCTGCCTCTGCTCCCAGGGGCCGGCCTGGCCTGGTG | G > C | Exon | 11748 |
| Q | GTGGCCTCCCAGTCAAGCGAGGGGGTGGATCCCTGCCCC | A > T | Intron | 12018 |
| R | CTGGGCGGCGTTCACCCCATGGAGTTGGGCCCCACAGCC | T > C | Exon | 13263 |
| R | AGTTGGGCCCCACAGCCACTGGACAGCCCTGGCCCCTGG | C > T | Exon | 13292 |
| R | GGGCTCATGCCTCCTGCCTCCTTCCAGATGGGCAGCACCC | C > T | Intron | 13370 |
| R | TATGCCCCTCCCCAGCCCCAGGGTCTCCTGCTGACCATAT | T > G | Intron | 13431 |

FIGS. 15A–15B, 16A–16B and 17A–17B illustrate the three different transcripts of Gene 216. Using an in-house program called gene view; the genomic structure of the gene is diagrammatically shown. The exons are shown to scale and the SNPs are identified by their location along the genomic BAC DNA. In addition, where the SNP results in an amino acid change, the change in amino acid is indicated.

The polymorphic sites discovered within the cDNA of Gene 216a, Gene 216b and 216c are underlined in FIGS. 3A–3F, 4A–4F and 5A–5G, respectively. The corresponding product. The reaction is incubated at the appropriate temperature according to the manufacturer's recommendations (NEB) for two to three hours, followed by a 4° C. incubation. After digestion, the reactions were size fractionated using the appropriate agarose gel depending on the assay specifications (2.5%, 3%, or metaphor). Gels are electrophoresed in 1×TBE Buffer at 170 Volts for approximately two hours.

The gel is illuminated using ultraviolet light and the image is saved as a Kodak 1D file. Using the Kodak 1D image analysis software, the images are scored and the data is exported to EXCEL.

2. ASO assay. The amplicon, containing the polymorphism, was PCR amplified using primers that were used to generate a fragment for sequencing (sequencing primers) or SSCP (SSCP primers). The appropriate population of individuals was PCR amplified in 96 well microtitre plates and re-arrayed into 384 well microtitre plates using a Tecan Genesis RSP200. The amplified products were loaded onto 2% agarose gels and size fractionated at 150V for 5 minutes. The DNA was transferred from the gel to Hybond N+ nylon membrane (Amersham-Pharmacia) using a Vacuum blotter (Bio-Rad). The filter containing the blotted PCR products was transferred to a dish containing 300 mls of pre-hybridization solution (5×SSPE {pH7.4}, 2% SDS, 5×Denhardts). The filter was left in the pre-hybridization solution at 40° C. for >1 hour. After pre-hybridization, 10 mls of the pre-hybridization solution and the filter were transferred to a washed glass bottle. The allele specific oligonucleotides (ASO) were designed with the polymorphism in the middle. The size of the oligonucleotide was dependent upon the GC content of the sequence around the polymorphism. Those ASOs that had a G or C polymorphism were designed so that the Tm was between 54–56° C. and those that had an A or T variance were designed so that the Tm was between 60–64° C. All oligonucleotides were phosphate free at the 5'end and purchased from Gibco BRL. For each polymorphism 2 ASOs were designed: one for each variant.

The two ASOs that represented the polymorphism were resuspended at a concentration of 1 µg/µl and separately end-labeled with $\gamma$-ATP$^{32}$ (6000 Ci/mmol) (NEN) using T4 polynucleotide kinase according to manufacturer recommendations (NEB). The end-labeled products were removed from the unincorporated $\gamma$-ATP$^{32}$ by passing the reactions through Sephadex G-25 columns according to manufacturers recommendation (Amersham-Pharmacia). The entire end-labeled product of one ASO was added to the bottle containing the appropriate filter and 10 mls of hybridization solution. The hybridization reaction was placed in a rotisserie oven (Hybaid) and left at 40° C. for a minimum of 4 hours. The other ASO was stored at –20° C.

After the prerequisite hybridization time had elapsed, the filter was removed from the bottle and transferred to 1 liter of wash solution (0.1×SSPE {pH7.4}, 0.1%SDS) pre-warmed to 45° C. After 15 minutes the filter was transferred to another liter of wash solution (0.1×SSPE {pH7.4}, 0.1%SDS) pre-warmed to 50° C. After 15 minutes the filter was wrapped in Saran, placed in an autoradiograph cassette and an X-ray film (Kodak) placed on top of the filter. Depending on the efficiency of the end-labeling reaction of the ASO and its hybridization to the filter an image would be observed on the film within an hour. After an image had been captured on film for the 50° C. wash, the process was repeated for wash steps at 55° C., 60° C. and 65° C. The image that captured the best result was used.

The ASO was removed from the filter by adding 1 liter of boiling strip solution (0.1×SSPE {pH7.4}, 0.1%SDS). This was repeated two more times. After removing the ASO the filter was pre-hybridized in 300 mls of pre-hybridization solution (5×SSPE {pH7.4}, 2% SDS, 5×Denhardts) at 40° C. for >1 hour. The second end-labeled ASO corresponding to the other variant was removed from storage at –20° C. and thawed to room temperature. The filter was placed into a glass bottle along with 10 mls of hybridization solution and the entire end-labeled product of the second ASO. The hybridization reaction was placed in a rotisserie oven (Hybaid) and left at 40° C. for a minimum of 4 hours. After the hybridization, the filter was washed at various temperatures and images captured on film as described above.

The two films that best captured the allele specific assay with the two ASOs were converted into digital images by scanning them into Adobe PhotoShop. These images were overlaid against each other in Graphic Converter and then scored and stored in FileMaker Pro 4.0.

M. ASSOCIATION STUDY ANALYSIS

In order to determine whether mutations in candidate genes are responsible for the asthma phenotype, association studies are performed using a case-control study design. To avoid issues of population admixture which can bias case-control studies, the unaffected controls were collected in both the US and the UK. A total of three hundred controls were collected, 200 in the UK and 100 in the US. Inclusion into the study required that the control individual was negative for asthma, as determined by self report of never having asthma, has no first degree relatives with asthma, and was negative for eczema and symptoms indicative of atopy within the past 12 months. Data from an abbreviated questionnaire similar to that administered to the affected sib pair families were collected. Results from skin prick tests to 4 common allergens were also collected. The results of the skin prick test were used to select a subset of control that were most likely to be asthma and atopy negative.

A subset of unrelated cases are selected from the affected sib pair families based on the evidence for linkage at the chromosomal location of interest. One affected sib from families demonstrating identity-by-decent (IBD) at the appropriate marker loci is selected. In the selection criteria, preference is given to families with multiple affected sibs all of whom are concordant at the marker locus as well as to families where affected and unaffected sibs are discordant.

Since the appropriate cases may vary for each SNP, a larger collection of individuals who are jointly IBD across a larger interval are genotyped and a subset used in the analyses. For each polymorphism, the frequency of the alleles in the control and case populations is compared using a Fisher exact test. It is expected that a mutation increasing susceptibility to the disease would be more prevalent in the cases than in the controls, while a protective mutation should be more prevalent in the control group. Similarly, the genotype frequencies of the SNPs are compared between cases and controls. P-values are computed for both the allele and genotype frequencies. A small p-value, is indicative of an association between the SNPs and the disease phenotype. The analysis is repeated for the US and UK population separately, to adjust for the possibility of genetic heterogeneity.

1. Association Test With Individual SNPs

Gene 216 has 21 exons spanning 17 kb. Seventeen exons have been completely screened by SSCP, of which ten exons are polymorphic. Seven of the 17 identified SNPs reside in the coding portion of the gene, six of which result in amino acid changes. The structure of the gene and the distribution of SNPs are shown in FIGS. 15A–15B, 16A–16B and 17A–17B.

Statistical analyses for all seven SNPs are presented in Table 11. Column one list the exon containing the SNP of interest. The control ("CNTL") allele frequency and sample size ("N") are in columns two and three. The affected individuals ("CASE") allele frequency and sample size ("N") are listed in columns four and five. The sixth column contains the significance value level of comparison between the control allele frequencies and the case allele frequencies.

The results demonstrate that five SNPs have allelic frequencies significantly different in the cases versus the controls in either the US or UK samples. In the US population, two SNPs in exon R were more frequent in the cases (20% and 29%, respectively) than in the control population (8% and 5%, respectively), and the differences were statistically significance (p=0.035 and p=0.0031). Both of these mutations resulted in amino acid changes; a methionine to threonine in the first SNP while a sefine replaced proline in the second SNP. In the UK and the combined sample, two SNPs in the adjacent exon (Q) reached statistical significant. A synonymous SNP was present in 27% of alleles of the controls and in only 15% for the cases for the UK population (26% vs 19% in combined sample), a difference which is highly significant (p=0.002 for UK sample, p=0.043 for combined sample). In the same exon, a SNP producing an amino acid change (a valine to an isoleucine) was observed more frequently in the controls than in the cases in the UK population (11% vs 5%, p=0.027), and this was also true for the combined sample (11% vs 5%, p=0.021). In addition, a SNP just outside exon O reached statistical significance in both the UK and combined sample (p=0.028 for UK sample, 14% in controls versus 8% of cases; p=0.029 in combined sample, 14% of cases versus 9% in controls).

2. Haplotype Analyses

In addition to analyzing individual SNPs, haplotype analyses were used to compare haplotype frequencies between the case and control groups. For these purposes, haplotypes for all polymorphisms are defined as those that lead to amino acid changes for a particular gene. The haplotypes are constructed using a maximum likelihood approach. The estimated frequency of each haplotype is compared between cases and controls by a permutation test. An overall comparison of the distribution of all haplotypes between the two groups is also performed.

Haplotype analyses were performed on Gene 216. The results are shown in Table 12. Column one is the amino acid sequence of the haplotype. The haplotype frequency in the control and the case is within columns two and three, respectively. Column four contains the significance of the difference of the case and the control. The most frequent haplotype was present more often in the controls than in the cases (p=0.038), and the second most frequent haplotype (24% in cases) was only present in about 8% of the controls (p=0.004). In the US and UK populations, a trend towards statistical significance was observed when comparing the haplotype distribution between the cases and controls (p=0.066 for US, p=0.093 for UK).

TABLE 11

| EXON | Frequencies | | | | ALLELE |
|---|---|---|---|---|---|
| | CNTL | N | CASE | N | P-VALUE |
| Combined sample | | | | | |
| R_2 | 0.89 | 190 | 0.89 | 120 | 1.0000 |
| R_1 | 0.11 | 217 | 0.11 | 130 | 1.0000 |
| Q_1 | 0.89 | 209 | 0.95 | 125 | 0.0213 |
| Q_2 | 0.26 | 217 | 0.19 | 131 | 0.0432 |
| O_+1 | 0.86 | 207 | 0.91 | 126 | 0.0289 |
| F_1 | 0.03 | 217 | 0.03 | 129 | 1.0000 |
| D_1 | 0.00 | 215 | 0.00 | 131 | 0.3786 |
| US sample | | | | | |
| R_2 | 0.92 | 68 | 0.80 | 25 | 0.0345 |
| R_1 | 0.08 | 77 | 0.24 | 27 | 0.0030 |
| Q_1 | 0.90 | 77 | 0.06 | 24 | 0.5726 |
| Q_2 | 0.25 | 77 | 0.35 | 27 | 0.1571 |
| O_+1 | 0.85 | 70 | 0.87 | 27 | 0.8223 |

TABLE 11-continued

| EXON | Frequencies | | | | ALLELE |
|---|---|---|---|---|---|
| | CNTL | N | CASE | N | P-VALUE |
| F_1 | 0.05 | 77 | 0.07 | 27 | 0.5136 |
| D_1 | 0.00 | 76 | 0.00 | 27 | 1.0000 |
| UK sample | | | | | |
| R_2 | 0.87 | 122 | 0.91 | 95 | 0.2211 |
| R_1 | 0.13 | 140 | 0.08 | 103 | 0.0764 |
| Q_1 | 0.89 | 132 | 0.95 | 101 | 0.0274 |
| Q_2 | 0.27 | 140 | 0.15 | 104 | 0.0020 |
| O_+1 | 0.86 | 137 | 0.92 | 99 | 0.0278 |
| F_1 | 0.02 | 140 | 0.02 | 102 | 1.0000 |
| D_1 | 0.00 | 139 | 0.00 | 104 | 0.4280 |

TABLE 12

| | Control | Case | P-value |
|---|---|---|---|
| US and UK Samples | | | |
| Pro-Met-Ile-Ser-Tyr | 74.7% | 79.2% | 0.1692 |
| Ser-Thr-Ile-Ser-Tyr | 10.5% | 11.7% | 0.6598 |
| Pro-Met-Val-Ser-Tyr | 10.0% | 5.0% | 0.0274 |
| Pro-Met-Ile-Asn-Tyr | 3.2% | 3.1% | 0.9850 |
| Pro-Thr-Val-Ser-Tyr | 0.8% | 0.0% | 0.3589 |
| Ser-Met-Ile-Ser-Tyr | 0.6% | 0.4% | 0.6641 |
| Ser-Met-Val-Ser-Tyr | 0.2% | 0.0% | 0.8713 |
| Pro-Met-Ile-Ser-His | 0.0% | 0.4% | 0.2210 |
| Ser-Thr-Val-Ser-Tyr | 0.0% | 0.1% | 0.0397 |
| Pro-Thr-Ile-Ser-Tyr | 0.0% | 0.0% | 0.7012 |
| Overall | | | 0.2244 |
| UK Samples | | | |
| Pro-Met-Ile-Ser-Tyr | 74.6% | 84.4% | 0.0120 |
| Ser-Thr-Ile-Ser-Tyr | 12.1% | 8.3% | 0.1901 |
| Pro-Met-Val-Ser-Tyr | 9.7% | 4.9% | 0.0604 |
| Pro-Met-Ile-Asn-Tyr | 2.0% | 1.6% | 0.7945 |
| Pro-Thr-Val-Ser-Tyr | 1.1% | 0.0% | 0.3842 |
| Ser-Met-Val-Ser-Tyr | 0.4% | 0.0% | 0.7954 |
| Pro-Met-Val-Asn-Tyr | 0.2% | 0.0% | 0.7767 |
| Pro-Met-Ile-Ser-His | 0.0% | 0.5% | 0.1826 |
| Ser-Thr-Ile-Asn-Tyr | 0.0% | 0.3% | 0.0868 |
| Ser-Thr-Val-Ser-Tyr | 0.0% | 0.1% | 0.0568 |
| Pro-Thr-Ile-Ser-Tyr | 0.0% | 0.0% | 0.5109 |
| Overall | | | 0.0930 |
| US Samples | | | |
| Pro-Met-Ile-Ser-Tyr | 75.2% | 60.6% | 0.0384 |
| Pro-Met-Val-Ser-Tyr | 10.4% | 6.1% | 0.4397 |
| Ser-Thr-Ile-Ser-Tyr | 7.8% | 24.1% | 0.0040 |
| Pro-Met-Ile-Asn-Tyr | 5.2% | 7.4% | 0.5083 |
| Ser-Met-Ile-Ser-Tyr | 1.5% | 1.9% | 0.9707 |
| Ser-Thr-Val-Ser-Tyr | 0.0% | 0.0% | 0.5606 |
| Overall | | | 0.0659 |

II. PREPARATION OF NUCLEIC ACIDS, VECTORS, TRANSFORMATIONS AND HOST CELLS

The nucleic acids of this invention can be produced in large quantities by replication in a suitable host cell. Natural or synthetic nucleic acid fragments, comprising at least ten contiguous bases coding for a desired peptide or polypeptide can be incorporated into recombinant nucleic acid constructs, usually DNA constructs, capable of introduction into and replication in a prokaryotic or eukaryotic cell. Usually the nucleic acid constructs will be suitable for replication in a unicellular host, such as yeast or bacteria, but may also be intended for introduction to (with and without integration within the genome) cultured mammalian or plant or other eukaryotic cells, cell lines, tissues, or organisms.

The purification of nucleic acids produced by the methods of the present invention is described, for example, in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, NY (1992).

The nucleic acids of the present invention can also be produced by chemical synthesis, e.g., by the phosphoramidite method described by Beaucage et al, *Tetra. Letts.*, 22:1859–1862 (1981) or the triester method according to Matteucci, et al, *J. Am. Chem. Soc.*, 103:3185 (1981), and can performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

These nucleic acids can encode full-length variant forms of proteins as well as the naturally-occurring protein. The variant proteins (which could be especially useful for detection and treatment of disorders) will have the variant amino acid sequences encoded by the polymorphisms described in Table 10, when said polymorphisms are read so as to be in-frame with the full-length coding sequence of which it is a component.

Nucleic acid constructs prepared for introduction into a prokaryotic or eukaryotic host will comprise a replication system recognized by the host, including the intended nucleic acid fragment encoding the selected protein or polypeptide, and will preferably also include transcription and translational initiation regulatory sequences operably linked to the protein encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals are also included, where appropriate, whether from a native Gene 216 protein or from other receptors or from secreted proteins of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, NY (1992).

An appropriate promoter and other necessary vector sequences will be selected so as to be functional in the host, and will include, when appropriate, those naturally associated with Gene 216 gene. Examples of workable combinations of cell lines and expression vectors are described in Sambrook et al, *Molecular Cloning. A Laboratory Manual*, 2nd Ed. (Cold Spring Harbor Laboratory, Cold Spring Harbor, N.Y. (1989) or Ausubel et al, *Current Protocols in Molecular Biology*, J. Wiley and Sons, NY (1992). Many useful vectors are known in the art and can be obtained from such vendors as Stratagene (supra), New England BioLabs, Beverly, Mass., U.S.A, Promega Biotech, and other biotechnology product suppliers. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in EP 73,675A. Appropriate non-native mammalian promoters might include the early and late promoters from SV40 (Fiers et al, *Nature*, 273:113 (1978)) or promoters derived from murine Moloney leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al, *FEBS Letts*. 241:119 (1988)), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the nucleic acids into the host cell by any method known in the art, including those described above, will be referred to herein as "transformation." The cells into which have been introduced nucleic acids described above are meant to also include the progeny of such cells.

Large quantities of the nucleic acids and proteins of the present invention may be prepared by expressing the Gene 216 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), *Cell Culture. Methods in Enzymology*, volume 58, Academic Press, Inc., Harcourt Brace Jovanovich, NY, (1979)). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the nucleic acids of the present invention will be useful not only for the production of the nucleic acids and proteins of the present invention, but also, for example, in studying the characteristics of Gene 216 proteins.

Antisense nucleic acid sequences are useful in preventing or diminishing the expression of Gene 216 gene, as will be appreciated by one skilled in the art. For example, nucleic acid vectors containing all or a fragment Gene 216 gene, complementary sequences of the former, or other sequences from the 20p13-p12 region may be placed under the control of a promoter in an antisense orientation and introduced into a cell. Such fragments can be 16 or more nucleotides in length. Expression of such an antisense construct within a cell will interfere with Gene 216 transcription and/or translation and/or replication.

The probes and primers based on the Gene 216 gene sequences disclosed herein are used to identify homologous Gene 216 gene sequences and proteins in other species. These Gene 216 gene sequences and proteins are used in the diagnostic/prognostic, therapeutic and drug screening methods described herein for the species from which they have been isolated.

III. PROTEIN EXPRESSION AND PURIFICATION

Expression and purification of the Gene 216 protein of the invention can be performed essentially as outlined below. To facilitate the cloning, expression and purification of membrane and secreted protein from the 20p13-p12, a gene expression system, such as the pET System (Novagen), for cloning and expression of recombinant proteins in *E. coli* is selected. Also, a DNA sequence encoding a peptide tag, the His-Tap, is fused to the 3' end of DNA sequences of interest to facilitate purification of the recombinant protein products. The 3' end is selected for fusion to avoid alteration of any 5' terminal signal sequence.

Nucleic acids chosen, for example, from the nucleic acids set forth SEQ ID NO:1–SEQ ID NO:3, or SEQ ID NO:7 (FIGS. 20A–20G) for cloning the genes are prepared by polymerase chain reaction (PCR). Synthetic oligonucleotide primers specific for the 5' and 3' ends of the nucleotide sequences are designed and purchased from Life Technologies (Gaithersburg, Md.). All forward primers (specific for the 5' end of the sequence) are designed to include an NcoI cloning site at the 5' terminus. These primers are designed to permit initiation of protein translation at the methionine residue encoded within the NcoI site followed by a valine residue and the protein encoded by the DNA sequence. All reverse primers (specific for the 3' end of the sequence) include an EcoRI site at the 5' terminus to permit cloning of the sequence into the reading frame of the pET-28b. The pET-28b vector provides a sequence encoding an additional 20 carboxyl-terminal amino acids including six histidine residues (at the C-terminus), which comprise the histidine affinity tag.

DNA prepared from the 20p13-p12 region is used as the source of template DNA for PCR amplification (Ausubel et al, *Current Protocols in Molecular Biology*, John Wilty & Sons (1994)). To amplify a DNA sequence containing the nucleotide sequence,. c DNA (50 ng) is introduced into a reaction vial containing 2 mM $MgCl_2$, 1 micromolar synthetic oligonucleotide primers (forward and reverse primers) complementary to and flanking a defined 20p13-p12 region, 0.2 mM of each of deoxynucleotide triphosphate, dATP, dGTP, dCTP, dTTP and 2.5 units of heat stable DNA polymerase (Amplitaq, Roche Molecular Systems, Inc., Branchburg, N.J.) in a final volume of 100 microliters.

Upon completion of thermal cycling reactions, each sample of amplified DNA is purified using the Qiaquick Spin PCR purification kit (Qiagen, Gaithersburg, Md.). All amplified DNA samples are subjected to digestion with the restriction endonucleases, e.g., NcoI and EcoRI (New England BioLabs, Beverly, Mass., U.S.A.) (Ausubel et al, *Current Protocols in Molecular Biology*, John Wiley & Sons, Inc. (1994)). DNA samples are then subjected to electrophoresis on 1.0% NuSeive (FMC BioProducts, Rockland, Me.) agarose gels. DNA is visualized by exposure to ethidium bromide and long wave UV irradiation. DNA contained in slices isolated from the agarose gel are purified using the Bio 101 GeneClean Kit protocol (Bio 101, Vista, Calif.).

The pET-28b vector is prepared for cloning by digestion with restriction endonucleases, e.g., NcoI and EcoRI (New England BioLabs, Beverly, Mass.) (Ausubel et al, *Current Protocols in Molecular Biology*, John Wiley & Sons, Inc. (1994)). The pET-28a vector, which encodes the histidine affinity tag that can be fused to the 5' end of an inserted gene, is prepared by digestion with appropriate restriction endonucleases.

Following digestion, DNA inserts are cloned (Ausubel et al, *Current Protocols in Molecular Biology*, John Wiley & Sons, Inc. (1994)) into the previously digested pET-28b expression vector. Products of the ligation reaction are then used to transform the BL21 strain of *E. coli* (Ausubel et al, *Current Protocols in Molecular Biology*, John Wiley & Sons, Inc. (1994)) as described below.

Competent bacteria, *E. coli* strain BL21 or *E. coli* strain BL21 (DE3), are transformed with recombinant pET expression plasmids carrying the cloned sequence according to standard methods (Ausubel et al, *Current Protocols in Molecular Biology*, John Wiley & Sons, Inc. (1994)). Briefly, 1 microliter of ligation reaction is mixed with 50 microliters of electrocompetent cells and subjected to a high voltage pulse, after which samples were incubated in 0.45 ml SOC medium (0.5% yeast extract, 2.0% tryptone, 10 mM NaCl, 2.5 mM KCl, 10 mM $MgCl_2$, 10 mM $MgSO_4$ and 20 mM glucose) at 37° C. with shaking for 1 hour. Samples are then spread on LB agar plates containing 25 µg/ml kanamycin sulfate for growth overnight. Transformed colonies of BL21 are then picked and analyzed to evaluate cloned inserts, as described below.

Individual BL21 clones transformed with recombinant pET-28b 20p13-p12 region nucleotide sequences are analyzed by PCR amplification of the cloned inserts using the same forward and reverse primers specific for the 20p13-p12 region sequences that are used in the original PCR amplification cloning reactions. Successful amplification verifies the integration of the sequence in the expresssion vector (Ausubel et al, *Current Protocols in Molecular Biology*, John Wiley & Sons, Inc. (1994)).

Individual clones of recombinant pET-28b vectors carrying properly cloned 20p13-p12 region nucleotide sequences are picked and incubated in 5 ml of LB broth plus 25 µg/ml kanamycin sulfate overnight. The following day plasmid DNA is isolated and purified using the Qiagen plasmid purification protocol (Qiagen Inc., Chatsworth, Calif.).

The pET vector can be propagated in any E. coli K-12 strain, e.g., HMS174, HB101, JM109, DH5 and the like, for purposes of cloning or plasmid preparation. Hosts for expression include E. coli strains containing a chromosomal copy of the gene for T7 RNA polymerase. These hosts are lysogens of bacteriophage DE3, a lambda derivative that carries the lacd gene, the lacUV5 promoter and the gene for T7 RNA polymerase. T7 RNA polymerase is induced by addition of isopropyl-β-D-thiogalactoside (IPTG), and the T7 RNA polymerase transcribes any target plasmid containing a functional T7 promoter, such as pET-28b, carrying its gene of interest. Strains include, for example, BL21(DE3) (Studier et al, Meth. Enzymol., 185:60–89 (1990)).

To express the recombinant sequence, 50 ng of plasmid DNA are isolated as described above to transform competent BL21(DE3) bacteria as described above (provided by Novagen as part of the pET expression kit). The lacZ gene (β-galactosidase) is expressed in the pET-System as described for the 20p13-p12 region recombinant constructions. Transformed cells were cultured in SOC medium for 1 hour, and the culture is then plated on LB plates containing 25 μg/ml kanamycin sulfate. The following day, the bacterial colonies are pooled and grown in LB medium containing kanamycin sulfate (25 μg/ml) to an optical density at 600 nM of 0.5 to 1.0 O.D. units, at which point 1 mM IPTG was added to the culture for 3 hours to induce gene expression of the 20p13-p12 region recombinant DNA constructions.

After induction of gene expression with IPTG, bacteria are collected by centrifugation in a Sorvall RC-3B centrifuge at 3500×g for 15 minutes at 4° C. Pellets are resuspended in 50 ml of cold mM Tris-HCl, pH 8.0, 0.1 M NaCl and 0.1 mM EDTA (STE buffer). Cells are then centrifuged at 2000×g for 20 minutes at 4° C. Wet pellets are weighed and frozen at −80° C. until ready for protein purification.

A variety of methodologies known in the art can be used to purify the isolated proteins (Coligan et al, Current Protocols in Protein Science, John Wiley & Sons (1995)). For example, the frozen cells can be thawed, resuspended in buffer and ruptured by several passages through a small volume microfluidizer (Model M-110S, Microfluidics International Corp., Newton, Mass.). The resultant homogenate is centrifuged to yield a clear supernatant (crude extract) and, following filtration, the crude extract is fractioned over columns. Fractions are monitored by absorbance at $OD_{280}$ nm and peak fractions may be analyzed by SDS-PAGE.

The concentrations of purified protein preparations are quantified spectrophotometrically using absorbance coefficients calculated from amino acid content (Perkins, Eur. J. Biochem., 157:169–180 (1986)). Protein concentrations are also measured by the method of Bradford, Anal. Biochem., 72:248–254 (1976) and Lowry et al, J. Biol. Chem., 193:265–275 (195 1) using bovine serum albumin as a standard.

SDS-polyacrylamide gels of various concentrations are purchased from BioRad (Hercules, Calif.), and stained with Coomassie blue. Molecular weight markers may include rabbit skeletal muscle myosin (200 kDa), E. coli β-galactosidase (116 kDa), rabbit muscle phosphorylase B (97.4 kDa), bovine serum albumin (66.2 kDa), ovalbumin (45 kDa), bovine carbonic anyhdrase (31 kDa), soybean trypsin inhibitor (21.5 kDa), egg white lysozyme (14.4 kDa) and bovine aprotinin (6.5 kDa).

Proteins can also be isolated by other conventional means of protein biochemistry and purification to obtain a substantially pure product, i.e., 80, 95, or 99% free of cell component contaminants, as described in Jacoby, Methods in Enzymology, Vol. 104, Academic Press, New York (1984); Scoopes, Protein Purification, Principles and Practice, 2$^{nd}$ Ed., Springer-Verlag, New York (1987); and Deutscher (ed.), Guide to Protein Purification, Methods in Enzymology, Vol. 182 (1990). If the protein is secreted, it can be isolated from the supernatant in which the host cell is grown; otherwise, it can be isolated from a lysate of the host cells.

Once a sufficient quantity of the desired protein has been obtained, it may be used for various purposes. One use of the protein or polypeptide is the production of antibodies specific for binding. These antibodies may be either polyclonal or monoclonal, and may be produced by in vitro or in vivo techniques well known in the art. Monoclonal antibodies to epitopes of any of the peptides identified and isolated as described can be prepared from murine hybridomas (Kohler, Nature, 256:495 (1975)). In summary, a mouse is inoculated with a few micrograms of protein over a period of two weeks. The mouse is then sacrificed. The cells that produce antibodies are then removed from the mouse's spleen. The spleen cells are then fused with polyethylene glycol with mouse myeloma cells. The successfully fused cells are diluted in a microtiter plate and growth of the culture is continued. The amount of antibody per well is measured by immunoassay methods such as ELISA (Engvall, Meth. Enzymol., 70:419 (1980)). Clones producing antibody can be expanded and further propagated to produce protein antibodies. Other suitable techniques involve in vitro exposure of lymphocytes to the antigenic polypeptides, or alternatively, to selection of libraries of antibodies in phage or similar vectors. See Huse et al, Science, 246:1275–1281 (1989). For additional information on antibody production see Davis et al, Basic Methods in Molecular Biology, Elsevier, N.Y., Section 21-2 (1989). Such antibodies are particularly useful in diagnostic assays for detection of variant protein forms, or as an active ingredient in a pharmaceutical composition.

III. TRANSFORMED HOSTS, DEVELOPMENT OF PHARMACEUTICALS AND RESEARCH TOOLS

Cells and animals that carry the Gene 216 gene can be used as model systems to study and test for substances that have potential as therapeutic agents. The cells are typically cultured mesenchymal stem cells. These may be isolated from individuals with somatic or germline Gene 216 gene. Alternatively, the cell line can be engineered to carry the Gene 216 genes, as described above. After a test substance is applied to the cells, the transformed phenotype of the cell is determined. Any trait of transformed cells can be assessed, including respiratory diseases including asthma, atopy, and response to application of putative therapeutic agents.

IV. DIAGNOSTIC APPLICATIONS

As discussed herein, chromosomal region 20p13-p12 has been genetically linked to a variety of diseases and disorders. The inventors provide nucleic acids and SNPs which can be useful in diagnosing individuals with chromosomal abnormalities linked to these diseases.

Antibody-based diagnostic methods. The invention provides methods for detecting disease-associated antigenic components in a biological sample, which methods comprise the steps of: (i) contacting a sample suspected to contain a disease-associated antigenic component with an antibody specific for an disease- associated antigen, extracellular or intracellular, under conditions in which a stable antigen-antibody complex can form between the antibody and disease-associated antigenic components in the sample; and (ii) detecting any antigen-antibody complex formed in step (i) using any suitable means known in the art, wherein the detection of a complex indicates the presence of disease-associated antigenic components in the sample. It will be understood that assays that utilize antibodies directed against sequences previously unidentified, or previously unidentified as being disease-associated, which sequences are disclosed herein, are within the scope of the invention.

Many immunoassay formats are known in the art, and the particular format used is determined by the desired application. An immunoassay can use, for example, a monoclonal antibody directed against a single disease-associated epitope, a combination of monoclonal antibodies directed against different epitopes of a single disease-associated antigenic component, monoclonal antibodies directed towards epitopes of different disease-associated antigens, polyclonal antibodies directed towards the same disease-associated antigen, or polyclonal antibodies directed towards different disease-associated antigens. Protocols can also, for example, use solid supports, or may involve immunoprecipitation.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

Kits suitable for antibody-based diagnostic applications typically include one or more of the following components:

(i) Antibodies: The antibodies may be pre-labeled; alternatively, the antibody may be unlabeled and the ingredients for labeling may be included in the kit in separate containers, or a secondary, labeled antibody is provided; and (ii) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

Nucleic-acid-based diagnostic methods: The invention provides methods for detecting disease-associated nucleic acids in a sample, such as in a biological sample, which methods comprise the steps of: (i) contacting a sample suspected to contain a disease-associated nucleic acid with one or more disease-associated nucleic acid probes under conditions in which hybrids can form between any of the probes and disease-associated nucleic acid in the sample; and (ii) detecting any hybrids formed in step (i) using any suitable means known in the art, wherein the detection of hybrids indicates the presence of the disease-associated nucleic acid in the sample. To detect disease-associated nucleic acids present in low levels in biological samples, it may be necessary to amplify the disease-associated sequences or the hybridization signal as part of the diagnostic assay. Techniques for amplification are known to those of skill in the art.

Disease-associated nucleic acids useful as probes in diagnostic methods include oligonucleotides at least about 15 nucleotides in length, preferably at least about 20 nucleotides in length, and most preferably at least about 25–55 nucleotides in length, that hybridize specifically with one or more disease-associated nucleic acids.

A sample to be analyzed, such as, for example, a tissue sample, may be contacted directly with the nucleic acid probes. Alternatively, the sample may be treated to extract the nucleic acids contained therein. It will be understood that the particular method used to extract DNA will depend on the nature of the biological sample. The resulting nucleic acid from the sample may be subjected to gel electrophoresis or other size separation techniques, or, the nucleic acid sample may be immobilized on an appropriate solid matrix without size separation.

Kits suitable for nucleic acid-based diagnostic applications typically include the following components:

(i) Probe DNA: The probe DNA may be prelabeled; alternatively, the probe DNA may be unlabeled and the ingredients for labeling may be included in the kit in separate containers; and (ii) Hybridization reagents: The kit may also contain other suitably packaged reagents and materials needed for the particular hybridization protocol, including solid-phase matrices, if applicable, and standards.

In cases where a disease condition is suspected to involve an alteration of the disease gene, specific oligonucleotides may be constructed and used to assess the level of disease mRNA in cells affected or other tissue affected by the disease.

For example, to test whether a person has a disease gene, polymerase chain reaction can be used. Two oligonucleotides are synthesized by standard methods or are obtained from a commercial supplier of custom-made oligonucleotides. The length and base composition are determined by standard criteria using the Oligo 4.0 primer Picking program (Wojchich Rychlik, 1992). One of the oligonucleotides is designed so that it will hybridize only to the disease gene DNA under the PCR conditions used. The other oligonucleotide is designed to hybridize a segment of genomic DNA such that amplification of DNA using these oligonucleotide primers produces a conveniently identified DNA fragment. Tissue samples may be obtained from hair follicles, whole blood, or the buccal cavity. The DNA fragment generated by this procedure is sequenced by standard techniques.

Other amplification techniques besides PCR may be used as alternatives, such as ligation-mediated PCR or techniques involving Q-beta replicase (Cahill et al, *Clin. Chem.*, 37(9): 1482–5 (1991)). Products of amplification can be detected by agarose gel electrophoresis, quantitative hybridization, or equivalent techniques for nucleic acid detection known to one skilled in the art of molecular biology (Sambrook et al, *Molecular Cloning. A Laboratory Manual*, Cold Spring Harbor Laboratory, Cold Spring, N.Y. (1989)). Other alterations in the disease gene may be diagnosed by the same type of amplification-detection procedures, by using oligonucleotides designed to identify those alterations.

V. GENOMIC SCREENING

The use of polymorphic genetic markers linked to the Gene 216 gene is very useful in predicting susceptibility to the diseases genetical linked to 20p13-p12. Similarly, as provided in Table 10 the identification of polymorphic genetic markers within the Gene 216 gene will allow the identification of specific allelic variants that are in linkage disequilibrium with other genetic lesions that affect one of the disease states discussed herein including respiratory disorders and obesity. SSCP allows the identification of polymorphisms within the genomic and coding region of the disclosed gene. Table 8 provides primers which one skilled in the art could identify exons which contain SNP's. Table 9 provides primers to identify the sequence change. This information can assist one skilled in the art to identify additional SNP's for use in genomic screening.

This method has been used successfully by others skilled in the art (e.g., Sheffield et al, *Genet.*, 4:1837–1844 (1995); LeBlanc-Straceski et al, *Genomics*, 19:341–9 (1994); Chen et al, *Genomics*, 25:1–8 (1995)). Use of these reagents with populations or individuals will predict their risk for disease described herein including respiratory disorders and obesity.

VI. TREATMENT OF DISORDERS

Thus, the present invention provides methods of screening for drugs comprising contacting such an agent with a novel protein of this invention or fragment thereof and assaying (i) for the presence of a complex between the agent and the protein or fragment, or (ii) for the presence of a complex between the protein or fragment and a ligand, by methods well known in the art. In such competitive binding assays the novel protein or fragment is typically labeled. Free protein or fragment is separated from that present in a protein:protein complex, and the amount of free (i.e., uncomplexed) label is a measure of the binding of the agent being tested to the novel protein or its interference with protein ligand binding, respectively.

This invention also contemplates the use of competitive drug screening assays in which neutralizing antibodies capable of specifically binding the Gene 216 protein compete with a test compound for binding to the Gene 216 protein or fragments thereof. In this manner, the antibodies can be used to detect the presence of any peptide which shares one or more antigenic determinants of a Gene 216 protein.

The goal of rational drug design is to produce structural analogs of biologically active proteins of interest or of small molecules with which they interact (e.g., agonists, antagonists, inhibitors) in order to fashion drugs which are, for example, more active or stable forms of the protein, or which, e.g., enhance or interfere with the function of a protein in vivo. See, e.g., Hodgson, *Bio/Technology*, 9:19–21 (1991). In one approach, one first determines the three-dimensional structure of a protein of interest or, for example, of the Gene 216 receptor or ligand complex, by x-ray crystallography, by computer modeling or most typically, by a combination of approaches. Less often, useful information regarding the structure of a protein may be gained by modeling based on the structure of homologous proteins. An example of rational drug design is the development of HIV protease inhibitors (Erickson et al, *Science*, 249:527–533 (1990)). In addition, peptides (e.g., Gene 216 protein) are analyzed by an alanine scan (Wells, *Methods in Enzymol.*, 202:390–411 (1991)). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved Gene 216 protein activity or stability or which act as inhibitors, agonists, antagonists, etc. of Gene 216 protein activity. By virtue of the availability of cloned Gene 216 gene sequences, sufficient amounts of the Gene 216 protein may be made available to perform such analytical studies as x-ray crystallography. In addition, the knowledge of the Gene 216 protein sequence will guide those employing computer modeling techniques in place of, or in addition to x-ray crystallography.

Cells and animals that carry the Gene 216 gene or an analog thereof can be used as model systems to study and test for substances that have potential as therapeutic agents. After a test substance is applied to the cells, the transformed phenotype of the cell is determined.

The therapeutic agents and compositions of the present invention are useful for preventing or treating respiratory disease. Pharmaceutical formulations suitable for therapy comprise the active agent in conjunction with one or more biologically acceptable carriers. Suitable biologically acceptable carriers include, but are not limited to, phosphate-buffered saline, saline, deionized water, or the like. Preferred biologically acceptable carriers are physiologically or pharmaceutically. acceptable carriers.

The compositions include an effective amount of active agent. Effective amounts are those quantities of the active agents of the present invention that afford prophyladic protection against a respiratory disease, or which result in amelioration or cure of an existing respiratory disease. Prophylactic methods incorporate a prophylactically effective amount of an active agent or composition. A prophylactically effective amount is an amount effective to prevent disease. Treatment methods incorporate a therapeutically effective amount of an active agent or composition. A therapeutically effective amount is an amount sufficient to ameliorate or eliminate the symptoms of disease. The effective amount will depend upon the agent, the severity of disease and the nature of the disease, and the particular host. The amount can be determined by experimentation known in the art, such as by establishing a matrix of dosage amounts and frequencies of dosage administration and comparing a group of experimental units or subjects to each point in the matrix. The prophylactically and/or therapeutically effective amounts can be administered in one administration or over repeated administrations. Therapeutic administration can be followed by prophylactic administration, once initial clinical symptoms of disease have been resolved.

The agents and compositions can be administered topically or systemically. Systemic administration includes both oral and parental routes. Parental routes include, without limitation, subcutaneous, intramuscular, intraperitoneal, intravenous, transdermal, and intranasal administration.

VII. GENE THERAPY

In recent years, significant technological advances have been made in the area of gene therapy for both genetic and acquired diseases. (Kay et al, *Proc. Natl. Acad. Sci. USA*, 94:12744–12746 (1997)) Gene therapy can be defined as the deliberate transfer of DNA for therapeutic purposes. Improvement in gene transfer methods has allowed for development of gene therapy protocols for the treatment of diverse types of diseases. Gene therapy has also taken advantage of recent advances in the identification of new therapeutic genes, improvement in both viral and nonviral gene delivery systems, better understanding of gene regulation, and improvement in cell isolation and transplantation. Gene therapy would be carried out according to generally accepted methods as described by, for example, Friedman, *Therapy for Genetic Diseases*, Friedman, Ed., Oxford University Press, pages 105–121 (1991).

Vectors for introduction of genes both for recombination and for extrachromosomal maintenance are known in the art, and any suitable vector may be used. Methods for introducing DNA into cells such as electroporation, calcium phosphate co-precipitation, and viral transduction are known in the art, and the choice of method is within the competence of one skilled in the art (Robbins, Ed., *Gene Therapy Protocols*, Human Press, NJ (1997)). Cells transformed with a Gene 216 gene can be used as model systems to study chromosome 20 disorders and to identify drug treatments for the treatment of such disorders.

Gene transfer systems known in the art may be useful in the practice of the gene therapy methods of the present invention. These include viral and nonviral transfer methods. A number of viruses have been used as gene transfer vectors, including polyoma, i.e., SV40 (Madzak et al, *J. Gen. Virol.*, 73:1533–1536 (1992)), adenovirus (Berkner, *Curr. Top. Microbiol. Immunol.*, 158:39–61 (1992); Berkner et al, *Bio Techniques*, 6:616–629 (1988); Gorziglia et al, *J. Virol.*, 66:4407–4412 (1992); Quantin et al, *Proc. Natl. Acad. Sci. USA*, 89:2581–2584 (1992); Rosenfeld et al, *Cell*, 68:143–155 (1992); Wilkinson et al, *Nucl. Acids Res.*, 20:2233–2239 (1992); Stratford-Perricaudet et al, *Hum. Gene Ther.*, 1:241–256 (1990)), vaccinia virus (Mackett et al, *Biotechnology*, 24:495–499 (1992)), adeno-associated virus (Muzyczka, *Curr. Top. Microbiol. Immunol.*, 158:91–123 (1992); Ohi et al, *Gene*, 89:279–282 (1990)), herpes viruses including HSV and EBV (Margolskee, *Curr. Top. Microbiol. Immunol.*, 158:67–90 (1992); Johnson et al, *J. Virol.*, 66:2952–2965 (1992); Fink et al, *Hum. Gene Ther.*, 3:11–19 (1992); Breakfield et al, *Mol. Neurobiol.*, 1:337–371 (1987;) Fresse et al, *Biochem. Pharmacol.*, 40:2189–2199 (1990)), and retroviruses of avian (Brandyopadhyay et al, *Mol. Cell Biol.*, 4:749–754 (1984); Petropouplos et al, *J. Virol.*, 66:3391–3397 (1992)), murine (Miller, *Curr. Top. Microbiol. Immunol.*, 158:1–30 24 (1992); Miller et al, *Mol. Cell Biol.*, 5:431–437 (1985); Sorge et al, *Mol. Cell Biol.*, 4:1730–1737 (1984); Mann et al, *J. Virol.*, 54:401–407 (1985)), and human origin (Page et al, *J. Virol.*, 64:5370–5276(1990); Buchschalcher et al, *J. Virol.*, 66:2731–2739 (1992)). Most human gene therapy protocols have been based on disabled murine retroviruses.

Nonviral gene transfer methods known in the art include chemical techniques such as calcium phosphate coprecipitation (Graham et al, *Virology*, 52:456–467 (1973); Pellicer et al, *Science*, 209:1414–1422 (1980)), mechanical techniques, for example microinjection (Anderson et al, *Proc. Natl. Acad. Sci. USA*, 77:5399–5403 (1980); Gordon et al, *Proc. Natl. Acad. Sci. USA*, 77:7380–7384 (1980); Brinster et al, *Cell*, 27:223–231 (1981); Constantini et al, *Nature*, 294:92–94 (1981)), membrane fusion-mediated transfer via liposomes (Feigner et al, *Proc. Natl. Acad Sci. USA*, 84:7413–7417 (1987); Wang et al, *Biochemistry*, 28:9508–9514 (1989); Kaneda et al, *J. Biol. Chem.*, 264:12126–12129 (1989); Stewart et al, *Hum. Gene Ther.*, 3:267–275 (1992); Nabel et al, *Science*, 249:1285–1288 (1990); Lim et al, *Circulation*, 83:2007–2011 (1992)), and direct DNA uptake and receptor-mediated DNA transfer (Wolff et al, *Science*, 247:1465–1468 (1990); Wu et al, *BioTechniques*, 11:474–485 (1991); Zenke et al, *Proc. Natl. Acad. Sci. USA*, 87:3655–3659 (1990); Wu et al, *J. Biol. Chem.*, 264:16985–16987 (1989); Wolff et al, *BioTechniques*, 11:474–485 (1991); Wagner et al, 1990; Wagner et al, *Proc. Natl. Acad. Sci. USA*, 88:4255–4259 (1991); Cotten et al, *Proc. Natl. Acad. Sci. USA*, 87:4033–4037 (1990); Curiel et al, *Proc. Natl. Acad. Sci. USA*, 88:8850–8854 (1991); Curiel et al, *Hum. Gene Ther.*, 3:147–154 (1991)).

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is non-specific, localized in vivo uptake and expression have been reported in tumor deposits, for example, following direct in situ administration (Nabel, *Hum. Gene Ther.*, 3:399–410 (1992)).

VIII. TRANSGENIC ANIMALS

This invention further relates to nonhuman transgenic animals capable of expressing an exogenous or non-naturally occurring variant Gene 216 gene. Such a transgenic animal can also have one or more endogenous genes inactivated or can, instead of expressing an exogenous variant gene, have one or more endogenous analogs inactivated. Any nonhuman animal can be used; however typical animals are rodents, such as mice, rats, or guinea pigs.

Animals for testing therapeutic agents can be selected after treatment of germline cells or zygotes. Thus, expression of an exogenous Gene 216 gene or a variant can be achieved by operably linking the gene to a promoter and optionally an enhancer, and then microinjecting the construct into a zygote. See, e.g., Hogan, et al., *Manipulating the Mouse Embryo, A Laboratory Manual*, Cold Spring Harbor Laboratory, Cold Spring Harbor, N.Y. Such treatments include insertion of the exogenous gene and disrupted homologous genes. Alternatively, the gene(s) of the animals may be disrupted by insertion or deletion mutation of other genetic alterations using conventional techniques, such as those described by, for example, Capecchi, *Science*, 244:1288 (1989); Valancuis et al, *Mol. Cell Biol.*, 11:1402 (1991); Hasty et al, *Nature*, 350:243 (1991); Shinkai et al, *Cell*, 68:855 (1992); Mombaerts et al, *Cell*, 68:869 (1992); Philpott et al, *Science*, 256:1448 (1992); Snouwaert et al, *Science*, 257:1083 (1992); Donehower et al, *Nature*, 356:215 (1992). After test substances have been administered to the animals, modulation of the disorder must be assessed. If the test substance reduces the incidence of the disorder, then the test substance is a candidate therapeutic agent. These animal models provide an extremely important vehicle for potential therapeutic products.

The disclosure of each of the patents, patent applications and publications cited in the specification is hereby incorporated by reference herein in its entirety.

Although the invention has been set forth in detail, one skilled in the art will recognize that numerous changes and modifications can be made, and that such changes and modifications may be made without departing from the spirit and scope of the invention.

What is claimed is:

1. An isolated nucleic acid which comprises a nucleotide sequence selected from the group consisting of:
   a. SEQ ID NO:2;
   b. a nucleotide sequence encoding amino acid sequence SEQ ID NO:5;
   c. a nucleotide sequence which is fully complementary to and of the same length as the nucleotide sequence of (a);
   d. a nucleotide sequence which exhibits at least 98% nucleotide sequence identity to the nucleotide sequence of (a); and
   e. a nucleotide sequence which is fully complementary to and of the same length as the nucleotide sequence of (d).

2. The isolated nucleic acid of claim 1 which is DNA.
3. The isolated nucleic acid of claim 1 which is RNA.
4. An expression vector containing the nucleic acid of claim 1.
5. A host cell containing the vector of claim 4.
6. The host cell of claim 5 which is a eukaryotic cell.
7. The host cell of claim 6 which is a human cell.
8. The host cell of claim 5 which is a prokaryotic cell.
9. Isolated DNA or RNA comprising:
   a. a nucleic acid which comprises SEQ ID NO:2; or
   b. a nucleic acid which is fully complementary to and of the same length as the nucleic acid of (a).
10. An isolated nucleic acid which exhibits at least 98% nucleotide sequence identity to the isolated DNA or RNA of claim 9.
11. An expression vector containing the DNA or RNA of claim 9.
12. A host cell containing the vector of claim 11.
13. The host cell of claim 5 which is a eukaryotic cell.
14. The host cell of claim 6 which is a human cell.
15. The host cell of claim 5 which is a prokaryotic cell.
16. An isolated nucleic acid which comprises at least 500 consecutive nucleotides of SEQ ID NO:2, and contains a G at single nucleotide polymorphism site Q1.
17. An isolated nucleic acid which is fully complementary to and of the same length as the polynucleotide of claim 16.

* * * * *